(12) United States Patent
Kong et al.

(10) Patent No.: US 12,312,378 B2
(45) Date of Patent: *May 27, 2025

(54) GLUCOSAMINE DERIVATIVES FOR THE PREVENTION OR TREATMENT OF JOINT DISORDERS

(71) Applicant: RISEN (SUZHOU) PHARMA TECH CO., LTD., Jiangsu (CN)

(72) Inventors: Xianqi Kong, Dollard-des-Ormeaux (CA); Jiasheng Lu, Shanghai (CN); Jiamin Gu, Suzhou (CN); Xiang Ji, Suzhou (CN); Daiqiang Hu, Suzhou (CN); Xiuchun Zhang, Suzhou (CN); Xinyong Lv, Suzhou (CN); Jinchao Ai, Suzhou (CN); Dongdong Wu, Suzhou (CN); Lin Wang, Suzhou (CN); Dongqing Zhu, Suzhou (CN); Xiaolin He, Suzhou (CN)

(73) Assignee: RISEN (SUZHOU) PHARMA TECH CO., LTD., Suzhou (CN)

( * ) Notice: Subject to any disclaimer, the term of this patent is extended or adjusted under 35 U.S.C. 154(b) by 0 days.

This patent is subject to a terminal disclaimer.

(21) Appl. No.: 18/211,796

(22) Filed: Jun. 20, 2023

(65) Prior Publication Data

US 2024/0051982 A1  Feb. 15, 2024

Related U.S. Application Data

(63) Continuation of application No. 16/954,491, filed as application No. PCT/CA2018/051608 on Dec. 17, 2018, now Pat. No. 11,718,636.

(60) Provisional application No. 62/621,987, filed on Jan. 25, 2018.

(30) Foreign Application Priority Data

Dec. 18, 2017  (CN) .......................... 201711364533.8

(51) Int. Cl.
| | | |
|---|---|---|
| C07H 5/06 | (2006.01) |
| A61K 9/00 | (2006.01) |
| A61P 19/02 | (2006.01) |
| C07H 15/04 | (2006.01) |
| C07H 15/12 | (2006.01) |
| C07H 15/14 | (2006.01) |
| C07H 15/18 | (2006.01) |
| C07H 15/203 | (2006.01) |
| C07H 15/26 | (2006.01) |
| C07H 19/01 | (2006.01) |
| C07H 19/02 | (2006.01) |
| C07H 19/24 | (2006.01) |
| C07J 9/00 | (2006.01) |

(52) U.S. Cl.
CPC ............. C07H 5/06 (2013.01); A61K 9/0014 (2013.01); A61K 9/0053 (2013.01); A61P 19/02 (2018.01); C07H 15/04 (2013.01); C07H 15/12 (2013.01); C07H 15/14 (2013.01); C07H 15/18 (2013.01); C07H 15/203 (2013.01); C07H 15/26 (2013.01); C07H 19/01 (2013.01); C07H 19/02 (2013.01); C07H 19/24 (2013.01); C07J 9/00 (2013.01); C07B 2200/05 (2013.01); C07B 2200/09 (2013.01)

(58) Field of Classification Search
CPC ........ C07H 15/12; C07H 15/14; C07H 15/18; C07H 15/203; C07H 15/26; C07H 15/04; C07H 15/22; C07H 19/01; C07H 19/02; C07H 9/06; C07H 13/04; C07H 13/06; C07H 13/08; C07H 13/10; C07H 13/12; C07H 13/02; C07J 41/0055; A61K 31/7008; A61K 31/7028; A61K 31/7052; A61P 19/00

See application file for complete search history.

(56) References Cited

U.S. PATENT DOCUMENTS

| | | |
|---|---|---|
| 3,427,300 A | 2/1969 | Sarett et al. |
| 3,987,029 A | 10/1976 | Kirby et al. |
| RE29,903 E | 2/1979 | Kirby |
| 2014/0128479 A1 | 5/2014 | Maggio |

FOREIGN PATENT DOCUMENTS

| | | |
|---|---|---|
| WO | 2005116086 A1 | 12/2005 |
| WO | 2006081616 A1 | 8/2006 |

OTHER PUBLICATIONS

Yan et al., Enzyme and Microbial Technology, 1999, p. 725-728.
(Continued)

*Primary Examiner* — Jonathan S Lau
(74) *Attorney, Agent, or Firm* — BCF LLP

(57) ABSTRACT

There are provided compounds of Formula (A) and pharmaceutically acceptable salts and esters thereof, and pharmaceutical compositions thereof, used for the prevention or treatment in a manual of joint and bone disorders such as arthritis and osteoporosis.

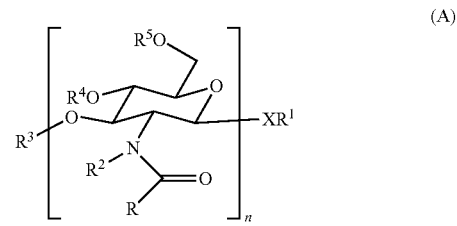

20 Claims, 9 Drawing Sheets

(56) References Cited

OTHER PUBLICATIONS

Ichikawa Yoshitaka et al., Synthesis of N-Acetylglucosamine derivatives as probes for specificity of chicken hepatic lectin, Glycoconjugate Journal, vol. 7, No. 4, p. 355-348, Jan. 1, 1990.
Sandor-Csaba Ats et al., Spacer-modified trisaccharide glycosides that mimic the biantennary Asn-inkedoligosaccharide acceptor of (1-4)-[beta]-d-galactorsyltransferase and can be used as competitive inhibitors and for irreversible deactivation, Carbohydrate research, vol. 233, p. 141-150, Sep. 1, 1992.
Dwivedi Deepti et al., Antomycobacterial serratamolides and diacly peptoglucosamine derivatives of Serratia sp., Journal of Natural Products, vol. 17, No. 4, Apr. 1, 2008.
Meindl et al., Darstellung und ensumatisch spaltbarkeit von [alpha]-Ketosiden der N-Propionyl-, N-Butyryl-un N-Bensoyl-d-Neuraminsaure, Manalshefle Fur Chemie/Chemical Monthly, Springer Vienne, vo. 97, No. 6, Jan. 1, 1966.
Inka Brockhausen et al., UDP-Gal: GlcNAc-R [beta] 1, 4-galactosyltransferase—a target enzyme for drug design. Acceptor specificity and inhibition of the enzyme, Glycoconjugate Journal, Springer New York, vol. 263, No. 7-8, p. 525-541, Nov. 1, 2006.
Koyayashi et al., Enzymatic synthesis of chondroitin and its derivatives catalyzed by Hyaluronidase, Journal of the American Chemical Society, American Chemical Society, vol. 125, No. 47, p. 14357-14369, Nov. 26, 2003.
Pohnlein et al., Enzumatic synthesis of amino sugar fatty acid esters, European Journal of Lipid Science Technology, vol. 116, No. 4, p. 423-428, Apr. 1, 2014.
Dang et al., Synthesis and characterization of N-acyl-tetra-O-acyl glucosamine derivatives, RSC Advances, 4(12), 5239-6245, 2014.
Hirano et al., Resolution of anomeric ethyl 2-amino-2-deoxy-D-gluxopyranoside by cation-exchange chromatography, and its N-acylation with carboxylic anhydrides, Journal of Organic Chemistry, 41(25) 4038-4040, 1976.
Pertel et al., Formation and opening of oxazoline ring in 2-amino-2-deoxy carbohydrates as a method of achieving intramolecular migration of an acyl radical from an amino group to a glucosidic hydroxul, Bioorganicheskaya Khimiya, 21(3), 226-229, 1995.
Inouye et al., Some fatty-acid derivatives of D-glucosamine, Journal of the American Chemical Society, 78, 4722-4724, 1956.
Morando et al., Mimicking Chitin: Chemical Synthesis, Conformational Analysis and Molecular Recognition of the B (1-3) N-Acetylchitopentaose Analogue, Chemistry—A European Journal, 16(14), 4239-4249, 2010.
Shajahan, A. et al., Carbohydrate-Neuroactive Hybrid Strategy for Metabolic Glycan Engineering of the Central Nervous System in Vivo, ACS Publications, J. Am. Chem. Soc., 2017, 139, 693-700.
Examiner's report issued in corresponding Japanese patent application No. 2023-192417 on Nov. 18, 2024.

GLUCOSAMINE DERIVATIVES FOR THE PREVENTION OR TREATMENT OF JOINT DISORDERS

CROSS-REFERENCE TO RELATED APPLICATIONS

This application is a Continuation of U.S. application Ser. No. 16/954,491 filed Jun. 16, 2020, now U.S. Pat. No. 11,718,636, which is a national phase entry under U.S.C. 371 of International Application No. PCT/CA2018/051608 filed Dec. 17, 2018 which claims priority from U.S. Provisional Application No. 62/621,987 filed Jan. 25, 2018, and from Chinese Application No. 201711364533.8 filed Dec. 18, 2017, the entire contents of each of which are hereby incorporated by reference.

FIELD

The present disclosure relates to glucosamine derivatives, compositions thereof, and methods of use thereof in therapeutic applications such as the prevention and treatment of arthritis and osteoporosis.

BACKGROUND

Osteoporosis is a condition in which the bones become less dense and more likely to fracture. In the United States, more than 53 million people either already have osteoporosis or are at high risk due to low bone mass. In osteoporosis, there is a loss of bone tissue that leaves bones less dense and more likely to fracture. It can result in a loss of height, severe back pain, and change in one's posture. Osteoporosis can impair a person's ability to walk and can cause prolonged or permanent disability.

Osteoporosis is known as a silent disease because it can progress undetected for many years without symptoms until a fracture occurs. Osteoporosis is diagnosed by a bone mineral density test, which is a safe and painless way to detect low bone density. The World Health Organization defines the presence of osteoporosis in humans in terms of low bone mineral density BMD. Individuals whose BMD is less than 2.5 standard deviations below the mean of young normals of their sex in respect of peak bone mass, are considered to have osteoporosis. Individuals whose BMD is less than 1.0 standard deviations below peak bone mass of their sex, are considered to have osteopenia. Osteoporosis results in a higher probability of fracturing bones. It is well known that women have a higher prevalence of osteoporosis and fractures compared to males, and that there is an increased prevalence of osteoporosis and associated increased incidence of fractures after the menopause. Low impact injuries can result in osteoporotic fractures, or so called "fragility fractures". Fractures can occur also after high impact, as a result of significant trauma, in individuals with normal bones or osteoporotic or osteopenic bones. The healing of high impact fractures depends on stimulation of new bone formation. Local osteoporosis can occur as a result of immobilization during the treatment of the fracture.

Although BMD is a reasonably good predictor of the risk of fracture in sites such as the hip or spine it is becoming increasingly recognized that there are a number of limitations to the usefulness of BMD measurements. One of the reasons is that DXA technology does not assess bone quality, which depends to a large extent on the micro-architecture of bone. Most drugs used in osteoporosis, such as the bi-phosphonates, increase BMD but do not improve the micro-architecture or the connectivity of bone. Parathyroid hormone administration results in an improvement of trabecular architecture. Glucosamine-based synthetic compounds are not known to improve BMD or bone microarchitecture.

Although currently there is no cure for the disease, the Food and Drug Administration has approved several medications to prevent and treat osteoporosis. In addition, a diet rich in calcium and vitamin D, regular weight-bearing exercise, and a healthy lifestyle can prevent or lessen the effects of the disease.

Arthritis is a general term for conditions that affect the joints and surrounding tissues. Joints are places in the body where bones come together, such as the knees, wrists, fingers, toes, and hips. Two common types of arthritis are osteoarthritis and inflammatory arthritis, such as rheumatoid arthritis.

Osteoarthritis (OA) is a painful, degenerative joint disease that often involves the hips, knees, neck, lower back, or small joints of the hands. OA usually develops in joints that are injured by repeated overuse from performing a particular task or playing a favorite sport or from carrying around excess body weight. Eventually this injury or repeated impact thins or wears away the cartilage that cushions the ends of the bones in the joint. As a result, the bones rub together, causing a grating sensation. Joint flexibility is reduced, bony spurs develop, and the joint swells. Usually, the first symptom of OA is pain that worsens following exercise or immobility. Treatment usually includes analgesics, topical creams, or nonsteroidal anti-inflammatory drugs, appropriate exercises or physical therapy; joint splinting; or joint replacement surgery for seriously damaged larger joints, such as the knee or hip. Glucosamine is a popular non-prescription, nutraceutical treatment for pain in OA.

Rheumatoid arthritis (RA) is an autoimmune inflammatory disease that usually involves various joints in the fingers, thumbs, wrists, elbows, shoulders, knees, feet, and ankles. An autoimmune disease is one in which the body releases enzymes that attack its own healthy tissues. In RA, these enzymes destroy the linings of joints. This causes pain, swelling, stiffness, malformation, and reduced movement and function. People with RA also may have systemic symptoms, such as fatigue, fever, weight loss, eye inflammation, anemia, subcutaneous nodules (bumps under the skin), or pleurisy (a lung inflammation).

Subjects suffering from osteoporosis and arthritis share many coping strategies. Many with one or both of these conditions benefit from exercise programs that may include physical therapy and rehabilitation. However, there is no real cure for either or both of these conditions and better treatments are needed.

Glycoconjugates play an important role in many biological processes. Carbohydrate groups can confer important physical properties such as conformational stability, protease resistance, charge and water-binding capacity, and biological recognition, where sequence diversity provides signals for protein targeting and cell-cell interactions (Paulson, J. C., Trends in Biochemical Sciences, 1989, 14(7): 272-6). Glycoconjugates of connective tissue matrices consist of hexosamines that are N-acetylated. However, the function of the N-acetyl moiety is not known.

The benefit of glucosamine (GlcN) in bone and joint disorders remains controversial. N-acetylation and other N-acylations of GlcN alter its biological properties fundamentally. N-butyryl glucosamine (GlcNBu) preserved strikingly the subchondral bone structure in a destructive arthritis rat model. Studies have shown that GlcNBu feeding in the OVX rat preserves bone mineral and some biomechanical properties (Anastassiades, T. et al., Translational Research, 2013, 162 (2):93-101). Pharmaceutical applications of GlcNBu have also been described (see for example, U.S. Pat. No. 6,479,469 (titled "Treatment of Arthritis and Compositions Therefore"), and U.S. Patent Application Publication No. 2006/0046976 (titled "Method for Increasing the Bone Mineral Density and Bone Micro-architecture or Connectivity of a Mammal using N-acylated Glucosamines), the contents of which are hereby incorporated by reference in their entirety.

However glucosamine and GlcNBu have limited therapeutic potential due to their poor pharmacokinetic properties. Glucosamine is usually administered in large doses (e.g., 3 g/day; see Barclay, T. S. et al., The Annals of Pharmacotherapy, 1998, 32(5): 574-579) due to its low oral bioavailability (F) as assessed using rats (F: 0.19-0.21; Aghazadeh-Habashi, A. et al.; J. Pharm. Pharm. Sci., 2002, 5:181-4). When glucosamine is given even in very large doses to humans, it is cleared quickly from the circulation to the point that serum levels cannot be detected after oral or IV administration. N-acetylglucosamine (GluNAc) has a longer half-life than glucosamine when administered to humans in polyvalent or monovalent form (Talent J. M. & Gracy R. W., Clinical therapeutics 1996, 18: 1184-90), but no efficacy data were recorded. GlcNBu also demonstrates low bioavailability, with an oral bioavailability range from 15% to 17% in Sprague Dawley (SD) rats. In addition to low bioavailability, GlcNBu is cleared quickly, with a half-life of only about 20 min. in rats (data from i.v., i.p., and p.o. studies; Aghazadeh-Habashi A. et al., Journal of Pharmacy & Pharmaceutical Sciences 2006, 9(3): 359-364).

SUMMARY

It is an object of the present invention to ameliorate at least some of the deficiencies present in the prior art. Embodiments of the present technology have been developed based at least in part on the inventors' appreciation that there is a need for treatments for bone and joint disorders such as osteoporosis and arthritis. These and other needs can be satisfied by the disclosure herein of GlcNBu derivatives and/or prodrugs, pharmaceutical compositions and uses thereof to treat osteoporosis, arthritis, and other bone and joint disorders.

In a first broad aspect, there are provided compounds of Formula A, or pharmaceutically acceptable salts or esters thereof:

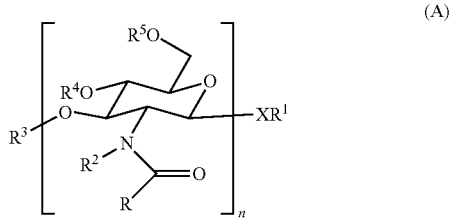

(A)

where X is O, N, or S; n is an integer from 1 to 6; R is a substituted or unsubstituted $C_2$ to $C_{18}$ substituent selected from linear or branched alkyl, alkenyl, alkynyl, aryl, heteroaryl, arylalkyl, alkylaryl, cycloalkyl, and alkyl comprising a cyclic or a heterocyclic moiety; $R^2$ is hydrogen, acyl, or alkyl; $R^1$, $R^3$, $R^4$, and $R^5$ are independently hydrogen, substituted or unsubstituted alkyl, aryl, arylalkyl, alkylaryl, cyclic or heterocyclic moiety, or acyl group derived from a carboxylic acid, an amino acid, or a peptide, optionally with a protecting group, a phosphonyl group, or a sulfonyl group, provided that $R^1$, $R^3$, $R^4$, and $R^5$ are not all hydrogen at the same time.

In one embodiment, $R^3$ and $R^4$, taken together with the atoms to which they are attached, form a substituted or unsubstituted heterocyclic ring.

In another embodiment, $R^4$ and $R^5$, together with the atoms to which they are attached, form a substituted or unsubstituted heterocyclic ring.

In one embodiment, one or more of $R^1$, $R^3$, $R^4$, and $R^5$ are independently in the form of $Q^1C(=O)—$, where $Q^1$ is selected from unsubstituted or substituted alkyl, alkenyl, alkynyl, aryl, heteroaryl, carbocyclic group with or without a substituent group, heterocyclic group with or without a substituent group, alkoxy, aryloxy, arylalkyloxy, and alkylaryloxy; and an amino or hydroxyl group in $Q^1$, if present, may or may not be further substituted.

In another embodiment, one or more of $R^1$, $R^3$, $R^4$, and $R^5$ are independently selected from alkoxycarbonyl, aryloxycarbonyl, and arylalkoxycarbonyl.

In an embodiment, R is a substituted or unsubstituted $C_2$ to $C_{12}$ substituent selected from linear or branched alkyl, alkenyl, alkynyl, aryl, heteroaryl, arylalkyl, alkylaryl, cycloalkyl, and alkyl comprising a cyclic or a heterocyclic moiety.

In one embodiment, a compound according to Formula (A) is in alpha-configuration at the anomeric center; in another embodiment, a compound according to Formula (A) is in beta-configuration at the anomeric center; and in a further embodiment, a compound according to Formula (A) is a mixture of alpha- and beta-configuration at the anomeric center.

In some embodiments, n is 1 to 4; in another embodiment, n is 2; in a further embodiment, n is 1.

In another aspect, there are provided compounds of Formula (I), or pharmaceutically acceptable salts or esters thereof:

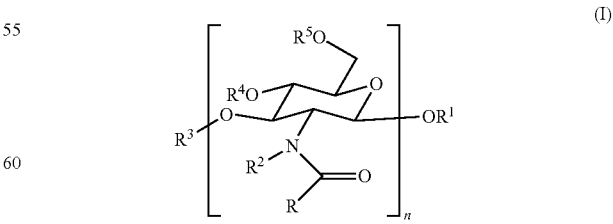

(I)

where R, $R^1$ through $R^5$, and n are as previously defined.

In one embodiment, a compound according to Formula (I) is in alpha-configuration at the anomeric center; in another embodiment, a compound according to Formula (I) is in beta-configuration at the anomeric center; and in a further embodiment, a compound according to Formula (I) is a mixture of alpha- and beta-configuration at the anomeric center.

In some embodiments of Formula (I), n is 1 to 4; in an embodiment, n is 2; and in another embodiment, n is 1.

In an embodiment of Formula (I), $R^2$ is hydrogen.

In another aspect, there are provided compounds of Formula (II), or pharmaceutically acceptable salts or esters thereof:

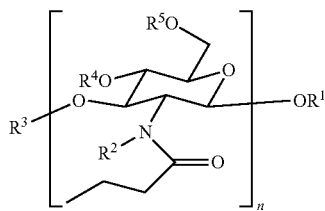

where $R^1$ through $R^5$ and n are as previously defined.

In one embodiment, a compound according to Formula (II) is in alpha-configuration at the anomeric center; in another embodiment, a compound according to Formula (II) is in beta-configuration at the anomeric center; and in a further embodiment, a compound according to Formula (II) is a mixture of alpha- and beta-configuration at the anomeric center.

In some embodiments of Formula (II), n is 1 to 4; in an embodiment, n is 2; and in another embodiment, n is 1.

In an embodiment of Formula (II), $R^2$ is hydrogen.

In another aspect, there are provided compounds of Formula (III), or pharmaceutically acceptable salts or esters thereof:

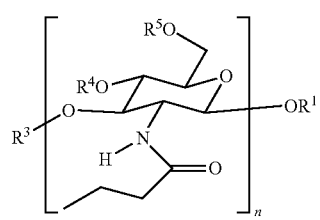

where $R^1$, $R^3$ through $R^5$ and n are as previously defined.

In another aspect, there are provided compounds of Formula (IV), or pharmaceutically acceptable salts or esters thereof:

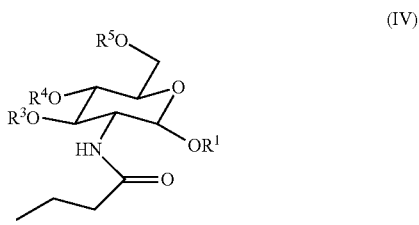

where $R^1$ and $R^3$ through $R^5$ are as previously defined.

In one embodiment of Formula (IV), $R^1$, $R^3$, $R^4$, and $R^5$ are independently H, $C_1$-$C_{12}$ alkyl, acyl, or an amino acid residue, provided that $R^1$, $R^3$, $R^4$, and $R^5$ are not all H at the same time.

In another embodiment of Formula (IV), $R^1$ is H, and $R^3$, $R^4$, and $R^5$ are independently H, $C_1$-$C_6$ alkyl, acyl, or a natural amino acid residue, provided that $R^3$, $R^4$, and $R^5$ are not all H at the same time.

In another embodiment of Formula (IV), $R^1$ and $R^3$ are H, and $R^4$ and $R^5$ are independently selected from H, $C_1$-$C_6$ acyl, or an unsubstituted or substituted natural amino acyl group.

In one embodiment, a compound according to Formula (IV) is in alpha-configuration at the anomeric center; in another embodiment, a compound according to Formula (IV) is in beta-configuration at the anomeric center; and in a further embodiment, a compound according to Formula (IV) is a mixture of alpha- and beta-configuration at the anomeric center.

In another embodiment of compounds provided herein, $R^2$ is hydrogen (H).

In some embodiments, the compound of Formula (A), (I), (II), (III), or (IV) is not a derivative of N-acetyl glucosamine.

In one embodiment, the C, H, O, and/or N atoms in the compound of Formula (A), (I), (II), (III), or (IV) are in natural abundance or are isotope-enriched.

In another embodiment, the C atoms in the compound of Formula (A), (I), (II), (III), or (IV) are independently $^{12}C$, $^{13}C$, or $^{14}C$; the H atoms are independently $^1H$, D ($^2H$), or T ($^3H$); the O-atoms are independently $^{16}O$, $^{17}O$, or $^{18}O$; and the N atoms are independently $^{14}N$ or $^{15}N$.

In some embodiments, at least one of the C, H, O and N atoms in the compound of Formula (A), (I), (II), (III), or (IV) is isotope-enriched.

In some embodiments, the compound of Formula (A), (I), (II), (III), or (IV) is a prodrug of GlcNBu. Without wishing to be limited by theory, in some cases the compound of Formula (A), (I), (II), (III), or (IV) may be converted to GlcNBu in vivo after administration in a subject, and thus serve as a prodrug of GlcNBu. In such embodiments the compound of Formula (A), (I), (II), (III), or (IV) may be used to increase the therapeutic efficacy of GlcNBu in the treatment of bone and joint disorders such as osteoporosis and/or arthritis by e.g. increasing bioavailability, stability, and/or reducing metabolism of GlcNBu, as compared to administration of GlcNBu itself.

In some embodiments, the compound of Formula (A), (I), (II), (III), or (IV) is a compound shown in Table 1, or a pharmaceutically-acceptable salt, ester, chelator, hydrate, solvate, stereoisomer, or polymorphic form thereof.

TABLE 1

Examples of GlcNBu derivatives.

| No. | Structure |
|---|---|
| 1 | *(structure: Boc-Tyr(OBoc)-O-CH2-GlcNBu)* |
| 2 | *(structure: Boc-Val-O-CH2-GlcNBu)* |
| 3 | *(structure: Boc-Gly-Val-O-CH2-GlcNBu)* |
| 4 | *(structure: H2N-Gly-Val-O-CH2-GlcNBu · HCl)* |
| 5 | *(structure: H-Val-O-CH2-GlcNBu · HCl)* |
| 6 | *(structure: per-O-butyryl GlcNBu)* |

TABLE 1-continued

Examples of GlcNBu derivatives.

| No. | Structure |
|---|---|
| 7 | 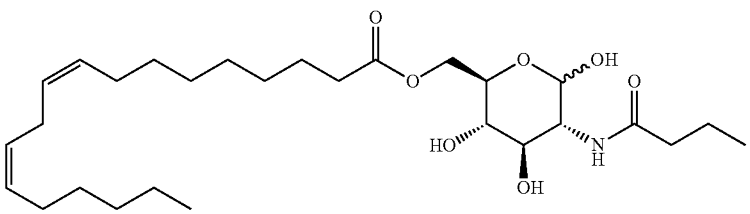 [SMILES: CCCCC/C=C\C/C=C\CCCCCCCC(=O)OC[C@H]1OC(O)[C@H](NC(=O)CCC)[C@@H](O)[C@@H]1O] |
| 8 | 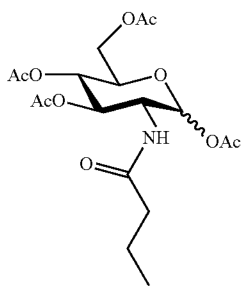 |
| 9 | 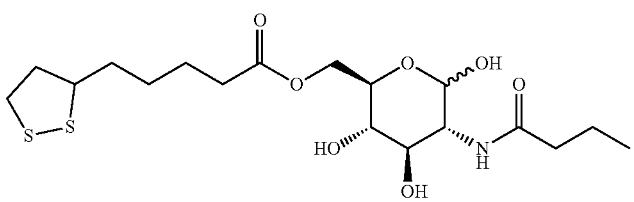 [SMILES: CCCC(=O)N[C@H]1C(O)O[C@H](COC(=O)CCCCC2CCSS2)[C@@H](O)[C@@H]1O] |
| 10 | 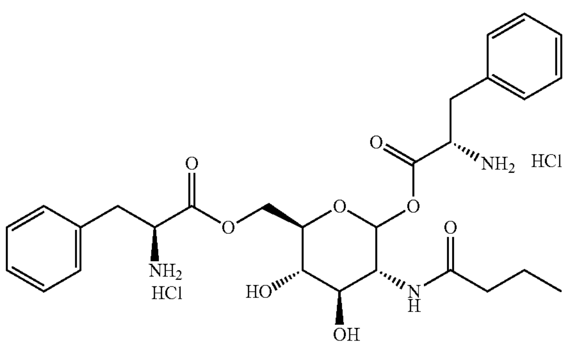 [SMILES: CCCC(=O)N[C@H]1C(OC(=O)[C@@H](N)Cc2ccccc2)O[C@H](COC(=O)[C@@H](N)Cc2ccccc2)[C@@H](O)[C@@H]1O ; Cl ; Cl] |
| 11 | 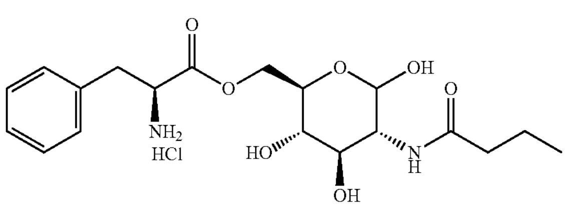 [SMILES: CCCC(=O)N[C@H]1C(O)O[C@H](COC(=O)[C@@H](N)Cc2ccccc2)[C@@H](O)[C@@H]1O ; Cl] |

TABLE 1-continued

Examples of GlcNBu derivatives.

| No. | Structure |
|---|---|
| 12 | (structure) |
| 13 | (structure) |
| 14 | (structure) |
| 15 | (structure) |
| 16 | (structure) |

TABLE 1-continued
Examples of GlcNBu derivatives.
| No. | Structure |
|---|---|
| 17 | 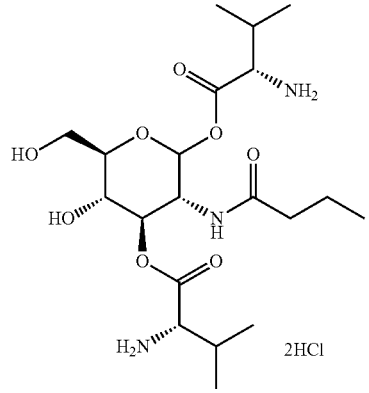 [SMILES: CCCC(=O)N[C@H]1C(OC(=O)[C@@H](N)C(C)C)O[C@H](CO)[C@@H](O)[C@@H]1OC(=O)[C@@H](N)C(C)C] 2HCl |
| 18 | 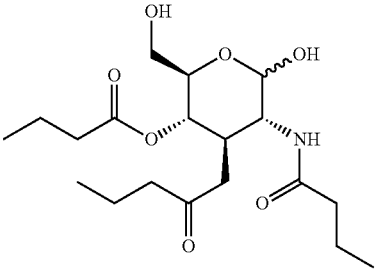 [SMILES: CCCC(=O)C[C@H]1[C@H](OC(=O)CCC)[C@@H](CO)OC(O)[C@@H]1NC(=O)CCC] |
| 19 | 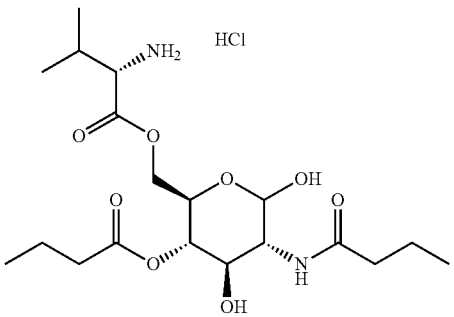 [SMILES: CCCC(=O)N[C@H]1C(O)O[C@H](COC(=O)[C@@H](N)C(C)C)[C@@H](OC(=O)CCC)[C@@H]1O ; Cl] |
| 20 | 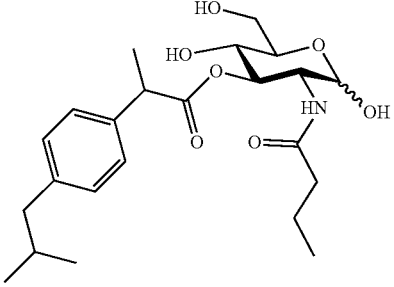 |

TABLE 1-continued

Examples of GlcNBu derivatives.

| No. | Structure |
|---|---|
| 21 | (structure shown) |
| 22 | (structure shown) |
| 23 | (structure shown) |
| 24 | (structure shown) |
| 25 | (structure shown) |

In some embodiments, the compound of Formula (A), (I), (II), (III), or (IV) is a compound shown in Table 2, or a pharmaceutically-acceptable salt, ester, chelator, hydrate, solvate, stereoisomer, or polymorphic form thereof.

TABLE 2

Other examples of GlcNBu derivatives.

| No. | Structure |
|---|---|
| 26 | (structure: 6-O-butyryl GlcNBu) |
| 27 | (structure: 4-O-butyryl GlcNBu) |
| 28 | (structure: 1-O-butyryl GlcNBu) |
| 29 | (structure: ethyl GlcNBu glycoside) |
| 30 | (structure: 4-hydroxyphenethyl GlcNBu glycoside) |
| 31 | (structure: 2-hydroxybenzyl GlcNBu glycoside) |

TABLE 2-continued

Other examples of GlcNBu derivatives.

| No. | Structure |
|-----|-----------|
| 32 | 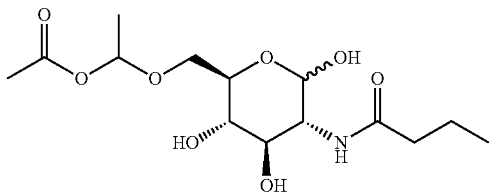 [SMILES: CCCC(=O)N[C@H]1C(O)O[C@H](COC(C)OC(C)=O)[C@@H](O)[C@@H]1O] |
| 33 | 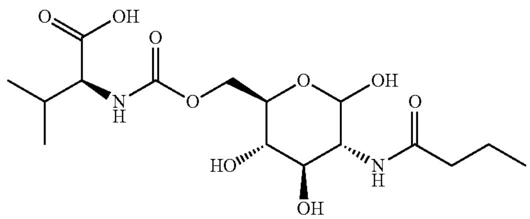 [SMILES: CCCC(=O)N[C@H]1C(O)O[C@H](COC(=O)N[C@H](C(=O)O)C(C)C)[C@@H](O)[C@@H]1O] |
| 34 | 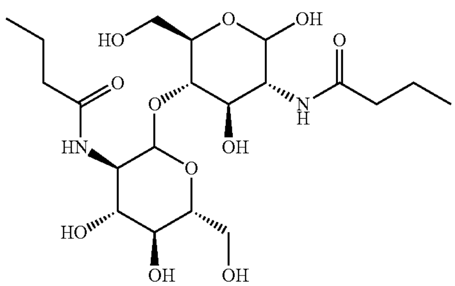 [SMILES: CCCC(=O)N[C@H]1C(O[C@H]2[C@H](O)[C@@H](NC(=O)CCC)C(O)O[C@@H]2CO)O[C@H](CO)[C@@H](O)[C@@H]1O] |
| 35 | 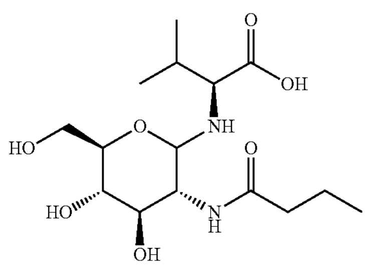 [SMILES: CCCC(=O)N[C@H]1C(N[C@H](C(=O)O)C(C)C)O[C@H](CO)[C@@H](O)[C@@H]1O] |
| 36 | 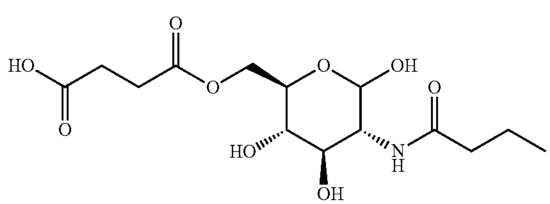 [SMILES: CCCC(=O)N[C@H]1C(O)O[C@H](COC(=O)CCC(=O)O)[C@@H](O)[C@@H]1O] |
| 37 | 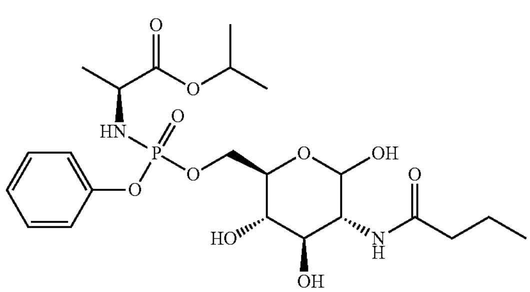 [SMILES: CCCC(=O)N[C@H]1C(O)O[C@H](COP(=O)(N[C@@H](C)C(=O)OC(C)C)Oc2ccccc2)[C@@H](O)[C@@H]1O] |

TABLE 2-continued

Other examples of GlcNBu derivatives.

| No. | Structure |
|---|---|
| 38 | 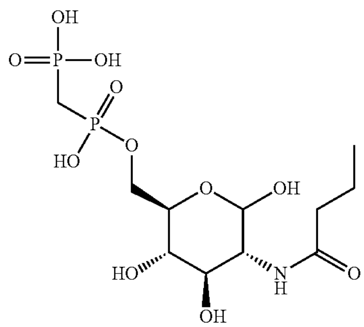 [SMILES: CCCC(=O)N[C@H]1C(O)O[C@H](COP(=O)(O)CP(=O)(O)O)[C@@H](O)[C@@H]1O] |
| 39 | 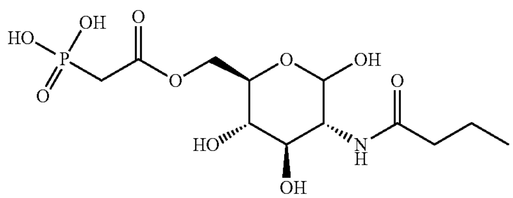 [SMILES: CCCC(=O)N[C@H]1C(O)O[C@H](COC(=O)CP(=O)(O)O)[C@@H](O)[C@@H]1O] |
| 40 | 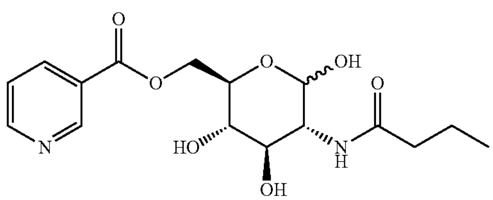 [SMILES: CCCC(=O)N[C@H]1C(O)O[C@H](COC(=O)c2cccnc2)[C@@H](O)[C@@H]1O] |
| 41 | 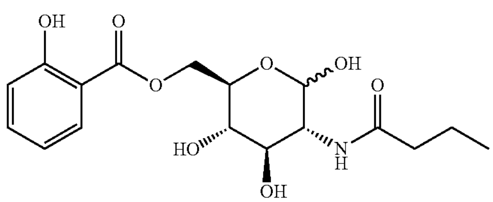 [SMILES: CCCC(=O)N[C@H]1C(O)O[C@H](COC(=O)c2ccccc2O)[C@@H](O)[C@@H]1O] |
| 42 | 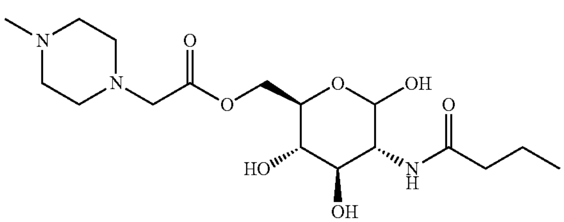 [SMILES: CCCC(=O)N[C@H]1C(O)O[C@H](COC(=O)CN2CCN(C)CC2)[C@@H](O)[C@@H]1O] |
| 43 | 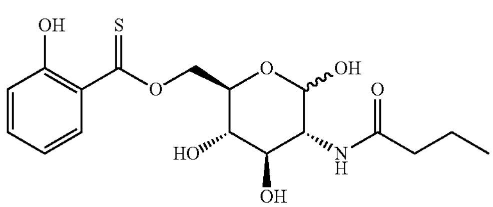 |

TABLE 2-continued

Other examples of GlcNBu derivatives.

| No. | Structure |
|---|---|
| 44 | 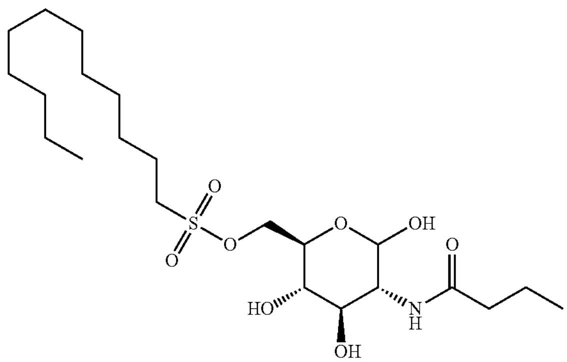 [SMILES: CCCCCCCCCCCCS(=O)(=O)OC[C@H]1OC(O)[C@H](NC(=O)CCC)[C@@H](O)[C@@H]1O] |
| 45 | 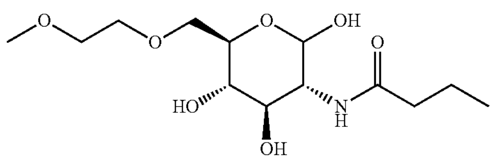 [SMILES: CCCC(=O)N[C@H]1C(O)O[C@H](COCCOC)[C@@H](O)[C@@H]1O] |
| 46 | 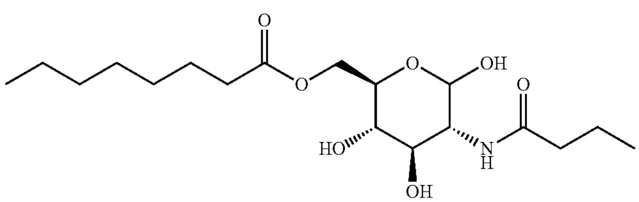 [SMILES: CCCCCCCC(=O)OC[C@H]1OC(O)[C@H](NC(=O)CCC)[C@@H](O)[C@@H]1O] |
| 47 | 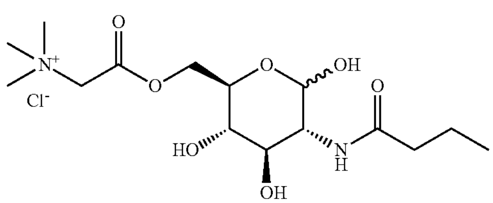 [SMILES: CCCC(=O)N[C@H]1C(O)O[C@H](COC(=O)C[N+](C)(C)C)[C@@H](O)[C@@H]1O ; [Cl-]] |
| 48 | 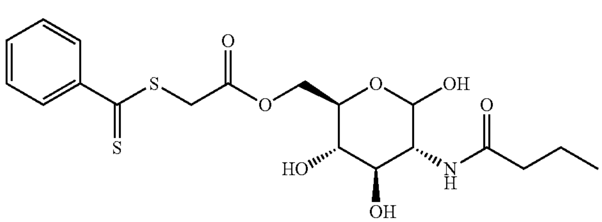 [SMILES: CCCC(=O)N[C@H]1C(O)O[C@H](COC(=O)CSC(=S)c2ccccc2)[C@@H](O)[C@@H]1O] |
| 49 | 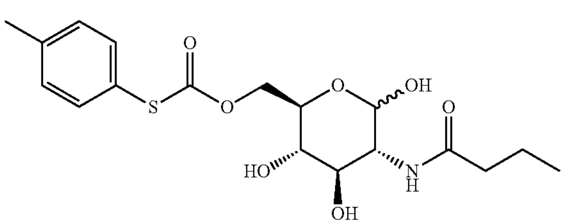 [SMILES: CCCC(=O)N[C@H]1C(O)O[C@H](COC(=O)Sc2ccc(C)cc2)[C@@H](O)[C@@H]1O] |

TABLE 2-continued

Other examples of GlcNBu derivatives.

| No. | Structure |
|---|---|
| 50 | 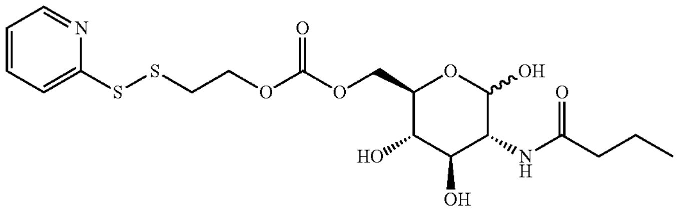 [SMILES: CCCC(=O)N[C@H]1C(O)O[C@H](COC(=O)OCCSSc2ccccn2)[C@@H](O)[C@@H]1O] |
| 51 | 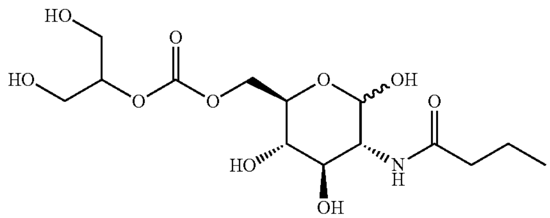 [SMILES: CCCC(=O)N[C@H]1C(O)O[C@H](COC(=O)OC(CO)CO)[C@@H](O)[C@@H]1O] |
| 52 | 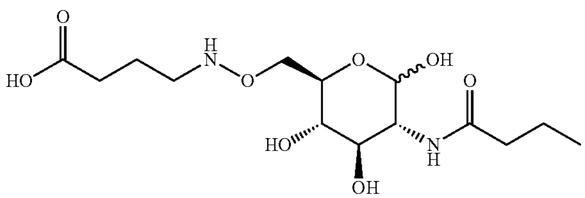 [SMILES: CCCC(=O)N[C@H]1C(O)O[C@H](CONCCCC(=O)O)[C@@H](O)[C@@H]1O] |
| 53 | 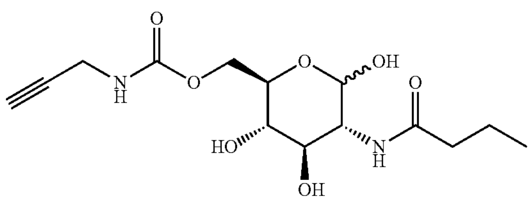 [SMILES: C#CCNC(=O)OC[C@H]1OC(O)[C@H](NC(=O)CCC)[C@@H](O)[C@@H]1O] |
| 54 | 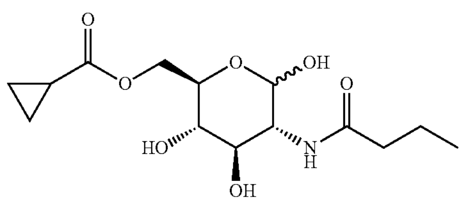 [SMILES: CCCC(=O)N[C@H]1C(O)O[C@H](COC(=O)C2CC2)[C@@H](O)[C@@H]1O] |
| 55 | 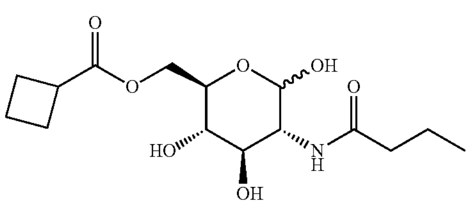 [SMILES: CCCC(=O)N[C@H]1C(O)O[C@H](COC(=O)C2CCC2)[C@@H](O)[C@@H]1O] |
| 56 | 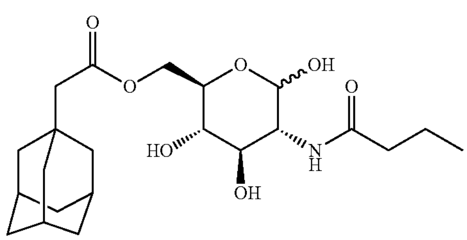 [SMILES: CCCC(=O)N[C@H]1C(O)O[C@H](COC(=O)CC23CC4CC(CC(C4)C2)C3)[C@@H](O)[C@@H]1O] |

TABLE 2-continued

Other examples of GlcNBu derivatives.

| No. | Structure |
|---|---|
| 57 | 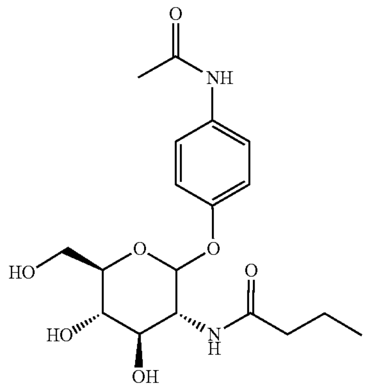 [SMILES: CCCC(=O)N[C@H]1C(Oc2ccc(NC(C)=O)cc2)O[C@H](CO)[C@@H](O)[C@@H]1O] |
| 58 | 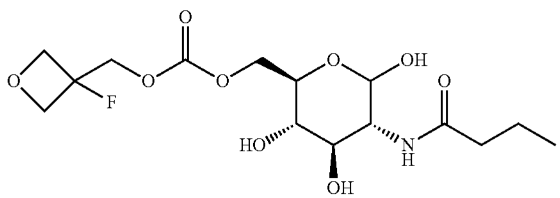 [SMILES: CCCC(=O)N[C@H]1C(O)O[C@H](COC(=O)OCC2(F)COC2)[C@@H](O)[C@@H]1O] |
| 59 | 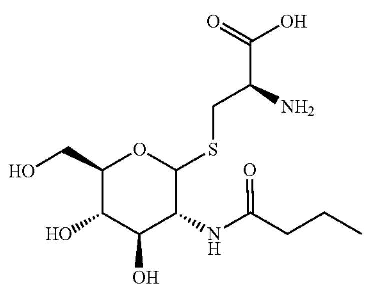 [SMILES: CCCC(=O)N[C@H]1C(SC[C@H](N)C(=O)O)O[C@H](CO)[C@@H](O)[C@@H]1O] |
| 60 | 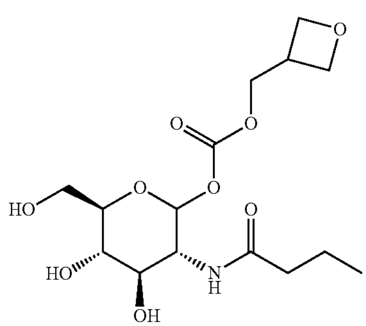 [SMILES: CCCC(=O)N[C@H]1C(OC(=O)OCC2COC2)O[C@H](CO)[C@@H](O)[C@@H]1O] |
| 61 | 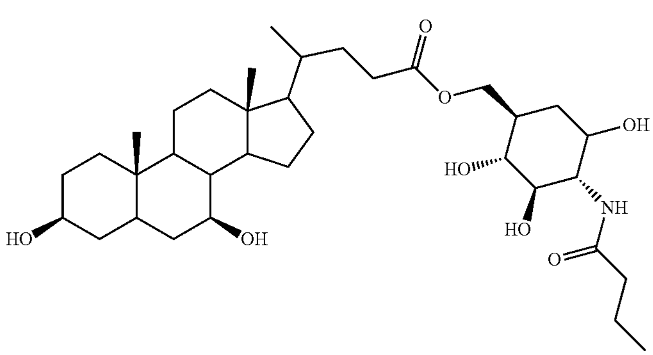 [SMILES: CCCC(=O)N[C@H]1C(O)C[C@H](COC(=O)CCC(C)C2CCC3C4C(CC[C@]23C)[C@@]2(C)CC[C@H](O)CC2C[C@@H]4O)[C@@H](O)[C@@H]1O] |

TABLE 2-continued

Other examples of GlcNBu derivatives.

| No. | Structure |
| --- | --- |
| 62 | 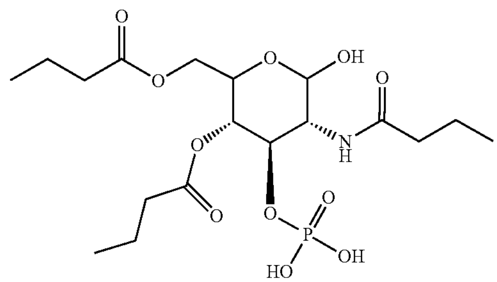 [SMILES: CCCC(=O)N[C@H]1C(O)OC(COC(=O)CCC)[C@@H](OC(=O)CCC)[C@@H]1OP(=O)(O)O] |
| 63 | 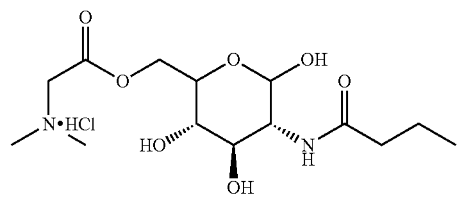 |
| 64 | 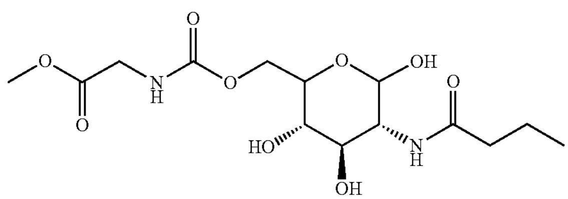 [SMILES: CCCC(=O)N[C@H]1C(O)OC(COC(=O)NCC(=O)OC)[C@@H](O)[C@@H]1O] |
| 65 | 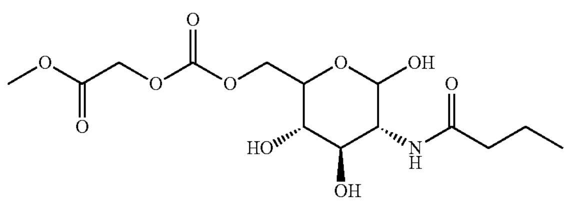 [SMILES: CCCC(=O)N[C@H]1C(O)OC(COC(=O)OCC(=O)OC)[C@@H](O)[C@@H]1O] |
| 66 | 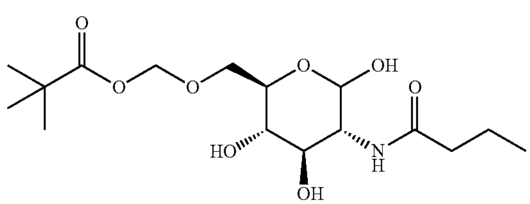 [SMILES: CCCC(=O)N[C@H]1C(O)O[C@H](COCOC(=O)C(C)(C)C)[C@@H](O)[C@@H]1O] |
| 67 | 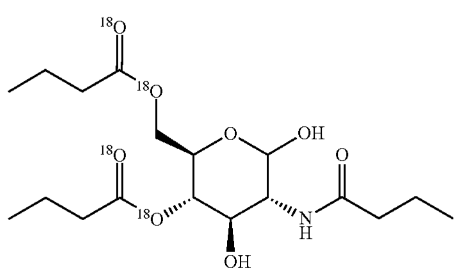 [SMILES: CCCC(=O)N[C@H]1C(O)O[C@H](C[18O]C(=[18O])CCC)[C@@H]([18O]C(=[18O])CCC)[C@@H]1O] |

TABLE 2-continued
Other examples of GlcNBu derivatives.
| No. | Structure |
|---|---|
| 68 | 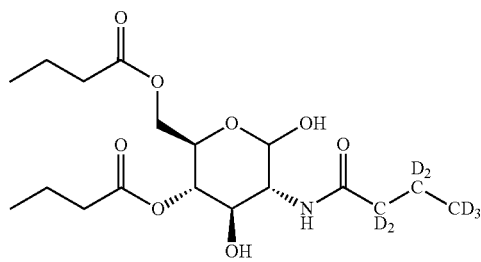 |
| 69 | 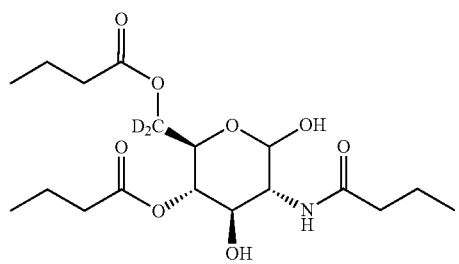 |
| 70 | 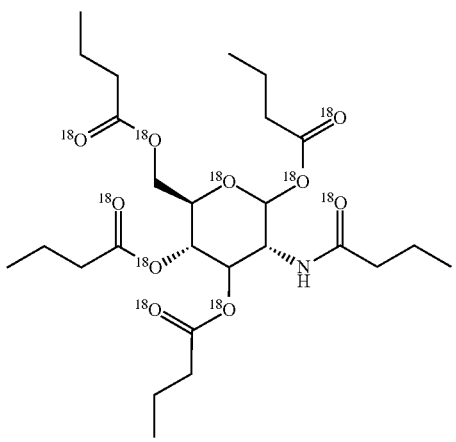 [SMILES: CCCC(=[18O])N[C@H]1C([18O]C(=[18O])CCC)[18O][C@H](C[18O]C(=[18O])CCC)[C@@H]([18O]C(=[18O])CCC)C1[18O]C(=[18O])CCC] |
| 71 | 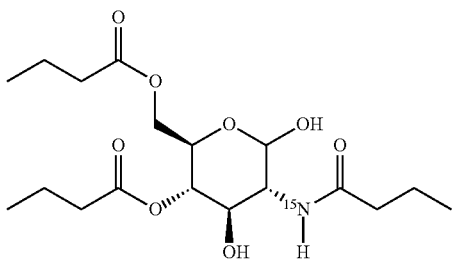 [SMILES: CCCC(=O)[15NH][C@H]1C(O)O[C@H](COC(=O)CCC)[C@@H](OC(=O)CCC)[C@@H]1O] |
In some embodiments, the compound of Formula (A), (I), (II), (III), or (IV) is a compound shown in Table 3, or a pharmaceutically-acceptable salt, ester, chelator, hydrate, solvate, stereoisomer, or polymorphic form thereof.

TABLE 3
Further examples of GlcNBu derivatives.
| No. | Structure |
|---|---|
| 72 | 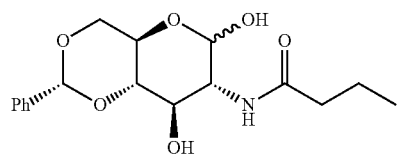 |
| 73 | 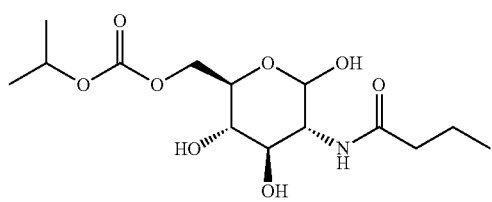 [SMILES: CCCC(=O)N[C@H]1C(O)O[C@H](COC(=O)OC(C)C)[C@@H](O)[C@@H]1O] |
| 74 | 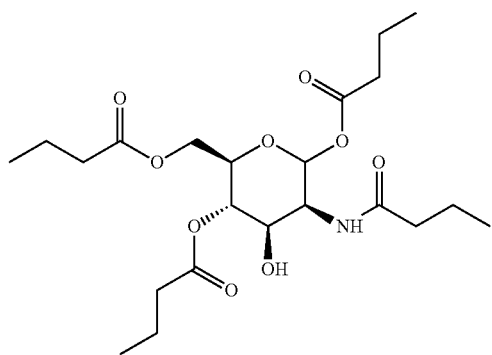 |
| 75 | 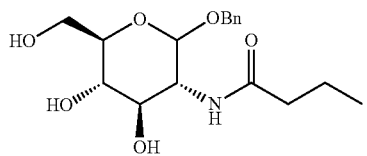 [SMILES: CCCC(=O)N[C@H]1C(OCc2ccccc2)O[C@H](CO)[C@@H](O)[C@@H]1O] |
| 76 | 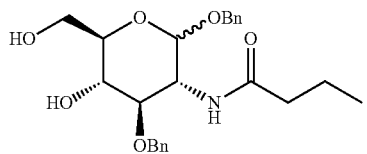 [SMILES: CCCC(=O)N[C@H]1C(OCc2ccccc2)O[C@H](CO)[C@@H](O)[C@@H]1OCc1ccccc1] |
| 77 | 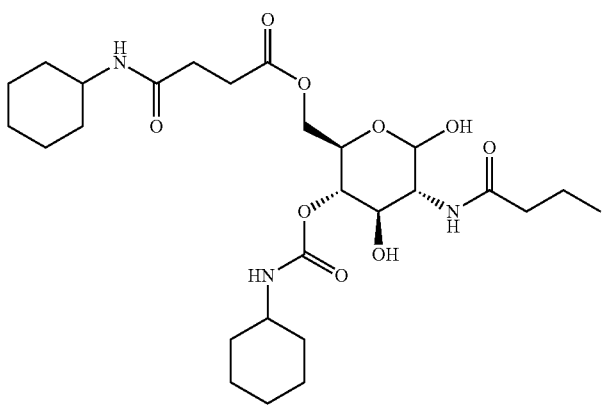 [SMILES: CCCC(=O)N[C@H]1C(O)O[C@H](COC(=O)CCC(=O)NC2CCCCC2)[C@@H](OC(=O)NC2CCCCC2)[C@@H]1O] |

TABLE 3-continued

Further examples of GlcNBu derivatives.

| No. | Structure |
|---|---|
| 78 | 6-O-valeryl, 4-O-valeryl GlcNBu |
| 79 | 6-O-succinyl, 4-O-succinyl GlcNBu |
| 80 | 6-O-propionyl, 4-O-propionyl GlcNBu |
| 81 | GlcNBu-d7 (deuterated butanoyl) |
| 82 | 6-O-(4-aminobutanoyl) GlcNBu·HCl |
| 83 | 6-O-(4-aminobutanoyl), 4-O-butanoyl GlcNBu·HCl |

TABLE 3-continued

Further examples of GlcNBu derivatives.

| No. | Structure |
|---|---|
| 84 | 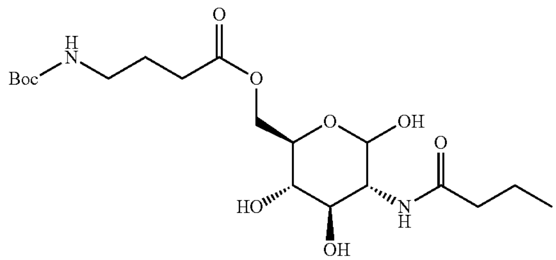 [SMILES: CCCC(=O)N[C@H]1C(O)O[C@H](COC(=O)CCCNC(=O)OC(C)(C)C)[C@@H](O)[C@@H]1O] |
| 85 | 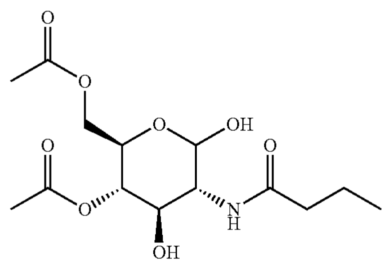 [SMILES: CCCC(=O)N[C@H]1C(O)O[C@H](COC(C)=O)[C@@H](OC(C)=O)[C@@H]1O] |
| 86 | 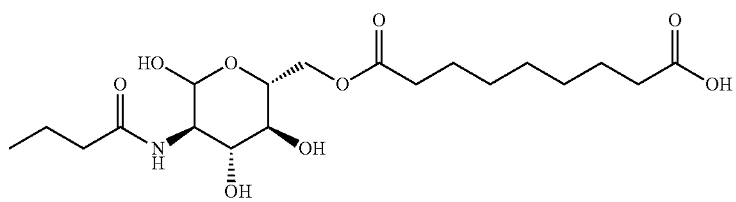 [SMILES: CCCC(=O)N[C@H]1C(O)O[C@H](COC(=O)CCCCCCCC(=O)O)[C@@H](O)[C@@H]1O] |
| 87 | 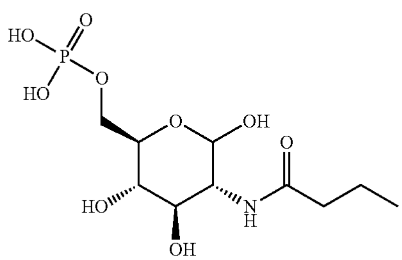 [SMILES: CCCC(=O)N[C@H]1C(O)O[C@H](COP(=O)(O)O)[C@@H](O)[C@@H]1O] |
| 88 | 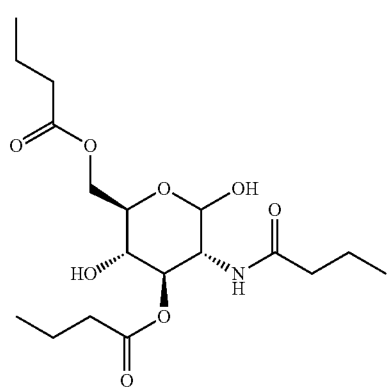 [SMILES: CCCC(=O)N[C@H]1C(O)O[C@H](COC(=O)CCC)[C@@H](O)[C@@H]1OC(=O)CCC] |

TABLE 3-continued
Further examples of GlcNBu derivatives.
| No. | Structure |
|-----|-----------|
| 89 | 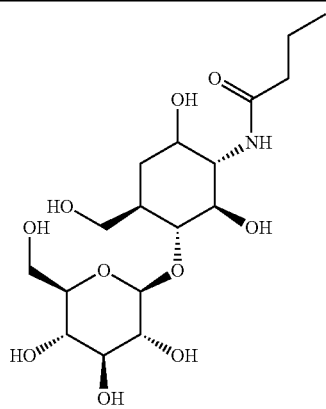 |
| 90 | 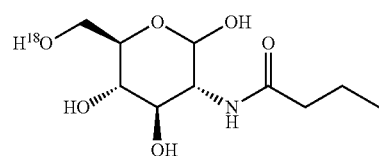 [SMILES: CCCC(=O)N[C@H]1C(O)O[C@H](C[18OH])[C@@H](O)[C@@H]1O] |
| 91 | 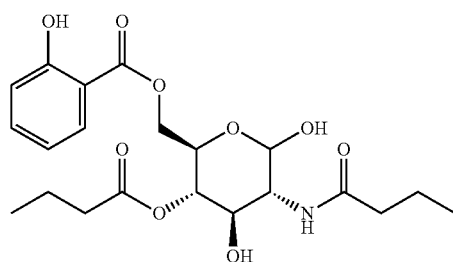 [SMILES: CCCC(=O)N[C@H]1C(O)O[C@H](COC(=O)c2ccccc2O)[C@@H](OC(=O)CCC)[C@@H]1O] |
| 92 | 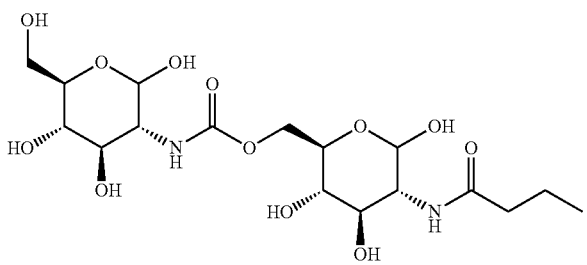 [SMILES: CCCC(=O)N[C@H]1C(O)O[C@H](COC(=O)N[C@H]2C(O)O[C@H](CO)[C@@H](O)[C@@H]2O)[C@@H](O)[C@@H]1O] |
| 93 | 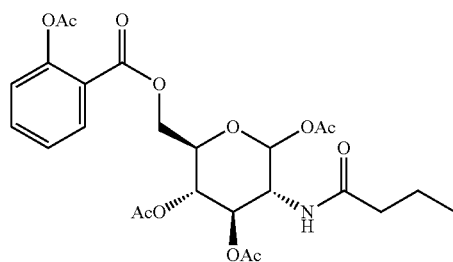 [SMILES: CCCC(=O)N[C@H]1C(OC(C)=O)O[C@H](COC(=O)c2ccccc2OC(C)=O)[C@@H](OC(C)=O)[C@@H]1OC(C)=O] |
| 94 | 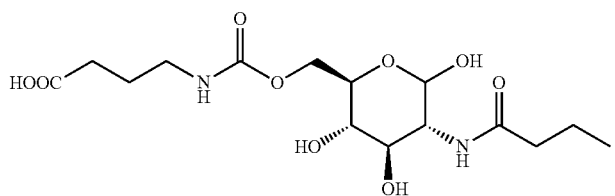 [SMILES: CCCC(=O)N[C@H]1C(O)O[C@H](COC(=O)NCCCC(=O)O)[C@@H](O)[C@@H]1O] |

TABLE 3-continued
Further examples of GlcNBu derivatives.
| No. | Structure |
|---|---|
| 95 | 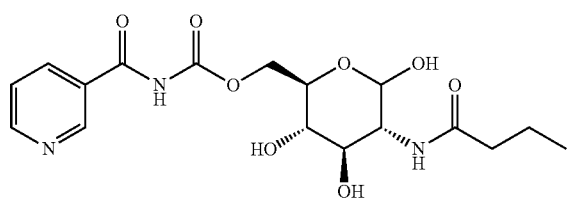 [SMILES: CCCC(=O)N[C@H]1C(O)O[C@H](COC(=O)NC(=O)c2cccnc2)[C@@H](O)[C@@H]1O] |
| 96 | 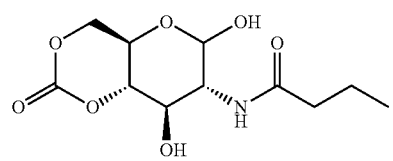 [SMILES: CCCC(=O)N[C@H]1C(O)O[C@@H]2COC(=O)O[C@H]2[C@@H]1O] |
| 97 | 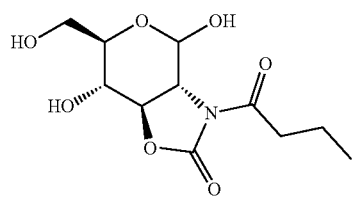 [SMILES: CCCC(=O)N1C(=O)O[C@H]2[C@H](O)[C@@H](CO)OC(O)[C@@H]21] |
| 98 | 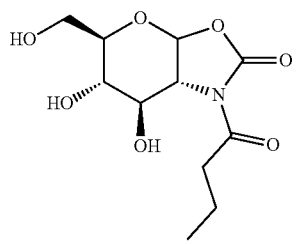 |
| 99 | 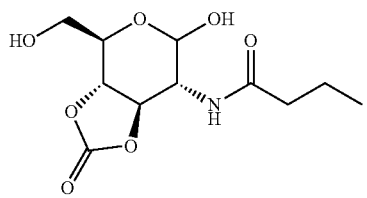 [SMILES: CCCC(=O)N[C@H]1C(O)O[C@H](CO)[C@H]2OC(=O)O[C@@H]21] |
| 100 | 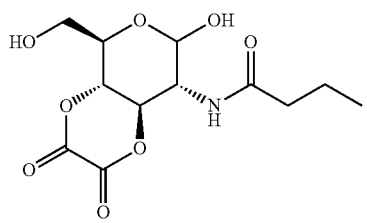 [SMILES: CCCC(=O)N[C@H]1C(O)O[C@H](CO)[C@H]2OC(=O)C(=O)O[C@@H]21] |
| 101 | 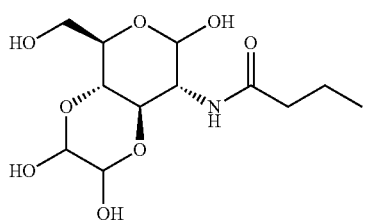 |

TABLE 3-continued

Further examples of GlcNBu derivatives.

| No. | Structure |
|---|---|
| 102 | [Structure: 1-methylpiperidine-4-carbonyl group linked via NH-C(O)-O- to C6 of GlcNBu sugar] |
| 103 | [Structure: (dimethylamino)methyl-NH-C(O)-O- linked to C6 of GlcNBu sugar] |
| 104 | [Structure: H₂N-CH₂CH₂-S-NH-C(O)-O- linked to C6 of GlcNBu sugar] |
| 105 | [Structure: GlcNBu with N-phosphate (HO)₂P(O)- on the acetamido nitrogen] |
| 106 | [Structure: GlcNBu with N-acyl nicotinoyl group on the acetamido nitrogen] |
| 107 | [Structure: GlcNBu with N-S-CH₂CH₂-NH₂ on the acetamido nitrogen] |
| 108 | [Structure: GlcNBu with N-CH₂-N(CH₃)₂ on the acetamido nitrogen] |

TABLE 3-continued

Further examples of GlcNBu derivatives.

| No. | Structure |
|---|---|
| 109 | 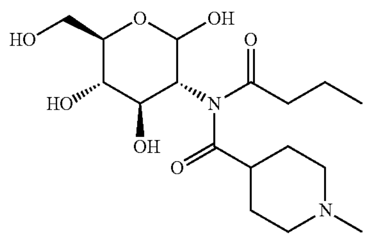 [SMILES: CCCC(=O)N(C(=O)C1CCN(C)CC1)[C@H]1C(O)O[C@H](CO)[C@@H](O)[C@@H]1O] |
| 110 | 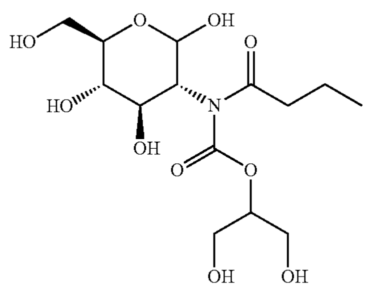 [SMILES: CCCC(=O)N(C(=O)OC(CO)CO)[C@H]1C(O)O[C@H](CO)[C@@H](O)[C@@H]1O] |
| 111 | 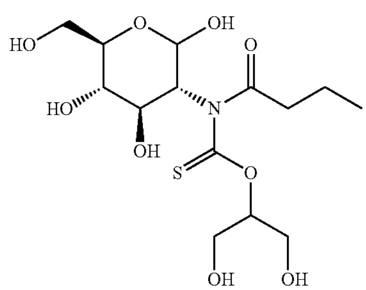 [SMILES: CCCC(=O)N(C(=S)OC(CO)CO)[C@H]1C(O)O[C@H](CO)[C@@H](O)[C@@H]1O] |
| 112 | 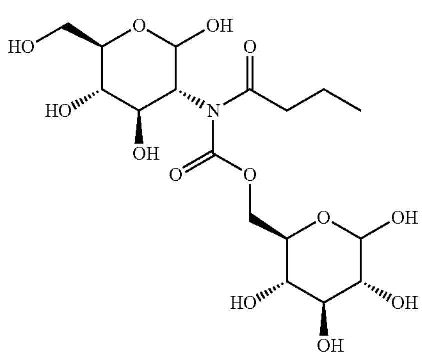 [SMILES: CCCC(=O)N(C(=O)OC[C@H]1OC(O)[C@H](O)[C@@H](O)[C@@H]1O)[C@H]1C(O)O[C@H](CO)[C@@H](O)[C@@H]1O] |
| 113 | 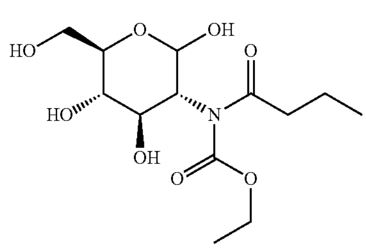 [SMILES: CCCC(=O)N(C(=O)OCC)[C@H]1C(O)O[C@H](CO)[C@@H](O)[C@@H]1O] |

TABLE 3-continued
Further examples of GlcNBu derivatives.
| No. | Structure |
|---|---|
| 114 | 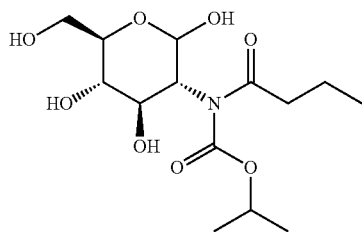 [SMILES: CCCC(=O)N(C(=O)OC(C)C)[C@H]1C(O)O[C@H](CO)[C@@H](O)[C@@H]1O] |
| 115 | 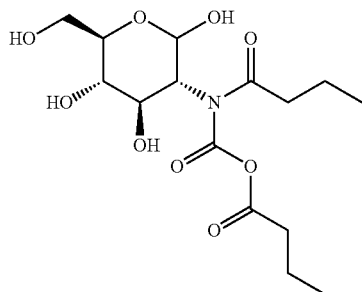 [SMILES: CCCC(=O)OC(=O)N(C(=O)CCC)[C@H]1C(O)O[C@H](CO)[C@@H](O)[C@@H]1O] |
| 116 | 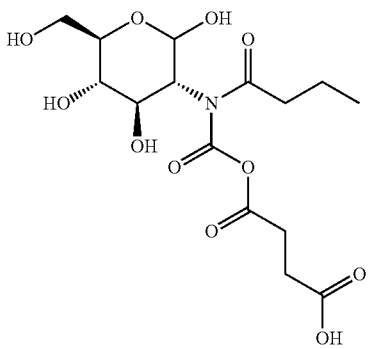 [SMILES: CCCC(=O)N(C(=O)OC(=O)CCC(=O)O)[C@H]1C(O)O[C@H](CO)[C@@H](O)[C@@H]1O] |
| 117 | 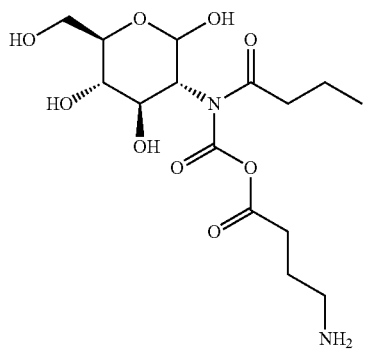 [SMILES: CCCC(=O)N(C(=O)OC(=O)CCCN)[C@H]1C(O)O[C@H](CO)[C@@H](O)[C@@H]1O] |
| 118 | 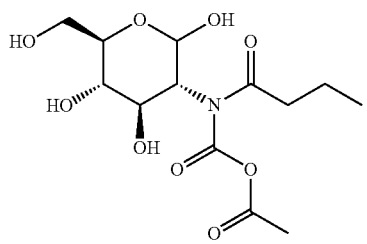 [SMILES: CCCC(=O)N(C(=O)OC(C)=O)[C@H]1C(O)O[C@H](CO)[C@@H](O)[C@@H]1O] |

TABLE 3-continued
Further examples of GlcNBu derivatives.
| No. | Structure |
|---|---|
| 119 | 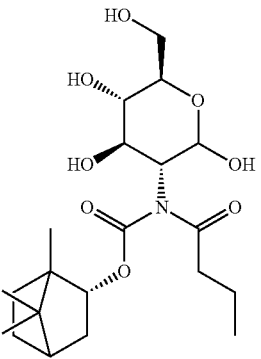 [SMILES: CCCC(=O)N(C(=O)O[C@@H]1CC2CCC1(C)C2(C)C)[C@H]1C(O)O[C@H](CO)[C@@H](O)[C@@H]1O] |
| 120 | 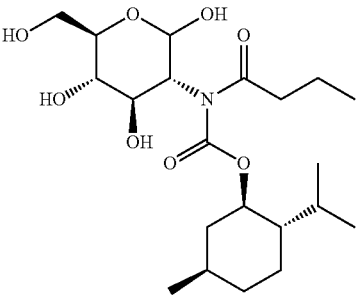 [SMILES: CCCC(=O)N(C(=O)O[C@@H]1C[C@H](C)CC[C@H]1C(C)C)[C@H]1C(O)O[C@H](CO)[C@@H](O)[C@@H]1O] |
| 121 | 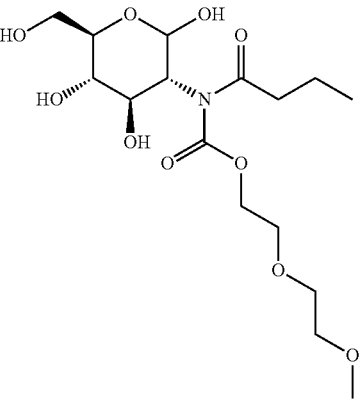 [SMILES: CCCC(=O)N(C(=O)OCCOCCOC)[C@H]1C(O)O[C@H](CO)[C@@H](O)[C@@H]1O] |
| 122 | 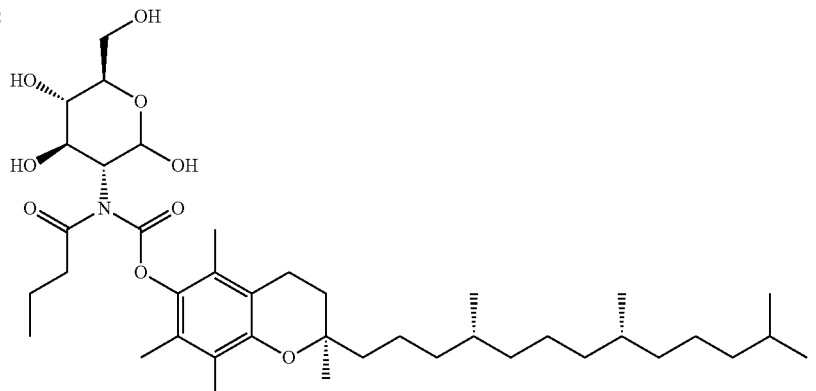 |

TABLE 3-continued
Further examples of GlcNBu derivatives.
| No. | Structure |
|---|---|
| 123 | 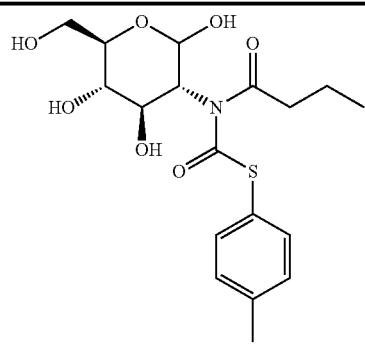 |
| 124 | 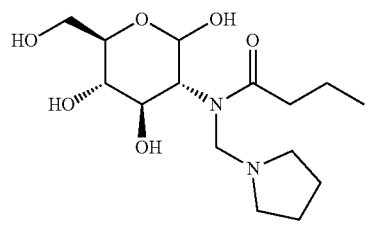 [SMILES: CCCC(=O)N(CN1CCCC1)[C@H]1C(O)O[C@H](CO)[C@@H](O)[C@@H]1O] |
| 125 | 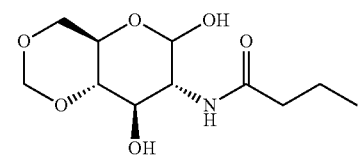 [SMILES: CCCC(=O)N[C@H]1C(O)O[C@@H]2COCO[C@H]2[C@@H]1O] |
| 126 | 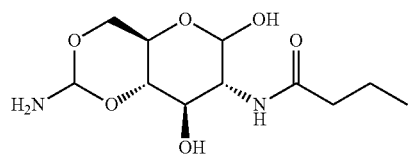 |
| 127 | 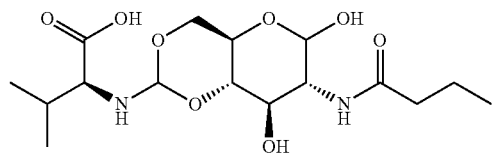 |
| 128 | 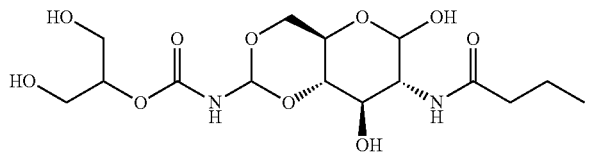 |
| 129 | 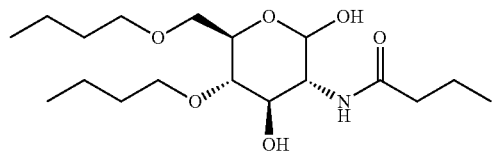 [SMILES: CCCCOC[C@H]1OC(O)[C@H](NC(=O)CCC)[C@@H](O)[C@@H]1OCCCC] |
| 130 | 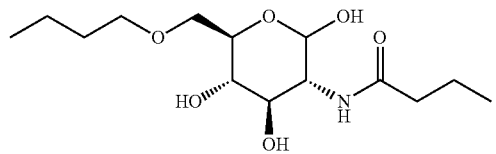 [SMILES: CCCCOC[C@H]1OC(O)[C@H](NC(=O)CCC)[C@@H](O)[C@@H]1O] |

TABLE 3-continued
Further examples of GlcNBu derivatives.
| No. | Structure |
|---|---|
| 131 | 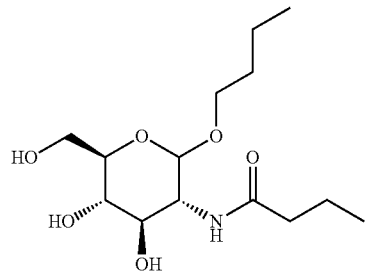 [SMILES: CCCCOC1O[C@H](CO)[C@@H](O)[C@H](O)[C@H]1NC(=O)CCC] |
| 132 | 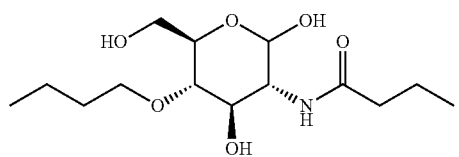 [SMILES: CCCCO[C@H]1[C@H](O)[C@@H](NC(=O)CCC)C(O)O[C@@H]1CO] |
| 133 | 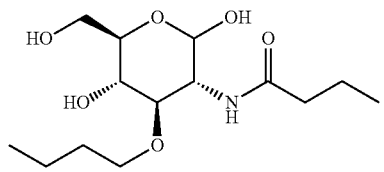 [SMILES: CCCCO[C@H]1[C@H](O)[C@@H](CO)OC(O)[C@@H]1NC(=O)CCC] |
| 134 | 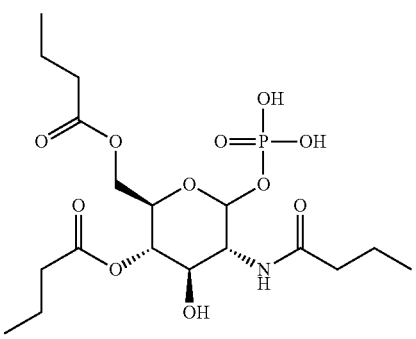 [SMILES: CCCC(=O)N[C@H]1C(OP(=O)(O)O)O[C@H](COC(=O)CCC)[C@@H](OC(=O)CCC)[C@@H]1O] |
| 135 | 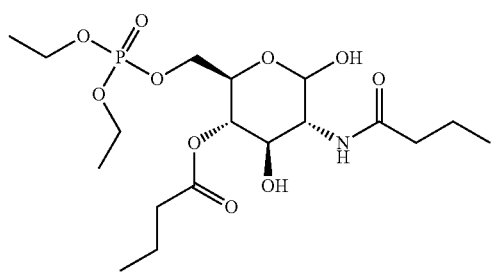 [SMILES: CCCC(=O)N[C@H]1C(O)O[C@H](COP(=O)(OCC)OCC)[C@@H](OC(=O)CCC)[C@@H]1O] |
| 136 | 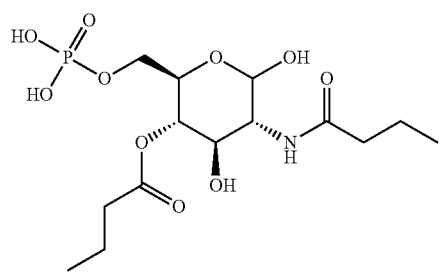 [SMILES: CCCC(=O)N[C@H]1C(O)O[C@H](COP(=O)(O)O)[C@@H](OC(=O)CCC)[C@@H]1O] |

TABLE 3-continued
Further examples of GlcNBu derivatives.
| No. | Structure |
|---|---|
| 137 | 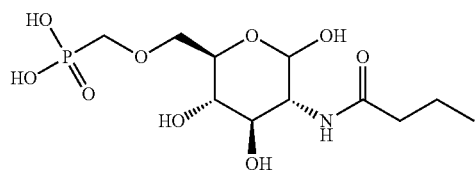 [SMILES: CCCC(=O)N[C@H]1C(O)O[C@H](COCP(=O)(O)O)[C@@H](O)[C@@H]1O] |
| 138 | 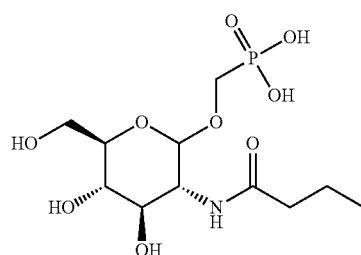 |
| 139 | 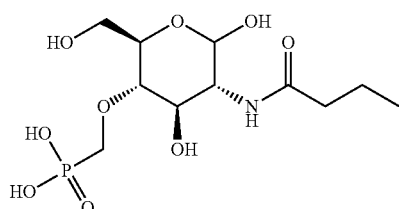 |
| 140 | 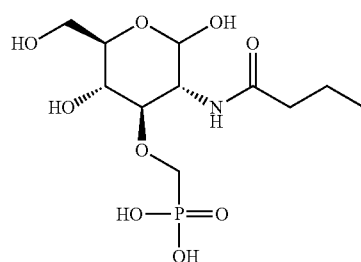 [SMILES: CCCC(=O)N[C@H]1C(O)O[C@H](CO)[C@@H](O)[C@@H]1OCP(=O)(O)O] |
| 141 | 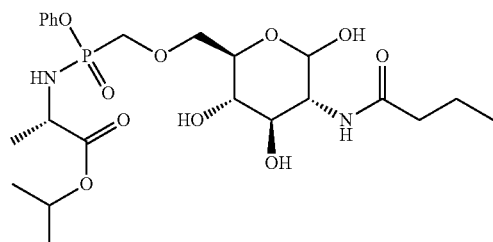 |
| 142 | 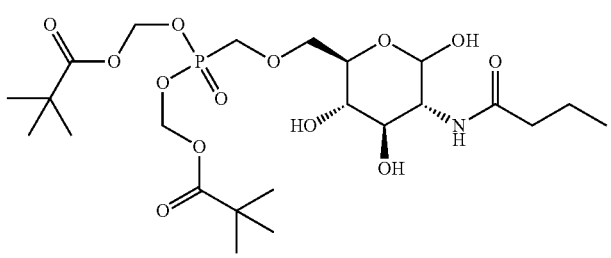 [SMILES: CCCC(=O)N[C@H]1C(O)O[C@H](COCP(=O)(OCOC(=O)C(C)(C)C)OCOC(=O)C(C)(C)C)[C@@H](O)[C@@H]1O] |

TABLE 3-continued

Further examples of GlcNBu derivatives.

| No. | Structure |
|---|---|
| 143 | 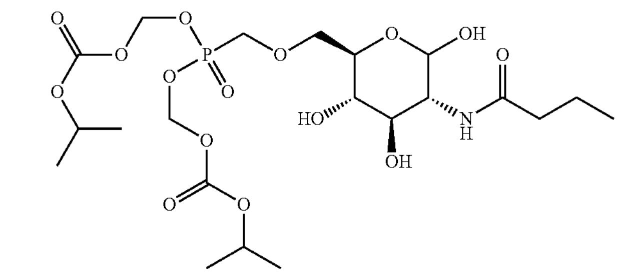 [SMILES: CCCC(=O)N[C@H]1C(O)O[C@H](COCP(=O)(OCOC(=O)OC(C)C)OCOC(=O)OC(C)C)[C@@H](O)[C@@H]1O] |
| 144 | 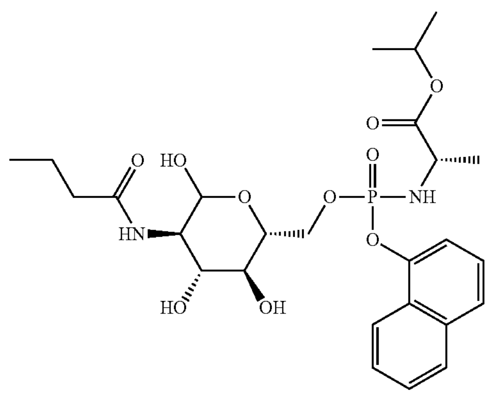 [SMILES: CCCC(=O)N[C@H]1C(O)O[C@H](COP(=O)(N[C@@H](C)C(=O)OC(C)C)Oc2cccc3ccccc23)[C@@H](O)[C@@H]1O] |
| 145 | 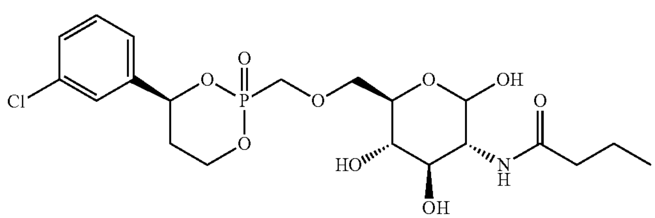 [SMILES: CCCC(=O)N[C@H]1C(O)O[C@H](COCP2(=O)OCC[C@@H](c3cccc(Cl)c3)O2)[C@@H](O)[C@@H]1O] |
| 146 | 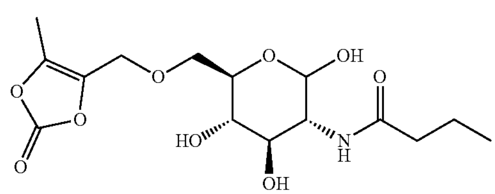 [SMILES: CCCC(=O)N[C@H]1C(O)O[C@H](COCc2oc(=O)oc2C)[C@@H](O)[C@@H]1O] |
| 147 | 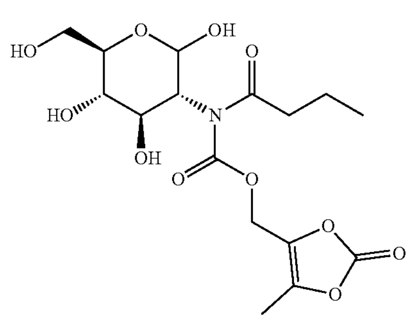 [SMILES: CCCC(=O)N(C(=O)OCc1oc(=O)oc1C)[C@H]1C(O)O[C@H](CO)[C@@H](O)[C@@H]1O] |

TABLE 3-continued
Further examples of GlcNBu derivatives.
| No. | Structure |
|-----|-----------|
| 148 | 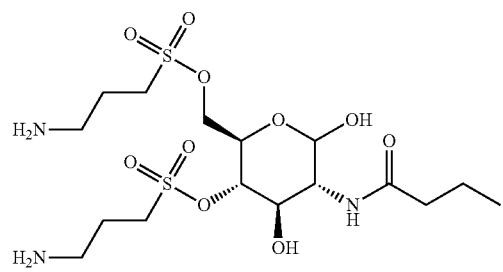 [SMILES: CCCC(=O)N[C@H]1C(O)O[C@H](COS(=O)(=O)CCCN)[C@@H](OS(=O)(=O)CCCN)[C@@H]1O] |
| 149 | 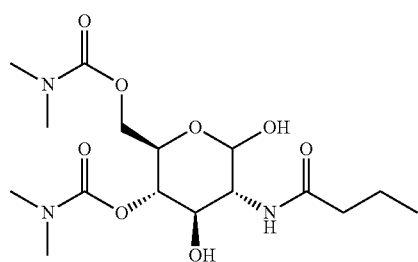 [SMILES: CCCC(=O)N[C@H]1C(O)O[C@H](COC(=O)N(C)C)[C@@H](OC(=O)N(C)C)[C@@H]1O] |
| 150 | 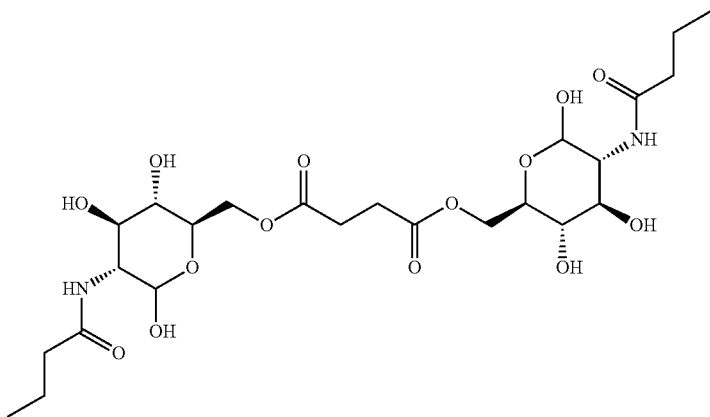 [SMILES: CCCC(=O)N[C@H]1C(O)O[C@H](COC(=O)CCC(=O)OC[C@H]2OC(O)[C@H](NC(=O)CCC)[C@@H](O)[C@@H]2O)[C@@H](O)[C@@H]1O] |
| 151 | 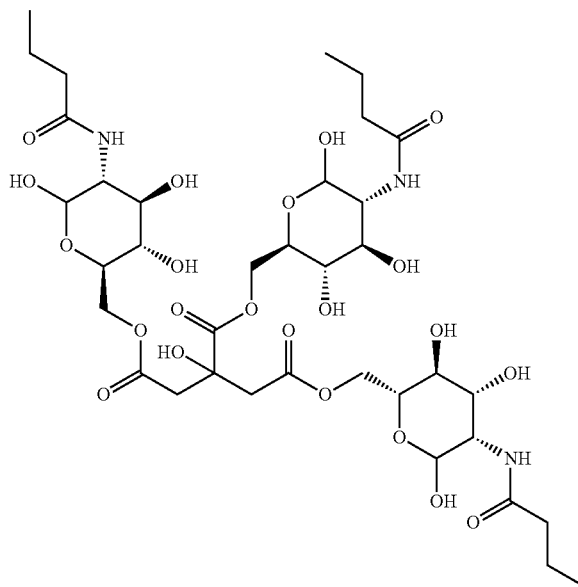 |

TABLE 3-continued

Further examples of GlcNBu derivatives.

| No. | Structure |
|-----|-----------|
| 152 | 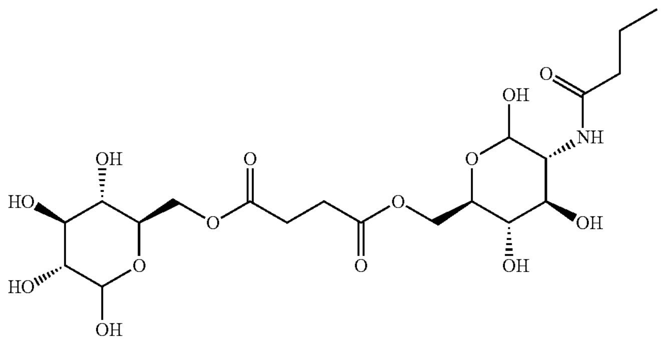 [SMILES: CCCC(=O)N[C@H]1C(O)O[C@H](COC(=O)CCC(=O)OC[C@H]2OC(O)[C@H](O)[C@@H](O)[C@@H]2O)[C@@H](O)[C@@H]1O] |
| 153 | 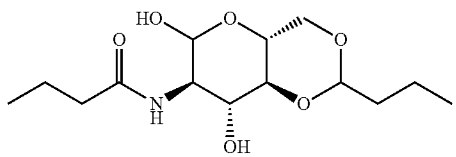 |
| 154 | 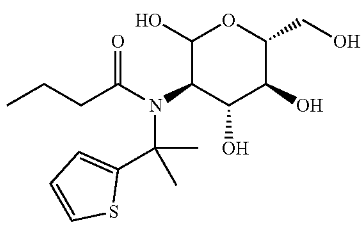 [SMILES: CCCC(=O)N([C@H]1C(O)O[C@H](CO)[C@@H](O)[C@@H]1O)C(C)(C)c1cccs1] |
| 155 | 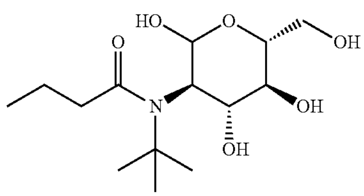 [SMILES: CCCC(=O)N([C@H]1C(O)O[C@H](CO)[C@@H](O)[C@@H]1O)C(C)(C)C] |
| 156 | 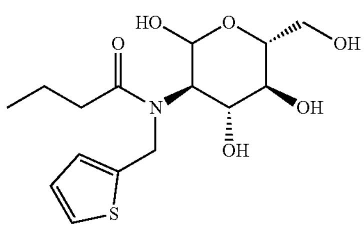 [SMILES: CCCC(=O)N(Cc1cccs1)[C@H]1C(O)O[C@H](CO)[C@@H](O)[C@@H]1O] |
| 157 | 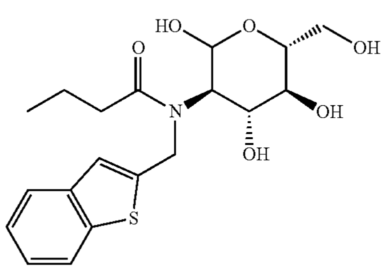 [SMILES: CCCC(=O)N(Cc1cc2ccccc2s1)[C@H]1C(O)O[C@H](CO)[C@@H](O)[C@@H]1O] |

TABLE 3-continued
Further examples of GlcNBu derivatives.
| No. | Structure |
|---|---|
| 158 | 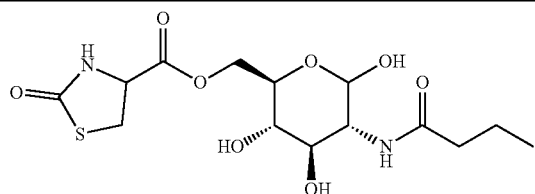 |
| 159 | 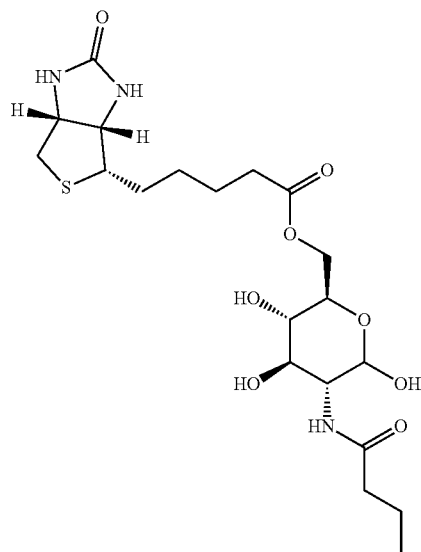 [SMILES: CCCC(=O)N[C@H]1C(O)O[C@H](COC(=O)CCCC[C@@H]2SC[C@@H]3NC(=O)N[C@@H]32)[C@@H](O)[C@@H]1O] |
| 160 | 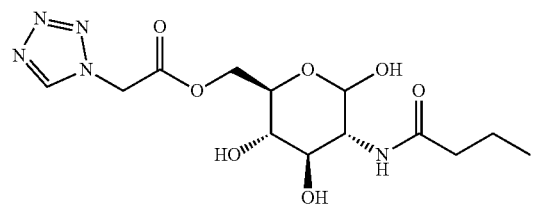 [SMILES: CCCC(=O)N[C@H]1C(O)O[C@H](COC(=O)Cn2cnnn2)[C@@H](O)[C@@H]1O] |
| 161 | 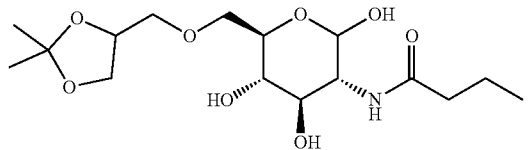 [SMILES: CCCC(=O)N[C@H]1C(O)O[C@H](COCC2COC(C)(C)O2)[C@@H](O)[C@@H]1O] |
| 162 | 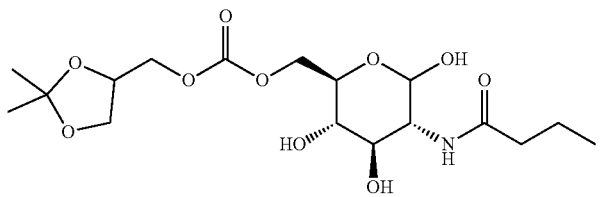 [SMILES: CCCC(=O)N[C@H]1C(O)O[C@H](COC(=O)OCC2COC(C)(C)O2)[C@@H](O)[C@@H]1O] |
| 163 | 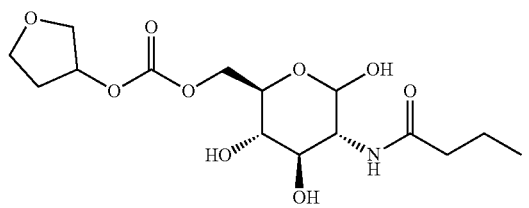 [SMILES: CCCC(=O)N[C@H]1C(O)O[C@H](COC(=O)OC2CCOC2)[C@@H](O)[C@@H]1O] |

TABLE 3-continued
Further examples of GlcNBu derivatives.
| No. | Structure |
|---|---|
| 164 | 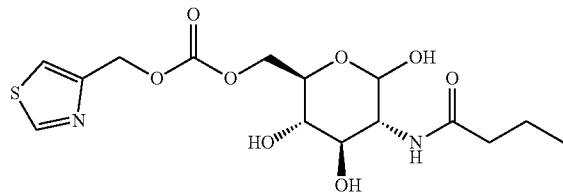 [SMILES: CCCC(=O)N[C@H]1C(O)O[C@H](COC(=O)OCc2cscn2)[C@@H](O)[C@@H]1O] |
| 165 | 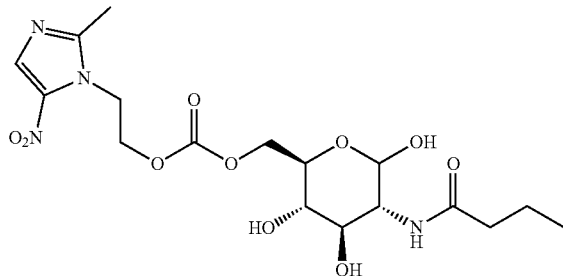 [SMILES: CCCC(=O)N[C@H]1C(O)O[C@H](COC(=O)OCCn2c([N+](=O)[O-])cnc2C)[C@@H](O)[C@@H]1O] |
| 166 | 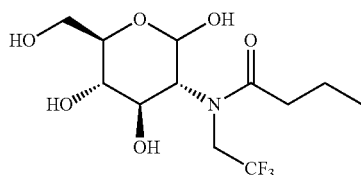 |
| 167 | 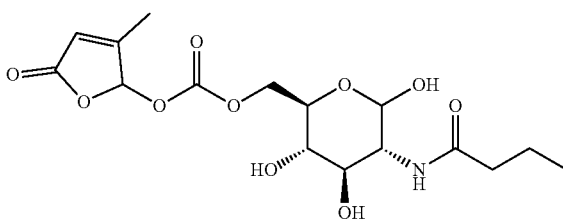 [SMILES: CCCC(=O)N[C@H]1C(O)O[C@H](COC(=O)OC2OC(=O)C=C2C)[C@@H](O)[C@@H]1O] |
| 168 | 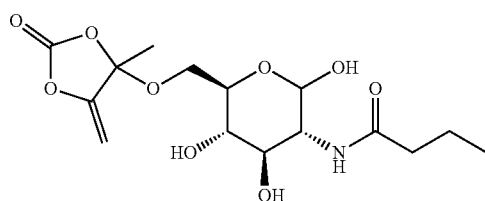 [SMILES: C=C1OC(=O)OC1(C)OC[C@H]1OC(O)[C@H](NC(=O)CCC)[C@@H](O)[C@@H]1O] |
| 169 | 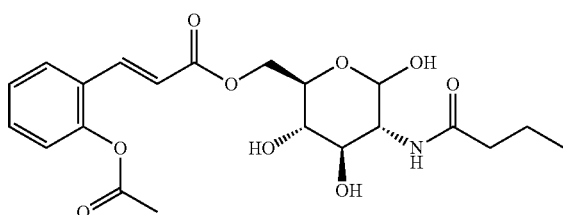 [SMILES: CCCC(=O)N[C@H]1C(O)O[C@H](COC(=O)/C=C/c2ccccc2OC(C)=O)[C@@H](O)[C@@H]1O] |
| 170 | 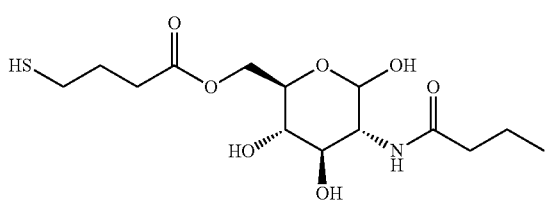 [SMILES: CCCC(=O)N[C@H]1C(O)O[C@H](COC(=O)CCCS)[C@@H](O)[C@@H]1O] |

TABLE 3-continued

Further examples of GlcNBu derivatives.

| No. | Structure |
|---|---|
| 171 | 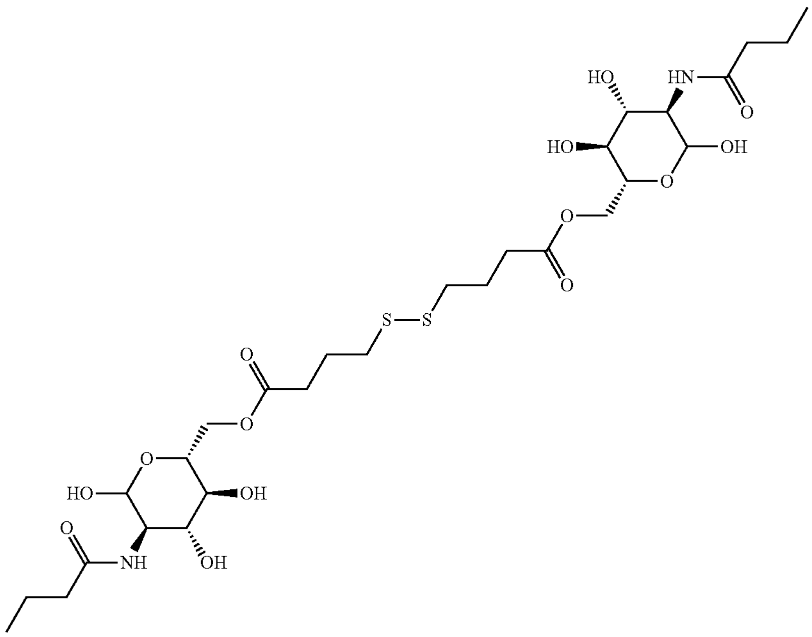 [SMILES: CCCC(=O)N[C@H]1C(O)O[C@H](COC(=O)CCCSSCCCC(=O)OC[C@H]2OC(O)[C@H](NC(=O)CCC)[C@@H](O)[C@@H]2O)[C@@H](O)[C@@H]1O] |
| 172 | 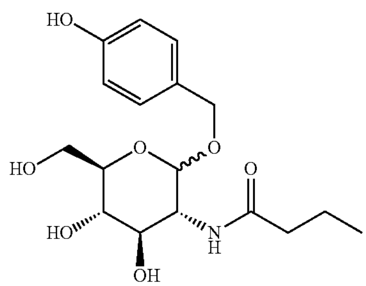 [SMILES: CCCC(=O)N[C@H]1C(OCc2ccc(O)cc2)O[C@H](CO)[C@@H](O)[C@@H]1O] |

In a second broad aspect, there are provided pharmaceutical compositions comprising a compound described herein, or a pharmaceutically acceptable salt thereof, and a pharmaceutically acceptable carrier. In some embodiments, there are provided pharmaceutical compositions comprising a compound of any one of Formulae (A), and (I) to (IV), or a pharmaceutically acceptable salt thereof, and a pharmaceutically acceptable carrier. In some embodiments, there are provided pharmaceutical compositions comprising a compound of any one of Formulae (A), and (I) to (IV), or a pharmaceutically acceptable salt thereof, wherein the compound is not a derivative of N-acetyl glucosamine.

In a third broad aspect, there are provided methods of preventing or treating a bone or joint disease or disorder in a subject in need thereof comprising administering to the subject an effective amount of a compound and/or a pharmaceutical composition described herein. In one embodiment, the bone or joint disease is osteoporosis. In one embodiment, the bone or joint disease is arthritis. Non-limiting examples of bone or joint diseases and disorders that may be treated according to methods provided herein include osteoporosis, osteopenia, and arthritis, including osteoarthritis, inflammatory arthritis (e.g., rheumatoid arthritis, psoriatic arthritis, etc.), traumatic arthritis, degenerative arthritis, dysplastic arthritis, and related conditions.

In some embodiments, compounds of Formulae (A), and (I) to (IV) and/or pharmaceutical compositions thereof are administered to increase the therapeutic effectiveness of GlcNBu in a subject, as compared to administration of GlcNBu.

In some embodiments, compounds of Formulae (A), and (I) to (IV) and/or pharmaceutical compositions thereof are administered to increase the bioavailability of GlcNBu, the AUC of GlcNBu in blood or plasma, the $C_{max}$ of GlcNBu, the $T_{max}$ of GlcNBu, the $t_{1/2}$ of GlcNBu, the therapeutic bio-distribution of GlcNBu, and/or the bioabsorption of GlcNBu in a subject, as compared to administration of GlcNBu itself.

In some embodiments, the effective therapeutic level of GlcNBu in a selected tissue of a subject is increased after administration of a compound of any of Formulae (A), and (I) to (IV) and/or a pharmaceutical composition thereof, as compared to administration of GlcNBu itself.

In some embodiments, compounds of Formulae (A), and (I) to (IV) and/or pharmaceutical compositions thereof are administered to reduce the metabolism of GlcNBu in a subject, as compared to administration of GlcNBu itself.

In some embodiments, compounds of Formulae (A), and (I) to (IV) and/or pharmaceutical compositions thereof are administered to reduce the side effects of GlcNBu in a subject, as compared to administration of GlcNBu itself.

In some embodiments, compounds of Formulae (A), and (I) to (IV) and/or pharmaceutical compositions thereof are administered to enhance cartilage formation in a subject.

In some embodiments, compounds of Formulae (A), and (I) to (IV) and/or pharmaceutical compositions thereof are administered to enhance chondrocyte cell proliferation or growth in a subject.

In some embodiments, compounds of Formulae (A), and (I) to (IV) and/or pharmaceutical compositions thereof are administered to alleviate the symptoms of joint stiffness and/or restricted mobility in a subject.

In some embodiments, compounds of Formulae (A), and (I) to (IV) and/or pharmaceutical compositions thereof are administered to enhance the production of glycosaminoglycan in a subject.

In some embodiments, compounds of Formulae (A), and (I) to (IV) and/or pharmaceutical compositions thereof are administered to increase bone mineral density (BMD) in a subject.

In some embodiments, compounds of Formulae (A), and (I) to (IV) and/or pharmaceutical compositions thereof are administered to improve bone micro-architecture and/or bone connectivity in a subject.

In some embodiments, compounds of Formulae (A), and (I) to (IV) and/or pharmaceutical compositions thereof are administered to treat low BMD in a subject.

In some embodiments, compounds of Formulae (A), and (I) to (IV) and/or pharmaceutical compositions thereof are administered to prevent or diminish the risk of fractures in a subject.

In some embodiments, compounds of Formulae (A), and (I) to (IV) and/or pharmaceutical compositions thereof are administered to treat or prevent bone fractures, e.g., low impact fractures and/or high impact factures, in a subject.

In another broad aspect, there are provided kits comprising one or more compound or pharmaceutical composition described herein. A kit may further comprise one or more additional therapeutic agents and/or instructions, for example, instructions for using the kit to treat a subject having a bone or joint disorder such as osteoporosis or arthritis.

BRIEF DESCRIPTION OF THE DRAWINGS

For a better understanding of the invention and to show more clearly how it may be carried into effect, reference will now be made by way of example to the accompanying drawings, which illustrate aspects and features according to embodiments of the present invention, and in which.

DETAILED DESCRIPTION

Definitions

Figure 1:
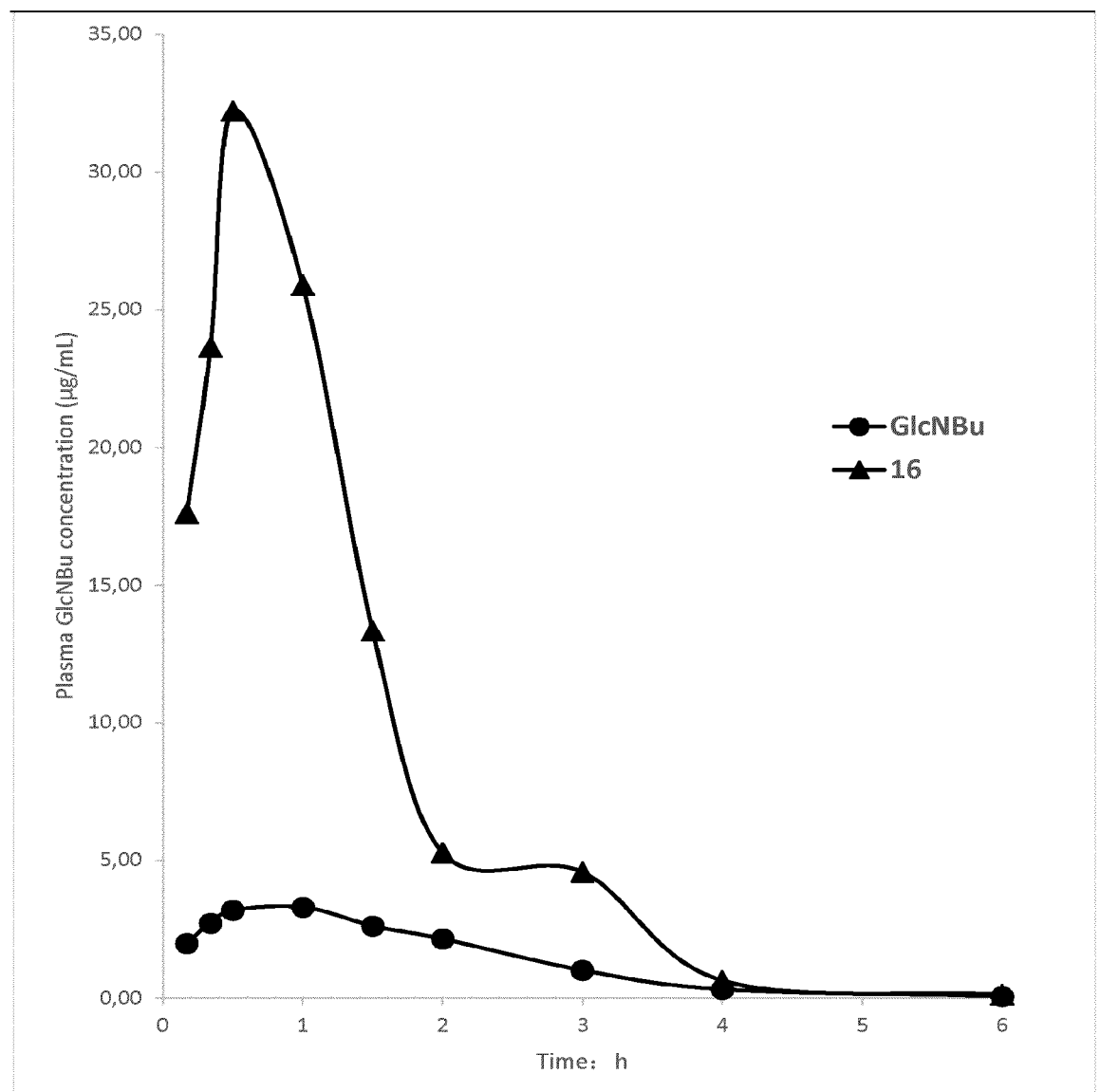
FIG. 1 shows mean plasma GLcNBu concentration versus time curves following oral administration of GlcNBu and Compound 16 at a dose of 0.93 mmol/kg.

In order to provide a clear and consistent understanding of the terms used in the present specification, a number of definitions are provided below. Moreover, unless defined otherwise, all technical and scientific terms as used herein have the same meaning as commonly understood to one of ordinary skill in the art to which this invention pertains.

The use of the word "a" or "an" when used in conjunction with the term "comprising" in the claims and/or the specification may mean "one", but it is also consistent with the meaning of "one or more", "at least one", and "one or more than one". Similarly, the word "another" may mean at least a second or more.

As used in this specification and claim(s), the words "comprising" (and any form of comprising, such as "comprise" and "comprises"), "having" (and any form of having, such as "have" and "has"), "including" (and any form of including, such as "include" and "includes") or "containing" (and any form of containing, such as "contain" and "contains"), are inclusive or open-ended and do not exclude additional, unrecited elements or process steps.

The term "about" is used to indicate that a value includes an inherent variation of error for the device or the method being employed to determine the value.

The term "derivative" as used herein, is understood as being a substance similar in structure to another compound but differing in some slight structural detail.

The present description refers to a number of chemical terms and abbreviations used by those skilled in the art. Nevertheless, definitions of selected terms are provided for clarity and consistency.

As used herein, the term "alkyl" refers to saturated hydrocarbons having from one to twelve carbon atoms, including linear, branched, and cyclic alkyl groups. Examples of alkyl groups include, without limitation, methyl, ethyl, propyl, butyl, pentyl, hexyl, heptyl, octyl, nonyl, decyl, isopropyl, tert-butyl, sec-butyl, isobutyl, cyclopropyl, cyclopentyl, cyclohexyl, cycloheptyl, cyclooctyl, and the like. The term alkyl includes both unsubstituted alkyl groups and substituted alkyl groups. The term "$C_1$-$C_n$alkyl", wherein n is an integer from 2 to 12, refers to an alkyl group having from 1 to the indicated "n" number of carbon atoms. Alkyl residues may be substituted or unsubstituted. In some embodiments, for example, alkyl may be substituted by hydroxyl, amino, carboxyl, carboxylic ester, amide, carbamate, or aminoalkyl.

As used herein, the term "acyclic" refers to an organic moiety without a ring system. The term "aliphatic group" includes organic moieties characterized by straight or branched-chains, typically having between 1 and 15 carbon atoms. Aliphatic groups include non-cyclic alkyl groups, alkenyl groups, and alkynyl groups.

As used herein, the term "alkenyl" refers to unsaturated hydrocarbons having from two to twelve carbon atoms, including linear, branched, and cyclic non aromatic alkenyl groups, and comprising between one to six carbon-carbon double bonds. Examples of alkenyl groups include, without limitation, vinyl, allyl, 1-propen-2-yl, 1-buten-3-yl, 1-buten-4-yl, 2-buten-4-yl, 1-penten-5-yl, 1,3-pentadien-5-yl, cyclopentenyl, cyclohexenyl, ethylcyclopentenyl, ethylcylohexenyl, and the like. The term alkenyl includes both unsubstituted alkenyl groups and substituted alkenyl groups. The term "$C_2$-$C_n$alkenyl", wherein n is an integer from 3 to 12, refers to an alkenyl group having from 2 to the indicated "n" number of carbon atoms.

As used herein, the term "alkynyl" refers to unsaturated hydrocarbons having from two to twelve carbon atoms, including linear, branched, and cyclic non aromatic alkynyl groups, and comprising between one to six carbon-carbon triple bonds. Examples of alkynyl groups include, without limitation, ethynyl, 1-propyn-3-yl, 1-butyn-4-yl, 2-butyn-4-yl, 1-pentyn-5-yl, 1,3-pentadiyn-5-yl, and the like. The term alkynyl includes both unsubstituted alkynyl groups and substituted alkynyl groups. The term "$C_2$-$C_n$alkynyl", wherein n is an integer from 3 to 12, refers to an alkynyl group having from 2 to the indicated "n" number of carbon atoms.

Unless the number of carbons is otherwise specified, "lower" as in "lower aliphatic," "lower alkyl," "lower alkenyl," and "lower alkylnyl", as used herein means that the moiety has at least one (two for alkenyl and alkynyl) and equal to or less than 6 carbon atoms.

The terms "cycloalkyl", "alicyclic", "carbocyclic" and equivalent expressions refer to a group comprising a saturated or partially unsaturated carbocyclic ring in a single, spiro (sharing one atom), or fused (sharing at least one bond) carbocyclic ring system having from three to fifteen ring members. Examples of cycloalkyl groups include, without limitation, cyclopropyl, cyclobutyl, cyclopentyl, cyclopenten-1-yl, cyclopenten-2-yl, cyclopenten-3-yl, cyclohexyl, cyclohexen-1-yl, cyclohexen-2-yl, cyclohexen-3-yl, cycloheptyl, bicyclo[4,3,0]nonanyl, norbornyl, and the like. The term cycloalkyl includes both unsubstituted cycloalkyl groups and substituted cycloalkyl groups. The term "$C_3$-$C_n$cycloalkyl", wherein n is an integer from 4 to 15, refers to a cycloalkyl group having from 3 to the indicated "n" number of carbon atoms in the ring structure. Unless the number of carbons is otherwise specified, "lower cycloalkyl" groups as herein used, have at least 3 and equal to or less than 8 carbon atoms in their ring structure.

Cycloalkyl residues can be saturated or contain one or more double bonds within the ring system. In particular they can be saturated or contain one double bond within the ring system. In unsaturated cycloalkyl residues the double bonds can be present in any suitable positions. Monocycloalkyl residues are, for example, cyclopropyl, cyclobutyl, cyclopentyl, cyclopentenyl, cyclohexyl, cyclohexenyl, cycloheptyl, cycloheptenyl, cyclooctyl, cyclononyl, cyclodecyl, cycloundecyl, cyclododecyl or cyclotetradecyl, which can also be substituted, for example by $C_{1-4}$ alkyl. Examples of substituted cycloalkyl residues are 4-methylcyclohexyl and 2,3-dimethylcyclopentyl. Examples of parent structures of bicyclic ring systems are norbornane, bicyclo[2.2.1]heptane, bicyclo[2.2.2]octane and bicyclo[3.2.1]octane.

The term "heterocycloalkyl" and equivalent expressions refer to a group comprising a saturated or partially unsaturated carbocyclic ring in a single, spiro (sharing one atom), or fused (sharing at least one bond) carbocyclic ring system having from three to fifteen ring members, including one to six heteroatoms (e.g., N, O, S, P) or groups containing such heteroatoms (e.g., NH, $NR_x$ ($R_x$ is alkyl, acyl, aryl, heteroaryl or cycloalkyl), $PO_2$, SO, $SO_2$, and the like). Heterocycloalkyl groups may be C-attached or heteroatom-attached (e.g., via a nitrogen atom) where such is possible. Examples of heterocycloalkyl groups include, without limitation, pyrrolidino, tetrahydrofuranyl, tetrahydrodithienyl, tetrahydropyranyl, tetrahydrothiopyranyl, piperidino, morpholino, thiomorpholino, thioxanyl, piperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3,1,0]hexanyl, 3-azabicyclo[4,1,0]heptanyl, 3H-indolyl, quinolizinyl, and sugars, and the like. The term heterocycloalkyl includes both unsubstituted heterocycloalkyl groups and substituted heterocycloalkyl groups. The term "$C_3$-$C_n$heterocycloalkyl", wherein n is an integer from 4 to 15, refers to a heterocycloalkyl group having from 3 to the indicated "n" number of atoms in the ring structure, including at least one hetero group or atom as defined above. Unless the number of carbons is otherwise specified, "lower heterocycloalkyl" groups as herein used, have at least 3 and equal to or less than 8 carbon atoms in their ring structure.

The terms "aryl" and "aryl ring" refer to aromatic groups having "4n+2".pi.(pi) electrons, wherein n is an integer from 1 to 3, in a conjugated monocyclic or polycyclic system (fused or not) and having six to fourteen ring atoms. A polycyclic ring system includes at least one aromatic ring. Aryl may be directly attached, or connected via a $C_1$-$C_3$alkyl group (also referred to as arylalkyl or aralkyl). Examples of aryl groups include, without limitation, phenyl, benzyl, phenetyl, 1-phenylethyl, tolyl, naphthyl, biphenyl, terphenyl, indenyl, benzocyclooctenyl, benzocycloheptenyl, azulenyl, acenaphthylenyl, fluorenyl, phenanthernyl, anthracenyl, and the like. The term aryl includes both unsubstituted aryl groups and substituted aryl groups. The term "$C_6$-$C_n$aryl", wherein n is an integer from 6 to 15, refers to an aryl group having from 6 to the indicated "n" number of atoms in the ring structure, including at least one hetero group or atom as defined above.

The terms "heteroaryl" and "heteroaryl ring" refer to an aromatic groups having "4n+2".pi.(pi) electrons, wherein n is an integer from 1 to 3, in a conjugated monocyclic or polycyclic system (fused or not) and having five to fourteen ring members, including one to six heteroatoms (e.g. N, O, S) or groups containing such heteroatoms (e.g. NH, $NR_x$ ($R_x$ is alkyl, acyl, aryl, heteroaryl or cycloalkyl), SO, and the like). A polycyclic ring system includes at least one heteroaromatic ring. Heteroaryls may be directly attached, or connected via a $C_1$-$C_3$alkyl group (also referred to as heteroarylalkyl or heteroaralkyl). Heteroaryl groups may be C-attached or heteroatom-attached (e.g., via a nitrogen atom), where such is possible. Examples of heteroaryl groups include, without limitation, pyridyl, imidazolyl, pyrimidinyl, pyrazolyl, triazolyl, tetrazolyl, furyl, thienyl; isooxazolyl, thiazolyl, oxazolyl, isothiazolyl, pyrrollyl, quinolinyl, isoquinolinyl, indolyl, isoindolyl, chromenyl, isochromenyl, benzimidazolyl, benzofuranyl, cinnolinyl, indazolyl, indolizinyl, phthalazinyl, pyridazinyl, pyrazinyl, triazinyl, isoindolyl, pteridinyl, purinyl, oxadiazolyl, thiadiazolyl, furazanyl, benzofurazanyl, benzothiophenyl, benzothienyl, benzothiazolyl, benzoxazolyl, quinazolinyl, quinolizinyl, quinolonyl, isoquinolonyl, quinoxalinyl, naphthyridinyl, furopyridinyl, carbazolyl, phenanthridinyl, acridinyl, perimidinyl, phenanthrolinyl, phenazinyl, phenothiazinyl, phenoxazinyl, dibenzofurnayl, and the like. The term heteroaryl includes both unsubstituted heteroaryl groups and substituted heteroaryl groups. The term "$C_5$-$C_n$heteroaryl", wherein n is an integer from 6 to 15, refers to a heteroaryl group having from 5 to the indicated "n" number of atoms in the ring structure, including at least one hetero group or atom as defined above.

The terms "heterocycle" or "heterocyclic" include heterocycloalkyl and heteroaryl groups. Examples of heterocycles include, without limitation, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, 4αH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, xanthenyl, and the like. The term heterocycle includes both unsubstituted heterocyclic groups and substituted heterocyclic groups.

The term "amine" or "amino," as used herein, refers to an unsubstituted or substituted moiety of the formula —$NR^aR^b$, in which $R^a$ and $R^b$ are each independently hydrogen, alkyl, aryl, or heterocyclyl, or $R^a$ and $R^b$, taken together with the nitrogen atom to which they are attached, form a heterocyclic ring. The term amino includes compounds or moieties in which a nitrogen atom is covalently bonded to at least one carbon or heteroatom. Thus, the terms "alkylamino" and "dialkylamino" as used herein mean an amine group having respectively one and at least two $C_1$-$C_6$alkyl groups attached thereto. The terms "arylamino" and "diarylamino" include groups wherein the nitrogen is bound to at least one or two aryl groups, respectively. The terms "amide" or "aminocarbonyl" include compounds or moieties which contain a nitrogen atom which is bound to the carbon of a carbonyl or a thiocarbonyl group. The term "acylamino" refers to an amino group directly attached to an acyl group as defined herein.

The term "nitro" means —$NO_2$; the terms "halo" and "halogen" refer to bromine, chlorine, fluorine or iodine substituents; the terms "thiol", "thio", or "mercapto" mean SH; and the terms "hydroxyl" or "hydroxy" mean —OH. The term "alkylthio" refers to an alkyl group, having a sulfhydryl group attached thereto. Suitable alkylthio groups include groups having 1 to about 12 carbon atoms, preferably from 1 to about 6 carbon atoms. The term "alkylcarboxyl" as used herein means an alkyl group having a carboxyl group attached thereto.

The terms "alkoxy" or "lower alkoxy" as used herein mean an alkyl group having an oxygen atom attached thereto. Representative alkoxy groups include groups having 1 to about 6 carbon atoms, e.g., methoxy, ethoxy, propoxy, tert-butoxy and the like. Examples of alkoxy groups include methoxy, ethoxy, isopropyloxy, propoxy, butoxy, pentoxy, fluoromethoxy, difluoromethoxy, trifluoromethoxy, chloromethoxy, dichloromethoxy, trichloromethoxy groups, and the like. The term "alkoxy" includes both unsubstituted or substituted alkoxy groups, etc., as well as perhalogenated alkyloxy groups.

The terms "carbonyl" or "carboxy" include compounds and moieties which contain a carbon connected with a double bond to an oxygen atom. Examples of moieties which contain a carbonyl include aldehydes, ketones, carboxylic acids, amides, esters, anhydrides, etc.

The term "acyl" refers to a carbonyl group that is attached through its carbon atom to a hydrogen (i.e., formyl), an aliphatic group ($C_1$-$C_6$alkyl, $C_1$-$C_6$alkenyl, $C_1$-$C_6$alkynyl, e.g., acetyl), a cycloalkyl group ($C_3$-$C_8$cycloalkyl), a heterocyclic group ($C_3$-$C_8$heterocycloalkyl and $C_5$-$C_6$heteroaryl), an aromatic group ($C_6$aryl, e.g., benzoyl), and the like. Acyl groups may be unsubstituted or substituted acyl groups (e.g., salicyloyl).

It should be understood that "substitution" or "substituted with" includes the implicit proviso that such substitution is in accordance with the permitted valence of the substituted atom and the substituent, and that the substitution results in a stable compound, i.e., a compound which does not spontaneously undergo transformation such as by rearrangement, cyclization, elimination, etc. As used herein, the term "substituted" is meant to include all permissible substituents of organic compounds. In a broad aspect, the permissible substituents include acyclic and cyclic, branched and unbranched, carbocyclic and heterocyclic, aromatic and nonaromatic substituents of organic compounds. The permissible substituents can be one or more. The term "substituted", when in association with any of the foregoing groups refers to a group substituted at one or more position with substituents such as acyl, amino (including simple amino, mono and dialkylamino, mono and diarylamino, and alkylarylamino), acylamino (including carbamoyl, and ureido), alkylcarbonyloxy, arylcarbonyloxy, alkoxycarbonyloxy, alkoxycarbonyl, carboxy, carboxylate, aminocarbonyl, mono and dialkylaminocarbonyl, cyano, azido, halogen, hydroxyl, nitro, trifluoromethyl, thio, alkylthio, arylthio, alkylthiocarbonyl, thiocarboxylate, lower alkyl, lower alkenyl, lower alkynyl, cycloalkyl, heterocycloalkyl, aryl, heteroaryl, lower alkoxy, aryloxy, aryloxycarbonyloxy, benzyloxy, benzyl, sulfinyl, alkylsulfinyl, sulfonyl, sulfate, sulfonate, sulfonamide, phosphate, phosphonato, phosphinato, oxo, guanidine, imino, formyl and the like. Any of the above substituents can be further substituted if permissible, e.g., if the group contains an alkyl group, an aryl group, or other.

The term "solvate" refers to a physical association of a compound with one or more solvent molecules, whether organic or inorganic. This physical association includes hydrogen bonding. In certain instances, a solvate will be capable of isolation, for example when one or more solvent molecules are incorporated in the crystal lattice of a crystalline solid. "Solvate" encompasses both solution-phase and isolable solvates. Exemplary solvates include, without limitation, hydrates, ethanolates, methanolates, hemiethanolates, and the like.

Isotopic enrichment is a process by which the relative abundance of the isotopes of a given element are altered, thus producing a form of the element that has been enriched (i.e., increased) in one particular isotope and reduced or depleted in its other isotopic forms. As used herein, an "isotope-enriched" compound or derivative refers to a compound in which one or more specific isotopic form has been increased, i.e., one or more of the elements has been enriched (i.e., increased) in one or more particular isotope. Generally, in an isotope-enriched compound or derivative, a specific isotopic form of an element at a specific position of the compound is increased. It should be understood however that isotopic forms of two or more elements in the compound may be increased. Further, an isotope-enriched compound may be a mixture of isotope-enriched forms that are enriched for more than one particular isotope, more than one element, or both.

Under normal conditions, the natural abundances for deuterium (D or $^2$H) (a stable isotope of hydrogen with a mass approximately twice that of the usual isotope), nitrogen-15 ($^{15}$N), carbon-13 ($^{13}$C), oxygen-18 ($^{18}$O), and oxygen-17 ($^{17}$O) are 0.016%, 0.37%, 1.11%, 0.204%, and 0.037%, respectively. As used herein, an "isotope-enriched" compound or derivative possesses a level of an isotopic form that is higher than the natural abundance of that form. The level of isotope-enrichment will vary depending on the natural abundance of a specific isotopic form. In some embodiments, the level of isotope-enrichment for a compound, or for an element in a compound, may be from about 2 to about 100 molar percent (%), e.g., about 2%, about 5%, about 17%, about 30%, about 51%, about 83%, about 90%, about 95%, about 96%, about 97%, about 98%, greater than about 98%, about 99%, or 100%. In one embodiment, the level of isotope-enrichment in an isotope-enriched compound of the invention (a compound of any one of Formula (A), (I), (II), (III), or (IV), etc.) is about 5% or higher, or about 10% or higher. In another embodiment, the level of isotope-enrichment in an isotope-enriched compound of the invention is about 20% or higher, or about 50% or higher. In yet another embodiment, the level of isotope-enrichment in an isotope-enriched compound of the invention is about 75% or higher, or about 90% or higher. In still another embodiment, the level of isotope-enrichment in an isotope-enriched compound of the invention is about 95% or higher, or 100%. It should be understood that the level of isotope-enrichment for a particular compound, or a particular element of a compound, will be selected based on several properties of the compound such as its chemical, pharmacokinetic, and therapeutic profiles, with the aim of improving the compound's therapeutic efficacy, therapeutic bio-distribution, bioavailability, metabolism, stability, and/or pharmacokinetic profile.

As used herein, an "element of natural abundance" and an "atom of natural abundance" refers to the element or atom respectively having the atomic mass most abundantly found in nature. For example, hydrogen of natural abundance is H (protium); nitrogen of natural abundance is $^{14}$N; oxygen of natural abundance is $^{16}$O; carbon of natural abundance is $^{12}$C; and so on. A "non-isotope enriched" compound is a compound in which all the atoms or elements in the compound are isotopes of natural abundance, i.e., all the atoms or elements have the atomic mass most abundantly found in nature. This is in contrast to an isotope-enriched compound in which one or more element is enriched for one or more specific isotopic form that is not the isotope of natural abundance.

As used herein, "D" refers to deuterium ($^2$H) and "T" refers to tritium ($^3$H).

A "pharmaceutically acceptable salt" of a compound means a salt of a compound that is pharmaceutically acceptable. Desirable are salts of a compound that retain or improve the biological effectiveness and properties of the free acids and bases of the parent compound as defined herein or that take advantage of an intrinsically basic, acidic or charged functionality on the molecule and that are not biologically or otherwise undesirable. Examples of pharmaceutically acceptable salts are also described, for example, in Berge et al., "Pharmaceutical Salts", J. Pharm. Sci. 66, 1-19 (1977). Non-limiting examples of such salts include:

(1) acid addition salts, formed on a basic or positively charged functionality, by the addition of inorganic acids such as hydrochloric acid, hydrobromic acid, hydroiodic acid, sulfuric acid, sulfamic acid, nitric acid, phosphoric acid, carbonate forming agents, and the like; or formed with organic acids such as acetic acid, propionic acid, lactic acid, oxalic, glycolic acid, pivalic acid, t-butylacetic acid, β-hydroxybutyric acid, valeric acid, hexanoic acid, cyclopentanepropionic acid, pyruvic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, cyclohexylaminosulfonic acid, benzenesulfonic acid, sulfanilic acid, 4-chlorobenzenesulfonic acid, 2-napthalenesulfonic acid, 4-toluenesulfonic acid, camphorsulfonic acid, 3-phenyl propionic acid, lauryl sulphonic acid, lauryl sulfuric acid, oleic acid, palmitic acid, stearic acid, lauric acid, embonic (pamoic) acid, palmoic acid, pantothenic acid, lactobionic acid, alginic acid, galactaric acid, galacturonic acid, gluconic acid, glucoheptonic acid, glutamic acid, naphthoic acid, hydroxynapthoic acid, salicylic acid, ascorbic acid, stearic acid, muconic acid, and the like;

(2) base addition salts, formed when an acidic proton present in the parent compound either is replaced by a metal ion, including, an alkali metal ion (e.g., lithium, sodium, potassium), an alkaline earth ion (e.g., magnesium, calcium, barium), or other metal ions such as aluminum, zinc, iron and the like; or coordinates with an organic base such as ammonia, ethylamine, diethylamine, ethylenediamine, N,N'-dibenzylethylenediamine, ethanolamine, diethanolamine, triethanolamine, tromethamine, N-methylglucamine, piperazine, chloroprocain, procain, choline, lysine and the like.

Pharmaceutically acceptable salts may be synthesized from a parent compound that contains a basic or acidic moiety, by conventional chemical methods. Generally, such salts are prepared by reacting the free acid or base forms of compounds with a stoichiometric amount of the appropriate base or acid in water or in an organic solvent, or in a mixture of the two. Salts may be prepared in situ, during the final isolation or purification of a compound or by separately reacting a compound in its free acid or base form with the desired corresponding base or acid, and isolating the salt thus formed. The term "pharmaceutically acceptable salts"

also include zwitterionic compounds containing a cationic group covalently bonded to an anionic group, as they are "internal salts". It should be understood that all acid, salt, base, and other ionic and non-ionic forms of compounds described herein are intended to be encompassed. For example, if a compound is shown as an acid herein, the salt forms of the compound are also encompassed. Likewise, if a compound is shown as a salt, the acid and/or basic forms are also encompassed.

As used herein, "AUC" refers to the area under a curve representing the concentration of a compound in a biological sample from a subject as a function of time following administration of the compound to the subject. Non-limiting examples of such biological samples include biological fluids such as plasma, blood, cerebrospinal fluid (CSF), and saliva; organ homogenates such as brain and liver homogenates; and the like. The AUC can be determined by measuring the concentration of a compound in a biological sample such as the plasma, blood, CSF or brain homogenate using methods such as liquid chromatography-tandem mass spectrometry (LC/MS/MS), at various time intervals, and calculating the area under the concentration-versus-time curve. Suitable methods for calculating the AUC from a drug concentration-versus-time curve are well known in the art. As relevant to the disclosure here, an AUC for GlcNBu can be determined by measuring the concentration of GlcNBu in the plasma, blood, or tissue homogenate of a subject following oral administration of a compound described herein to the subject.

"Bioavailability" refers to the rate and amount of a compound that reaches the systemic circulation of a subject following administration of the compound or a prodrug thereof to the subject and can be determined by evaluating, for example, the plasma or blood concentration-versus-time profile for the compound. Parameters useful in characterizing a plasma or blood concentration-versus-time curve include the area under the curve (AUC), the time to peak concentration ($T_{max}$), and the maximum compound concentration ($C_{max}$). "$C_{max}$" is the maximum concentration of a compound in the biological sample of a subject following administration of a dose of the compound to the subject. "$T_{max}$" is the time to the maximum concentration ($C_{max}$) of a compound in the biological sample of a subject following administration of a dose of the compound to the subject. "$t_{1/2}$" is the terminal elimination half-life of a compound in the biological sample of a subject following administration of a dose of the compound to the subject. Bioavailability is often expressed as F (%) referring to the ratio in percentage of the AUC of the compound for a specific mode of administration (e.g., orally) over AUC of the compound after intravenous (TV) administration.

"Bioequivalence" refers to equivalence of the rate and extent of absorption of a therapeutic agent, such as a compound, after administration of equal doses of the agent to a patient. As used herein, two plasma or blood concentration profiles are bioequivalent if the 90% confidence interval for the ratio of the mean response of the two profiles is within the limits of 0.8 and 1.25. The mean response includes at least one of the characteristic parameters of a profile such as Cmax, Tmax, or AUC.

As used herein the term "effective amount" refers to the amount or dose of a therapeutic agent, such as a compound, upon single or multiple dose administration to a subject, which provides the desired therapeutic, diagnostic, or prognostic effect in the subject. An effective amount can be readily determined by an attending physician or diagnostician using known techniques and by observing results obtained under analogous circumstances. In determining the effective amount or dose of compound administered, a number of factors are considered including, but not limited to: the size, age, and general health of the subject; the specific disease involved; the degree of or involvement or the severity of the disease or condition to be treated; the response of the individual subject; the particular compound administered; the mode of administration; the bioavailability characteristics of the preparation administered; the dose regimen selected; the use of concomitant medication(s); and other relevant considerations.

"Pharmaceutically acceptable" refers to drugs, medicaments, inert ingredients etc., which the term describes, suitable for use in contact with the cells or tissues of humans and animals without undue toxicity, incompatibility, instability, irritation, allergic response, and the like, commensurate with a reasonable benefit/risk ratio. It generally refers to a compound or composition that is approved or approvable by a regulatory agency of the Federal or state government or listed in the U.S. Pharmacopoeia or other generally recognized pharmacopoeia for use in animals and more particularly in humans.

"Pharmaceutically acceptable vehicle" refers to a diluent, adjuvant, excipient, vehicle or carrier with which a compound is administered. The terms "Pharmaceutically acceptable vehicle" and "Pharmaceutically acceptable carrier" are used interchangeably herein.

"Pharmaceutical composition" refers to a composition comprising a compound as described herein and at least one component comprising a pharmaceutically acceptable carrier, diluent, adjuvant, excipient, or vehicle, such as a preserving agent, a filler, a disintegrating agent, a wetting agent, an emulsifying agent, a suspending agent, a sweetening agent, a flavoring agent, a perfuming agent, an antibacterial agent, an antifungal agent, a lubricating agent, a dispensing agent, and the like, depending on the nature of the mode of administration and dosage forms. "Preventing" or "prevention" is intended to refer to at least the reduction of likelihood of the risk of (or susceptibility to) acquiring a disease or disorder (i.e., causing at least one of the clinical symptoms of the disease not to develop in a patient that may be exposed to or predisposed to the disease but does not yet experience or display symptoms of the disease).

"Treating" or "treatment" of any disease or disorder refers, in some embodiments, to ameliorating at least one disease or disorder (i.e., arresting or reducing the development of the disease or at least one of the clinical symptoms thereof). In certain embodiments "treating" or "treatment" refers to ameliorating at least one physical parameter, which may or may not be discernible by the patient. In certain embodiments, "treating" or "treatment" refers to inhibiting the disease or disorder, either physically, (e.g., stabilization of a discernible symptom), physiologically, (e.g., stabilization of a physical parameter), or both. In some embodiments, "treating" or "treatment" refers to improving the quality of life or reducing the symptoms or side effects of a bone or joint disorder such as osteoporosis or arthritis in a subject in need thereof. "Therapeutically effective amount" means the amount of a compound that, when administered to a subject for treating or preventing a disease, is sufficient to effect such treatment or prevention of the disease. The "therapeutically effective amount" will vary depending on the compound, the disease and its severity, and the age, weight, etc., of the subject having the disease to be treated or prevented. As used herein, the term "therapeutically effective amount" refers to an amount of a compound or composition sufficient to prevent, treat, inhibit, reduce, ameliorate or eliminate one or more causes, symptoms, or complications of a bone or joint disease such as osteoporosis, osteopenia, or arthritis. In certain embodiments, a desired therapeutic effect is the attainment of one or more of the following in a subject: enhanced cartilage formation; enhanced chondrocyte cell proliferation or growth; reduced joint stiffness; increased mobility, or reduction in restricted mobility; enhanced production of glycosaminoglycan; increased bone mineral density (BMD); improved bone micro-architecture and/or bone connectivity; and reduced risk of fractures.

"Therapeutic effectiveness" means the ability of a compound or composition to provide a desired therapeutic effect. As used herein, the term "increasing therapeutic effectiveness" refers to increasing the therapeutic effect provided by a particular active therapeutic agent. In certain embodiments "increasing therapeutic effectiveness" refers to improving the pharmacokinetics of a therapeutic agent, e.g., attaining one or more target pharmacokinetic parameter, such that ability to attain a desired therapeutic effect with the therapeutic agent is improved or increased. In some embodiments, "increasing therapeutic effectiveness" means increasing one or more of the following: bioavailability of GlcNBu; AUC of GlcNBu in blood or plasma; $C_{max}$ of GlcNBu; $T_{max}$ of GlcNBu; $t_{1/2}$ of GlcNBu; bio-distribution of GlcNBu; level of GlcNBu in a selected tissue; and/or bioabsorption of GlcNBu; in a subject, as compared to administration of GlcNBu itself. In some embodiments, "increasing therapeutic effectiveness" means decreasing one or more of the following: metabolism of GlcNBu; and side effects of GlcNBu; in a subject, as compared to administration of GlcNBu itself. In some embodiments, "increasing therapeutic effectiveness" means that the dose and/or dosing frequency of a compound or composition sufficient to provide a desired therapeutic effect in a subject is decreased.

The term "subject" includes animals, including mammals and humans, particularly humans.

The term "prodrug" and equivalent expressions refer to agents which can be converted in vitro or in vivo directly or indirectly to an active form (see, e.g., R. B. Silverman, 1992, "The Organic Chemistry of Drug Design and Drug Action," Academic Press, Chap. 8; Bundgaard, Hans; Editor. Neth. (1985), "Design of Prodrugs". 360 pp. Elsevier, Amsterdam; Stella, V.; Borchardt, R.; Hageman, M.; Oliyai, R.; Maag, H.; Tilley, J. (Eds.) (2007), "Prodrugs: Challenges and Rewards, XVIII, 1470 p. Springer). Prodrugs can be used to alter the bio-distribution (e.g., to allow agents which would not typically enter the reactive site of a protease) or the pharmacokinetics for a particular agent. A wide variety of groups have been used to modify compounds to form prodrugs, for example, esters, ethers, phosphates, etc. When a prodrug is administered to a subject, the group is cleaved, enzymatically or non-enzymatically, reductively, oxidatively, or hydrolytically, or otherwise to reveal the active form. As used herein, "prodrug" includes pharmaceutically acceptable salts thereof, or pharmaceutically acceptable solvates as well as crystalline forms of any of the foregoing. Prodrugs are frequently, although not necessarily, pharmacologically inactive until converted to the active form.

The term "ester" refers to compounds that can be represented by the formula RCOOR (carboxylic ester) or the formula $RSO_3R'$ (sulfonate ester), usually respectively formed by the reaction between a carboxylic or a sulfonic acid and an alcohol usually with the elimination of water.

The term "amino acid" generally refers to an organic compound comprising both a carboxylic acid group and an amine group. The term "amino acid" includes both "natural" and "unnatural" or "non-natural" amino acids. Additionally, the term amino acid includes O-alkylated and N-alkylated amino acids, as well as amino acids having nitrogen or oxygen-containing side chains (such as Lys, Cys, or Ser) in which the nitrogen or oxygen atom has been acylated or alkylated. Amino acids may be pure L or D isomers or mixtures of L and D isomers, including (but not limited to) racemic mixtures.

The term "natural amino acid" and equivalent expressions refer to L-amino acids commonly found in naturally-occurring proteins. Examples of natural amino acids include, without limitation, alanine (Ala), cysteine (Cys), aspartic acid (Asp), glutamic acid (Glu), phenylalanine (Phe), glycine (Gly), histidine (His), isoleucine (Ile), lysine (Lys), leucine (Leu), methionine (Met), asparagine (Asn), proline (Pro), glutamine (Gln), arginine (Arg), serine (Ser), threonine (Thr), valine (Val), tryptophan (Trp), tyrosine (Tyr), β-alanine (β-Ala), and γ-aminobutyric acid (GABA).

The term "unnatural amino acid" refers to any derivative of a natural amino acid including D forms, and α- and β-amino acid derivatives. The terms "unnatural amino acid" and "non-natural amino acid" are used interchangeably herein. It is noted that certain amino acids, e.g., hydroxyproline, that are classified as a non-natural amino acid herein, may be found in nature within a certain organism or a particular protein. Amino acids with many different protecting groups appropriate for immediate use in the solid phase synthesis of peptides are commercially available. In addition to the twenty most common naturally occurring amino acids, the following examples of non-natural amino acids and amino acid derivatives may be used according to the invention (common abbreviations in parentheses): 2-aminoadipic acid (Aad), 3-aminoadipic acid (β-Aad), 2-aminobutyric acid (2-Abu), α,β-dehydro-2-aminobutyric acid (8-AU), 1-aminocyclopropane-1-carboxylic acid (ACPC), aminoisobutyric acid (Aib), 3-aminoisobutyric acid (β-Aib), 2-amino-thiazoline-4-carboxylic acid, 5-aminovaleric acid (5-Ava), 6-aminohexanoic acid (6-Ahx), 2-aminoheptanoic acid (Ahe), 8-aminooctanoic acid (8-Aoc), 11-aminoundecanoic acid (11-Aun), 12-aminododecanoic acid (12-Ado), 2-aminobenzoic acid (2-Abz), 3-aminobenzoic acid (3-Abz), 4-aminobenzoic acid (4-Abz), 4-amino-3-hydroxy-6-methylheptanoic acid (Statine, Sta), aminooxyacetic acid (Aoa), 2-aminotetraline-2-carboxylic acid (ATC), 4-amino-5-cyclohexyl-3-hydroxypentanoic acid (ACHPA), para-aminophenylalanine (4-NH$_2$-Phe), 2-aminopimelic acid (Apm), biphenylalanine (Bip), para-bromophenylalanine (4-Br-Phe), ortho-chlorophenylalanine (2-C$_1$-Phe), meta-chlorophenylalanine (3-Cl-Phe), para-chlorophenylalanine (4-C$_1$-Phe), meta-chlorotyrosine (3-C$_1$-Tyr), para-benzoylphenylalanine (Bpa), tert-butylglycine (TLG), cyclohexylalanine (Cha), cyclohexylglycine (Chg), desmosine (Des), 2,2-diaminopimelic acid (Dpm), 2,3-diaminopropionic acid (Dpr), 2,4-diaminobutyric acid (Dbu), 3,4-dichlorophenylalanine (3,4-C$_{1-2}$-Phe), 3,4-difluororphenylalanine (3,4-F$_2$-Phe), 3,5-diiodotyrosine (3,5-I$_2$-Tyr), N-ethylglycine (EtGly), N-ethylasparagine (EtAsn), ortho-fluorophenylalanine (2-F-Phe), meta-fluorophenylalanine (3-F-Phe), para-fluorophenylalanine (4-F-Phe), meta-fluorotyrosine (3-F-Tyr), homoserine (Hse), homophenylalanine (Hfe), homotyrosine (Htyr), hydroxylysine (Hyl), allo-hydroxylysine (aHyl), 5-hydroxytryptophan (5-OH-Trp), 3- or 4-hydroxyproline (3- or 4-Hyp), para-iodophenylalanine (4-I-Phe), 3-iodotyrosine (3-1-Tyr), indoline-2-carboxylic acid (Idc), isodesmosine (Ide), allo-isoleucine (a-Ile), isonipecotic acid (Inp), N-methylisoleucine (MeIle), N-methyllysine (MeLys), meta-methyltyrosine (3-Me-Tyr), N-methylvaline (MeVal), 1-naphthylalanine (1-Nal), 2-naphthylalanine (2-Nal), para-nitrophenylalanine (4-NO$_2$-Phe), 3-nitrotyrosine (3-NO$_2$-Tyr), norleucine (Nle), norvaline (Nva), ornithine (Orn), ortho-phosphotyrosine (H$_2$PO$_3$-Tyr), octahydroindole-2-carboxylic acid (Oic), penicillamine (Pen), pentafluorophenylalanine (F$_5$-Phe), phenylglycine (Phg), pipecolic acid (Pip), propargylglycine (Pra), pyroglutamic acid (PGLU), sarcosine (Sar), tetrahydroisoquinoline-3-carboxylic acid (Tic), thienylalanine, and thiazolidine-4-carboxylic acid (thioproline, Th).

For compounds provided herein, it is intended that, in some embodiments, salts thereof are also encompassed, including pharmaceutically acceptable salts. Those skilled in the art will appreciate that many salt forms (e.g., TFA salt, tetrazolium salt, sodium salt, potassium salt, etc.) are possible; appropriate salts are selected based on considerations known in the art. The term "pharmaceutically acceptable salt" refers to salts prepared from pharmaceutically acceptable non-toxic acids or bases including inorganic acids and bases and organic acids and bases. For example, for compounds that contain a basic nitrogen, salts may be prepared from pharmaceutically acceptable non-toxic acids including inorganic and organic acids. Suitable pharmaceutically acceptable acid addition salts for the compounds of the present invention include without limitation acetic, benzenesulfonic (besylate), benzoic, camphorsulfonic, citric, ethenesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric acid, p-toluenesulfonic, and the like. When the compounds contain an acidic side chain, suitable pharmaceutically acceptable base addition salts for the compounds of the present invention include without limitation metallic salts made from aluminum, calcium, lithium, magnesium, potassium, sodium and zinc or organic salts made from lysine, N,N'-dibenzylethylenediamine, chloroprocaine, choline, diethanolamine, ethylenediamine, meglumine (N-methylglucamine), and procaine.

Compositions

In an embodiment, there is provided a pharmaceutical composition comprising a compound of the invention, e.g., a compound of any one of Formulae (A), and (I) to (IV), or a pharmaceutically acceptable salt, ester, or solvate thereof, and a pharmaceutically acceptable carrier. In an embodiment, there is provided a pharmaceutical composition comprising a compound in Tables 1, 2, and 3 or a pharmaceutically acceptable salt thereof, and a pharmaceutically acceptable carrier. In another embodiment, there is provided a pharmaceutical composition comprising a compound of any one of Formulae (A), and (I) to (IV) or a compound in Tables 1, 2 and 3, or a pharmaceutically acceptable salt thereof, and a pharmaceutically acceptable carrier, with the proviso that the compound is not derived from N-acetyl glucosamine.

The preparation of pharmaceutical compositions can be carried out as known in the art (see, for example, Remington: The Science and Practice of Pharmacy, 20$^{th}$ Edition, 2000). For example, a therapeutic compound and/or composition, together with one or more solid or liquid pharmaceutical carrier substances and/or additives (or auxiliary substances) and, if desired, in combination with other pharmaceutically active compounds having therapeutic or prophylactic action, are brought into a suitable administration form or dosage form which can then be used as a pharmaceutical in human or veterinary medicine. Pharmaceutical preparations can also contain additives, of which many are known in the art, for example fillers, disintegrants, binders, lubricants, wetting agents, stabilizers, emulsifiers, dispersants, preservatives, sweeteners, colorants, flavorings, aromatizers, thickeners, diluents, buffer substances, solvents, solubilizers, agents for achieving a depot effect, salts for altering the osmotic pressure, coating agents and/or antioxidants.

The term "pharmaceutically acceptable carrier" is intended to encompass any carrier, diluent, adjuvant, excipient, or vehicle, as described herein. Examples of suspending agents include without limitation ethoxylated isostearyl alcohols, polyoxyethylene sorbitol and sorbitan esters, microcrystalline cellulose, aluminum metahydroxide, bentonite, agar-agar and tragacanth, or mixtures of these substances. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monosterate and gelatin. Examples of suitable carriers, diluents, solvents, or vehicles include without limitation water, ethanol, polyols, suitable mixtures thereof, vegetable oils (such as olive oil), and injectable organic esters such as ethyl oleate. Examples of excipients include without limitation lactose, milk sugar, sodium citrate, calcium carbonate, and dicalcium phosphate. Examples of disintegrating agents include without limitation starch, alginic acids, and certain complex silicates. Examples of lubricants include without limitation magnesium stearate, sodium lauryl sulphate, talc, as well as high molecular weight polyethylene glycols.

A pharmaceutically acceptable carrier may include any and all solvents, dispersion media, coatings, antibacterial agents, antifungal agents, isotonic agents, absorption delaying agent, and the like that are physiologically compatible. In one embodiment, the carrier is suitable for oral administration. Alternatively, the carrier may be suitable for intravenous, intraperitoneal, intramuscular, sublingual or parenteral administration. In other embodiments, the carrier is suitable for topical administration, transdermal administration, or for administration via inhalation. Pharmaceutically acceptable carriers may include sterile aqueous solutions or dispersions and sterile powders for the extemporaneous preparation of sterile injectable solutions or dispersion. The use of such media and agents for pharmaceutically active substances is well known in the art. Except insofar as any conventional media or agent is incompatible with the active compound, use thereof in the pharmaceutical compositions provided herein is contemplated.

A pharmaceutical composition provided herein can be administered orally, for example in the form of pills, tablets, lacquered tablets, sugar-coated tablets, granules, hard and soft gelatin capsules, aqueous, alcoholic or oily solutions, syrups, emulsions or suspensions, or rectally, for example in the form of suppositories. Administration can also be carried out parenterally, for example subcutaneously, intramuscularly or intravenously in the form of solutions for injection or infusion. Other suitable administration forms are, for example, percutaneous or topical administration, for example in the form of ointments, creams, tinctures, sprays or transdermal therapeutic systems, or the inhalative administration in the form of nasal sprays or aerosol mixtures, or, for example, microcapsules, implants or wafers.

In some embodiments, pharmaceutical compositions provided herein are suitable for oral administration. For example, a pharmaceutical composition may be in the form of a hard shell gelatin capsule, a soft shell gelatin capsule, a cachet, a pill, a tablet, a lozenge, a powder, a granule, a pellet, a pastille, or a dragee. Alternatively, a pharmaceutical composition may be in the form of a solution, an aqueous liquid suspension, a non-aqueous liquid suspension, an oil-in-water liquid emulsion, a water-in-oil liquid emulsion, an elixir, a syrup, an ointment, or a medical patch. Pharmaceutical compositions may or may not be enteric coated. In some embodiments, pharmaceutical compositions are formulated for controlled release, such as delayed or extended release.

In further embodiments, compounds and compositions thereof may be formulated in multi-dose forms, i.e., in the form of multi-particulate dosage forms (e.g., hard gelatin capsules or conventional tablets prepared using a rotary tablet press) comprising one or more bead or minitab populations for oral administration. The conventional tablets rapidly disperse on entry into the stomach. The one or more coated bead or minitab populations may be compressed together with appropriate excipients into tablets (for example, a binder, a diluent/filler, and a disintegrant for conventional tablets).

Tablets, pills, beads, or minitabs of the compounds and compositions of the compounds may be coated or otherwise compounded to provide a dosage form affording the advantage of controlled release, including delayed or extended release, or to protect from the acid conditions of the stomach. For example, the tablet or pill can include an inner dosage and an outer dosage component, the latter being in the form of a coating over the former. The two components can be separated by a polymer layer that controls the release of the inner dosage.

In certain embodiments, the layer may comprise at least one enteric polymer. In further embodiments, the layer may comprise at least one enteric polymer in combination with at least one water-insoluble polymer. In still further embodiments, the layer may comprise at least one enteric polymer in combination with at least one water-soluble polymer. In yet further embodiments, the layer may comprise at least one enteric polymer in combination with a pore-former.

In certain embodiments, the layer may comprise at least one water-insoluble polymer. In still further embodiments, the layer may comprise at least one water-insoluble polymer in combination with at least one water-soluble polymer. In yet further embodiments, the layer may comprise at least one water-insoluble polymer in combination with a pore-former.

Representative examples of water-soluble polymers include polyvinylpyrrolidone (PVP), hydroxypropyl methylcellulose (HPMC), hydroxypropylcellulose (HPC), polyethylene glycol, and the like.

Representative examples of enteric polymers include esters of cellulose and its derivatives (cellulose acetate phthalate, hydroxypropyl methylcellulose phthalate, hydroxypropyl methylcellulose acetate succinate), polyvinyl acetate phthalate, pH-sensitive methacrylic acid-methylmethacrylate copolymers and shellac. These polymers may be used as a dry powder or an aqueous dispersion. Some commercially available materials that may be used are methacrylic acid copolymers sold under the trademark Eudragit (LI 00, S I 00, L30D) manufactured by Rohm Pharma, Cellacefate (cellulose acetate phthalate) from Eastman Chemical Co., Aquateric (cellulose acetate phthalate aqueous dispersion) from FMC Corp. and Aqoat (hydroxypropyl methylcellulose acetate succinate aqueous dispersion) from Shin Etsu K.K.

Representative examples of useful water-insoluble polymers include ethylcellulose, polyvinyl acetate (for example, Kollicoat SR #30D from BASF), cellulose acetate, cellulose acetate butyrate, neutral copolymers based on ethyl acrylate and methylmethacrylate, copolymers of acrylic and methacrylic acid esters with quaternary ammonium groups such as Eudragit NE, RS and RS30D, RL or RL30D and the like.

Any of the above polymers may be further plasticized with one or more pharmaceutically acceptable plasticizers. Representative examples of plasticizers include triacetin, tributyl citrate, triethyl citrate, acetyl tri-n-butyl citrate diethyl phthalate, castor oil, dibutyl sebacate, acetylated monoglycerides and the like or mixtures thereof. The plasticizer, when used, may comprise about 3 to 30 wt. % and more typically about 10 to 25 wt. % based on the polymer. The type of plasticizer and its content depends on the polymer or polymers and nature of the coating system (e.g., aqueous or solvent based, solution or dispersion based and the total solids).

Pharmaceutical compositions typically must be sterile and stable under the conditions of manufacture and storage. A composition can be formulated as a solution, microemulsion, liposome, or other ordered structure suitable to high drug concentration. The carrier can be a solvent or dispersion medium containing, for example, water, ethanol, polyol (for example, glycerol, propylene glycol, liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of injectable compositions can be brought about by including in the composition an agent which delays absorption, for example, monostearate salts and gelatin. Moreover, a compound can be administered in a time release formulation, for example in a composition which includes a slow release polymer. The compound can be prepared with carriers that will protect against rapid release, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, polylactic acid and polylactic, polyglycolic copolymers (PLG).

Many methods for the preparation of such formulations are generally known to those skilled in the art. Sterile injectable solutions can be prepared by incorporating a compound, such as a compound of Formulae (A), and (I)-(IV) provided herein, in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, common methods of preparation are vacuum drying and freeze-drying which yields a powder of the active ingredient plus any additional desired ingredient from a previously sterile-filtered solution thereof. Compounds may also be formulated with one or more additional compounds that enhance their solubility.

It is often advantageous to formulate compositions (such as parenteral compositions) in dosage unit form for ease of administration and uniformity of dosage. The term "unit dosage form" refers to a physically discrete unit suitable as unitary dosages for human subjects and other animals, each unit containing a predetermined quantity of active material calculated to produce the desired therapeutic effect, in association with a suitable pharmaceutical carrier. The specification for the dosage unit forms of the invention may vary and are dictated by and directly dependent on (a) the unique characteristics of the therapeutic compound and the particular therapeutic effect to be achieved, and (b) the limitations inherent in the art of compounding such a therapeutic compound. Dosages are discussed further below.

In some embodiments, there are provided pharmaceutical compositions that comprise an effective amount of a compound and/or composition described herein, and a pharmaceutically acceptable carrier. In an embodiment, there are provided pharmaceutical compositions for the treatment or prevention of a bone or joint disorder comprising a compound described herein, or a pharmaceutically acceptable salt thereof, and a pharmaceutically acceptable carrier. In an embodiment, there are provided pharmaceutical compositions for the treatment or prevention of osteoporosis comprising a compound described herein, or a pharmaceutically acceptable salt thereof, and a pharmaceutically acceptable carrier. In an embodiment, there are provided pharmaceutical compositions for the treatment or prevention of arthritis comprising a compound described herein, or a pharmaceutically acceptable salt thereof, and a pharmaceutically acceptable carrier.

In some embodiments, there are provided pharmaceutical compositions that comprise an effective amount of a GlcNBu prodrug and a pharmaceutically acceptable carrier. Such compositions may be used for the treatment or prevention of a bone or joint disorder such as osteoporosis and arthritis and for other methods as described herein. In some such embodiments, the GlcNBu prodrug may be a compound of Formulae (A), and (I) to (IV) or a pharmaceutically acceptable salt thereof. In some embodiments, treatment or prevention are within the context of the present invention if there is a measurable difference between the performances of subjects treated using the compounds and methods provided herein as compared to members of a placebo group, historical control, or between subsequent tests given to the same subject.

It should be understood that the dosage or amount of a compound and/or composition used, alone or in combination with one or more active compounds to be administered, depends on the individual case and is, as is customary, to be adapted to the individual circumstances to achieve an optimum effect. Dosing and administration regimens are within the purview of the skilled artisan, and appropriate doses depend upon a number of factors within the knowledge of the ordinarily skilled physician, veterinarian, or researcher (e.g., see Wells et al. eds., Pharmacotherapy Handbook, 2nd Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000)). For example, dosing and administration regimens may depend on the nature and the severity of the disorder to be treated, and also on the sex, age, weight and individual responsiveness of the human or animal to be treated, on the efficacy and duration of action of the compounds used, on whether the therapy is acute or chronic or prophylactic, and/or on whether other active compounds are administered in addition to the therapeutic molecule(s).

Thus the dose(s) of a compound or composition will vary depending upon a variety of factors including, but not limited to: the activity, biological and pharmacokinetic properties and/or side effects of the compound being used; the age, body weight, general health, gender, and diet of the subject; the time of administration, the route of administration, the rate of excretion, and any drug combination, if applicable; the effect which the practitioner desires the compound to have upon the subject; and the properties of the compound being administered (e.g., bioavailability, stability, potency, toxicity, etc.). Such appropriate doses may be determined as known in the art. When one or more of the compounds or compositions described herein is to be administered to a human, a physician may for example, prescribe a relatively low dose at first, subsequently increasing the dose until an appropriate response is obtained.

There are no particular limitations on the dose of each of the compounds for use in compositions provided herein. Exemplary doses include milligram or microgram amounts of the compound per kilogram of subject or sample weight (e.g., about 50 micrograms per kilogram to about 3000 milligrams per kilogram, about 1 milligram per kilogram to about 100 milligrams per kilogram, about 1 milligram per kilogram to about 50 milligram per kilogram, about 1 milligram per kilogram to about 10 milligrams per kilogram, or about 3 milligrams per kilogram to about 5 milligrams per kilogram). Additional exemplary doses include doses of about 5 to about 500 mg, about 25 to about 300 mg, about 25 to about 200 mg, about 50 to about 150 mg, or about 50, about 100, about 150 mg, about 200 mg, about 250 mg, about 500 mg, about 1000 mg, about 2000 mg and, about 3000 mg for example, daily or twice daily, or lower or higher amounts.

In some embodiments, the dose range for adult humans is generally from 0.005 mg to 10 g/day orally. Tablets or other forms of presentation provided in discrete units may conveniently contain an amount of a compound (e.g., of Formula I, Formula II, or Formula III) which is effective at such dosage or as a multiple of the same, for instance, units containing 5 mg to 500 mg, usually around 10 mg to 200 mg. A dosage unit (e.g., an oral dosage unit) can include from, for example, 1 to 30 mg, 1 to 40 mg, 1 to 100 mg, 1 to 300 mg, 1 to 500 mg, 2 to 500 mg, 3 to 100 mg, 5 to 20 mg, 5 to 100 mg (e.g. 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 150 mg, 200 mg, 250 mg, 300 mg, 350 mg, 400 mg, 450 mg, 500 mg, 1000 mg, 2000 mg, or 3000 mg) of a compound described herein.

In some embodiments, the dosage range for oral administration is generally about 0.001 mg to about 3000 mg of a compound per kg body mass. In some embodiments, the oral dose is 0.01 mg to 100 mg per kg body mass, 0.1 mg to 50 mg per kg body mass, 0.5 mg to 20 mg per kg body mass, or 1 mg to 10 mg per kg body mass. In some embodiments, the oral dose is 5 mg of a compound per kg body mass.

Administration of compounds and compositions provided herein can be carried out using known procedures, at dosages and for periods of time effective to achieve a desired purpose. Dosage regimens can be adjusted to provide the optimum therapeutic response. For example, several divided doses may be administered daily or the dose may be proportionally reduced as indicated by the exigencies of the therapeutic situation. In some embodiments, a compound or composition is administered at an effective dosage sufficient to prevent or treat a bone or joint disease, e.g., osteoporosis and/or arthritis, in a subject. Further, a compound or composition may be administered using any suitable route or means, such as without limitation via oral, parenteral, intravenous, intraperitoneal, intramuscular, sublingual, topical, transdermal, or nasal administration, via inhalation, or via such other routes as are known in the art.

The compounds and compositions provided herein may be administered once, twice, three, or four times daily, using any suitable mode described above. Also, in certain embodiments, administration or treatment with the compounds according to any of the formulae described herein may be continued for a number of weeks; for example, commonly treatment would continue for at least 2 weeks, 4 weeks, 8 weeks, 12 weeks, 16 weeks, 20 weeks, 24 weeks, 28 weeks, 32 weeks, 36 weeks, 40 weeks, 44 weeks, 48 weeks, 52 weeks, 56 weeks, 60 weeks, 64 weeks, 68 weeks, 72 weeks, 76 weeks, 80 weeks, 84 weeks, 88 weeks, 92 weeks, 96 weeks, 100 weeks, or 104 weeks. In yet further embodiments, administration or treatment with the compounds according to any of the formulae described herein may be continued for a number of months; for example, commonly treatment would continue for at least 2 months, 4 months, 6 months, 8 months, 10 months, 12 months, 15 months, 18 months, 20 months, or 24 months. In still further embodiments, administration or treatment with the compounds according to any of the formulae described herein may be continued indefinitely.

Therapeutic Methods

In some embodiments, there are provided methods of treating or preventing a bone or joint disorder in a subject in need thereof comprising administering an effective amount of a compound, GlcNBu prodrug, or pharmaceutical composition thereof as described herein to the subject, such that the bone or joint disorder is prevented or treated in the subject.

A wide range of bone or joint disorders may be treated or prevented by the methods provided herein, including without limitation osteoporosis, osteopenia, and/or arthritis. Many types of arthritis are known and may be treated or prevented using methods provided herein, including without limitation osteoarthritis, inflammatory arthritis (e.g., rheumatoid arthritis, psoriatic arthritis, etc.), traumatic arthritis, degenerative arthritis, and dysplastic arthritis.

In an embodiment, there is provided a method of enhancing cartilage formation in a subject.

In an embodiment, there is provided a method of enhancing chondrocyte cell proliferation or growth in a subject.

In an embodiment, there is provided a method of alleviating the symptoms of joint stiffness and/or restricted mobility in a subject.

In an embodiment, there is provided a method of enhancing the production of glycosaminoglycan in a subject.

In an embodiment, there is provided a method of increasing bone mineral density (BMD) in a subject.

In an embodiment, there is provided a method of improving bone micro-architecture and/or bone connectivity in a subject.

In an embodiment, there is provided a method of treating or preventing low BMD in a subject.

In an embodiment, there is provided a method of preventing or diminishing the risk of fractures in a subject.

In an embodiment, there is provided a method of treating or preventing bone fractures, e.g., low impact fractures and/or high impact factures, in a subject.

In some embodiments, there are provided methods of increasing the therapeutic effectiveness of GlcNBu in a subject in need thereof, comprising administering an effective amount of a compound, GlcNBu prodrug, or pharmaceutical composition thereof as described herein to the subject, such that the therapeutic effectiveness of GlcNBu is increased as compared to administration of GlcNBu.

In some embodiments, one or more of the following is increased by administration of the compound, GlcNBu prodrug, or pharmaceutical composition provided herein: bioavailability of GlcNBu; AUC of GlcNBu in blood or plasma; $C_{max}$ of GlcNBu; $T_{max}$ of GlcNBu; $t_{1/2}$, of GlcNBu; therapeutic bio-distribution of GlcNBu; therapeutic level of GlcNBu in a selected tissue; and/or bioabsorption of GlcNBu in a subject, as compared to administration of GlcNBu itself. In some embodiments, one or more of the following is reduced by administration of the compound, GlcNBu prodrug, or pharmaceutical composition provided herein: metabolism of GlcNBu; and side effects of GlcNBu in a subject, as compared to administration of GlcNBu itself.

In some embodiments, there are provided methods of attaining a target pharmacokinetic parameter for GlcNBu in a subject, comprising administering an effective amount of a compound, GlcNBu prodrug, or pharmaceutical composition thereof as described herein to the subject, such that the target pharmacokinetic parameter for GlcNBu is attained in the subject. Non-limiting examples of target pharmacokinetic parameters include a target bioavailability, AUC in blood or plasma, $C_{max}$, $T_{max}$, bio-distribution, level in a selected tissue, half-life ($t_{1/2}$), bioabsorption, and amount or rate of metabolism. Pharmacokinetic parameters may be calculated using methods known in the art.

In some embodiments of methods provided herein, the subject is a mammal, e.g., a human.

In some embodiments of methods provided herein, there are provided methods of treating or preventing a bone or joint disorder in a subject in need thereof comprising administering an effective amount of a compound, GlcNBu prodrug, or pharmaceutical composition thereof as described herein in combination with one or more other therapeutic agent to the subject, such that the bone or joint disorder is prevented or treated in the subject. It should be understood that compounds and/or compositions provided herein may be used alone or in combination with other suitable therapies for bone or joint disorders, including therapies for osteoporosis, arthritis, etc. Non-limiting examples of such other therapies for bone or joint disorders include bisphosphonates, denosumab, calcitonic, selective estrogen receptor modulators (SERMs) such as raloxifene, teriparatide, duloxetine, and nonsteroidal anti-inflammatory drugs (NSAIDs). Compounds and/or compositions described herein may be administered alone or in combination with the one or more additional therapy for bone or joint disorders. The latter can be administered before, after or simultaneously with the administration of the compounds and/or compositions described herein.

EXAMPLES

The present invention will be more readily understood by referring to the following examples, which are provided to illustrate the invention and are not to be construed as limiting the scope thereof in any manner.

Unless defined otherwise or the context clearly dictates otherwise, all technical and scientific terms used herein have the same meaning as commonly understood by one of ordinary skill in the art to which this invention belongs. It should be understood that any methods and materials similar or equivalent to those described herein can be used in the practice or testing of the invention.

Example 1. Preparation of 2-N-butyryl-6-O—(N,O-bis(t-butoxycarbonyl)-L-tyrosyl)-D-glucosamine (Compound 1)

To a mixture of L-tyrosine (3.62 g, 20 mmol, 1 eq.) in water (50 mL) under stirring was added a solution of $Boc_2O$ (13.08 g, 60 mmol, 3 eq.) in isopropanol (IPA, 25 mL, followed by dropwise addition of 8 M KOH aqueous solution until the pH of the reaction mixture reached 12. The mixture was stirred at r.t for 3 h, acidified to pH 3 with 1 M HCl aqueous solution, and then extracted with ethyl acetate (100 mL). The organic layer was washed with water (50 mL) and brine (50 mL) subsequently, and then evaporated to dryness on a rotary evaporator, giving N,O-bis(t-butoxycarbonyl)-L-tyrosine (7.68 g, 100%). This compound (7.68 g, 20 mmol, 1 eq.) was added to DMF (50 mL), followed by addition of N-butyryl-D-glucosamine (GlcNBu, 4.98 g, 20 mmol, 1 eq.), N-hydroxybenzotrizole (HOBt, 4.05 g, 30 mmol, 1.5 eq.), N-(3-dimethylaminopropyl)-N'-ethylcarbodiimide (EDCI, 7.64 g, 40 mmol, 2 eq.), and N,N-diisopropylethylamine (DIPEA, 7.74 g, 60 mmol, 3 eq.). The mixture was stirred at r.t. for 16 h, followed by addition of water (50 mL) and ethyl acetate (50 mL). The organic layer was separated, washed with water (50 mL) and then with brine (50 mL), and evaporated to dryness. The residue was purified on a silica-gel column (MeOH/DCM=1/50~1/40), providing the title compound (2.21 g, 17.9%): $^1$H NMR (CD$_3$OD, 500 MHz) δ ppm 0.95 (t, 3H), 1.39 (s, 9H), 1.52 (s, 9H), 1.64 (dt, 2H), 2.22 (t, 2H), 2.92-2.96 (m, 0.8H), 3.16-3.20 (m, 1H), 3.34-3.52 (m, 1.2H), 3.71 (t, 0.8H), 3.87 (dd, 0.8H), 4.01-4.04 (m, 0.8H), 4.27-4.30 (m, 1H), 4.40-4.49 (m, 1.8H), 4.60 (d, 0.2H), 5.10 (d, 0.8H), 7.04 (d, 2H), 7.26 (d, 2H); $^{13}$C NMR (CD$_3$OD, 125 MHz) δ ppm 12.55, 18.96, 26.47, 27.27, 36.54, 37.49, 54.29, 55.00, 64.38, 69.23, 71.06, 79.30, 82.84, 91.22, 120.82, 129.99, 134.70, 150.03, 152.12, 156.40, 171.98, 175.14.

Example 2. Preparation of 2-N-butyryl-6-O—(N-(t-butoxycarbonyl)-L-valyl)-D-glucosamine (Compound 2)

To a mixture of N-Boc-L-valine (2.17 g, 10 mmol, 1 eq.) in DMF (50 mL) were added GlcNBu (2.49 g, 10 mmol, 1 eq.), HOBt (1.62 g, 12 mmol, 1.2 eq.), EDCI (2.88 g, 15 mmol, 1.5 eq.), and DIPEA (3.88 g, 30 mmol, 3 eq.). The mixture was stirred at r.t. for 16 h, followed by addition of water (50 mL) and ethyl acetate (50 mL), and mixed well. The organic layer was separated, washed with water (50 mL) and brine (50 mL) subsequently, and evaporated to dryness. The residual material was purified on a silica-gel column (MeOH/DCM, 1/35 to 1/30, v/v), giving the title compound (1.43 g, 32.0%): $^1$H NMR (CD$_3$OD, 500 MHz) δ ppm 0.92-0.96 (m, 9H), 1.44 (s, 9H), 1.65 (dt, 2H), 2.12 (tt, 1H), 2.20-2.22 (m, 2H), 3.42-3.50 (m, 1.3H), 3.60 (t, 0.7H), 3.70 (t, 0.3H), 3.84 (dd, 0.3H), 3.93-4.06 (m, 1.3H), 4.22-4.27 (m, 1H), 4.42-4.49 (m, 1H), 4.58 (d, 0.7H), 5.00 (d, 0.3H); $^{13}$C NMR (CD$_3$OD, 125 MHz) δ ppm 13.94, 18.31, 19.59, 28.72, 31.96, 38.90, 39.29, 55.69, 58.64, 60.62, 65.39, 70.68, 72.68, 80.61, 92.59, 97.11, 158.25, 173.65, 176.52, 177.11.

Example 3. Preparation of 2-N-butyryl-6-O—(N—(N-Boc-L-glycyl)-L-valyl)-D-glucosamine (Compound 3)

To a mixture of 2-N-butyryl-6-O-(L-valyl)-D-glucosamine hydrochloride (see Example 5 for its preparation, 3.84 g, 10 mmol, 1 eq.) in dichloromethane (DCM, 50 mL) was added triethylamine (2.0 g, 20 mmol, 2 eq.). The mixture was stirred at r.t. for 10 min., followed by addition of N-Boc-glycine N-hydroxysuccinimide ester (2.72 g, 10 mmol, 1 eq.). The mixture was stirred for 1 h, quenched with brine. The organic layer was separated, washed with brine (50 mL), and evaporated to dryness. The residual material was purified on a silica-gel column (MeOH/DCM, 1/100 to 1/30), providing the title compound (3.81 g, 75.6%): $^1$H NMR (CD$_3$OD, 500 MHz) δ ppm 0.90-0.97 (m, 9H), 1.45 (s, 9H), 1.66 (dt, 2H), 2.14-2.24 (m, 3H), 3.38-3.46 (m, 0.7H), 3.68-4.03 (m, 4.5H), 4.24-4.58 (m, 3H), 5.07 (s, 0.7H), 5.48 (s, 0.3H); $^{13}$C NMR (CD$_3$OD, 125 MHz) δ ppm 13.96, 18.29, 20.36, 28.69, 38.91, 44.42, 55.73, 59.02, 59.17, 65.12, 70.66, 72.43, 80.75, 92.62, 158.48, 172.63, 172.89, 176.54.

Example 4. Preparation of 2-N-butyryl-6-O—(N-(L-glycyl)-L-valyl)-D-glucosaminehydrochloride (Compound 4)

To compound 3 (5.05 g, 10 mmol, 1 eq.) in DCM (50 mL) was added 4M HCl in dioxane (5 mL). The mixture was stirred at room temperature (r.t.) for 1 hour (h). Solvent was removed on a rotary evaporator, giving the title compound (4.41 g, 100.0%): $^1$H NMR (D$_2$O, 500 MHz) δ ppm 0.86-0.91 (m, 9H), 1.57 (dt, 2H), 2.12-2.17 (m, 3H), 3.22-3.42 (m, 3H), 3.50-3.57 (m, 2H), 3.64 (t, 0.6H), 3.74-3.77 (m, 0.6H), 3.82-3.93 (m, 0.6H), 3.14-3.53 (m, 3.3H), 4.98 (t, 0.6H).

Example 5. Preparation of 2-N-butyryl-6-O-(L-valyl)-D-glucosamine hydrochloride (Compound 5)

To a stirred mixture of compound 2 (0.9 g, 2 mmol, 1 eq.) in DCM (9 mL) was added 4M HCl in dioxane (92.7. mL). The mixture was stirred at r.t. for 1 h, and evaporated to dryness, affording the title compound (0.77 g, 100%): $^1$H NMR (CD$_3$OD, 500 MHz) δ ppm 0.78-0.82 (m, 3H), 0.96 (d, 6H), 1.5 (dt, 2H), 2.14-2.19 (m, 2H), 2.25-2.32 (m, 1H), 3.38-3.47 (m, 1.35H), 3.56-3.69 (m, 1.35H), 3.77-3.80 (m, 0.65H), 3.99-4.00 (m, 1.75H), 4.39-4.49 (m, 2H), 4.63 (d, 0.4H), 5.07 (d, 0.6H); $^{13}$C NMR (CD$_3$OD, 125 MHz) δ ppm 12.51, 17.01, 17.15, 18.92, 29.28, 37.44, 37.87, 53.78, 56.30, 58.28, 64.66, 69.08, 69.76, 70.08, 70.32, 90.85, 94.93, 169.48, 177.54, 177.76; m/z (ESI$^+$) 349.0.

Example 6. Preparation of 1,3,4,6-tetra-O-2-N-pentabutyryl-D-glucosamine (Compound 6)

To a mixture of GlcNBu (2.17 g, 5 mmol, 1 eq.) in pyridine (15 mL) were added 4-dimethylamonopyridine (DMAP, 0.06 g, 0.5 mmol, 0.1 eq.) and butyric anhydride (3.96 g, 25 mmol, 5 eq.). The mixture was stirred at r.t. for 16 h. Solvent was removed on a rotary evaporator, and the residual material was purified on a silica-gel column (EA/PE, 1/10 to 1/3), giving the title compound (2.5 g, 94.3%): $^1$H NMR (CDCl$_3$, 500 MHz) δ ppm 0.86-0.99 (m, 15H), 1.52-1.73 (m, 10H), 2.03-2.081 (m, 2H), 2.20-2.40 (m, 8H), 3.76-3.79 (m, 0.4H), 3.96-3.97 (m, 0.6H), 4.06-4.23 (m, 2H), 4.30-4.36 (m, 0.4H), 4.44-4.48 (m, 0.6H), 5.10-5.27 (m, 2H), 5.49 (d, 1H), 5.66 (d, 0.4H), 6.20 (d, 0.6H); $^{13}$C NMR (CDCl$_3$, 125 MHz) δ ppm 13.64, 18.09, 18.39, 18.95, 35.89, 35.93, 35.99, 36.06, 36.09, 38.43, 51.24, 52.81, 61.47, 67.19, 67.43, 70.01, 70.40, 73.17, 90.46, 92.69, 171.31, 171.75, 171.84, 172.26, 172.75, 173.34, 173.91, 174.54; m/z (ESI$^-$) 528.2.

Example 7. Preparation of 2-N-butyryl-6-O-linolyl-D-glucosamine (Compound 7)

To linoleic acid (2.8 g, 10 mmol, 1 eq.) in DMF (60 mL) were added GlcNBu (2.49 g, 10 mmol, 1 eq.), HOBt (1.62 g, 12 mmol, 1.2 eq), EDCI (2.88 g, 15 mmol, 1.5 eq.), DIPEA (3.88 g, 30 mmol, 3 eq.). The mixture was stirred at r.t. for 16 h, followed by addition of water (50 mL) and ethyl acetate (50 mL) and well mixed. The organic layer was separated, washed with water (50 mL) and brine (50 mL) subsequently, and evaporated to dryness. The residual material was purified on a silica-gel column (MeOH/DCM, 1/70 to 1/50), finishing the title compound (0.60 g, 11.7%): $^1$H NMR (CD$_3$OD, 500 MHz) δ ppm 0.89-0.97 (m, 6H), 1.29-1.38 (m, 16H), 1.61-1.68 (m, 4H), 2.04-2.07 (m, 4H), 2.22 (t, 2H), 2.34 (t, 2H), 2.77 (t, 2H), 3.35 (t, 0.8H), 3.42-3.62 (m, 0.5H), 3.70 (t, 0.8H), 3.84-3.86 (m, 0.9H), 3.93-3.99 (m, 1H), 4.19-4.22 (m, 0.9H), 4.36-4.38 (m, 0.9H), 4.58 (d, 0.1H), 5.07 (d, 0.9H), 5.29-5.39 (m, 4H); $^{13}$C NMR (CD$_3$OD, 125 MHz) δ ppm 12.56, 13.03, 18.96, 24.60, 26.75, 28.81, 29.07, 37.49, 47.07, 47.59, 54.29, 63.37, 69.33, 71.06, 71.18, 91.22, 127.64, 127.67, 129.47, 129.52, 174.07, 175.11; m/z (ESI$^+$) 512.2.

Example 8. Preparation of 2-N-butyryl-1,3,4,6-tetra-O-tetraacetyl-D-glucosamine (Compound 8)

To a mixture of GlcNBu (2.17 g, 5 mmol, 1 eq.) in pyridine (15 mL) were added DMAP (0.06 g, 0.5 mmol, 0.1 eq.), acetic anhydride (2.55 g, 25 mmol, 5 eq.). The mixture was stirred at r.t. for 16 h. Solvent was removed on a rotary evaporator; and the residual material was purified on a silica-gel column (EA/PE, 1/10 to 1/3), giving the title compound (2.0 g, 95.9%): $^1$H NMR (CDCl$_3$, 500 MHz) δ ppm 0.87-0.90 (t, 3H), 1.52-1.63 (m, 2H), 2.02-2.04 (m, 6H), 2.07-2.12 (m, 6H), 2.15-2.21 (m, 2H), 3.79 (s, 0.35H), 3.98-4.13 (m, 1.65H), 4.23-4.35 (m, 1.35H), 4.46-4.51 (m, 0.65H), 5.09-5.26 (m, 2H), 5.50-5.54 (m, 1H), 5.67 (d, 0.35H), 6.18 (d, 0.65H); $^{13}$C NMR (CDCl$_3$, 125 MHz) δ ppm 13.66, 19.08, 19.14, 20.72, 20.87, 38.54, 38.73, 51.06, 52.92, 61.68, 61.76, 67.60, 67.76, 69.86, 70.75, 73.13, 90.82, 92.84, 168.73, 169.24, 169.37, 169.68, 170.86, 171.29, 171.90, 172.96, 173.08; m/z (ESI$^-$) 416.2.

Example 9. Preparation of 2-N-butyryl-6-O-lipoyl-D-glucosamine (Compound 9)

To a mixture of lipoic acid (2.06 g, 10 mmol, 1 eq.) in DMF (60 mL) were added GlcNBu (2.49 g, 10 mmol, 1 eq.), HOBt (1.62 g, 12 mmol, 1.2 eq), EDCI (2.88 g, 15 mmol, 1.5 eq.), and DIPEA (3.88 g, 30 mmol, 3 eq.). The mixture was stirred at r.t. for 16 h, followed by addition of water (50 mL) and ethyl acetate (50 mL). The organic layer was separated, washed with water (50 mL) and brine (50 mL), and evaporated to dryness. The residual material was purified on a silica-gel column (MeOH/DCM, 1/70 to 1/40), providing the title compound (0.20 g, 4.6%): $^1$H NMR (DMSO, 500 MHz) δ ppm 0.84 (t, 3H), 1.23-1.69 (m, 8.8H), 1.82-2.09 (m, 3.2H), 2.31-2.44 (m, 2.5H), 2.80 (s, 1H), 3.08-3.21 (m, 2H), 3.45-3.54 (m, 0.8H), 3.58-3.66 (m, 1.6H), 3.79 (d, 0.8H), 4.02 (d, 0.8H), 4.30 (d, 0.8H), 4.69 (d, 0.7H), 4.90 (s, 0.9H), 5.17 (d, 0.8H), 6.53 (d, 0.8H), 7.54 (d, 0.8H); $^{13}$C NMR (DMSO, 125 MHz) δ ppm 14.12, 19.14, 24.70, 28.55, 33.74, 34.51, 37.56, 38.54, 54.48, 55.38, 56.49, 69.68, 70.65, 71.57, 91.16, 172.65, 173.28; m/z (ESI$^+$) 438.0.

Example 10. Preparation of 2-N-butyryl-1,6-di-O-di(L-phenylalanyl)-D-glucosamine hydrochloride (Compound 10)

To a mixture of L-phenylalanine (3.30 g, 20 mmol, 1 eq.) in MeOH (50 mL) were added Boc$_2$O (6.54 g, 30 mmol, 1.5 eq.) and triethylamine (3.5 g, 35 mmol, 1.75 eq.). The mixture was stirred at 50° C. for 1 h. Solvent was removed on a rotary evaporator; and the residual material was taken into DMF (100 mL), followed by addition of GlcNBu (4.98 g, 20 mmol, 1 eq.), HOBt (4.05 g, 30 mmol, 1.5 eq.), EDCI (7.64 g, 40 mmol, 2 eq.), and DIPEA (7.74 g, 60 mmol, 3 eq.). The mixture was stirred at r.t. for 16 h, followed by addition of water (50 mL) and ethyl acetate (50 mL). The organic layer was separated, washed with water (50 mL) and brine (50 mL), subsequently. Solvent was removed (rotary evaporation); and the residual material was purified (silica-gel column; eluent, MeOH/DCM, 1/80 to 1/65), giving the corresponding intermediate (1.1 g, 7.40%). This intermediate (1.1 g, 1.48 mmol, 1 eq.) was dissolved in DCM (11 mL), followed by addition (while a stirring was applied) of 4M HCl in dioxane (1.1 mL). The mixture was stirred at r.t. for 1 h, and then the solvent was removed by rotary evaporator, affording the title compound (0.74 g, 83.0%): $^1$H NMR (D$_2$O, 500 MHz) δ ppm 0.70-0.83 (m, 3H), 1.20-1.26 (m, 0.5H), 1.55 (d, 1.8H), 2.19-2.52 (m, 2H), 3.12-3.38 (m, 5H), 3.44 (d, 0.8H), 3.58-3.70 (m, 1H), 3.78-3.99 (m, 1.5H), 4.21 (t, 0.8H), 4.41-4.47 (m, 3.2H), 5.00-5.35 (m, 0.4H), 6.23-6.42 (m, 0.4H), 7.20-7.37 (m, 10H); $^{13}$C NMR (D$_2$O, 125 MHz) δ ppm 12.58, 12.69, 17.65, 18.94, 35.27, 35.51, 35.67, 37.49, 52.45, 53.73, 53.91, 54.41, 64.85, 69.02, 69.62, 69.85, 70.31, 88.93, 89.16, 90.90, 92.90, 94.98, 127.92, 128.10, 129.16, 129.25, 129.34, 133.63, 134.10, 169.23, 171.84, 174.35, 177.56; m/z (ESI$^+$) 544.1.

Example 11. Preparation of 2-N-Butyryl-6-O-(L-phenylalanyl)-D-glucosamine hydrochloride (Compound 11)

To a mixture of L-phenylalanine (3.30 g, 20 mmol, 1 eq.) in MeOH (50 mL) was added (while stirring applied) Boc$_2$O (6.54 g, 30 mmol, 1.5 eq.) and triethylamine (3.5 g, 35 mmol, 1.75 eq.). The mixture was stirred at r.t. for 1 h. Solvent was removed by rotary evaporation; and the residual material was taken into DMF (100 mL), followed by addition of GlcNBu (4.98 g, 20 mmol, 1 eq.), HOBt (4.05 g, 30 mmol, 1.5 eq.), EDCI (7.64 g, 40 mmol, 2 eq.), and DIPEA (7.74 g, 60 mmol, 3 eq.). The mixture was stirred at r.t. for 16 h, followed by addition, to the mixture, of water (50 mL) and ethyl acetate (50 mL). The organic layer was separated, washed with water (50 mL) and brine (50 mL), subsequently. After the solvent was evaporated, the residual material was purified on a silica-gel column (MeOH/DCM, 1/65 to 1/40), giving 6-O—(N-Boc-L-phenylalanyl)-2-N-butyryl-D-glucosamine (1.7 g, 17.1%) as an intermediate. This intermediate (1.7 g, 3.42 mmol, 1 eq.) was dissolved in DCM (17 mL). To the stirred solution was added 4 M HCl solution in dioxane (1.7 mL). The mixture was stirred at r.t. for 1 h, and evaporated to dryness, providing the title compound (1.30 g, 88.1%): $^1$H NMR (D$_2$O, 500 MHz) δ ppm 0.71-0.83 (m, 3H), 1.17-1.29 (m, 0.7H), 1.53-1.58 (m, 2H), 2.20-2.23 (m, 2H), 2.69 (d, 0.2H), 3.20-3.34 (m, 3H), 3.47 (t, 0.4H), 3.59-3.70 (m, 1.2H), 3.78 (d, 0.6H), 4.00 (d, 0.6H), 4.38-4.50 (m, 2.8H), 4.67 (d, 0.4H), 5.09 (d, 0.6H), 7.26-7.38 (m, 5H); $^{13}$C NMR (D$_2$O, 125 MHz) δ ppm 12.58, 18.94, 35.55, 37.49, 37.91, 53.73, 53.91, 56.29, 64.84, 68.99, 69.61, 69.84, 70.31, 90.90, 94.98, 128.10, 129.23, 129.32, 133.67, 169.33, 177.56, 177.80; m/z (ESI$^+$) 397.0.

Example 12. Preparation of 1,3,4-tri-O-2-N-tetrabutyryl-6-O-(L-valyl)-D-glucosamine hydrochloride (Compound 12)

To a mixture of compound 2 (1.50 g, 3.3 mmol, 1 eq.) in pyridine (15 mL) were added, while stirring applied, butyric anhydride (1.85 g, 11.7 mmol, 3.5 eq.) and DMAP (0.04 g, 0.3 mmol, 0.1 eq.). The mixture was stirred at 40° C. for 1 h and at r.t. overnight. Solvent was evaporated; and the residual material was purified on a silica-gel column (A/PE, 1/5 to 1/2), providing an N-Boc intermediate (0.7 g, 34.9%). This intermediate (0.7 g, 1.2 mmol, 1 eq.) was taken into DCM (7 mL), followed by addition of 4 M HCl in dioxane (0.7 mL) with stirring. The mixture was stirred at r.t. for 1 h and then evaporated to dryness, finishing with the title compound (0.7 g, quantitative): $^1$H NMR (MeOH, 500 MHz) δ ppm 0.87-1.09 (m, 18H), 1.58-1.71 (m, 8H), 2.13-2.51 (m, 9 H), 3.99-4.43 (m, 4.8H), 5.07-5.37 (m, 2.3H), 6.10-6.25 (m, 0.9H), 7.88-8.10 (m, 0.7H); $^{13}$C NMR (MeOH, 125 MHz) δ ppm 12.50, 12.56, 16.84, 17.69, 17.89, 29.51, 35.02, 35.28, 35.45, 50.40, 58.05, 63.21, 68.19, 69.26, 69.91, 89.75, 168.45, 171.84, 172.30, 172.78, 175.15; m/z (ESI$^+$) 558.9.

Example 13. Preparation of 2-N-butyryl-6-O-(L-histidyl)-D-glucosamine hydrochloride (Compound 13)

To a mixture of L-histidine (3.10 g, 20 mmol, 1 eq.) in MeOH (50 mL) were added Boc$_2$O (13.1 g, 60 mmol, 3.0 eq.) and triethylamine (7.0 g, 70 mmol, 3.5 eq.). The mixture was stirred at 50° C. until a clear solution was obtained (around 2 h). Solvent was removed on a rotary evaporator; and the residual material was taken into DMF (100 mL), followed by addition of GlcNBu (4.98 g, 20 mmol, 1 eq.), HOBt (4.05 g, 30 mmol, 1.5 eq.), EDCI (7.64 g, 40 mmol, 2 eq.), DIPEA (7.74 g, 60 mmol, 3 eq.). The mixture was stirred at r.t. for 16 h. To the reaction mixture were added water (50 mL) and ethyl acetate (50 mL). After the mixture was stirred very well, the organic layer was separated and washed with water (50 mL) and brine (50 mL) subsequently. Solvent was removed; and the residual material was purified on a silica-gel column (MeOH/DCM, 1/60 to 1/30), giving a di-Boc protected intermediate (1.3 g, 11.1%). This intermediate (1.3 g, 2.21 mmol, 1 eq.) was dissolved in DCM (13 mL). To the stirred solution was added a solution of 4 M HCl in dioxane (1.3 mL); and the mixture was stirred at r.t. for 1 h, and then evaporated to dryness, giving the title compound (0.75 g, 73.5%): $^1$H NMR (D$_2$O, 500 MHz) δ ppm 0.92 (t, 3H), 1.64 (q, 2H), 2.29 (q, 2H), 3.36-3.87 (m, 6H), 4.07 (d, 0.45H), 3.20-3.34 (m, 3H), 3.47 (t, 0.4H), 4.47-4.61 (m, 3H), 5.19 (d, 0.55H), 7.50 (s, 1H), 8.75 (s, 1H); $^{13}$C NMR (D$_2$O, 125 MHz) δ ppm 12.61, 18.97, 25.00, 37.52, 37.93, 51.71, 53.85, 5636, 65.41, 68.97, 69.71, 70.04, 70.25, 73.41, 90.84, 95.01, 118.31, 126.22, 134.36, 168.17, 177.63, 177.87; m/z (ESI$^+$) 386.7.

Example 14. Preparation of 2-N-butyryl-3,4,6-tri-O-acetyl-D-glucosamine (Compound 14)

To a mixture of compound 8 (4.17 g, 10 mmol, 1 eq.) in THF (60 mL) was added benzylamine (1.2 g, 11 mmol, 1.1 eq.). The mixture was stirred at r.t. for 16 h, followed by addition of water (50 mL) and ethyl acetate (50 mL) while stirring was continued. The organic layer was separated, washed with water (50 mL) and brine (50 mL). Solvent was removed by rotary evaporation, and the residual material was purified on a silica-gel column (EA/PE, 1/3 to 3/1), providing the title compound (3.0 g, 80.0%): $^1$H NMR (CDCl$_3$, 500 MHz) δ ppm 0.89 (t, 3H), 1.54-1.61 (m, 2H), 1.98 (s, 3H), 2.01 (s, 3H), 2.07 (s, 3H), 2.09-2.19 (m, 2H), 3.64-3.68 (m, 0.2H), 3.94-3.99 (m, 0.2H), 4.08-4.12 (m, 1H), 4.17-4.29 (m, 2.4H), 4.60-4.63 (m, 0.2H), 4.73 (d, 0.8H), 5.01-5.12 (m, 1.2H), 5.21-5.30 (m, 1.6H), 5.59 (d, 0.2H), 5.96 (d, 0.8H), 6.34 (m, 0.2H); $^{13}$C NMR (CDCl$_3$, 125 MHz) δ ppm 13.55, 13.68, 18.96, 20.73, 29.77, 38.36, 38.62, 52.27, 56.95, 62.22, 67.56, 68.13, 68.42, 71.02, 91.68, 97.74, 169.44, 169.56, 171.00, 171.10, 171.48, 172.28, 173.56, 176.56; m/z (ESI$^+$) 375.8.

Example 15. Preparation of 2-N-1,3-di-O-tributyryl-D-glucosamine (Compound 15)

To a mixture of GlcNBu (10.0 g, 40 mmol, 1 eq.) in DMF (200 mL) were added (dimethoxymethyl)benzene (60.8 g, 400 mmol, 10 eq.) and p-toluenesulfonic acid monohydrate (0.76 g, 4 mmol, 0.1 eq.). The mixture was stirred at 50° C. for 16 h. After cooled to r.t., the mixture was poured into water (800 mL) and stirred for 1 h. The solid material was collected by filtration, washed with water (100 mL) and pet-ether (100 mL), and dried, giving 4,6-O-benzalidene-2-N-butyryl-D-glucosamine (8.0 g, 59.0%). This compound (3.37 g, 10 mmol, 1 eq.) was taken into pyridine (33 mL), followed by addition of DMAP (0.12 g, 1 mmol, 0.1 eq.) and butyric anhydride (3.95 g, 25 mmol, 2.5 eq.). The mixture was stirred at r.t. for 16 h, and then poured into water (330 mL). The resulting mixture was stirred at r.t. for 1 h, and solid material was collected by filtration, washed with water (50 mL) and pet-ether (50 mL) subsequently, and dried, providing 4,6-O-benzylidene-1,2-di-O-2-N-butyryl-D-glucosamine (2.9 g, 60.8%). The glucosamine derivative thus obtained (2.9 g, 6 mmol, 1 eq.) was added to DCM (58 mL), followed by addition of water (1 mL) and trifluoroacetic acid (1 mL). The mixture was stirred at r.t. for 10 min, and then diluted with water (50 mL) and stirred briefly. The organic layer was separated, washed with water (50 mL) and saturated aqueous sodium bicarbonate solution (50 mL). The organic layer was evaporated to dryness; and the residual material was purified on a silica-gel column (MeOH/DCM, 1/40 to 1/20), giving the title compound (1.3 g, 55.0%): $^1$H NMR (CD$_3$OD, 500 MHz) δ ppm 0.84-0.94 (m, 9H), 1.52-1.66 (m, 6H), 2.04-2.42 (m, 6H), 3.44-3.82 (m, 4H), 3.92-4.24 (m, 1H), 5.04-5.17 (m, 1H), 5.69-6.06 (m, 1H), 7.82-8.05 (m, 1H); $^{13}$C NMR (CD$_3$OD, 125 MHz) δ ppm 13.88, 13.94, 19.11, 19.20, 19.40, 36.67, 36.76, 36.95, 37.02, 38.61, 48.48, 48.65, 48.83, 49.00, 49.17, 61.91, 69.25, 74.01, 75.99, 76.35, 78.66, 91.89, 93.69, 173.35, 173.67, 174.76, 175.11, 176.42, 176.50; m/z (ESI$^-$) 387.9.

Example 16. Preparation of 2-N-4,6-O-tributyryl-D-glucosamine (Compound 16)

4,6-O-benzalidene-2-N-butyryl-D-glucosamine (3.37 g, 10 mmol, 1 eq.) was added to DMF (50 mL). The mixture was cooled to −10° C. under nitrogen atmosphere, followed by batch-wise addition of NaH (oil dispersion, 1.08 g, 27 mmol, 2.7 eq.). The temperature of the mixture was kept below 0° C. during the addition of NaH, and then increased to r.t. slowly. After stirring at r.t. for 2 h, the mixture was poured into water (300 mL). The resultant mixture was stirred at r.t. for 1 h. Solid material was collected by filtration, washed with water (50 mL) and pet-ether (50 mL) subsequently, and dried, giving 4,6-O-benzylidene-1,3-O-dibenzyl-2-N-butyryl-D-glucosamine (4.5 g, 87.1%) as an intermediate. To this intermediate (4.5 g, 8.7 mmol, 1 eq.) was added DCM (90 mL), followed by addition of water (1.5 mL) and trifluoroacetic acid (18 mL). The mixture was stirred at r.t. for 10 min, then diluted with water (50 mL), and stirred briefly. The organic layer was separated, washed with water (50 mL) and saturated aqueous sodium bicarbonate solution (50 mL). The organic layer was evaporated to dryness; and the residual material was triturated with warm pet-ether, then collected by filtration and dried, providing 1,3-O-dibenzyl-2-N-butyryl-D-glucosamine (3.2 g, 85.7%). This compound (2.5 g, 5.8 mmol, 1 eq.) was taken into pyridine (25 mL), followed by addition of DMAP (0.04 g, 0.29 mmol, 0.05 eq.) and butyryl anhydride (2.3 g, 14.5 mmol, 2.5 eq.). After stirring at r.t. for 16 h, the reaction mixture was poured into water (250 mL) and then stirred at r.t. for 1 h. The insoluble material was collected, washed with water (50 mL) and pet-ether (50 mL), and dried, giving 1,3-O-dibenzyl-2-N-4,6-di-O-tributyryl-D-glucosamine (2.9 g, 87.8%). Compound thus obtained (2.9 g) was taken into MeOH (15 mL), followed by addition of palladium-carbon (10%, 1.45 g) and acetic acid (15 mL), and hydrogenolysized under hydrogen atmosphere (hydrogen balloon) for 48 h. The mixture was filtered, and the filtrate was concentrated to dryness. The residual material was purified on a silica-gel column (MeOH/DCM, 1/100 to 1/30), giving the title compound (1.3 g, 65.6%): $^1$H NMR (CD$_3$OD, 500 MHz) δ ppm 0.78-1.03 (m, 9H), 1.52-1.66 (m, 6H), 2.18-2.31 (m, 6H), 3.30 (s, 0.3H), 3.62 (s, 0.7H), 3.78-4.11 (m, 4.3H), 4.63 (s, 0.3H), 4.86 (t, 1H), 5.07 (s, 0.8H); $^{13}$C NMR (CD$_3$OD, 125 MHz) δ ppm 12.67, 17.97, 18.98, 35.46, 35.58, 37.51, 37.53, 37.92, 54.38, 54.46, 57.51, 62.31, 69.00, 71.13, 71.49, 71.83, 91.17, 95.69, 172.87, 172.94, 173.55, 173.63, 173.86, 175.13, 175.21, 175.62; m/z (ESI$^+$) 389.8.

Example 17. Preparation of 2-N-butyryl-1,3-di-O-(L-valyl)-D-glucosamine hydrochloride (Compound 17)

To 4,6-O-benzylidene-2-N-butyryl-D-glucosamine (3.37 g, 10 mmol, 1 eq) in DMF (100 mL) were added N-Boc-L-valine (4.77 g, 22 mmol, 2.2 eq.), HOBt (4.05 g, 30 mmol, 3 eq.), EDCI (7.64 g, 40 mmol, 4 eq.), DIPEA (7.74 g, 60 mmol, 6 eq.). The mixture was stirred at r.t. for 16 h, followed by addition of water (50 mL) and ethyl acetate (50 mL). The mixture was stirred well; and organic layer was separated, washed with water (50 mL) and brine (50 mL), and evaporated to dryness. The residual material was purified on a silica-gel column (EA/PE, 1/6), providing 1,3-O-bis(N-Boc-L-valyl)-2-N-butyryl-glucosamine (2.0 g, 27.2%). The compound obtained above (2.0 g, 2.7 mmol, 1 eq.) was dissolved in DCM (20 mL), followed by addition of 4 M HCl in dioxane (2 mL). The mixture was stirred at r.t. for 1 h, and evaporated to dryness, giving the title compound (1.1 g, 77.5%): $^1$H NMR (D$_2$O, 500 MHz) δ ppm 0.87-1.16 (m, 15H), 1.55-1.60 (m, 2H), 2.22-2.58 (m, 4H), 3.63-4.01 (m, 4.5H), 4.17-4.27 (m, 1.9H), 4.53 (d, 0.6H), 5.21-5.41 (m, 1H), 6.27 (s, 0.6H); $^{13}$C NMR (D$_2$O, 125 MHz) δ ppm 12.79, 12.93, 16.30, 16.80, 17.11, 17.17, 17.42, 17.80, 18.64, 18.89, 29.02, 29.23, 37.36, 37.63, 50.09, 51.61, 58.28, 67.33, 68.05, 71.13, 73.91, 73.96, 91.03, 92.98, 168.75, 169.36, 171.87, 177.34; m/z (ESI$^+$) 448.2.

Example 18. Preparation of 2-N-3,4-O-tributyryl-D-glucosamine (Compound 18)

To a mixture of GlcNBu (10 g, 40 mmol, 1 eq.) in toluene (100 mL) were added p-toluenesulfonic acid monohydrate (0.76 g, 4 mmol, 0.1 eq.) and benzyl alcohol (60 mL). The mixture was refluxed, in a Dean-Stark apparatus to remove water, for 16 h. The mixture was cooled to r.t., stirred, and followed by addition of pet-ether (30 mL). After stirred thoroughly, the solid material was collected, and re-dissolved in hot ethyl acetate (100 mL). The hot ethyl acetate solution was cooled to r.t., and the solid material was collected and dried, giving 1-O-benzyl-2-N-butyryl-D-glucosamine (4.0 g, 29.4%). This material (3.4 g, 10 mmol, 1 eq.) was added into pyridine (50 mL). The mixture was cooled to 0° C. under nitrogen atmosphere, followed by addition of DMAP (0.12 g, 1 mmol, 0.1 eq.) and TBDMSCl (3.0 g, 20 mmol, 2 eq.), subsequently. The mixture was gradually warmed to 50° C., and stirred at 50° C. for 12 h, and then cooled to r.t. The mixture was concentrated to dryness on a rotary evaporator; and the residual material was purified on a silica-gel column (MeOH/DCM, 1/30), giving the corresponding intermediate, 1-O-benzyl-2-N-butyryl-6-O-(tert-butyldimethylsilyl-D-glucosamine, (2.0 g, 44.5%). The intermediate (4.5 g, 10 mmol, 1 eq.) was added to pyridine (50 mL), followed by addition of DMAP (0.12 g, 1 mmol, 0.1 eq.) and butyric anhydride (3.9 g, 25 mmol, 2.5 eq.). After stirred at r.t. overnight, the mixture was concentrated on a rotary evaporator. The residual material was purified on a silica-gel column (MeOH/DCM, 1/100), giving 1-O-benayl-2-N-3,4-O-tributyryl-6-O-(tert-butyldimentyl-silyl)-D-glucosamine (5.9 g, 99.8%). The compound obtained above (5.9 g, 10 mmol, 1 eq.) was dissolved in methanol (50 mL) and acetic acid (50 mL), followed by addition of Pd/C (10% palladium on carbon, 0.6 g), hydrogenolysized under hydrogen atmosphere (hydrogen balloon) for 48 h. The reaction mixture was filtered, and the filtrate was evaporated to dryness. The residual material was purified on a silica-gel column (MeOH/DCM, 1/60), giving the debenzylated intermediate (4.0 g, 79.8%). This intermediate (1.5 g, 3.0 mmol, 1 eq.) was taken into DCM (15 mL), followed by addition of a solution of 4 M HCl in dioxane (1.5 mL). The mixture was stirred at r.t. for 30 min, and evaporated to dryness, providing the title compound (1.1 g, 94.8%): $^1$H NMR (CD$_3$OD, 500 MHz) δ ppm 0.89-0.97 (m, 9H), 1.54-1.67 (m, 6H), 2.12-2.36 (m, 6H), 3.52-3.64 (m, 1.5H), 4.03-4.25 (m, 2.2H), 4.39 (d, 0.5H), 4.97-5.09 (m, 1.4H), 5.19-5.36 (m, 1H), 7.62-7.76 (m, 0.5H); $^{13}$C NMR (CD$_3$OD, 125 MHz) δ ppm 13.98, 19.30, 19.39, 20.34, 36.86, 37.02, 37.09, 38.78, 53.50, 53.66, 62.08, 64.38, 70.15, 70.61, 70.67, 72.41, 92.65, 92.82, 173.91, 174.66, 175.23, 176.14; m/z (ESI$^+$) 389.9.

Example 19. Preparation of 2-N-4-O-dibutyryl-6-O-(L-valyl)-D-glucosamine hydrochloride (Compound 19)

To a mixture of 1,3-O-dibenzyl-2-N-butyryl-D-glucosamine (4.29 g, 10 mmol, 1 eq.) in DMF (50 mL) were added N-Boc-L-valine (2.6 g, 12 mmol, 1.2 eq.), HOBt (4.05 g, 30 mmol, 3 eq.), EDCI (7.64 g, 40 mmol, 4 eq.), and DIPEA (7.74 g, 60 mmol, 6 eq.). The mixture was stirred at r.t. for 16 h, followed by addition of water (50 mL) and ethyl acetate (50 mL) and stirred. The organic layer was separated, washed with water (50 mL) and brine (50 mL), subsequently. Solvent was removed, and the residual material was purified on a silica-gel column (EA/PE, 1/6), providing 1,3-O-dibenzyl-2-N-butyryl-6-O—(N-Boc-L-valyl)-D-glucosamine (2.4 g, 35.5%). This compound (1.4 g, 2.2 mmol, 1 eq.) was taken into pyridine (14 mL), followed by addition of DMAP (0.02 g, 0.2 mmol, 0.1 eq.) and butyric anhydride (0.53 g, 3.3 mmol, 1.5 eq.); and the mixture was stirred at r.t. overnight. Solvent was removed on a rotary evaporator, the residual material was purified on a silica-gel column (MeOH/DCM, 1/100), giving 1,3-O-dibenzyl-2-N-4-O-dibutyryl-6-O—(N-Boc-L-valyl)-D-glucosamine (1.5 g, 99.8%). The compound obtained above (1.7 g, 2.4 mmol, 1 eq.) was added to a mixture of methanol (50 mL) and acetic acid (50 mL), followed by addition of 10% palladium on carbon (0.2 g). The mixture was stirred under hydrogen atmosphere for 48 h, then filtered. Solvent was removed by rotary evaporation; and the residual material was purified (silica gel column; eluent MeOH/DCM, 1/30), giving debenzylated intermediate (1.15 g, 91.2%). The intermediate (1.15 g, 2.2 mmol, 1 eq.) was treated in DCM (15 mL) with a solution of 4 MHCl in dioxane (1.5 mL) at r.t. for 30 min. The mixture was evaporated to dryness, giving the title compound (0.99 g, 98.1%): $^1$H NMR (CD$_3$OD, 500 MHz) δ ppm 0.94-0.98 (m, 6H), 1.10 (t, 6H), 1.62-1.67 (m, 4H), 2.22-2.38 (m, 5H), 3.67-6.97 (m, 3.2H), 4.08-4.36 (m, 2.7H), 4.73 (d, 0.3H), 5.11 (d, 0.7H); $^{13}$C NMR (CD$_3$OD, 125 MHz) δ ppm 13.94, 13.97, 18.18, 18.44, 19.33, 30.82, 36.88, 38.78, 39.20, 55.75, 58.66, 59.51, 65.49, 68.28, 70.04, 72.33, 72.71, 92.51, 96.96, 169.87, 174.47, 176.67, 177.17; m/z (ESI$^+$) 420.0.

Example 20. Preparation of 2-N-butyryl-3-O-(2-(4-isobutylphenyl)propanoyl)-D-glucosamine (Compound 20)

1-O-benzyl-4,6-O-benzylidene-2-N-butyryl-D-glucosamine (4.27 g, 10 mmol, 1 eq.) was added to DMF (50 mL), followed by addition of isobutyric acid (2.06 g, 10 mmol, 1 eq.), HOBt (4.05 g, 30 mmol, 1.5 eq.), EDCI (7.64 g, 40 mmol, 2 eq.), and DIPEA (7.74 g, 60 mmol, 3 eq.). The mixture was stirred at r.t. for 16 h. Water (50 mL) and ethyl acetate (50 mL) were added to the mixture, and stirred briefly. The organic layer was separated, washed with water (50 mL) and brine (50 mL), subsequently. Solvent was removed on a rotary evaporator, and the residual material was purified on a silica-gel column (MeOH/DCM, 1/50 to 1/40), providing 1-O-benzyl-4,6-O-benzylidene-2-N-butyryl-3-O-(2-(4-isobutylphenyl)propanoyl)-D-glucosamine (5.0 g, 81.3%). This compound (6.1 g, 10 mmol, 1 eq.) was added to DCM (60 mL), followed by addition of water (2 mL) and trifluoroacetic acid (22 mL). The mixture was stirred at r.t. for 10 min, and then water (50 mL) was added. The organic layer was separated, washed with water (50 mL) and saturated aqueous then sodium bicarbonate, and evaporated to dryness. The residual material was purified on a silica-gel column (MeOH/DCM, 1/100 to 1/30), giving 1-O-benzyl-2-N-butyryl-3-O-(2-(4-isobutylphenyl)propanoyl)-D-glucosamine (5.1 g, 96.7%). The compound thus obtained (5.3 g, 10 mmol, 1 eq.) was dissolved in methanol (25 mL), followed by addition of palladium on carbon (10%, 2.0 g) and acetic acid (25 mL). The mixture was hydrogenolysized under hydrogen atmosphere (balloon) for 48 h. The mixture was filtered, and the filtrate was evaporated to dryness. The residual material was purified on a silica-gel column (MeOH/DCM, 1/30 to 1/10), providing the title compound (3.9 g, 89.2%): $^1$H NMR (CDCl$_3$, 500 MHz) δ ppm 0.83-0.87 (m, 9H), 1.41-1.52 (m, 5H), 1.76-1.84 (m, 1H), 1.96-2.0 (m, 2H), 2.40-2.41 (m, 2H), 3.24-4.17 (m, 8H), 4.62-5.24 (m, 2H), 5.64-6.07 (m, 1H), 6.31-6.59 (m, 1H), 7.05 (d, 2H), 7.15 (d, 2H); $^{13}$C NMR (CDCl$_3$, 125 MHz) δ ppm 13.59, 16.59, 18.86, 30.10, 38.17, 44.97, 52.23, 61.99, 69.43, 71.57, 73.78, 91.44, 127.14, 129.37, 137.39, 140.69, 174.04, 175.95; m/z (ESI$^+$) 438.0.

Example 21. Preparation of 2-N-butyryl-3-O-(L-valyl)-D-glucosamine hydrochloride (Compound 21)

To N-Boc-L-valine (100 mg, 0.46 mmol, 1.1 eq.) in DMF (5 mL) were added 1-O-benzyl-2-N-butyryl-4,6-O-isopropylidene-D-glucosamine (150 mg, 0.40 mmol, 1 eq.), HOBt (65 mg, 0.48 mmol, 1.2 eq.), EDCI (115 mg, 0.60 mmol, 1.5 eq.), and DIPEA (1 mL), subsequently. The mixture was stirred at r.t. overnight, diluted with ethyl acetate (50 mL). The mixture was washed with water (3×50 mL), and concentrated to dryness. The residual material was purified on a silica-gel column (MeOH/DCM, 1/30 to 1/10), providing an off-white solid (210 mg). This material (210 mg) was dissolved in a mixture of methanol (20 mL), DCM (2 mL), and water (1 mL). After addition of Pd(OH)$_2$/C (0.5 g), the mixture was stirred under hydrogen atmosphere at r.t. overnight. The mixture was filtered, and the filtrate was evaporated to dryness. The residual material was taken into DCM (5 mL) containing 1.50 mL solution of 4 M HCl in dioxane, and stirred at r.t. for 1 h. The solid material was collected by filtration, and dried under vacuum at 60° C., giving the title compound (90 mg, 58.6%): $^1$H NMR (CD$_3$OD, 500 MHz) δ ppm 0.93-0.97 (t, 3H), 1.03-1.32 (d, 6H), 1.59-1.65 (m, 2H), 1.97-2.35 (m, 3H), 3.33-4.19 (m, 7.3H), 5.02-5.36 (m, 2.2H); $^{13}$C NMR (CD$_3$OD, 125 MHz) δ ppm 12.66, 16.68, 17.08, 18.77, 29.33, 37.51, 47.14, 48.16, 58.25, 68.57, 71.31, 76.13, 91.41, 167.80, 168.71; m/z (ES$^+$) 349.6, (ES$^-$) 383.8.

Example 22. Preparation of 2-N-butyryl-6-O-(2-(4-isobutylphenyl)propanoyl)-D-glucosamine (Compound 22)

To a mixture of GlcNBu (1.25 g, 5 mmol, 1 eq.) in DMF (15 mL) were added, in sequence, HOBt (810 mg, 6 mmol, 1.2 eq.), EDCI (1.15 mg, 6 mmol, 1.2 eq.), DIPEA (1 mL), and ibuprofen (1.24 g, 6 mmol, 1.2 eq.). The mixture was stirred at r.t. overnight, and evaporated to dryness. The residual material was purified on a silica gel column (MeOH/DCM, 1/30 to 1/10), giving the title compound (523 mg, 23.9%): $^1$H NMR (D$_2$O, 500 MHz) δ ppm 0.80-0.95 (m, 9H), 1.38-1.44 (m, 3H), 1.54-1.66 (m, 2H), 1.74-1.84 (m, 1H), 2.14-2.22 (t, 2H), 2.36-2.42 (d, 2H), 3.22-5.04 (m, 8H), 7.01-7.20 (m, 4H); 13C NMR (D$_2$O, 125 MHz) δ ppm 12.59, 17.70, 18.97, 30.00, 37.54, 44.63, 54.26, 63.58, 69.48, 70.85, 71.04, 71.09, 91.19, 95.75, 126.90, 128.95, 137.89, 140.30, 175.03, 175.08, 175.11, 175.77; m/z (ESI$^+$) 438.0.

Example 23. Preparation of 2-N-3-O-dibutyryl-D-glucosamine (Compound 23)

1-O-Benzyl-2-N-butyryl-D-glucosamine (3.4 g, 10 mmol, 1 eq.) was added into DMF (5 mL) and stirred, followed by addition of (dimethoxymethyl)benzene (6.1 g, 40 mmol, 4 eq.) and p-toluenesulfonic acid monohydrate (0.19 g, 1 mmol, 0.1 eq.). The mixture was stirred at 50° C. for 16 h, cooled to r.t., and poured into water (80 mL). The mixture was stirred for 1 h, and the solid material was collected, washed with water and pet-ether (in sequence, 10 mL each), and dried, giving 1-O-benzyl-4,6-O-benzylidene-2-N-butyryl-D-glucosamine (4.1 g, 96%). This compound (4.27 g, 10 mmol, 1 eq.) was dissolved in pyridine (50 mL), followed by addition of, while efficient stirring was applied, DMAP (0.12 g, 1 mmol, 0.1 eq.) and butyric anhydride (2.37 g, 15 mmol, 1.5 eq.). After the completion of the addition, the mixture was stirred at r.t. for 16 h. The reaction mixture was poured into water (300 mL) and the mixture was stirred at r.t. for 1 h. The solid material was collected, washed with water (50 mL) and then with pet-ether (50 mL), and dried, providing 1-O-benzyl-4,6-O-benzylidene-2-N-3-O-dibutyryl-D-glucosamine (4.5 g, 90.3%). This compound (3 g, 6 mmol, 1 eq.) was suspended in DCM (58 mL), followed by addition, while stirring was applied, of water (1 mL) and trifluoroacetic acid (11 mL). The mixture was stirred at r.t. for 10 min., and diluted with water (50 mL). The organic layer was separated, washed with water (50 mL) and saturated aqueous sodium bicarbonate solution (50 mL), and evaporated to dryness. The residual material was purified on a silica-gel column (MeOH/DCM, 1/100 to 1/30), giving 1-O-benzyl-2-N-3-O-dibutyryl-D-glucosamine (2.1 g, 86.7%). The compound thus obtained (2.1 g, 5.1 mmol, 1 eq.) was put in methanol (10 mL), followed by addition of palladium on carbon (10%, 1.05 g) and then acetic acid (10 mL). The mixture was stirred under hydrogen atmosphere for 48 h. The mixture was filtered, and the filtrate was evaporated to dryness. The residual material was purified on a silica-gel column (MeOH/DCM, 1/30 to 1/10), giving the title compound (0.45 g, 27.3%): $^1$H NMR (CD$_3$OD, 500 MHz) δ ppm 0.90-0.95 (m, 6H), 1.54-1.65 (m, 4H), 2.10-2.17 (m, 2H), 2.25-2.36 (m, 2H), 3.36-3.38 (m, 0.2H), 3.48-3.58 (m, 1H), 3.67-3.81 (m, 2H), 3.85-3.90 (m, 1H), 4.05-4.10 (m, 0.8H), 4.59 (s, 0.2H), 4.70 (d, 0.2H), 4.99 (t, 0.2H), 5.06 (d, 0.8H), 5.19-5.23 (m, 0.8H), 7.60 (d, 0.8H), 8.0 (d, 0.1H); $^{13}$C NMR (CD$_3$OD, 125 MHz) δ ppm 12.62, 17.99, 18.94, 35.63, 35.72, 37.47, 37.52, 47.12, 47.63, 52.32, 61.01, 61.16, 68.50, 71.58, 73.40, 75.52, 76.48, 91.39, 95.27, 173.57, 174.01, 174.72, 174.80, 174.88; m/z (ESI$^-$) 320.0.

Example 24. Preparation of
2-N-butyryl-4,6-O-diisobutyryl-D-glucosamine
(Compound 24)

2-N-Butyryl-1,3-O-dibenzyl-D-glucosamine (2.5 g, 5.8 mmol, 1 eq.) was taken into pyridine (25 mL), followed by addition of DMAP (0.04 g, 0.29 mmol, 0.05 eq.) and isobutyric anhydride (2.3 g, 14.5 mmol, 2.5 eq.). The mixture was stirred at r.t. for 16 h, and then poured into water (250 mL). After the mixture was stirred at r.t. for 1 h, the solid material was collected, washed with water (50 mL) and then with pet-ether (50 mL), and dried, providing 2-N-butyryl-1,3-O-dibenzyl-4,6-O-diisobutyryl-D-glucosamine (2.9 g, 87.8%). This compound (2.9 g, 5.1 mmol, 1 eq.) was added into methanol (15 mL), followed by addition of Pd/C (10%, 1.45 g) and then acetic acid (15 mL). The mixture was stirred under a hydrogen atmosphere (hydrogen balloon) for 48 h. The mixture was filtered, and the filtrate was evaporated to dryness. The residual material was purified on a silica-gel column (MeOH/DCM, 1/100 to 1/30), giving the title compound (1.3 g, 65.6%): $^1$H NMR (CD$_3$OD, 500 MHz) δ ppm 0.94-0.98 (m, 3H), 1.15-1.18 (m, 12H), 1.60-1.68 (m, 2H), 2.20-2.26 (m, 2H), 2.54-2.63 (m, 2H), 3.63-4.18 (m, 5H), 4.55-4.69 (m, 0.2H), 4.91 (t, 1H), 5.11 (d, 0.8H); $^{13}$C NMR (CD$_3$OD, 125 MHz) δ ppm 13.95, 19.25, 19.41, 20.28, 35.07, 35.12, 38.86, 39.24, 55.85, 58.94, 63.62, 68.76, 70.39, 72.12, 72.48, 73.27, 92.52, 96.99, 176.53, 177.52, 178.33; m/z (ESI$^+$) 390.0.

Example 25. Preparation of
2-N-butyryl-4,6-O-dihexanoyl-D-glucosamine
(Compound 25)

2-N-Butyryl-1,3-O-dibenzyl-D-glucosamine (2.5 g, 5.8 mmol, 1 eq.) was taken into pyridine (25 mL), followed by addition of DMAP (0.04 g, 0.29 mmol, 0.05 eq.) and hexanoic anhydride (3.1 g, 14.5 mmol, 2.5 eq.). The mixture was stirred at r.t. for 16 h, and then poured into water (250 mL). After the mixture was stirred at r.t. for 1 h, the solid material was collected, washed with water (50 mL) and then with pet-ether (50 mL), and dried, providing 2-N-butyryl-1,3-O-dibenzyl-4,6-O-dihexanoyl-D-glucosamine (3.2 g, 87.2%). This compound (3.2 g, 5.1 mmol, 1 eq.) was added into methanol (15 mL), followed by addition of Pd/C (10%, 1.6 g) and then acetic acid (15 mL). The mixture was stirred under a hydrogen atmosphere (hydrogen balloon) for 48 h. The mixture was filtered, and the filtrate was evaporated to dryness. The residual material was purified on a silica-gel column (MeOH/DCM, 1/100 to 1/30), giving the title compound (1.9 g, 84.0%): $^1$H NMR (CD$_3$OD, 500 MHz) δ ppm 0.86-0.94 (m, 6H), 1.11-1.29 (m, 8H), 1.57-1.64 (m, 4H), 2.16-2.34 (m, 4H), 2.50-2.59 (m, 0.5H), 3.34 (s, 1H), 3.60-4.18 (m, 4.2H), 4.67 (t, 0.2H), 4.88-5.12 (m, 1.6H); $^{13}$C NMR (CD$_3$OD, 125 MHz) δ ppm 13.94, 14.24, 19.18, 20.35, 32.39, 38.86, 38.91, 39.29, 55.79, 55.86, 63.68, 68.68, 68.83, 70.37, 72.57, 72.89, 92.56, 97.08, 174.45, 175.18, 176.53, 176.62, 177.60, 178.42; m/z (ESI$^+$) 446.2.

Example 26. Preparation of
2-N-6-O-dibutyryl-D-glucosamine (Compound 26)

Et$_3$N (1.0 g, 10 mmol, 1 eq) was added to a solution of butyric acid (0.88 g, 10 mmol, 1 eq) in THF (20 mL). The solution was cooled to 0° C. under N$_2$ atmosphere, followed by addition of 4-nitrobenzene-1-sulfonyl chloride (2.2 g, 10 mmol, 1 eq). The reaction mixture was stirred at r.t. for 2 h. Et$_3$N (1.0 g, 10 mmol, 1 eq) was added to the reaction mixture, followed by addition of 2-N-butyryl-1,3-di-O-benzyl-D-glucosamine (4.3 g, 10 mmol, 1 eq) and DMAP (0.12 g, 1 mmol, 1 eq). The mixture was stirred at r.t. for 16 h, and concentrated under reduced pressure. The residual material was purified by flash column chromatography (eluent: MeOH/DCM=1/100~1/30) to afford 2-N-3-O-dibutyryl-1,3-di-O-benzyl-D-glucosamine (3.5 g, 70.1%). Pd/C (10%, 1.7 g) was added to a solution of 2-N-3-O-dibutyryl-1,3-di-O-benzyl-D-glucosamine (3.5 g, 7.0 mmol, 1 eq) in MeOH (17 mL), followed by addition of acetic acid (17 mL). The mixture was stirred at r.t. under H$_2$ atmosphere for 48 h. The mixture was filtered. The filtration was concentrated under reduced pressure. The residual material was purified by flash column chromatography (eluent: MeOH/DCM=1/100~1/30) to afford the title compound (2.1 g, 94.2%); $^1$H NMR (500 MHz, CD$_3$OD) δ ppm 0.98 (tdd, J=7.4, 5.4, 1.7 Hz, 6H), 1.59-1.75 (m, 4H), 2.20-2.28 (m, 2H), 2.35 (t, J=7.6 Hz, 2H), 3.42-3.35 (m, 1H), 3.67-3.77 (m, 1H), 3.87 (dd, J=10.8, 3.6 Hz, 1H), 3.94-4.06 (m, 1H), 4.16-4.30 (m, 1H), 4.35-4.46 (m, 1H), 4.58-4.66 (d, J=8.4 Hz, 0.2H), 5.07-5.11 (d, J=3.6 Hz, 0.8H); m/z (ESI$^-$): 318.0.

Example 27. Preparation of
2-N-4-O-dibutyryl-D-glucosamine (Compound 27)

Et$_3$SiH (11.2 g, 96.6 mmol, 10.0 eq) was added to a solution of 1,3-di-O-benzyl-4,6-O-benzylidene-2-N-butyryl-D-glucosamine (5 g, 9.66 mmol, 1 eq) in DCM (100 mL). The mixture was cooled to 0° C. under N$_2$ atmosphere, followed by addition of BF$_3$-Et$_2$O (2.74 g, 19.320 mmol, 2.0 eq). The mixture was stirred at r.t. for 16 h. DCM (100 mL) and H$_2$O (100 mL) were added to the reaction mixture. The organic layer was washed with H$_2$O (100 mL) and brine (100 mL), and concentrated under reduced pressure. The residual material was purified by flash column chromatography (eluent: MeOH/DCM=1/100~1/50) to afford 1,3,6-tri-O-benzyl-2-N-butyryl-D-glucosamine (3.0 g, 60%). Butyric anhydride (1 g, 6.351 mmol, 1.1 eq) and DMAP (35 mg, 0.289 mmol, 0.05 eq) were added to a solution of 1,3,6-tri-O-benzyl-2-N-butyryl-D-glucosamine (3 g, 5.773 mmol, 1 eq) in pyridine (30 mL). The mixture was stirred at 35° C. for 16 h. The mixture was concentrated under reduced pressure. The residual material was purified by flash column chromatography (eluent: EA/PE=1/50~1/10) to afford 1,3,6-tri-O-benzyl-2-N-4-O-dibutyryl-D-glucosamine (1.85 g, 54.4%). AcOH (9.25 mL) was added to a solution of 1,3,6-tri-O-benzyl-2-N-4-O-dibutyryl-D-glucosamine (1.85 g, 3.137 mmol, 1 eq) in MeOH (9.25 mL), followed by addition of 10% Pd/C (1.4 g). The mixture was stirred at 35° C. under $H_2$ atmosphere for 72 h. The mixture was filtered. The filtration was concentrated under reduced pressure. The residual material was purified by flash column chromatography (eluent: MeOH/DCM=1/100~1/30) to afford the title compound (920 mg, 92%); $^1$H NMR (500 MHz, $CD_3OD$) δ ppm 0.92-1.09 (m, 6H), 1.59-1.80 (m, 4H), 2.16-2.56 (m, 4H), 3.51-3.66 (m, 2H), 3.84-3.94 (m, 1H), 3.95-4.07 (m, 2H), 4.70 (d, J=8.0 Hz, 0.07H), 4.81-4.89 (m, 1H), 5.18 (d, J=3.5 Hz, 1H); $^{13}$C NMR (125 MHz, $CD_3OD$) δ ppm 12.54, 17.98, 18.97, 35.60, 37.46, 54.46, 57.55, 61.14, 68.99, 69.71, 71.99, 91.06, 173.26, 175.14; m/z (ESI$^+$) 320.0.

Example 28. Preparation of 2-N-butyryl-1-O-(2-(4-hydroxyphenyl)ethyl)-D-glucosamine (Compound 30)

Acetic anhydride (20.4 g, 200 mmol, 5 eq) was added to a solution of 2-N-butyryl-D-glucosamine (10 g, 40 mmol, 1 eq) in pyridine (50 mL), and the mixture was stirred at r.t. overnight. The mixture was evaporated in vacuo and purified by flash column chromatography (eluent: DCM) to afford 1,3,4,6-tetra-O-acetyl-2-N-butyryl-D-glucosamine (14.5 g, 87.0%). Phenylmethanamine (70 mL) was added to a solution of 1,3,4,6-tetra-O-acetyl-2-N-butyryl-D-glucosamine (14.5 g, 35 mmol, 1 eq) in THF (70 mL) in drop-wise at 0° C. The mixture was stirred at 0° C. for 2 h and concentrated in vacuo. The residue was purified by flash column chromatography (eluent: EA/PE=1/30~1/2) to afford 3,4,6-tri-O-acetyl-2-N-butyryl-D-glucosamine (5.6 g, 43.1%). A solution of 3,4,6-tri-O-acetyl-2-N-butyryl-D-glucosamine (5.2 g, 13.8 mmol, 1 eq) in DCM (26 mL) was cooled to 0° C. under $N_2$ atmosphere. DBU (0.42 g, 2.7 mmol, 0.2 eq) was added to the reaction mixture followed by addition of 2,2,2-trichloroacetonitrile (7.0 g, 48.3 mmol, 3.5 eq). The reaction mixture was stirred at r.t. for 3 h and concentrated in vacuo. The residue was purified by flash column chromatography (eluent: MeOH/DCM=0/100~1/100) to afford 3,4,6-tri-O-acetyl-2-N-butyrylamino-2-deoxy-D-glucopyranosyl trichloroacetimidate (5.2 g, 72.2%). 4-(2-Hydroxyethyl)phenyl acetate (0.87 g, 4.8 mmol, 1 eq) was added to a solution of 3,4,6-tri-O-acetyl-2-N-butyrylamino-2-deoxy-D-glucopyranosyl trichloroacetimidate (2.5 g, 4.8 mmol, 1 eq) in DCM (100 mL). The reaction mixture was cooled to −20° C. under $N_2$ atmosphere. The mixture was stirred at −20° C. for 2 h and concentrated in vacuo. The residue was purified by flash column chromatography (eluent: EA/PE=1/10~1/1) to afford 2-N-butyryl-3,4,6-tri-O-acetyl-1-O-(2-(4-acetoxyphenyl)ethyl-D-glucosamine (500 mg, 19.4%). MeONa (50.4 mg, 0.9 mmol, 1 eq) was added to a solution of 2-N-butyryl-3,4,6-tri-O-acetyl-1-O-(2-(4-acetoxyphenyl)ethyl)-D-glucosamine (500 mg, 0.9 mmol, 1 eq) in MeOH (5 mL). The reaction mixture was stirred at r.t. for 2 h and concentrated in cacuo. The residue was purified by flash column chromatography (eluent: MeOH/DCM=1/10~1/5) to afford the title compound (300 mg, 87.0%). $^1$H NMR (400 MHz, $CD_3OD$) δ ppm 1.0 (t, J=7.0 Hz, 3H), 1.64-1.69 (m, 2H), 2.18 (t, J=7.5 Hz, 2H), 2.78 (t, J=5.0 Hz, 2H), 3.28-3.32 (m, 1H), 3.47 (t, J=8.8 Hz, 1H), 3.61-3.73 (m, 3H), 3.90 (d, J=12.0 Hz, 1H), 4.06-4.10 (m, 1H), 4.45 (d, J=8.2 Hz, 1H), 6.70 (d, J=7.3 Hz, 2H), 7.05 (d, J=7.3 Hz, 2H); $^{13}$C NMR (125 MHz, $CD_3OD$) δ ppm 12.78, 18.80, 34.02, 37.89, 55.22, 60.73, 69.98, 70.57, 73.77, 75.79, 100.93, 115.18, 130.07, 130.83, 153.66, 177.26; m/z (ESI$^+$): 369.9.

Example 29. Preparation of 2-N-butyryl-6-O-(2-hydroxybenzoyl)-D-glucosamine (Compound 41)

Potassium carbonate (50.78 g, 651 mmol, 3 eq) was added to a solution of 2-hydroxybenzoic acid (30 g, 217 mmol, 1 eq) in acetone (300 mL), followed by addition of (bromomethyl)benzene (37.15 g, 217 mmol, 1 eq). The mixture was stirred at 50° C. for 16 h. The mixture was filtered and concentrated under reduced pressure. The residual material was purified by flash column chromatography (eluent: EA/PE=1/10~1/1) to afford benzyl 2-(benzyloxy)benzoate (24 g, 34.7% yield). $H_2O$ (10 mL) was added to a solution of benzyl 2-(benzyloxy)benzoate (20 g, 62.8 mmol, 1 eq) and NaOH (7.54 g, 188.5 mmol, 1 eq) in ethanol (100 mL). The reaction mixture was stirred at 80° C. for 16 h. The mixture was concentrated under reduced pressure. $H_2O$ (50 mL) was added to the mixture. The aqueous phase was washed with DCM (50 mL×3) and 1N HCl was added to the aqueous phase to adjust pH to 4; and the aqueous phase was washed with DCM (50 mL×3). The organic layer was washed by brine (50 mL), and dried ($Na_2SO_4$). The organic layer was concentrated under reduced pressure to afford 2-(benzyloxy)benzoic acid (13 g, 92.8% yield) as a yellow solid. Di(1H-imidazol-1-yl)methanone (12.87 g, 79.4 mmol, 1.1 eq) was added to a solution of 2-(benzyloxy)benzoic acid (16.5 g, 72.3 mmol, 1 eq) in THF (200 mL) under $N_2$. The mixture was stirred at 25° C. for 1 h. The organic layer was concentrated under reduced pressure, purified by flash column chromatography (eluent: EA/PE=1/10~1/1) to afford (2-(benzyloxy)phenyl)(1H-imidazol-1-yl)methanone (12.5 g, 60% yield) as an oil. The mixture of 1,3-di-O-benzyl-2-N-butyryl-D-glucosamine (17.52 g, 40.8 mmol, 1 eq) and DBU (1.24 g, 8.14 mmol, 0.2 eq) in MeCN (200 mL) was stirred at 50° C. for 20 min under $N_2$, followed by addition of (2-(benzyloxy)phenyl)(1H-imidazol-1-yl)methanone (12.5 g, 45 mmol, 1.1 eq). The mixture was stirred at 50° C. for 16 h, concentrated under reduced pressure. The residual material was purified by flash column chromatography (eluent: MeOH/DCM=1/100-3/100) to afford 1,3-di-O-benzyl-6-(2-benzyloxybenzoyl)-2-N-butyryl-D-glucosamine (17.3 g, 66.28% yield) as a white solid. To the solution of the compound (3.5 g, 5.4 mmol, 1 eq) obtained above in MeOH (25 mL) and AcOH (25 mL) was added Pd/C (2 g, 10%, wet) under $H_2$. The mixture was stirred at 25° C. for 32 h. The mixture was filtered and concentrated under reduced pressure. The residual material was purified by flash column chromatography (eluent: MeOH/DCM=1/100~1/30) to afford the title compound (1.05 g, 50% yield) as a white solid. $^1$H NMR (500 MHz, $CD_3OD$) δ ppm 1.00 (t, J=7.0 Hz, 3H), 1.70 (dt, J=14.5, 7.5 Hz, 2H), 2.28 (t, J=6.5 Hz, 2H), 3.53 (t, J=9.0 Hz, 1H), 3.58-4.25 (m, 3H), 4.51-4.64 (m, 1H), 4.69 (d, J=11.5 Hz, 1H), 4.72-5.55 (m, 1H), 6.97 (dd, J=20.5 Hz, 8 Hz, 2H), 7.53 (t, J=7 Hz, 1H), 7.96 (d, J=7.5 Hz, 1H). $^{13}$C NMR (125 MHz, $CD_3OD$) δ ppm 175.69, 175.17, 169.74, 161.35, 135.46, 129.79, 118.88, 116.97, 112.26, 95.77, 91.31, 74.45, 73.84, 71.25, 71.08, 70.86, 69.32, 64.18, 64.06, 57.24, 54.34, 37.91, 37.50, 18.95, 12.54. m/z (ESI+): 369.9.

Example 30. Preparation of 6-O-(1-admantaneacetyl)-2-N-butyryl-D-glucosamine (Compound 56)

Et$_3$N (1.0 g, 10 mmol, 1 eq) was added to a solution of 1-adamantylacetic acid (1.94 g, 10 mmol, 1 eq) in THF (20 mL). The solution was cooled to 0° C. under N$_2$ atmosphere, followed by addition of 4-nitrobenzene-1-sulfonyl chloride (2.2 g, 10 mmol, 1 eq). The reaction mixture was stirred at r.t. for 2 h. Et$_3$N (1.0 g, 10 mmol, 1 eq) was added to the reaction mixture, followed by addition of 2-N-butyryl-1,3-di-O-benzyl-D-glucosamine (4.3 g, 10 mmol, 1 eq) and DMAP (0.12 g, 1 mmol, 1 eq). The mixture was stirred at r.t. for 16 h, and concentrated under reduced pressure. The residual material was purified by flash column chromatography (eluent: MeOH/DCM=1/100~1/30) to afford 6-O-(1-admantaneacetyl)-2-N-butyryl-1,3-di-O-benzyl-D-glucosamine (4.6 g, 76.3%). 10% Pd/C (2.3 g) was added to a solution of 6-O-(1-admantaneacetyl)-2-N-butyryl-1,3-di-O-benzyl-D-glucosamine (4.6 g, 7.6 mmol, 1 eq) in MeOH (23 mL), followed by addition of acetic acid (23 mL). The mixture was stirred at r.t. under H$_2$ atmosphere for 48 h. The mixture was filtered. The filtration was concentrated under reduced pressure. The residual material was purified by flash column chromatography (eluent: MeOH/DCM=1/100~1/30) to give the title compound (2.4 g, 75.0%); $^1$H NMR (400 MHz, CD$_3$OD) δ ppm 0.99 (t, J=7.5 Hz, 3H), 1.65-1.80 (m, 14H), 1.98-2.28 (m, 7H), 3.34-4.48 (m, 6.2H), 5.11 (d, J=3.1 Hz 0.8H); $^{13}$C NMR (125 MHz, CD$_3$OD) δ ppm 12.57, 18.98, 28.69, 32.38, 36.35, 36.43, 37.50, 41.91, 42.07, 48.51, 54.29, 62.90, 69.37, 71.04, 71.13, 91.22, 172.05, 175.12; m/z (ESI$^+$): 426.0.

Example 31. Preparation of 4,6-di-O-butyryl-2-N-(butyryl-$_{d7}$)-D-glucosamine (Compound 68)

Following the same procedure in Example 16, the title compound was prepared. $^1$H NMR (CD$_3$OD, 500 MHz) δ ppm 0.78-1.03 (m, 6H), 1.52-1.66 (m, 4H), 2.18-2.31 (m, 4H), 3.30 (s, 0.3H), 3.62 (s, 0.7H), 3.78-4.11 (m, 4.3H), 4.63 (s, 0.3H), 4.86 (t, 1H), 5.07 (s, 0.8H); $^{13}$C NMR (CD$_3$OD, 125 MHz) δ ppm 13.96, 19.33, 36.83, 36.94, 55.75, 58.90, 62.25, 63.80, 70.34, 72.50, 72.88, 73.46, 92.56, 97.06, 174.35, 175.07, 176.66; m/z (ESI$^+$) 397.1.

Example 32. Preparation of 4,6-O-benzylidene-2-N-butyryl-D-glucosamine (Compound 72)

(Dimethoxymethyl)benzene (30.5 g, 200.594 mmol, 10 eq) was added to a solution of GlcNBu (5.0 g, 20.059 mmol, 1 eq) in DMF (50 mL), followed by addition of p-toluenesulfonic acid monohydrate (0.191 g, 1.003 mmol, 0.05 eq). The reaction mixture was stirred at 50° C. for 16 h. The mixture was cooled to r.t., and poured into H$_2$O (250 mL). The mixture was stirred at r.t. for 1 h. The solid was filtered, then washed with H$_2$O (50 mL) and PE (100 mL), and dried to afford the title compound (5.22 g, 77.0%); $^1$H NMR (500 MHz, CD$_3$OD) δ ppm 0.93-1.09 (m, 3H), 1.62-1.80 (m, 2H), 2.20-2.38 (m, 2H), 3.34 (s, 1H), 3.53-3.62 (m, 1H), 3.74-3.87 (m, 1H), 3.97 (t, J=9.5 Hz, 1H), 4.01-4.10 (m, 1H), 4.18-4.39 (m, 1H), 4.76 (d, J=7.5 Hz, 0.19H), 5.17 (d, J=3.0 Hz, 1H), 5.65 (s, 1H), 7.35-7.47 (m, 4H), 7.55-7.57 (m, 2H).

Example 33. Preparation of 6-O-isopropyloxycarbonyl-2-N-butyryl-D-glucosamine (Compound 73)

GlcNBu (2.49 g, 10 mmol, 1.0 eq) was dissolved in pyridine (25 mL), cooled to 0° C. under N$_2$ atmosphere. To the cold solution was added isopropyl carbonochloridate (1.2 g, 10 mmol, 1.0 eq). The reaction mixture was stirred at r.t. overnight, and concentrated in vacuum. The residual material was purified by flash column chromatography (eluent: MeOH/DCM=1/100~1/20) to afford the title compound (2.01 g, 60.0%); $^1$H NMR (CD$_3$OD, 500 MHz) δ ppm 0.99 (t, J=7.5 Hz, 3H), 1.30 (d, J=6.5 Hz, 6H), 1.65-1.72 (m, 2H), 2.26 (t, J=7.2 Hz, 2H), 3.38 (t, J=9.4 Hz, 1H), 3.74 (t, J=9.4 Hz, 1H), 3.88-3.91 (m, 1H), 4.00-4.03 (m, 1H), 4.27-4.30 (m, 1H), 4.41-4.4 (m, 1H), 4.83-4.90 (m, 1H), 5.11 (d, J=3.4 Hz, 1H); $^{13}$C NMR (CD$_3$OD, 125 MHz) δ ppm 12.56, 13.05, 18.97, 20.57, 37.48, 54.25, 66.54, 69.33, 71.04, 71.64, 91.20, 154.89, 175.13; m/z (ESI$^+$): 335.9.

Example 34. Preparation of 2-N-1,4,6-tri-O-tetrabutyryl-D-glucosamine (Compound 74)

Imidazole (3.18 g, 46.785 mmol, 2.0 eq) was added to a solution of 1-O-benzyl-4,6-O-benzylidene-2-N-butyryl-D-glucosamine (10.0 g, 23.392 mmol, 1.5 eq) in DMF (100 mL). The mixture was cooled to 0° C. under N$_2$ atmosphere, followed by addition of TBSCl (5.29 g, 35.089 mmol, 1.5 eq). The reaction mixture was stirred at r.t. for 16 h. Ethyl acetate (100 mL) and H$_2$O (100 mL) were added to reaction mixture. The organic layer was washed with H$_2$O (100 mL) and brine (100*3 mL), and concentrated under reduced pressure. The residual material was purified by flash column chromatography (eluent: EA/PE=1/20~1/5) to afford 1-O-benzyl-4,6-O-benzylidene-3-O-(tert-butyldimethylsilyl)-2-N-butyryl-D-glucosamine (10.0 g, 78.9%). PtO$_2$ (3 g) was added to a solution of 1-O-benzyl-4,6-O-benzylidene-3-O-(tert-butyldimethylsilyl)-2-N-butyryl-D-glucosamine (10 g, 18.459 mmol, 1 eq) in MeOH (100 mL). The mixture was stirred at 30° C. under H$_2$ atmosphere for 48 h. The mixture was filtered. The filtration was concentrated under reduced pressure. The residual material was purified by flash column chromatography (eluent: MeOH/DCM=1/50~1/10) to afford 3-O-(tert-butyldimethylsilyl)-2-N-butyryl-D-glucosamine (4.8 g, 71.6%). Butyric anhydride (6.89 g, 43.574 mmol, 3.3 eq) and DMAP (81 mg, 0.660 mmol, 0.05 eq) were added to a solution of 3-O-(tert-butyldimethylsilyl)-2-N-butyryl-D-glucosamine (4.8 g, 13.204 mmol, 1.0 eq) in pyridine (48 mL). The mixture was stirred at 35° C. for 16 h. The mixture was concentrated under reduced pressure. The residual material was purified by flash column chromatography (eluent: EA/PE=1/20~1/5) to afford 3-O-(tert-butyldimethylsilyl)-1,4,6-tri-O-2-N-tetrabutyryl-D-glucosamine (6.5 g, 85.8%). The obtained compound (6.5 g, 11.328 mmol, 1 eq) was dissolved in DCM (65 mL), followed by addition of 4M HCl in 1,4-dioxane (6.5 mL). The mixture was stirred at r.t. for 16 h, and concentrated under reduced pressure. The residual material was purified by flash column chromatography (eluent: MeOH/DCM=1/100~1/50) to afford the title compound (4.5 g, 86.5%); $^1$H NMR (500 MHz, CD$_3$OD) δ ppm 0.87-1.08 (m, 12H), 1.57-1.78 (m, 8H), 2.15-2.52 (m, 8H), 3.86-3.94 (m, 1H), 3.98-4.05 (m, 1H), 4.05-4.13 (m, 1H), 4.13-4.19 (m, 1H), 4.19-4.29 (m, 1H), 5.02 (t, J=10.0

Hz, 1H), 6.21 (d, J=3.5 Hz, 1H), 8.21 (d, J=8.0 Hz, 0.25H); $^{13}$C NMR (125 MHz, CD$_3$OD) δ ppm 12.52, 12.59, 17.86, 17.92, 18.91, 19.41, 35.21, 35.36, 35.43, 37.24, 37.86, 53.00, 53.46, 61.82, 68.57, 70.07, 70.65, 89.90, 171.90, 172.69, 173.42, 175.27; m/z (ESI$^+$) 481.9 (M+Na).

Example 35. Preparation of 1-O-benzyl-2-N-butyryl-D-glucosamine (Compound 75)

AcCl (21.4 g, 272.808 mmol, 3.4 eq) was added to a solution of GlcNBu (20.0 g, 80.238 mmol, 1.0 eq) in BnOH (200 mL). The reaction mixture was stirred at r.t. for 0.5 h, then at 70° C. for 2 h. The mixture was concentrated under vacuum pressure. EtOH (200 mL) was added, and the mixture was stirred for 0.5 h. The mixture was filtered, and dried to afford the title compound (4.7 g). The filtration was concentrated to 100 mL under reduced pressure, followed by addition of iPr$_2$O (200 mL). The mixture was stirred for 0.5 h, and the second crop of the title compound (15.21 g) was obtained (by filtration and drying). The total yield was 73.1%. $^1$H NMR (500 MHz, CD$_3$OD) δ ppm 0.97 (t, J=7.5 Hz, 3H), 1.51-1.78 (m, 2H), 2.23 (t, J=7.5 Hz, 2H), 3.09 (dd, J=10.5, 3.5 Hz, 0.19H), 3.38-3.47 (m, 1H), 3.67-3.81 (m, 3H), 3.81-3.91 (m, 2H), 3.95 (dd, J=11.0, 3.5 Hz, 1H), 4.53 (d, J=12.0 Hz, 1H), 4.78 (d, J=12.0 Hz, 1H), 5.36 (d, J=3.5 Hz, 0.14H), 7.18-7.54 (m, 5H); $^{13}$C NMR (125 MHz, CD$_3$OD) δ ppm 12.63, 18.97, 37.43, 53.88, 54.82, 60.82, 61.32, 68.68, 70.03, 70.37, 71.03, 71.19, 71.95, 72.68, 89.40, 96.10, 127.44, 127.94, 127.98, 137.52, 175.08; m/z (ESI$^-$) 337.9.

Example 36. Preparation of 2-N-butyryl-1,3-di-O-benzyl-D-glucosamine (Compound 76)

BnBr (11.15 g, 65.210 mmol, 2.2 eq) was added to a solution of 4,6-O-benzylidene-2-N-butyryl-D-glucosamine (10.0 g, 29.641 mmol, 1.0 eq) in DMF (150 mL). The mixture was cooled to −10° C. under N$_2$ atmosphere, followed by addition of NaH (3.2 g, 80.031 mmol, 2.7 eq, 60% in mineral oil). The reaction mixture was stirred at r.t. for 2 h. EA (200 mL) and H$_2$O (200 mL) were added to the reaction mixture. The organic layer was washed with H$_2$O (100 mL) and brine (100×3 mL), and concentrated under reduced pressure. The residual material was purified by flash column chromatography (eluent: EA/PE=1/100~1/50) to afford 4,6-O-benzylidene-2-N-butyryl-1,3-di-O-benzyl-D-glucosamine (11.5 g, 75.0%). H$_2$O (3.45 mL) was added to a solution of 4,6-O-benzylidene-2-N-butyryl-1,3-di-O-benzyl-D-glucosamine (11.5 g, 22.217 mmol, 1.0 eq) in TFA (46 mL). The mixture was stirred at r.t. for 1 h, then added into H$_2$O (115 mL). The mixture was stirred for 0.5 h, filtered and the filter cake was added into saturated sodium bicarbonate (115 mL). The mixture was stirred for 0.5 h, filtered and the filter cake was added into EA (11.5 mL) and PE (115 mL). The mixture was stirred at 50° C. for 1 h, filtered and the filter cake was dried to afford the title compound (6.1 g, 64%); $^1$H NMR (500 MHz, CD$_3$OD) δ ppm 0.87-0.98 (m, 3H), 1.54-1.67 (m, 2H), 2.07-2.23 (m, 2H), 3.52-3.65 (m, 1H), 3.71-3.83 (m, 3H), 3.85-4.01 (m, 1H), 4.07-4.18 (m, 1H), 4.52-4.60 (m, 1H), 4.63-4.74 (m, 1H), 4.81 (d, J=12.0 Hz, 1H), 4.86 (d, J=3.5 Hz, 1H), 4.92 (s, 1H), 7.24-7.49 (m, 10H), 8.10 (d, J=9.0 Hz, 0.15H); $^{13}$C NMR (125 MHz, CD$_3$OD) δ ppm 12.63, 18.97, 37.43, 53.88, 54.82, 60.82, 61.32, 68.68, 70.03, 70.37, 71.03, 71.19, 71.95, 72.68, 89.40, 96.10, 127.44, 127.94, 127.98, 137.52, 175.08; m/z (ESI$^+$) 430.1.

Example 37. Preparation of 2-N-butyryl-3-O-cyclohexylaminocarbonyl-6-O-(4-cyclohexylamino-4-oxo-butyryl)-D-glucosamine (Compound 77)

DMAP (0.12 g, 1 mmol, 0.1 eq) was added to a solution of 2-N-butyryl-1,3-di-O-benzyl-D-glucosamine (4.3 g, 10 mmol, 1 eq) in pyridine (43 mL), followed by addition of dihydrofuran-2,5-dione (1.0 g, 10 mmol, 1 eq). The reaction mixture was stirred at r.t. for 16 h, and concentrated under reduced pressure. The residual material was purified by flash column chromatography (eluent: MeOH/DCM=1/20~1/10) to afford 2-N-butyryl-1,3-di-O-benzyl-6-O-(4-hydroxy-4-oxo-butyryl)-D-glucosamine (3.0 g, 56.7%). DCC (1.4 g, 6.8 mmol, 1.2 eq) was added to a solution of 2-N-butyryl-1,3-di-O-benzyl-6-O-(4-hydroxy-4-oxo-butyryl)-D-glucosamine (3.0 g, 5.7 mmol, 1.0 eq) in DCM (30 mL), the mixture was stirred at r.t. for 16 h, and concentrated under reduced pressure. The residual material was purified by flash column chromatography (eluent: MeOH/DCM=1/100~1/40) to afford 2-N-butyryl-1,3-di-O-benzyl-4-O-cyclohexylaminocarbonyl-6-O-(4-cyclohexylamino-4-oxo-butyryl)-D-glucosamine (3.0 g, 73.0%). 10% Pd/C (1.5 g) was added to a solution of the above-obtained compound (3.0 g, 4.1 mmol, 1 eq) in MeOH (15 mL), followed by addition of acetic acid (15 mL). The mixture was stirred at r.t. under H$_2$ atmosphere for 48 h. The mixture was filtered. The filtration was concentrated under reduced pressure. The residual material was purified by flash column chromatography (eluent: MeOH/DCM=1/100~1/30) to afford the title compound (2.0 g, 88.5%); $^1$H NMR (CD$_3$OD, 500 MHz) δ ppm 0.95 (t, J=7.0 Hz, 3H), 1.11-1.99 (m, 21H), 2.01 (s, 2H), 2.66-2.68 (m, 4H), 3.33-4.60 (m, 8.44H), 5.08 (s, 0.78H), 7.76 (s, 0.57H), 8.23 (s, 0.76H); $^{13}$C NMR (CD$_3$OD, 125 MHz) δ ppm 12.64, 19.00, 24.63, 28.77, 37.52, 37.57, 50.36, 50.48, 51.00, 54.19, 63.85, 69.28, 70.84, 71.07, 71.17, 91.22, 95.77, 154.25, 154.33, 170.08, 173.02, 175.09, 175.17, 175.71; m/z (ESI$^+$): 556.3.

Example 38. Preparation of 2-N-butyryl-4,6-di-O-pentanoyl-D-glucosamine (Compound 78)

Pentanoic anhydride (2.23 g, 12 mmol, 3 eq) was added to a solution of 2-N-butyryl-1,3-di-O-benzyl-D-glucosamine (2 g, 4 mmol, 1 eq) and DMAP (0.025 g, 0.2 mmol, 0.05 eq) in pyridine (10 mL). The mixture was stirred at 35° C. for 16 h. Pyridine was removed under reduced pressure. The residue was dissolved by ethyl alcohol (30 mL), and added to H$_2$O (150 mL), and the solid was collected and dried, giving 2-N-butyryl-1,3-di-O-benzyl-4,6-di-O-pentanoyl-D-glucosamine (2.3 g, 92% yield), as a light yellow solid. The above-obtained compound (2.3 g, 4 mmol, 1 eq) was dissolved in MeOH (10 mL) and AcOH (10 mL), and the solution was added to Pd/C (1.2 g, 10%, wet) under H$_2$. The mixture was stirred at 25° C. for 40 h. The mixture was filtered and concentrated under reduced pressure. The residual material was purified by flash column chromatography (eluent: MeOH/DCM=1/100~1/30) to afford the title compound (1 g, 60% yield). $^1$H NMR (500 MHz, CD$_3$OD) δ 5.15 (s, 0.82H), 4.70 (s, 0.16H), 4.26-4.03 (m, 3H), 3.99 (d, J=10.3 Hz, 1H), 3.89 (t, J=9.7 Hz, 1H), 3.70 (s, 0.48H), 2.50-2.34 (m, 4H), 2.26 (d, J=6.7 Hz, 2H), 1.77-1.57 (m, 6H), 1.41 (s, 4H), 0.98 (d, J=7.1 Hz, 9H). $^{13}$C NMR (125 MHz, CD$_3$OD) δ 175.13, 173.79, 173.05, 95.66, 91.15, 72.05, 71.47, 71.07, 68.94, 67.27, 62.41, 57.50, 54.36, 37.88, 37.44, 33.35, 33.23, 26.61, 21.84, 18.95, 12.66, 12.53. m/z (ESI$^+$) 417.9.

Example 39. Preparation of 2-N-butyryl-4,6-di-O-(4-hydroxy-4-oxo-butyryl)-D-glucosamine (Compound 79)

The dihydrofuran-2,5-dione (3 g, 30 mmol, 3 eq) was added to a solution of 2-N-butyryl-1,3-di-O-benzyl-D-glucosamine (4.29 g, 10 mmol, 1 eq) and DMAP (0.06 g, 0.5 mmol, 0.05 eq) in pyridine (22 mL). The mixture was stirred at 35° C. for 16 h. Pyridine was removed under reduced pressure. The residual material was purified by flash column chromatography (eluent: MeOH/DCM=1/100~1/20) to afford 2-N-butyryl-1,3-di-O-benzyl-4,6-di-O-(4-hydroxy-4-oxo-butyryl)-D-glucosamine (1.6 g, 25.8% yield) as a white solid. The above-obtained compound (1.5 g, 2 mmol, 1 eq) was dissolved in MeOH (10 mL) and AcOH (10 mL), followed by addition of Pd/C (0.75 g, 10%, wet) under H$_2$. The mixture was stirred at 25° C. for 40 h. The mixture was filtered and concentrated under reduced pressure. The residual material was purified by flash column chromatography (eluent: MeOH/DCM=1/100~1/10) to afford title compound (0.518 g, 57.68% yield) as a white solid. $^1$H NMR (500 MHz, CD$_3$OD) δ 5.16 (s, 0.81H), 4.71 (d, J=6.0 Hz, 0.19H), 4.19 (t, J=16.4 Hz, 3H), 3.99 (s, 1H), 3.93 (t, J=9.6 Hz, 1H), 3.73 (s, 1H), 3.65 (s, 0.45H), 2.65 (t, J=20.7 Hz, 9H), 2.27 (d, J=6.3 Hz, 2H), 1.69 (d, J=6.5 Hz, 2H), 1.37 (d, J=34.1 Hz, 2H), 1.00 (s, 3H). $^{13}$C NMR (126 MHz, CD$_3$OD) δ 175.16, 174.85, 172.60, 172.10, 91.10, 72.04, 68.86, 67.12, 62.89, 62.85, 54.22, 48.45, 37.90, 37.45, 31.66, 29.34, 28.82, 28.67, 28.59, 28.45, 22.33, 18.97, 13.04, 12.54. m/z (ESI$^+$) 449.9, m/z (ESI$^-$) 447.9.

Example 40. Preparation of 2-O-butyryl-4,6-di-O-propanoyl-D-glucosamine (Compound 80)

Propionic anhydride (1.56 g, 12 mmol, 3 eq) was added to a solution of N-butyryl-1,3-di-O-benzyl-D-glucosamine (2 g, 4 mmol, 1 eq) and DMAP (0.025 g, 0.2 mmol, 0.05 eq) in pyridine (10 mL). The mixture was stirred at 35° C. for 16 h. Pyridine was removed under reduced pressure. The residue was dissolved by ethyl alcohol (30 mL), and added to H$_2$O (150 mL), the solid was collected and dried to afford N-butyryl-1,3-di-O-benzyl-4,6-di-O-propanoyl-D-glucosamine (1.5 g, 65% yield) as a white solid. This white solid (1.5 g, 2 mmol, 1 eq) was dissolved in MeOH (7.5 mL) and AcOH (7.5 mL), followed by addition of Pd/C (0.75 g, 10%, wet) under H$_2$. The mixture was stirred at 25° C. for 40 h. The mixture was filtered and concentrated under reduced pressure. The residual material was purified by flash column chromatography (eluent: MeOH/DCM=1/100~1/30) to afford the title compound (0.596 g, 82.54% yield) as a white solid. $^1$H NMR (500 MHz, CD$_3$OD) δ 5.16 (d, J=3.4 Hz, 0.87H), 4.95 (d, J=9.8 Hz, 1H), 4.71 (d, J=7.8 Hz, 0.09H), 4.25 (dd, J=12.1, 4.6 Hz, 1H), 4.16 (m, 1H), 4.08 (dd, J=12.1, 2.2 Hz, 1H), 4.00 m, 1H), 3.94-3.87 (m, 1H), 2.49-2.36 (m, 4H), 2.27 (t, J=7.4 Hz, 2H), 1.69 (dd, J=14.8, 7.4 Hz, 2H), 1.17 (td, J=7.6, 3.8 Hz, 6H), 1.04-0.94 (m, 3H). $^{13}$C NMR (126 MHz, CD$_3$OD) δ 175.14, 174.47, 173.82, 91.15, 71.56, 68.91, 67.30, 62.42, 54.33, 37.44, 26.91, 26.77, 18.96, 12.53, 7.93, 7.91. m/z (ESI$^+$) 361.9.

Example 41. Preparation of 2-N-(butyryl-$_{d7}$)-D-glucosamine (Compound 81)

To a suspension of glucosamine hydrochloride (2.5 g, 11.59 mmol, 1 eq) in pyridine (50 mL), HMDS (24.2 mL, 115.9 mmol, 10 eq) was added followed by TMSCl (14.7 mL, 115.9 mmol, 10 eq). The resulting mixture was stirred at r.t. for 3 h. The mixture was evaporated in vacuo and purified by flash column chromatography (eluent: EA/PE=1/30~1/10) to afford 1,3,4,6-tetra-O-trimethylsilyl-D-glucosamine (4.0 g, 85.6%). Butyric-$_{d7}$ acid (0.771 g, 8.1 mmol, 1 eq) was added to a solution of 1,3,4,6-tetra-O-trimethylsilyl-D-glucosamine (3.8 g, 8.1 mmol, 1 eq) in DCM (38 mL), followed by addition of DCC (2.01 g, 9.7 mmol, 1.2 eq). The mixture was stirred at r.t. for 3 h. The mixture was evaporated in vacuo and purified by flash column chromatography (eluent: EA/PE=1/30~1/15) to afford 2-N-butyryl-1,3,4,6-tetra-O-trimethylsilyl-D-glucosamine (3.0 g, 67.8%). The above-obtained compound (3.0 g, 5.5 mmoL, 1 eq) was dissolved in DCM (30 mL), followed by addition of 4 M HCl in Dioxane (1 mL). The mixture was stirred at r.t. for 3 h and concentrated in vacuo to give the title compound (1.4 g, 99.9%); $^1$H NMR (400 MHz, D$_2$O) δ ppm 3.38-3.50 (m, 1.67H), 3.61-3.87 (m, 4.63H), 4.65 (d, J=8.0 Hz, 0.4H), 5.14 (d, J=3.0 Hz, 0.6H); $^{13}$C NMR (125 MHz, D$_2$O) δ ppm 53.94, 56.50, 60.57, 60.72, 69.90, 70.12, 70.52, 71.53, 90.85, 94.96, 177.64, 177.87; m/z (ESI$^-$): 255.0.

Example 42. Preparation of 6-O-(4-aminobutyryl)-2-N-butyryl-D-glucosamine hydrochloride (Compound 82)

4M HCl/dioxane (0.8 mL, 3.2 mmol, 2 eq) was added to a solution of 6-O-(4-tert-butyloxycarbonylaminobutyryl)-2-N-butyryl-D-glucosamine (700 mg, 1.6 mmol, 1 eq) in dioxane (15 mL). The mixture was stirred at r.t. for 3 h, some solid appeared, and the solvent was removed. The residual material was dissolved with water and dried at −40° C. under vacuum to give the title compound (400 mg, 67.1%); $^1$H NMR (500 MHz, D$_2$O) δ 5.13 (d, J=3.5 Hz, 0.35H), 4.47-4.22 (m, 1.35H), 4.07-3.93 (m, 0.42H), 3.84 (dd, J=10.6, 3.2 Hz, 1.02H), 3.72 (dd, J=10.7, 9.1 Hz, 1.18H), 3.67-3.54 (m, 1.25H), 3.56-3.32 (m, 1.45H), 3.00 (s, 2H), 2.53 (d, J=2.3 Hz, 2H), 2.22 (d, J=6.9 Hz, 2H), 2.00-1.81 (m, 2H), 1.56 (d, J=7.3 Hz, 2H), 0.85 (dt, J=11.5, 5.7 Hz, 3H); $^{13}$C NMR (125 MHz, D$_2$O) δ 177.81, 177.56, 176.90, 174.60, 95.02, 90.92, 73.51, 73.27, 70.36, 70.11, 69.84, 69.23, 63.49, 62.51, 60.62, 56.42, 55.32, 53.89, 38.68, 37.94, 37.53, 30.53, 21.96, 18.97, 12.62; m/z (ESI$^-$) 370.9.

Example 43. Preparation of 6-O-(4-aminobutyryl)-2-N-4-O-dibutyryl-D-glucosamine hydrochloride (Compound 83)

Butyric anhydride (2 g, 12.6 mmol, 3.15 eq) was added to a solution of 6-O-(4-tert-butoxyaminobutyryl)-1,3-di-O-benzyl-2-N-butyryl-D-glucosamine (3 g, 4.9 mmol, 1 eq) and DMAP (25 mg, 0.2 mmol, 0.05 eq) in pyridine (30 mL). The mixture was stirred at r.t. for 16 h, pyridine was removed and dissolved with DCM, the organic layer washed with water and saturated sodium bicarbonate solution, and dried with anhydrous magnesium sulfate. The organic layer was concentrated under reduced pressure. The residual material was purified by flash column chromatography (eluent: MeOH/DCM=1/100~1/50) to afford 6-O-(4-tert-butoxyaminobutyryl)-1,3-di-O-benzyl-2-N-4-O-dibutyryl-D-glucosamine (3 g, 89%). The compound thus obtained (3 g, 8.1 mmol, 1 eq) was dissolved in MeOH (15 mL) and acetic acid (15 mL), followed by addition of Pd/C (10%, 1.2 g). The mixture was stirred at r.t. under $H_2$ atmosphere for 48 h. The mixture was filtered. The filtration was concentrated under reduced pressure. The residual material was purified by flash column chromatography (eluent: MeOH/DCM=1/100~1/50) to afford 6-O-(4-tert-butoxyaminobutyryl)-2-N-4-O-dibutyryl-D-glucosamine (2 g, 90%). This Boc derivative (1 g, 2 mmol, 1 eq) was dissolved in DCM (40 mL), followed by addition of 4M HCl/dioxane (1 mL, 4 mmol, 2 eq). The mixture was stirred at r.t. for 3 h, some solid appeared, and the solvent was removed. The residual material was dissolved with water and dried at −40° C. under vacuum to give the title compound (380 mg, 43.4%); $^1$H NMR (500 MHz, $D_2O$) δ 5.19 (d, J=3.0 Hz, 0.62H), 4.92 (t, J=9.4 Hz, 0.9H), 4.31 (td, J=12.9, 3.1 Hz, 0.98H), 4.21 (d, J=10.1 Hz, 0.61H), 4.12 (dd, J=27.3, 12.6 Hz, 0.94H), 3.97-3.88 (m, 1.23H), 3.85 (d, J=9.7 Hz, 0.32H), 3.78-3.69 (m, 0.69H), 3.02 (t, J=7.5 Hz, 2H), 2.60-2.48 (m, 2H), 2.38 (dd, J=9.1, 5.1 Hz, 2H), 2.24 (t, J=7.2 Hz, 2H), 2.04-1.84 (m, 2H), 1.67-1.45 (m, 4H), 0.95-0.76 (m, 6H); $^{13}$C NMR (125 MHz, $D_2O$) δ 177.84, 177.61, 175.71, 174.32, 95.15, 90.97, 71.45, 71.20, 70.58, 70.24, 68.40, 67.16, 62.38, 56.43, 53.83, 38.65, 37.92, 37.51, 35.69, 30.53, 21.94, 18.96, 17.89, 12.77, 12.57; m/z (ESI$^-$) 440.8.

Example 44. Preparation of 6-O-(4-tert-butoxycarbonylaminobutyryl)-2-N-butyryl-D-glucosamine (Compound 84)

Triethylamine (15 mL, 108 mmol, 1.25 eq) was added to a solution of 4-aminobutanoic acid (9 g, 87 mmol, 1 eq) and (BOC)$_2$O (20.9 g, 96 mmol, 1.1 eq) in MeOH (200 mL). The mixture was stirred at 50° C. for 2 h. and solvent was removed under reduced pressure. The residual material was purified by flash column chromatography (eluent: MeOH/DCM=1/50~1/5) to afford 4-((tert-butoxycarbonylamino)butanoic acid (9.0 g, 75%). 4-((tert-Butoxycarbonyl)amino)butanoic acid (8 g, 39.4 mmol, 2 eq) was added to a solution of 1,3-di-O-benzyl-2-N-butyryl-D-glucosamine (8.5 g, 19.7 mmol, 1 eq) in DMF (200 mL), followed by addition of HOBt (8 g, 159.2 mmol, 3 eq), EDCI (15 g, 78.2 mmol, 4 eq), DIPEA (15 g, 116 mmol, 6 eq). The mixture was stirred at r.t. for 16 h. $H_2O$ (500 mL) were added to the reaction mixture. The white suspension was filtered, and the filter cake washed with water, then dried at 50° C. under vacuum to give 1,3-di-O-benzyl-6-O-(4-tert-butoxycarbonylaminobutyryl)-2-N-butyryl-D-glucosamine (11 g, 45%). The above-obtained compound (5 g, 8.1 mmol, 1 eq) was dissolved in MeOH (25 mL), followed by addition of acetic acid (25 mL), and then Pd/C (10%, 2.5 g). The mixture was stirred at r.t. under $H_2$ atmosphere for 48 h. The mixture was filtered. The filtration was concentrated under reduced pressure. The residual material was purified by flash column chromatography (eluent: MeOH/DCM=1/100~1/30) to afford the title compound (3.07 g, 86%); $^1$H NMR (500 MHz, CD$_3$OD) δ 5.53 (s, 0.48H), 5.13 (s, 0.93H), 4.42 (d, J=11.7 Hz, 0.96H), 4.35-4.19 (m, 0.96H), 4.04 (s, 0.93H), 3.90 (d, J=10.6 Hz, 0.93H), 3.75 (t, J=9.6 Hz, 0.96H), 3.40 (t, J=6.8 Hz, 1H), 3.12 (t, J=5.5 Hz, 2H), 2.42 (t, J=6.3 Hz, 2H), 2.27 (t, J=6.3 Hz, 2H), 1.90-1.76 (m, 2H), 1.69 (dd, J=13.7, 6.7 Hz, 2H), 1.48 (s, 9H), 1.01 (d, J=7.1 Hz, 3H); $^{13}$C NMR (125 MHz, CD$_3$OD) δ 175.13, 173.51, 157.13, 95.74, 91.21, 78.58, 74.45, 73.87, 71.25, 71.07, 70.90, 69.28, 63.54, 57.25, 54.32, 53.39, 39.22, 37.50, 30.86, 27.37, 24.90, 18.95, 12.55; m/z (ESI$^+$) 435.0, (ESI$^-$) 433.0.

Example 45. Preparation of 4,6-di-O-acetyl-2-N-butyryl-D-glucosamine (Compound 85)

DMAP (0.04 g, 0.29 mmol, 0.05 eq) was added to a solution of 1,3-di-O-benzyl-2-N-butyryl-D-glucosamine (2.5 g, 5.8 mmol, 1 eq) in pyridine (25 mL), followed by addition of acetic anhydride (1.5 g, 14.5 mmol, 2.5 eq). The reaction mixture was stirred at r.t. for 16 h, and poured into $H_2O$ (250 mL). The mixture was stirred at r.t. for 1 h. The solid was filtered, then washed with $H_2O$ (50 mL) and PE (50 mL), and dried to afford 4,6-di-O-acetyl-1,3-di-O-benzyl-2-N-butyryl-D-glucosamine (3.2 g, 87.2%). The compound thus obtained (3.2 g, 5.1 mmol, 1 eq) was dissolved in MeOH (15 mL) and acetic acid (15 mL), followed by addition of Pd/C (10%, 1.6 g). The mixture was stirred at r.t. under $H_2$ atmosphere for 48 h. The mixture was filtered. The filtration was concentrated under reduced pressure. The residual material was purified by flash column chromatography (eluent: MeOH/DCM=1/100~1/30) to afford the title compound (1.5 g, 88.9%); $^1$H NMR (CD$_3$OD, 500 MHz) δ ppm 0.95 (t, J=7.0 Hz, 3H), 1.60-1.67 (m, 2H), 2.04 (s, 3H), 2.08 (s, 3H), 2.23 (t, J=7.0 Hz, 2H), 3.65-3.72 (m, 0.44H), 3.86 (t, J=9.5 Hz, 0.87H), 3.94-4.21 (m, 3.82H), 4.66 (d, J=7.5 Hz, 0.16H), 4.86 (t, J=9.5 Hz, 1H), 5.11 (d, J=3.0 Hz, 0.85H), 7.84 (d, J=8.5 Hz, 0.6H); $^{13}$C NMR (CD$_3$OD, 125 MHz) δ ppm 13.94, 20.30, 20.71, 20.92, 38.80, 38.85, 39.23, 55.60, 55.68, 58.68, 63.88, 68.88, 70.20, 72.82, 73.01, 73.22, 92.45, 96.98, 171.87, 171.96, 172.48, 172.58, 176.48, 176.56; m/z (ESI$^+$): 333.9.

Example 46. Preparation of 2-N-butyryl-6-O-(9-hydroxy-9-oxononanoyl)-D-glucosamine (Compound 86)

BnBr (4.54 g, 26.565 mmol, 1.0 eq) and DBU (4.04 g, 26.565 mmol, 1.0 eq) were added to a solution of nonanedioic acid (5.0 g, 26.565 mmol, 1.0 eq) in THF (30 mL) at 0° C. under N$_2$ atmosphere. The mixture was stirred at r.t. for 16 h. Ethyl acetate (50 mL) and H$_2$O (50 mL) were added to reaction mixture. The organic layer was washed with H$_2$O (50 mL) and brine (50 mL), and concentrated under reduced pressure. The residual material was purified by flash column chromatography (eluent: MeOH/DCM=1/100~1/50) to afford 9-(benzyloxy)-9-oxononanoic acid (5.2 g, 70.4%). 9-(benzyloxy)-9-oxononanoic acid (4.9 g, 17.604 mmol, 1.0 eq) in anhydrous THF (10 mL) was added to a solution of Et$_3$N (1.78 g, 35.209 mmol, 1.0 eq) and NosCl (3.9 g, 19.604 mmol, 1.0 eq) in anhydrous THF (150 mL) at 0° C. under N$_2$ atmosphere. The mixture was stirred at r.t. for 2 h. Et$_3$N (1.78 g, 35.209 mmol, 1.0 eq), DMAP (430 mg, 3.521 mmol, 0.2 eq) and 1,3-di-O-benzyl-2-N-butyryl-D-glucosamine (7.56 g, 17.604 mmol, 1.0 eq) were added to the mixture. The reaction mixture was stirred at r.t. for 16 h. Et$_2$O (200 mL) and H$_2$O (200 mL) were added to the reaction mixture. The organic layer was washed with H$_2$O (200 mL) and 1 M sodium hydroxide solution (100*2 mL), dried by anhydrous sodium sulfate and concentrated under reduced pressure. The residual material was purified by flash column chromatography (eluent: MeOH/DCM=1/100~1/50) to afford 1,3-di-O-benzyl-2-N-butyryl-6-O-(9-benzyloxy-9-oxononanoyl)-D-glucosamine (7.4 g, 61.2%). The above-obtained compound (3.5 g, 5.074 mmol, 1 eq) was dissolved in MeOH (35 mL) and AcOH (35 mL), followed by addition of Pd/C (10%, 4.41 g). The mixture was stirred at 35° C. under $H_2$ atmosphere for 48 h. The mixture was filtered. The filtration was concentrated under reduced pressure. The residual material was purified by flash column chromatography (eluent: MeOH/DCM=1/100~1/50) to afford the title compound (898 mg, 20.4%); $^1$H NMR (500 MHz, $CD_3OD$) δ ppm 1.01 (t, J=7.5 Hz, 3H), 1.41 (s, 6H), 1.57-1.77 (m, 6H), 2.28 (t, J=7.5 Hz, 2H), 2.34 (t, J=7.5 Hz, 2H), 2.40 (t, J=7.5 Hz, 2H), 3.41 (t, J=9.5 Hz, 1H), 3.76 (t, J=9.0 Hz 1H), 3.86-3.98 (m, 1H), 3.98-4.11 (m, 1H), 4.26 (dd, J=11.5, 5.0 Hz, 1H), 4.43 (d, J=10.0 Hz, 1H), 5.13 (d, J=3.5 Hz, 1H), 7.81 (d, J=8.5 Hz, 1H); $^{13}$C NMR (125 MHz, $CD_3OD$) δ ppm 13.96, 20.36, 25.94, 26.01, 30.02, 34.92, 34.95, 38.91, 55.71, 64.76, 68.53, 70.75, 72.48, 72.58, 92.62, 175.50, 176.54, 177.72; m/z (ESI$^-$): 418.0.

Example 47. Preparation of
2-N-butyryl-6-O-phosphono-D-glucosamine
(Compound 87)

GlcNBu (2.49 g, 10 mmol, 1.0 eq) was dissolved in pyridine (25 mL), and this solution was cooled to −10° C. under $N_2$ atmosphere. To this solution was added diphenyl phosphorochloridate (2.68 g, 10 mmol, 1.0 eq). The reaction mixture was stirred at r.t. for 2-4 h, and concentrated in vacuum. The residual material was purified by flash column chromatography (eluent: MeOH/DCM=1/100~1/30) to afford 2-N-butyryl-6-O-(diphenylphosphono)-D-glucosamine (1.6 g, 73%). The above-obtained compound (1.6 g, 3.3 mmol, 1 eq) was dissolved in water (32 mL), followed by addition of $Pt_2O$ (0.16 g). The mixture was stirred at r.t. under $H_2$ atmosphere for 48 h. The mixture was filtered. The filtration was concentrated under reduced pressure to afford the title compound (1.09 g, 99.2%); $^1$H NMR ($D_2O$, 500 MHz) δ ppm 0.77-0.81 (m, 3H), 1.47-1.51 (m, 2H), 2.13-2.17 (m, 2H), 3.38-3.47 (m, 1.6H), 3.58 (t, J=9.0 Hz, 0.4H), 3.65 (t, J=9.5 Hz, 0.6H), 3.77-4.09 (m, 3.4H), 4.62 (d, J=8.0 Hz, 0.4H), 5.01 (d, J=3.0 Hz, 0.6H); $^{13}$C NMR ($D_2O$, 125 MHz) δ ppm 12.55, 18.88, 37.44, 37.84, 53.79, 56.36, 64.70, 69.35, 69.57, 70.23, 70.34, 90.86, 94.93, 177.46, 177.74; $^{31}$P NMR ($D_2O$, 200 MHz) δ ppm 1.02; m/z (ESI$^-$): 327.9.

Example 48. Preparation of
2-N-3,6-di-O-tributyryl-D-glucosamine (Compound 88)

Butyric anhydride (2.70 g, 17.034 mmol, 1.1 eq) and DMAP (95 mg, 0.774 mmol, 0.05 eq) were added to a solution of 1-O-benzyl-4,6-O-benzylidene-D-glucosamine (6.62 g, 15.486 mmol, 1.0 eq) in pyridine (66 mL). The mixture was stirred at 35° C. for 16 h. The mixture was concentrated under reduced pressure. The residual material was purified by flash column chromatography (eluent: EA/PE=1/20~1/5) to afford 1-O-benzyl-4,6-O-benzylidene-2-N-3-O-dibutyryl-D-glucosamine (6.2 g, 80.5%). This compound (7.93 g, 15.937 mmol, 1.0 eq) was placed in TFA (31.7 mL), followed by addition of $H_2O$ (2.4 mL). The mixture was stirred at r.t. for 5 min, then added into saturated sodium bicarbonate (150 mL). The mixture was stirred for 10 min, extracted by DCM (100 mL×3). The combined organic layer was washed with brine (100 mL), and concentrated under reduced pressure. The residual material was purified by flash column chromatography (eluent: MeOH/DCM=1/100~1/50) to afford 1-O-benzyl-2-N-3-O-dibutyryl-D-glucosamine (5.5 g, 84.2%). Butyric acid (646 mg, 7.327 mmol, 1.0 eq) in anhydrous THF (2 mL) was added to a solution of $Et_3N$ (741 mg, 7.327 mmol, 1.0 eq) and NosCl (1.62 g, 7.327 mmol, 1.0 eq) in anhydrous THF (60 mL) at 0° C. under $N_2$ atmosphere. The mixture was stirred at r.t. for 2 h. $Et_3N$ (741 mg, 7.327 mmol, 1.0 eq), DMAP (179 mg, 1.465 mmol, 0.2 eq) and 1-O-benzyl-2-N-3-O-dibutyryl-D-glucosamine (3 g, 7.327 mmol, 1.0 eq) were added to the mixture. The reaction mixture was stirred at r.t. for 16 h. $Et_2O$ (100 mL) and $H_2O$ (100 mL) were added to reaction mixture. The organic layer was washed with $H_2O$ (200 mL) and 1 M sodium hydroxide solution (100*2 mL), dried by anhydrous sodium sulfate and concentrated under reduced pressure. The residual material was purified by flash column chromatography (eluent: MeOH/DCM=1/100~1/50) to afford 1-O-benzyl-2-N-3,6-di-O-tributyryl-D-glucosamine (1.35 g, 38.5%). The compound thus obtained (1.35 g, 2.805 mmol, 1 eq) was dissolved in MeOH (7 mL), followed by addition of AcOH (7 mL), and then Pd/C (10%, 2.20 g). The mixture was stirred at 35° C. under $H_2$ atmosphere for 48 h. The mixture was filtered. The filtration was concentrated under reduced pressure. The residual material was purified by flash column chromatography (eluent: MeOH/DCM=1/100~1/50) to afford the title compound (741.5 mg, 67.9%); $^1$H NMR (500 MHz, $CD_3OD$) δ ppm 0.88-1.06 (m, 9H), 1.55-1.77 (m, 6H), 2.12-2.25 (m, 2H), 2.27-2.45 (m, 4H), 3.59 (t, J=9.5 Hz, 1H), 3.79-3.87 (m, 0.14H), 4.05-4.17 (m, 2H), 4.28 (dt, J=11.5, 5.0 Hz, 1H), 4.38-4.50 (m, 1H), 4.75 (d, J=8.0 Hz, 0.14H), 5.07 (d, J=3.5 Hz, 1H), 5.26 (t, J=10.5 Hz, 1H), 7.67 (d, J=9.0 Hz, 0.44H); $^{13}$C NMR (125 MHz, $CD_3OD$) δ ppm 12.53, 12.58, 17.98, 18.02, 18.92, 35.46, 35.69, 37.44, 52.25, 62.97, 68.75, 69.26, 73.14, 91.41, 173.84, 174.73; m/z (ESI$^+$): 390.0.

Example 49. Preparation of 2-N-butyryl-4-O-(D-glucopyranosyl)-D-glucosamine (Compound 89)

Acetic anhydride (34.27 g, 340 mmol, 6 eq) was added to a solution of D-glucose (10 g, 5.6 mmol, 1 eq) and DMAP (0.69 g, 0.056 mmol, 0.1 eq) in pyridine (150 mL). The mixture was stirred at 20° C. for 16 h. Pyridine was removed under reduced pressure. The residue was washed by PE (150 mL), and the solid was collected and dried to give 1,2,3,4,6-pentaacetyl-D-glucopyranose (12 g, 55% yield) as a white solid. Phenylmethanamine (2.866 g, 26.8 mmol, 1.1 eq) was added to a solution of 1,2,3,4,6-penta-O-acetyl-D-glucopyranose (9.5 g, 24.4 mmol, 1 eq) in THF (40 mL). The mixture was stirred at 25° C. for 25 h. The mixture was concentrated under reduced pressure and purified by flash column chromatography (eluent: MeOH/DCM=1/100~1/70) to afford 2,3,4,6-tetra-O-acetyl-D-glucopyranose (9 g) as an oil. This compound (9.5 g, 27.3 mmol, 1 eq) was dissolved in DCM (100 mL), followed by addition of DBU (0.831 g, 5.46 mmol, 0.2 eq) at 0° C. for 10 min, then 2,2,2-trichloroacetonitrile (11.23 g, 98.2 mmol, 3.6 eq), drop-wise. The mixture was stirred at 25° C. for 3 h, then concentrated under reduced pressure. The residual material was purified by flash column chromatography (eluent: MeOH/DCM=1/100~1/70) to afford 2,3,4,6-tetra-O-acetyl-D-glucopyranosyl trichloroacetimidate (8.5 g, 63% yield) as an oil. The solution of $BF_3$ in ether (1.695 g, 12 mmol, 2 eq) was drop added to the solution of 2-N-butyryl-1,3,6-tri-O-benzyl-D-glucosamine (3.102 g, 5.97 mmol, 1 eq) and 2,3,4,6-tetra-O-acetyl-D-glucopyranosyl trichloroacetimidate (4.4 g, 8.96 mmol, 1.5 eq) in DCM (100 mL). The mixture was stirred at 25° C. for 1 h, and then the pH of the mixture was adjusted to 7. The mixture was then washed by brine (30 mL×3), and dried by $Na_2SO_4$. The organic phase was concentrated under reduced pressure and purified by flash column chromatography (eluent: MeOH/DCM=1/

100~1/100) to afford the corresponding disaccharide derivative (2.5 g, 50% yield) as a white solid. This disaccharide derivative (2.45 g, 2.88 mmol, 1 eq) was dissolved in MeOH (25 mL) and AcOH (25 mL). To the solution was added Pd/C (1 g, 10%, wet) under $H_2$. The mixture was stirred at 25° C. for 16 h. The mixture was filtered and concentrated under reduced pressure. The residual material was purified by flash column chromatography (eluent: MeOH/DCM=1/100~1/20) to afford 2-N-butyryl-4-O-(2,3,4,5-tetra-O-acetyl-D-glucopyranosyl)-D-glucosamine (0.5 g, 31% yield) as a white solid. To a solution of this intermediate compound (0.5 g, 0.86 mmol, 1 eq) in MeOH (10 mL) was added sodium methoxide (0.023 g, 0.43 mmol, 0.5 eq). The mixture was stirred at 25° C. for 16 h, then concentrated under reduced pressure. The residual material was dissolved in $H_2O$ (1.5 mL), and stirred with acidic ion exchange resin. The mixture was filtered and the filtrate was concentrated under reduced pressure, affording the title compound (0.26 g, 73% yield). $^1$H NMR (500 MHz, D2O) δ 5.23 (s, 0.49H), 5.15 (s, 0.14H), 5.07 (s, 0.09H), 4.67-4.48 (m, 1H), 4.38 (s, 0.12H), 4.18 (dd, J=9.5, 5.0 Hz, 0.14H), 3.99 (d, J=10.5 Hz, 1H), 3.93 (d, J=14.0 Hz, 3H), 3.90-3.82 (m, 0.68H), 3.81-3.68 (m, 3H), 3.62 (s, 0.42H), 3.59-3.47 (m, 2H), 3.47-3.41 (m, 1H), 3.34 (q, J=11.0, 3.0 Hz, 1H), 2.49-2.11 (m, 2H), 1.64 (q, J=14.0, 7.0 Hz, 2H), 1.09-0.72 (m, 3H). $^{13}$C NMR (125 MHz, D2O) δ 178.64, 177.72, 177.49, 102.56, 94.84, 92.86, 90.53, 79.21, 78.82, 76.40, 75.96, 75.47, 75.11, 74.78, 73.16, 72.31, 71.56, 70.71, 70.21, 69.43, 69.05, 67.47, 60.54, 59.92, 56.18, 53.69, 52.61, 37.95, 37.52, 18.95, 12.59. m/z (ESI⁻) 410.

Example 50. Preparation of 2-N-butyryl-6-$^{18}$O-D-glucosamine (Compound 90)

Triphenylphosphine (667 mg, 2.54 mmol, 1.2 eq) was added to a solution of 2-N-butyryl-1,3,4-tri-O-benzyl-D-glucosamine (1.12 g, 2.2 mmol, 1 eq) and benzoic-$^{18}$O$_2$ acid (0.325 g, 2.58 mmol, 1.2 eq) in THF (50 mL), followed by addition of DEAD (0.44 g, 2.53 mmol, 1.2 eq). The mixture was stirred at r.t. for 16 h. Then the mixture was concentrated under reduced pressure. The residual material was purified by flash column chromatography (eluent: MeOH/DCM=1/200) to afford 6-$^{18}$O-6-O-($^{18}$O-benzoyl)-2-N-butyryl-1,3,4-tri-O-benzyl-D-glucosamine (1.2 g, 86.8%) with 98.7% abundance of $^{18}$O-isotope at 6-O-position and benzoyl oxygen. This isotope-labelled intermediate (1.2 g, 1.9 mmol, 1 eq) was dissolved in MeOH (90 mL), followed by addition of sodium methoxide (0.21 g, 3.8 mmol, 2 eq). The mixture was stirred at r.t. for 16 h, then concentrated under reduced pressure. The residual material was purified by flash column chromatography (eluent: MeOH/DCM=1/100) to afford 6-$^{18}$O-2-N-butyryl-1,3,4-tri-O-benzyl-D-glucosamine (0.89 g, 89.8%). This tribenzyl derivative (0.89 g, 1.7 mmol, 1 eq) was dissolved in MeOH (25 mL), followed by addition of acetic acid (25 mL), and then Pd/C (10%, 0.8 g). The mixture was stirred at 30° C. under $H_2$ atmosphere for 48 h, then filtered. The filtration was concentrated under reduced pressure. Then DCM (25 mL) was added to the residual material and the mixture was stirred for 10 min. The solid was collected by filtration, and dried, affording the title compound (0.36 g, 84.3%) with 97.5% abundance of $^{18}$O-isotope at 6-O-position: $^1$H NMR (500 MHz, D$_2$O) δ 5.23 (d, J=3.6 Hz, 0.65H), 4.74 (d, J=8.7 Hz, 0.4H), 3.98-3.85 (m, 2.57H), 3.84-3.68 (m, 1.94H), 3.61-3.44 (m, 1.47H), 2.32 (t, J=7.2 Hz, 2H), 1.66 (q, J=7.4 Hz, 2H), 0.95 (td, J=7.4, 3.9 Hz, 3H). $^{13}$C NMR (125 MHz, D$_2$O) δ 177.54, 94.99, 90.88, 75.93, 73.83, 71.55, 70.55, 70.16, 69.94, 60.75, 60.59, 56.55, 53.99, 37.98, 37.57, 18.99, 12.65; m/z (ESI⁻): 250.2: (ESI⁻): 252.1.

Example 51. Preparation of 2-N-4-O-dibutyryl-6-O-(2-hydroxybenzoyl)-D-glucosamine (Compound 91)

Butyric anhydride (0.742 g, 4.69 mmol, 1.5 eq) was added to a solution of 1,3-di-O-benzyl-2-N-butyryl-6-O-(2-benzyloxybenzoyl)-D-glucosamine (2 g, 3.13 mmol, 1 eq) and DMAP (0.038 g, 0.31 mmol, 0.1 eq) in pyridine (20 mL). The mixture was stirred at 35° C. for 2 h. Pyridine was removed under reduced pressure. The residual material was purified by flash column chromatography (eluent: MeOH/DCM=1/100~1/100) to afford 1,3-di-O-benzyl-2-N-4-O-dibutyryl-6-O-(2-benzyloxybenzoyl)-D-glucosamine (2 g, 90% yield) as a white solid. This solid (2. g, 2.82 mmol, 1 eq) was dissolved in MeOH (15 mL) and AcOH (15 mL), followed by addition of Pd/C (1 g, 10%, wet) under $H_2$. The mixture was stirred at 25° C. for 40 h. The mixture was filtered and concentrated under reduced pressure. The residual material was purified by flash column chromatography (eluent: MeOH/DCM=1/100~1/30) to afford the title compound (0.24 g, 20% yield) as a white solid. $^1$H NMR (500 MHz, CD$_3$OD) δ 7.94 (d, J=7.5 Hz, 1H), 7.49 (t, J=7.5 Hz, 1H), 6.93 (dd, J=18.0, 9.0 Hz, 2H), 5.59 (s, 0.007H), 5.49 (s, 0.002H), 5.19 (d, J=2.0 Hz, 0.85H), 5.06 (t, J=9.5 Hz, 0.97H), 4.77 (d, J=7.0 Hz, 0.17H), 4.57 (d, J=14.5 Hz, 0.32H), 4.49 (d, J=11.5 Hz, 0.83H), 4.39 (dd, J=12.0, 4.5 Hz, 0.96H), 4.31 (d, J=9.5 Hz, 0.82H), 4.04 (dd, J=10.5, 2.5 Hz, 0.83H), 3.94 (t, J=10.0 Hz, 0.81H), 3.85 (d, J=7.5 Hz, 0.14H), 3.80-3.71 (m, 0.26H), 2.45-2.32 (m, 2H), 2.25 (t, J=7.5 Hz, 2H), 1.78-1.54 (m, 4H), 0.96 (q, J=13.5, 6.5 Hz, 6H). $^{13}$C NMR (125 MHz, CD3OD) δ 175.69, 175.23, 173.14, 169.52, 161.31, 135.60, 129.97, 119.00, 116.98, 112.14, 95.74, 91.28, 72.05, 71.68, 71.30, 68.99, 67.22, 63.33, 63.15, 57.54, 54.42, 37.94, 37.52, 35.57, 18.98, 17.96, 12.63. m/z (ES⁺) 340.0, m/z (ES⁻) 338.0.

Example 52. Preparation of 2-N-butyryl-6-O-(2-N-D-glucosaminocarbonyl)-D-glucosamine (Compound 92)

TBSCl (18.7 g, 124 mmol, 2 eq) was added to a solution of 1,3-di-O-benzyl-2-N-butyryl-D-glucosamine (20 g, 62 mmol, 1 eq) and DMAP (0.75 g, 6.2 mmol, 0.1 eq) in pyridine (200 mL). The mixture was stirred at r.t. under N$_2$ atmosphere for 3 h, and pyridine was removed under reduced pressure. The residual material was dissolved with EtOH (40 mL) and added to H$_2$O (400 mL). The white suspension was filtered, and the filter cake washed with water, then dried at 50° C. under vacuum to give 1,3-di-O-benzyl-2-N-butyryl-6-O-trimethylsilyl-D-glucosamine (25 g, 74%). The product was dissolved (25 g, 46 mmol, 1 eq) in DMF (300 mL), followed by addition of benzyl bromide (9.6 g, 56.1 mmol, 1.2 eq). To the mixture was added NaH (2.8 g, 69.2 mmol, 2.7 eq) in batches while keeping the temperature below 0° C. The mixture was warmed to r.t. and stirred at r.t. for 4 h. The mixture was poured into H$_2$O (2000 mL). The mixture was stirred at r.t. for 1 h. The solid was collected by filtration, washed with H$_2$O (100 mL) and PE (100 mL) subsequently, and dried, giving 1,3,4-tri-O-benzyl-2-N-butyryl-6-O-trimethylsilyl-D-glucosamine (27 g, 92.6%). The obtained compound (27 g, 42.6 mmol, 1 eq) was dissolved in DCM (15 mL), treated with 4 M HCl in Dioxane (27 mL). The mixture was stirred at r.t. for 2 h, and concentrated under reduced pressure. The residual material was purified by flash column chromatography (eluent: MeOH/DCM=1/200~1/40) to afford 1,3,4-tri-O-benzyl-2-N-butyryl-D-glucosamine (16 g, 72.3%). The compound thus obtained (5.2 g, 10 mmol, 1 eq) and 4-nitrophenyl carbonochloridate (2.4 g, 12 mmol, 1.2 eq) were dissolved in DCM (100 mL), followed by addition of triethylamine (1.5 g, 15 mmol, 1.5 eq). The mixture was stirred at r.t. for 16 h, and solvent was removed under reduced pressure. The residual material was purified by flash column chromatography (eluent: MeOH/DCM=1/200) to afford 1,3,4-tri-O-benzyl-2-N-butyryl-6-O-(4-nitrobenzyloxycarbonyl)-D-glucosamine (4.3 g, 62.8%). This product (1.05 g, 1.5 mmol, 1 eq) and D-glucosamine hydrochloride (0.32 g, 1.5 mmol, 1 eq) were dissolved in DMF (50 mL), followed by addition of triethylamine (0.24 g, 2.4 mmol, 1.5 eq). The mixture was stirred at r.t. for 16 h, and solvent was removed under reduced pressure. The residual material was purified by flash column chromatography (eluent: MeOH/DCM=1/200) to give 1,3,4-tri-O-benzyl-2-N-butyryl-6-O-(2-N-D-glucosaminocarbonyl)-D-glucosamine (1.1 g, 98.9%). The latter compound (1.1 g, 1.5 mmol, 1 eq) was dissolved in MeOH (35 mL), followed by addition of Pd/C (10%, 0.8 g) and acetic acid (35 mL). The mixture was stirred at 30° C. under $H_2$ atmosphere for 16 h. The mixture was filtered. The filtration was concentrated under reduced pressure. The mixture was filtered. The filtration was concentrated under reduced pressure. Then DCM (15 mL) was added to residual material and stirred for 10 min, the solid was filtered, and dried to afford compound 92 (0.46 g, 66.6%). $^1$H NMR (500 MHz, $D_2O$) δ 5.20 (d, J=3.5 Hz, 0.64H), 5.16 (d, J=3.5 Hz, 0.81H), 4.40-4.21 (m, 1.5H), 4.00 (dd, J=9.6, 2.8 Hz, 0.7H), 3.93-3.78 (m, 2.37H), 3.78-3.64 (m, 2.66H), 3.64-3.57 (m, 0.77H), 3.55-3.39 (m, 2.62H), 3.33 (d, J=14.1 Hz, 0.19H), 2.25 (t, J=7.2 Hz, 2H), 1.59 (q, J=7.4 Hz, 2H), 0.88 (td, J=7.4, 4.0 Hz, 3H). $^{13}$C NMR (126 MHz, $D_2O$) δ 177.81, 177.57, 158.34, 158.08, 95.10, 91.23, 90.97, 81.77, 75.94, 73.95, 73.75, 73.60, 71.56, 71.08, 70.44, 70.08, 70.01, 69.85, 69.68, 69.63, 63.88, 60.77, 60.63, 58.42, 56.48, 55.64, 53.92, 37.99, 37.58, 19.00, 12.66; m/z ($ESI^-$): 453; ($ESI^+$): 455.1.

Example 53. Preparation of 1,3,4-tri-O-acetyl-2-N-butyryl-6-O-(2-acetyloxybenzoyl)-D-glucosamine (Compound 93)

Acetic anhydride (2.22 g, 2.2 mmol, 4 eq) was added to a solution of 2-N-butyryl-6-O-(2-hydroxybenzoyl)-D-glucosamine (2 g, 5.4 mmol, 1 eq) and DMAP (0.032 g, 0.27 mmol, 0.05 eq) in pyridine (50 mL). The mixture was stirred at 35° C. for 2 h. Pyridine was removed under reduced pressure. The residue was purified by flash column chromatography (eluent: MeOH/DCM=1/100~1/70) to afford the title compound (0.9 g, 31% yield) as a white solid. $^1$H NMR (500 MHz, $CD_3OD$) δ 8.02 (d, J=7.5 Hz, 1H), 7.64 (t, J=7.5 Hz, 1H), 7.39 (t, J=7.5 Hz, 1H), 7.16 (d, J=8.0 Hz, 1H), 6.14 (s, 1H), 5.34 (t, J=10.0 Hz, 1H), 5.15 (t, J=9.5 Hz, 1H), 4.51-4.39 (m, 2H), 4.36 (d, J=12.5 Hz, 1H), 4.24 (d, J=9.0 Hz, 1H), 2.37 (s, 3H), 2.19 (s, 3H), 2.15 (t, J=7.0 Hz, 2H), 2.02 (s, 3H), 1.98 (s, 3H), 1.79-1.42 (m, J=14.0, 6.9 Hz, 2H), 0.89 (t, J=7.0 Hz, 3H). $^{13}$C NMR (125 MHz, $CD_3OD$) δ 175.18, 170.52, 169.92, 169.81, 169.37, 164.16, 150.62, 133.96, 131.37, 125.83, 123.60, 122.90, 90.06, 70.35, 69.70, 68.59, 62.32, 50.40, 37.11, 19.64, 19.35, 19.25, 19.19, 18.89, 12.45. m/z ($ESI^+$) 537.9.

Example 54. Preparation of 2-N-butyryl-6-O-((3-carboxy-1-propyl)aminocarbonyl)-D-glucosamine (Compound 94)

1,3,4-Tri-O-benzyl-2-N-butyryl-6-O-(4-nitrobenzoyl)-D-glucosamine (1.4 g, 2 mmol, 1 eq) and 4-aminobutanoic acid (0.2 g, 2 mmol, 1 eq) were dissolved in DMF (200 mL), followed by addition of triethylamine (0.3 g, 3 mmol, 1.5 eq). The mixture was stirred at r.t. for 16 h, and DMF was removed under reduced pressure. The residual material was purified by flash column chromatography (eluent: MeOH/DCM=1/50) to afford 1,3,4-tri-O-benzyl-2-N-butyryl-6-O-((3-carboxy-1-propyl)aminocarbonyl)-D-glucosamine (1.05 g, 81.0%). The obtained compound (1.05 g, 1.65 mmol, 1 eq) was dissolved in MeOH (10 mL), followed by addition of Pd/C (10%, 0.8 g) and acetic acid (10 mL). The mixture was stirred at 30° C. under $H_2$ atmosphere for 16 h. The mixture was filtered. The filtration was concentrated under reduced pressure. The residual material was dissolved with water and dried at −40° C. under vacuum to give the title compound (510 mg, 81.7%); $^1$H NMR (500 MHz, $D_2O$) δ 8.09 (d, J=10.1 Hz, 0.03H), 8.01 (d, J=8.9 Hz, 0.26H), 5.14 (d, J=3.5 Hz, 0.59H), 4.68 (d, J=8.5 Hz, 0.43H), 4.44-4.09 (m, 1.87H), 4.05-3.78 (m, 1.43H), 3.77-3.60 (m, 1.35H), 3.60-3.37 (m, 1.40H), 3.14 (t, J=6.7 Hz, 2H), 2.38 (t, J=7.3 Hz, 2H), 2.23 (q, J=7.1 Hz, 2H), 1.76 (p, J=6.8 Hz, 2H), 1.58 (h, J=7.5 Hz, 2H), 0.87 (t, J=7.3 Hz, 3H). $^{13}$C NMR (125 MHz, $D_2O$) δ 178.22, 177.77, 177.52, 158.29, 158.24, 95.07, 90.93, 73.76, 73.60, 70.43, 70.14, 70.04, 69.78, 69.66, 63.52, 56.47, 53.90, 52.19, 39.67, 37.97, 37.56, 31.00, 30.96, 24.33, 18.98, 12.63; m/z ($ESI^-$): 376.9.

Example 55. General Method for Pharmacokinetic Study of Compounds of the Invention A test compound is dissolved in water at a concentration determined by the desired dose and dosing volume for the specific animal to which the compound is to be administered. A calculated volume of dosing solution is administered to the animal (PO, SQ, IP, or IV). A blood sample is collected following administration of the test compound at specific time points (such as 0 minutes (min), 5 min, 10 min, 15 min, 30 min, 1 hour (h), 1.5 h, 2 h, 3 h, 4, 6 h, etc.). The blood sample is converted to a plasma sample using standard techniques. The plasma samples are analyzed to determine the concentration of the test compound and, in some cases, GlcNBu.

Example 56. Pharmacokinetic Studies for Compounds in Sprague-Dawley (SD) Rats

According to the above general procedure, SD rats were grouped randomly into groups of six (n=6). The test compound, GlcNBu or a compound provided herein, was administered to the animals by oral gavage at a dose of 0.93 mmol/kg. For illustration purposes, GlcNBu was given at an oral dose of 232 mg/kg (0.93 mmol/kg), and compound 16 was administered at an equal molar dose (0.93 mmol/kg, i.e., 362 mg/kg). At pre-set time points, blood was taken through orbital venous plexus extraction, and the samples were analyzed using LC/MS-MS to determine the GlcNBu concentration in the plasma.

Figure 2A:
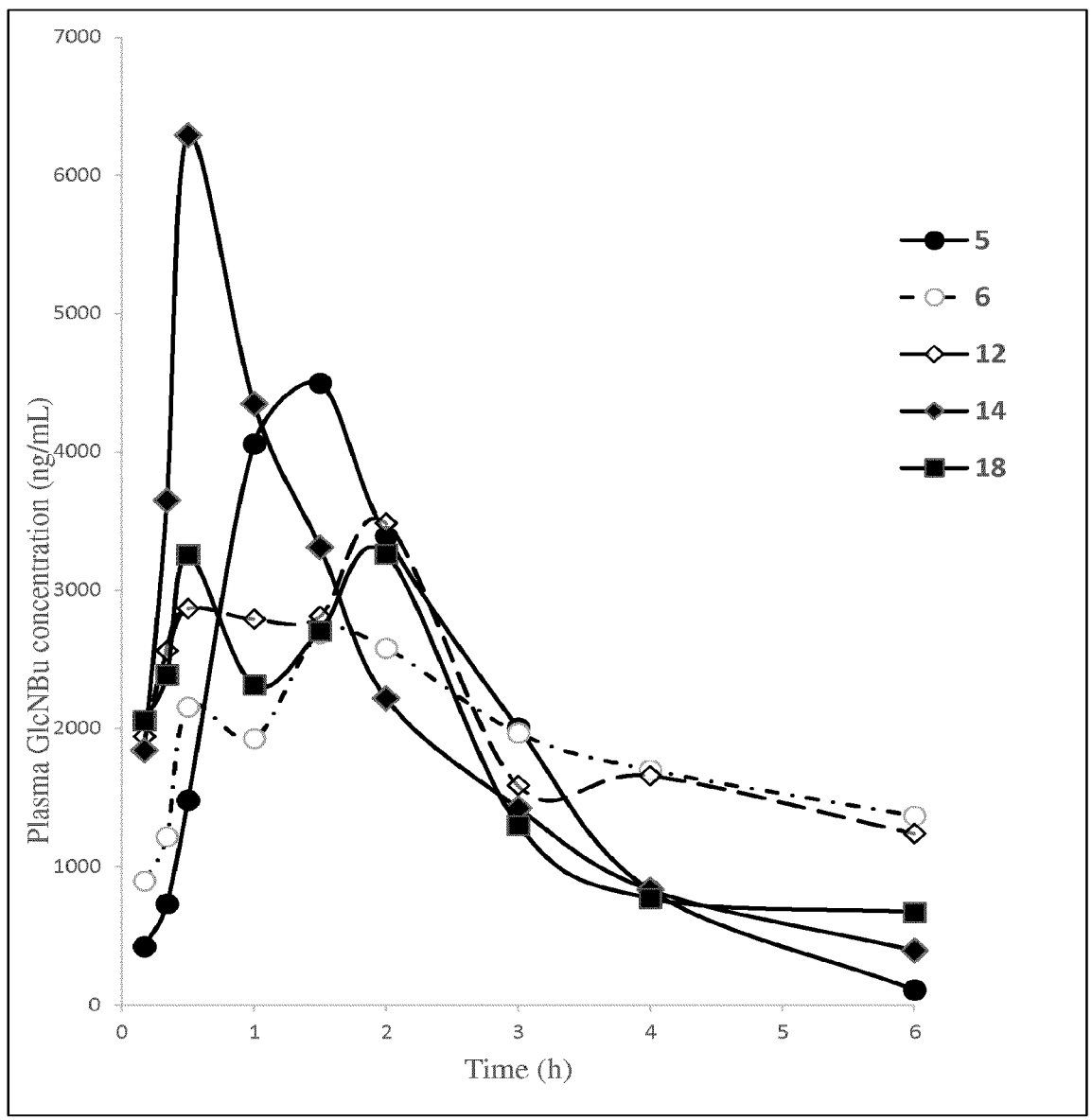
FIGS. 2A-2B show comparison of mean plasma GLcNBu concentration versus time curves following oral administration of Compounds 5, 6, 12, 14, and 18 (2A) and 41, 80, and 88 (2B) at a dose of 0.93 mmol/kg.
Figure 2B:
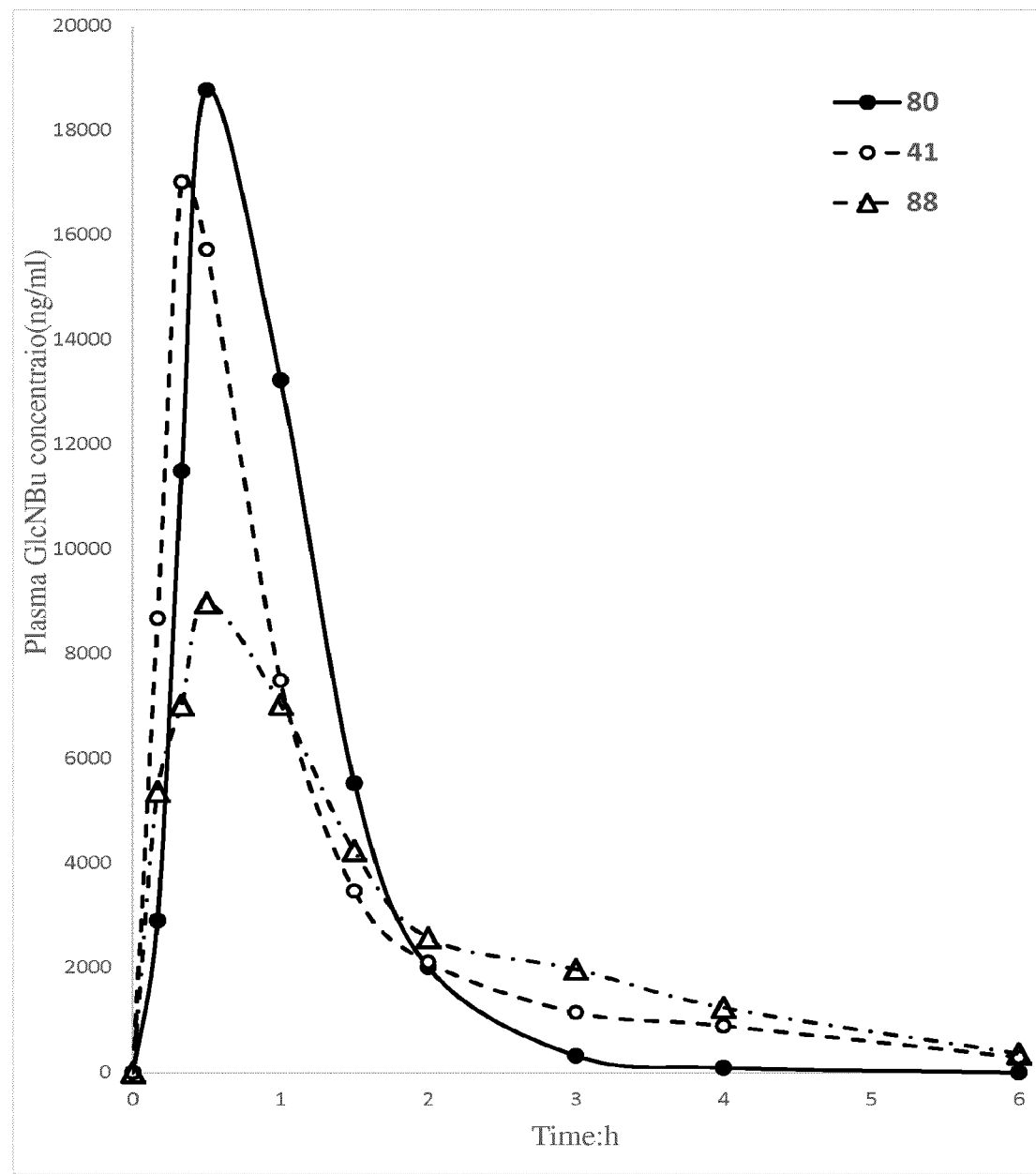
Figure 3:
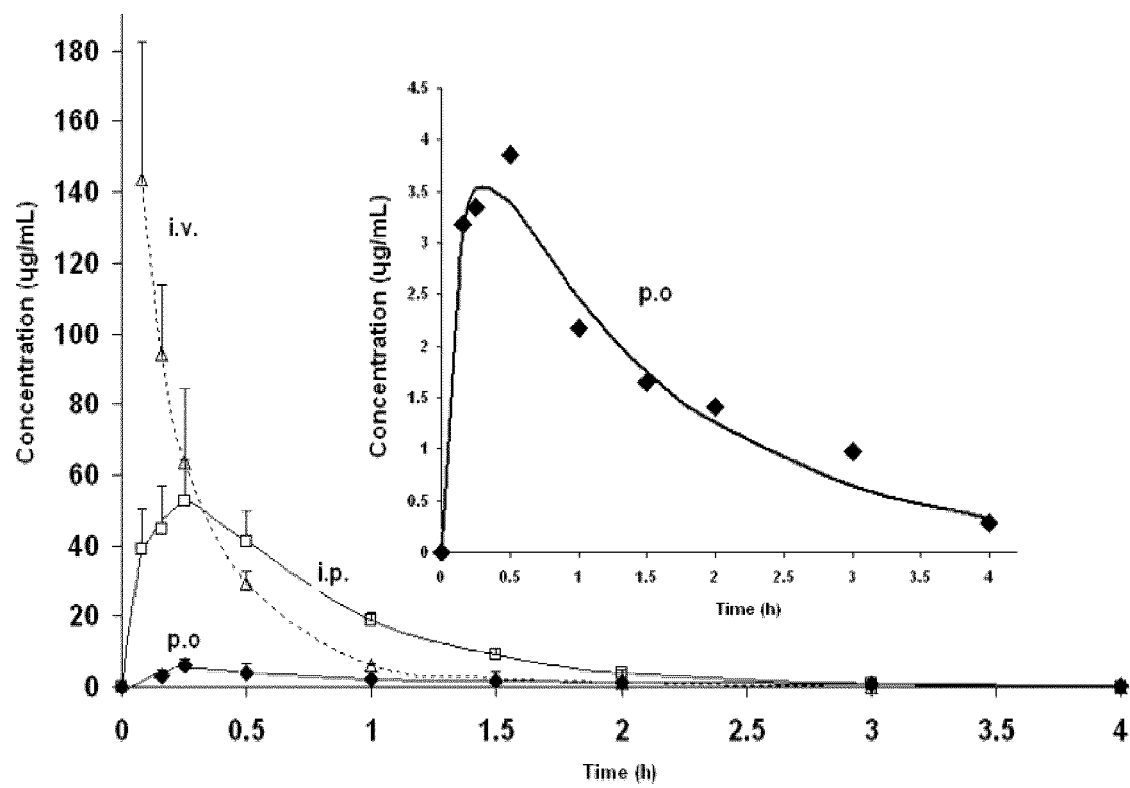
FIG. 3 shows mean plasma concentration versus time curves of GLcNBu following different routes of administration, as indicated (i.v., i.p., and p.o., respectively). The insert is the enlarged curve following oral administration (*J. Pharm. Pharmaceut. Sci.,* 9 (3): 359-364, 2006).
Figure 4A:
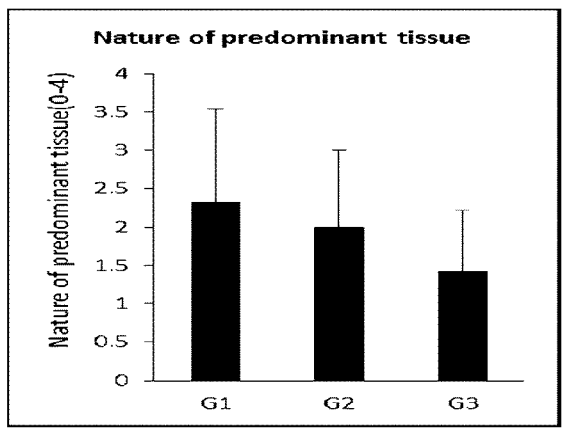
FIGS. 4A-4H show various histological parameters obtained in a MIA rat model for osteoarthritis for control animals (G1) and animals treated with compound 16 at 234 mg/kg (G2) or 468 mg/kg (G3), as follows: 4A: Nature of predominant tissue, 4B: Surface regularity, 4C: Chondrocyte clustering, 4D: Structural integrity, 4E: Degenerative changes in cartilage, 4F: Inflammatory response in subchondral bone region, 4G: Neo-vascularization, and 4H: Osteophytes.
Figure 4B:
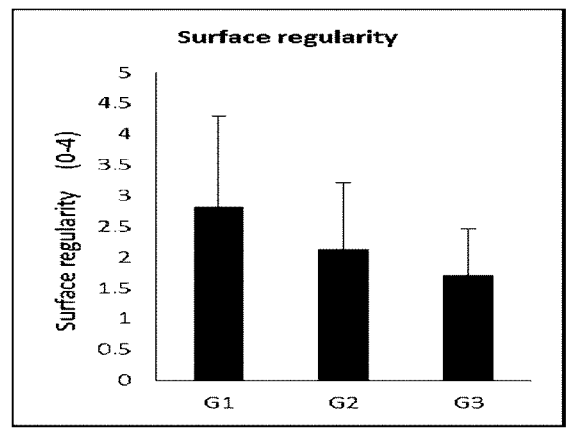
Figure 4C:
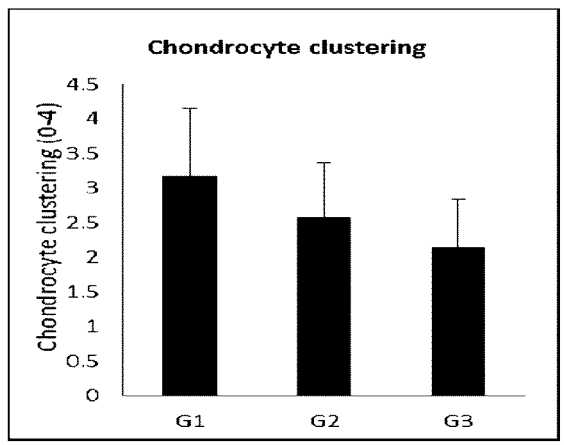
Figure 4D:
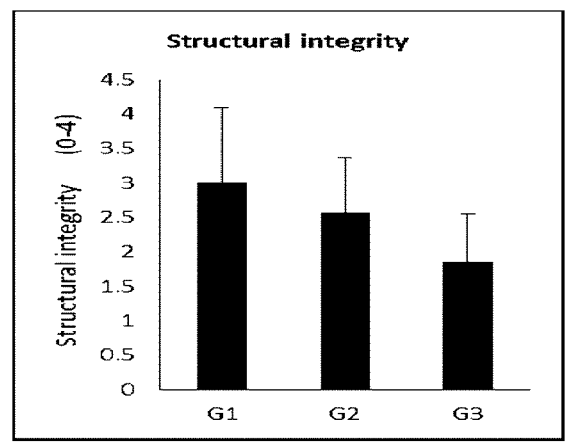
Figure 4E:
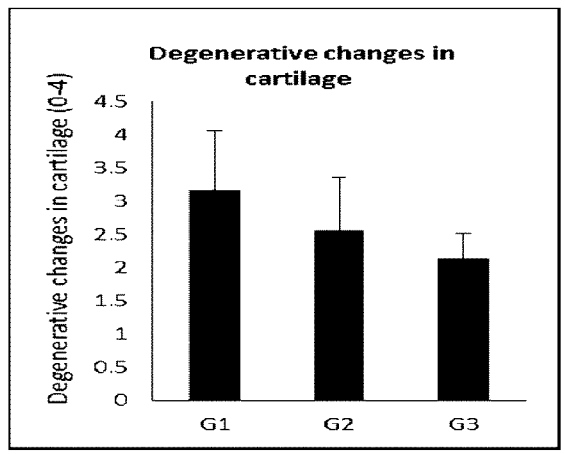
Figure 4F:
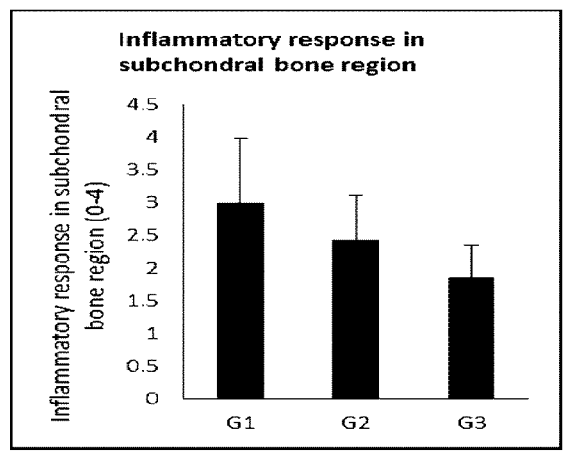
Figure 4G:
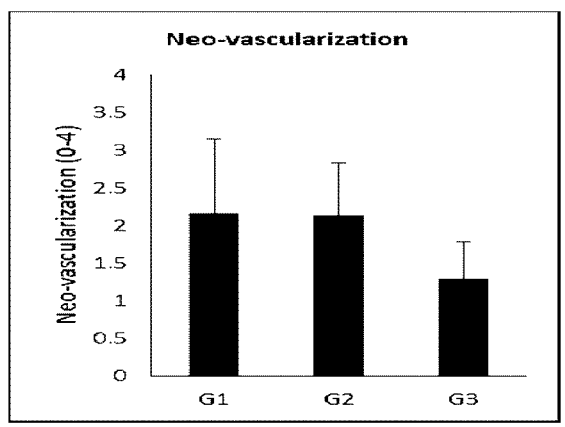
Figure 4H:
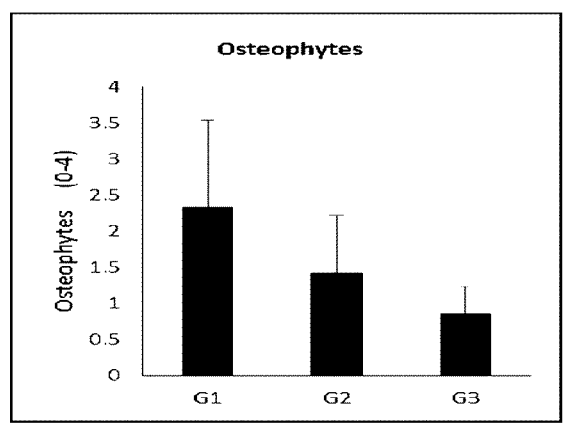

The results of an exemplary pharmacokinetic study are presented in FIGS. 1 and 2. The plasma GlcNBu concentration-time curves following an oral administration of GlcNBu and compound 16 are shown in FIG. 1. In the figure, Curves labeled with -●- and -▲- represent plasma GlcNBu concentration following oral administration of GlcNBu (232 mg/kg, or 0.93 mmol/kg) and compound 16 (232 mg/kg, or 0.93 mmol/kg), respectively. The results indicate that at the mole-equivalent oral dose, compound 16 improved plasma drug exposure significantly, with about 10-fold increase of Cmax for the plasma GlcNBu concentration. FIG. 2A and FIG. 2B show examples of other compounds of the invention, presented in plasma GlcNBu concentration versus time curves; a summary of pharmacokinetic parameters for these compounds is given in Table 4 and Table 5.

TABLE 4

PK parameters for GlcNBu after administration of the indicated compound.

| Parameter | Unit | Compound | | | | | |
|---|---|---|---|---|---|---|---|
| | | 5 | 6 | 12 | 14 | 18 | GlcNBu |
| AUC(0-t) | ug/L * h | 10850.9 | 11179.2 | 12412 | 10799 | 9895 | 7938 |
| AUC(0-∞) | ug/L * h | 10963.3 | 22557.6 | 16842 | 11704 | 10348 | 7992 |
| $t_{1/2}$ | h | 0.7 | 5.8 | 2.677 | 1.603 | 1.18 | 0.741 |
| Tmax | h | 1.5 | 1.5 | 2 | 1 | 1.25 | 1 |
| Vz/F | L/kg | 20.9 | 83.2 | 51.15 | 44.08 | 3.47 | 31.184 |
| CLz/F | L/h/kg | 20.4 | 9.9 | 13.24 | 19.05 | 1.96 | 29.157 |
| Cmax | ug/L | 4496 | 2685 | 3483 | 4345 | 3570 | 3303 |

TABLE 5

PK parameters for GlcNBu after administration of the indicated compound[1].

| Compound # | $AUC_{0-t}$ (μg/L * h) | $AUC_{0-\infty}$ (μg/L * h) | $t_{1/2}$ (h) | $T_{max}$ (h) | Vz/F (L/kg) | CLz/F (L/h/kg) | $C_{max}$ (μg/L) |
|---|---|---|---|---|---|---|---|
| 27 | 8597 | 8918 | 2 | 1 | 77 | 33 | 4890 |
| 30 | 512 | 810 | 2 | 2 | 86 | 25 | 276 |
| 41 | 19303 | 19890 | 1 | 0 | 23 | 11 | 17017 |
| 56 | 2190 | 2520 | 2 | 2 | 18 | 8 | 588 |
| 73 | 8740 | 9346 | 2 | 2 | 64 | 25 | 4300 |
| 74 | 662 | 889 | 1 | 0 | 28 | 22 | 426 |
| 75 | (—) | (—) | (—) | (—) | (—) | (—) | (—) |
| 76 | (—) | (—) | (—) | (—) | (—) | (—) | (—) |
| 77 | 874 | 1903 | 4 | 2 | 68 | 11 | 345 |
| 78 | 4582 | 5038 | 2 | 0 | 9 | 4 | 4960 |
| 79 | (—) | (—) | (—) | (—) | (—) | (—) | (—) |
| 80 | 19988 | 19990 | 0 | 1 | 1 | 1 | 18770 |
| 82 | 5932 | 5970 | 1 | 2 | 3 | 3 | 2287 |
| 83 | 3037 | 3638 | 2 | 3 | 183 | 60 | 657 |
| 84 | 6532 | 9919 | 4 | 1 | 10 | 2 | 1723 |
| 85 | 3156 | 3189 | 1 | 1 | 7 | 6 | 1180 |
| 86 | 1609 | 1941 | 1 | 2 | 187 | 113 | 678 |
| 87 | 7062 | 7157 | 1 | 0 | 4 | 3 | 3797 |
| 88 | 17129 | 17767 | 1 | 1 | 2 | 1 | 8967 |
| 89 | 1757 | 1942 | 1 | 2 | 10 | 10 | 1110 |
| 91 | 4355 | 5048 | 2 | 1 | 13 | 4 | 1700 |
| 92 | 1165 | 1166 | 1 | 1 | 11 | 25 | 901 |
| 93 | 1060 | 1080 | 1 | 0 | 27 | 20 | 906 |
| 94 | (—) | (—) | (—) | (—) | (—) | (—) | (—) |

[1](—): not detected

Example 57. Evaluation of a Novel Compound in Monosodium Iodoacetate-Induced Osteoarthritis (MIA) Model in Rat Knee Osteoarthritis was induced by intra-articular (i.a.) injection of MIA solution in the rat knee joint as follows: Briefly, rats were anesthetized with isoflurane and given a single i.a. administration of 2 mg of MIA dissolved in saline through the intrapatellar ligament of the right knee. MIA was administered in a volume of 50 μL. Basal readings were established using a group of control rats injected with 10% ethanol in water. Rats were randomized by initial body weight to groups of 6 or 7. After MIA injection, the MIA groups began treatment with either vehicle, or a test compound at a preset dose regime for a period of 28 days. Clinical observations were recorded, including body weight, joint swelling, and weight bearing, on pre-induction day (day 0), day 3, 5, 7, 14, 21 and/or 28. At the end of the study, the animals were euthanized by $CO_2$ and sacrificed. Joint samples including the tibia and femur were sectioned in the coronal plane and stained using both H&E and Safranin-O. Knee joints were examined and scored for cartilage degeneration, the presence of osteophytes, the amount and extent of calcified cartilage and subchondral bone damage, and the amount of synovial membrane inflammation using the Osteoarthritis Research Society International (OARSI) scoring system put forth in 2010 (Kraus, V. B. et al., Osteoarthritis Cartilage, 2010, Suppl 3:S35-52).

Example 58. Study of Compound 16 in MIA Model

Studies of compound 16 in the MIA model were conducted as described above. The MIA animals were randomized into four groups (n=6), and treated with vehicle (Group 1 (G1)), or compound 16 at 234 mg/kg (Group 2 (G2)) or 468 mg/kg (Group 3 (G3)). The weight bearing results are given in Table 6 below. On day 5, all the compound-treated groups showed significant increases in weight bearing on the back-right leg. The trend for increasing weight bearing was clear throughout the treatment period after day 5 for both treated groups, with significant increases at the high dose (G3) on day 14. Total histological scores from the vehicle group and the treated groups are shown in FIGS. 4A-4H.

TABLE 6

Weight bearing results for rats in MIA model treated with compound 16.

| Animal Group | | Pre-Injection (Day 0) % | Day 3 % | Day 5 % | Day 7 % | Day 14 % | Day 21 % | Day 28 % |
|---|---|---|---|---|---|---|---|---|
| 1 | Mean | 50.49 | 34.79 | 27.81 | 34.04 | 36.38 | 40.64 | 43.01 |
| | SD | 1.43 | 5.35 | 5.62 | 5.89 | 4.54 | 3.31 | 2.98 |
| 2 | Mean | 50.49 | 32.07 | 35.76** | 37.72 | 40.86 | 44.12 | 45.90 |
| | SD | 1.01 | 4.46 | 3.00 | 1.94 | 3.18 | 2.47 | 1.05 |
| 3 | Mean | 50.25 | 34.56 | 37.40** | 39.23 | 41.68* | 44.25 | 44.98 |
| | SD | 1.40 | 3.89 | 3.12 | 3.07 | 1.92 | 2.40 | 1.52 |

*Vs Group 1, $P < 0.05$;
**Vs Group 1, $P < 0.01$

The results indicate that osteophytes in the high dose group were significantly decreased compared with the vehicle group. The high dose treated group showed a clear trend of lowering all other mean values for each histological parameter evaluated in the study, including the Nature of Predominant Tissue, Surface Regularity, Structural Integrity, Chondrocyte Clustering, Degenerative Changes in Cartilage, Inflammatory Response in Subchondral Bone Region, and Neo-Vascularization. The lower morphological and numerical changes of chondrocytes and closer to normal nature of the tissue indicated that compound 16 slowed the articular cartilage degeneration in this MIA-induced OA rat model.

Example 59. Study of Compound 16 in Medial Meniscus Transection (MMT) Model in Rats In the rat MMT model, the unilateral knee (right knee) was cleaned and prepped for surgery. An incision was made over the medial aspect of the femoro-tibial joint. The medial collateral ligament was exposed via blunt dissection and transected to reflect the meniscus toward the femur. A full thickness cut was made through the meniscus at its narrowest point. The joint space was returned to normal, and the skin was closed and the animal allowed to recover. For the present study, at second day post MMT induction animals, G1 and G2 animals were treatment with vehicle and test compound 16 respectively. Animals were dosed 4 times every day, and were dosed by gavage for 4 weeks.

Figure 5:
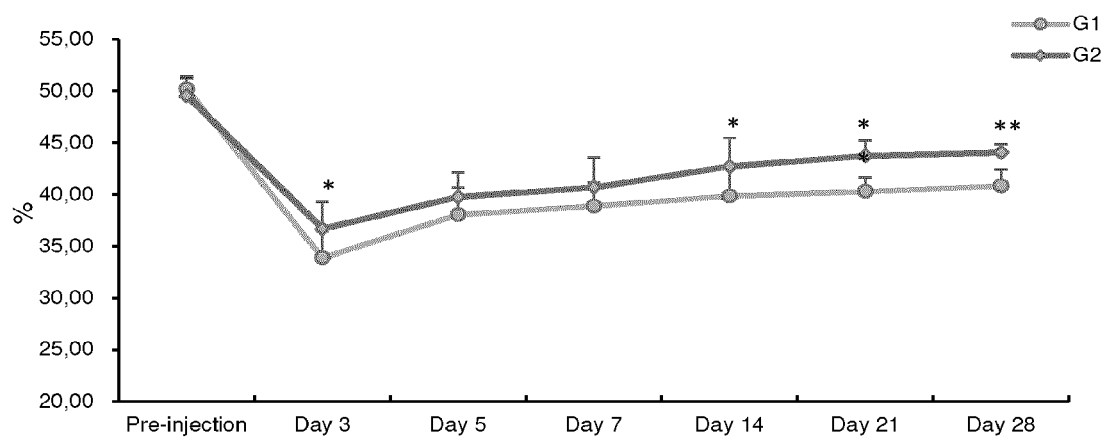
FIG. 5 shows weight bearing results for rats in a MMT model treated with compound 16 (G2) or vehicle (G1); *:Vs G1, P<0.05; **:Vs G1, P<0.01.
Figure 6A:
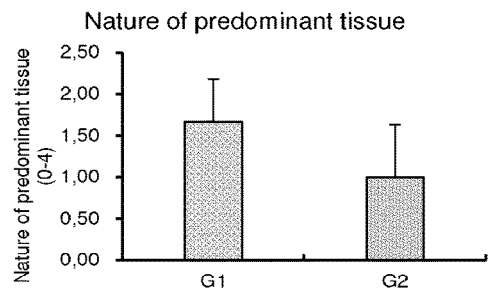
FIGS. 6A-6I show various histological parameters obtained in a MMT rat model for osteoarthritis for control animals (G1) and animals treated with compound 16 (G2), as follows: 6A: Nature of predominant tissue; 6B: Surface regularity; 6C: Structural integrity; 6D: Chondrocyte clustering (*:Vs G1, P<0.05); 6E: Degenerative changes in cartilage; 6F: Inflammatory response in subchondral bone region; 6G: Neo-vascularization; 6H: Osteophytes; and 6I: Total scoring.
Figure 6B:
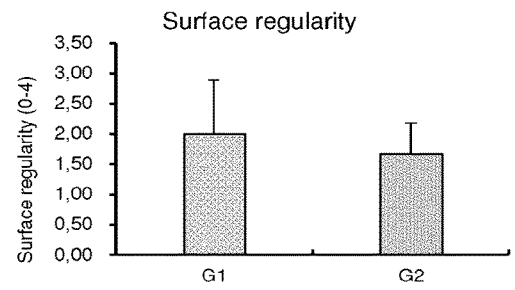
Figure 6C:
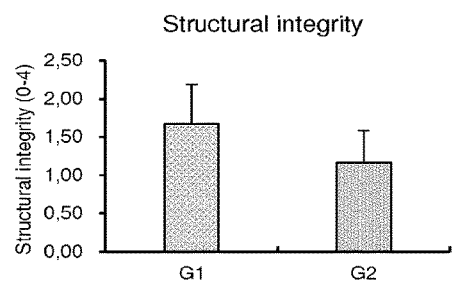
Figure 6D:
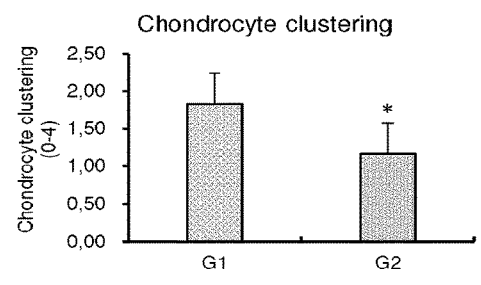
Figure 6E:
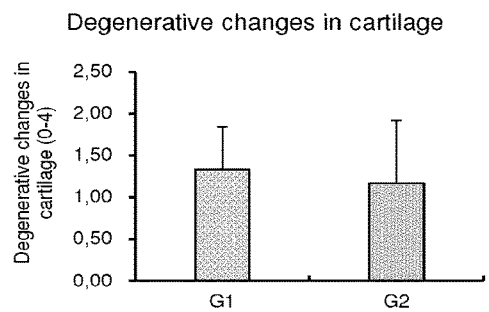
Figure 6F:
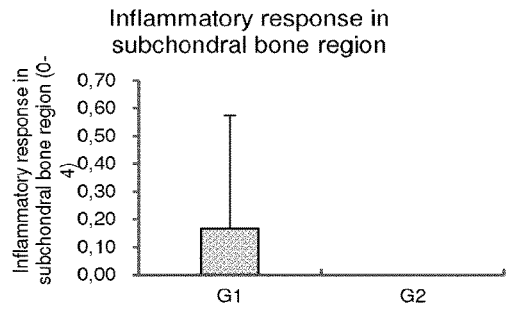
Figure 6G:
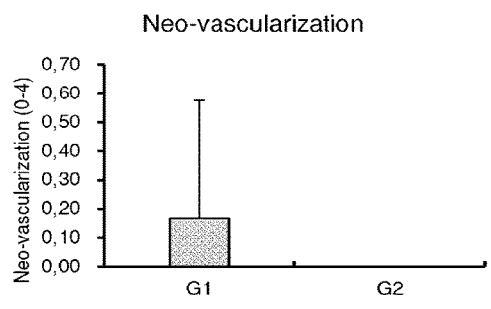
Figure 6H:
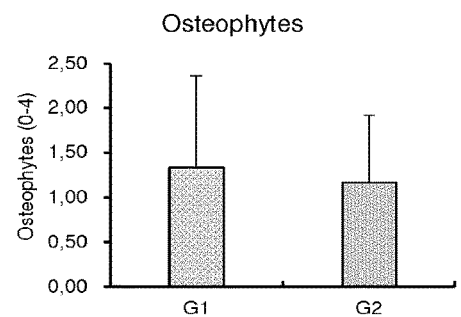
Figure 6I:
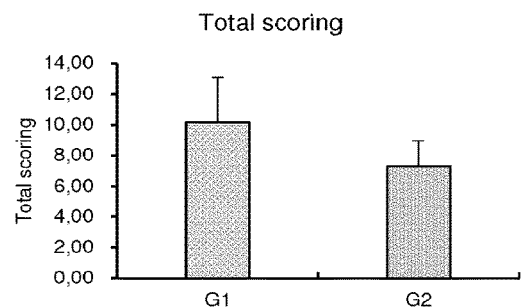

After MMT, weight bearing of the right paw was decreased sharply in both groups (see Table 7; FIG. 5) until Day 3. The rebounds of the weight bearing on the right paw after Day 3 were larger in G2 than in G1, moreover, it was significantly increased in G2 as compared with G1 on Day 3 and Days 14-28.

TABLE 7

Weight bearing results for rats in MMT model treated with compound 16.

| Group | Weight bearing (right paw, %) | Pre-injection % | Day 3 % | Day 5 % | Day 7 % | Day 14 % | Day 21 % | Day 28 % |
|---|---|---|---|---|---|---|---|---|
| G1 | Mean | 50.21 | 33.88 | 38.06 | 38.89 | 39.85 | 40.30 | 40.83 |
|    | SD   | 0.71  | 2.17  | 2.84  | 1.26  | 1.68  | 1.03  | 1.66  |
| G2 | Mean | 49.55 | 36.68* | 39.76 | 40.68 | 42.71* | 43.73** | 44.06** |
|    | SD   | 0.98  | 2.06  | 2.01  | 3.16  | 2.20  | 1.01  | 1.09  |

*VsG1, $P < 0.05$;
**VsG1, $P < 0.01$

Data (see Table 8; FIGS. 6A-6I) from histology parameters showed that the G2 had values in all parameters lower than that of the G1. Specifically, degeneration changes of chondrocyte clustering of the G2 (compound 16) was significantly lower as compared with the G1.

TABLE 8

Histopathology evaluation results.

| Histopathological parameter | G1 Mean | G1 SD | G2 Mean | G2 SD |
|---|---|---|---|---|
| Nature of predominant tissue (0-4) | 1.67 | 0.52 | 1.00 | 0.63 |
| Surface regularity (0-4) | 2.00 | 0.89 | 1.67 | 0.52 |
| Structural integrity (0-4) | 1.67 | 0.52 | 1.17 | 0.41 |
| Chondrocyte clustering (0-4) | 1.83 | 0.41 | 1.17* | 0.41 |
| Degenerative changes in cartilage (0-4) | 1.33 | 0.52 | 1.17 | 0.75 |
| Inflammatory response in subchondral bone region (0-4) | 0.17 | 0.41 | 0.00 | 0.00 |
| Neo-vascularization (0-4) | 0.17 | 0.41 | 0.00 | 0.00 |
| Osteophytes (0-4) | 1.33 | 1.03 | 1.17 | 0.75 |
| Total scoring | 10.17 | 2.93 | 7.33 | 1.63 |

*Vs G1, $P < 0.05$

Current experiments demonstrated that the G2 (compound 16) had significantly more weight bearing on the injured leg starting on Day 3 and Day 14 through Day 28, and significantly less cartilage clustering degeneration. The above observations demonstrate the efficacy and support the use of the test compound q.i.d. to treat an MMT-induced model of osteoarthritis.

From a certain perspective, embodiments of the present invention can be summarized as follows, structured in numbered clauses:

CLAUSE 1. A compound of Formula (A), or a pharmaceutically acceptable salt or ester thereof:

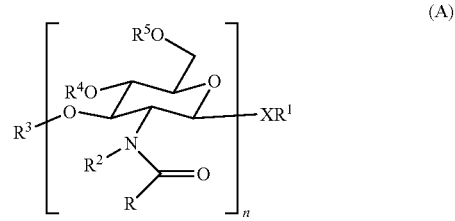

(A)

where:
X is O, N, or S;
R is a substituted or unsubstituted $C_2$ to $C_{18}$ substituent selected from linear or branched alkyl, alkenyl, alkynyl, aryl, heteroaryl, arylalkyl, alkylaryl, cycloalkyl, and alkyl comprising a cyclic or a heterocyclic moiety, or R is a substituted or unsubstituted $C_2$ to $C_{12}$ substituent selected from linear or branched alkyl, alkenyl, alkynyl, aryl, heteroaryl, arylalkyl, alkylaryl, cycloalkyl, and alkyl comprising a cyclic or a heterocyclic moiety;

$R^2$ is hydrogen, acyl, or alkyl; and $R^1$, $R^3$, $R^4$, and $R^5$ are independently hydrogen, substituted or unsubstituted alkyl, aryl, arylalkyl, alkylaryl, cyclic or heterocyclic moiety, or acyl group derived from a carboxylic acid, an amino acid, or a peptide, optionally with a protecting group, a phosphonyl group, or a sulfonyl group, provided that $R^1$, $R^3$, $R^4$, and $R^5$ are not all hydrogen at the same time, or one or more of $R^1$, $R^3$, $R^4$, and $R^5$ are independently selected from alkoxycarbonyl, aryloxycarbonyl, and arylalkoxycarbonyl, or $R^3$ and $R^4$, taken together with the atoms to which they are attached, form a substituted or unsubstituted heterocyclic ring, or $R^4$ and $R^5$, together with the atoms to which they are attached, form a substituted or unsubstituted heterocyclic ring; and n is an integer from 1 to 6.

CLAUSE 2. The compound of clause 1, wherein one or more of $R^1$, $R^3$, $R^4$, and $R^5$ is independently in the form of $Q^1C(=O)$—, where $Q^1$ is selected from unsubstituted or substituted alkyl, alkenyl, alkynyl, aryl, heteroaryl, carbocyclic, heterocyclic group with or without a substituent group, alkoxy, aryloxy, arylalkyloxy, and alkylaryloxy; and an amino or hydroxyl group in $Q^1$, if present, is optionally substituted.

CLAUSE 3. The compound of clause 1 or 2, wherein the compound is a compound of Formula (I), or a pharmaceutically acceptable salt or ester thereof:

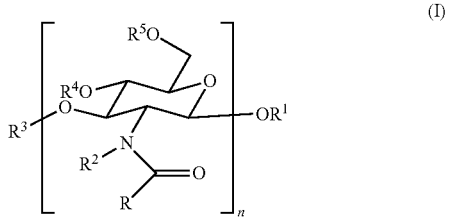

(I)

where R, $R^1$ through $R^5$, and n are defined as in clause 1.

CLAUSE 4. The compound of clause 1 or 2, wherein the compound is a compound of Formula (II), or a pharmaceutically acceptable salt or ester thereof:

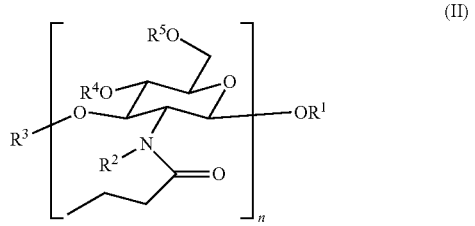

(II)

where $R^1$ through $R^5$, and n are defined as in clause 1.

CLAUSE 5. The compound of clause 1 or 2, wherein the compound is a compound of Formula (III), or a pharmaceutically acceptable salt or ester thereof:

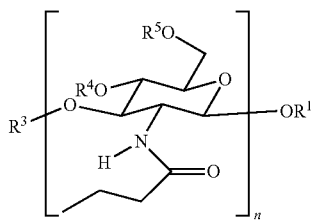

(III)

where $R^1$, $R^3$ through $R^5$, and n are defined as in clause 1.

CLAUSE 6. The compound of clause 1 or 2, wherein the compound is a compound of Formula (IV), or a pharmaceutically acceptable salt or ester thereof:

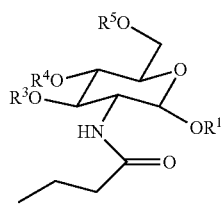

(IV)

where:

$R^1$, $R^3$, $R^4$, and $R^5$ are independently hydrogen, substituted or unsubstituted alkyl, aryl, arylalkyl, alkylaryl, cyclic or heterocyclic moiety, or acyl group derived from a carboxylic acid, an amino acid, or a peptide, optionally with a protecting group, a phosphonyl group, or a sulfonyl group, provided that $R^1$, $R^3$, $R^4$, and $R^5$ are not all hydrogen at the same time, or one or more of $R^1$, $R^3$, $R^4$, and $R^5$ are independently selected from alkoxycarbonyl, aryloxycarbonyl, and arylalkoxycarbonyl, or $R^3$ and $R^4$, taken together with the atoms to which they are attached, form a substituted or unsubstituted heterocyclic ring, or $R^4$ and $R^5$, together with the atoms to which they are attached, form a substituted or unsubstituted heterocyclic ring.

CLAUSE 7. The compound of clause 6, wherein $R^3$, $R^4$, and $R^5$ are independently H, $C_1$-$C_{12}$ alkyl, acyl, or an amino acid, provided that $R^1$, $R^3$, $R^4$, and $R^5$ are not all H at the same time.

CLAUSE 8. The compound of clause 6, wherein $R^1$ is H, and $R^3$, $R^4$, and $R^5$ are independently H, $C_1$-$C_6$ alkyl, acyl, or a natural amino acid residue, provided that $R^3$, $R^4$, and $R^5$ are not all H at the same time.

CLAUSE 9. The compound of clause 6, wherein $R^1$ and $R^3$ are H, and $R^4$ and $R^5$ are independently selected from H, $C_1$-$C_6$ acyl, or an unsubstituted or substituted natural amino acyl group.

CLAUSE 10. The compound of any one of clauses 1 to 9, wherein the compound is an alpha-anomer, a beta-anomer, or a mixture of alpha- and beta-anomers.

CLAUSE 11. The compound of any one of clauses 1 to 10, wherein the compound is not a derivative of N-acetyl glucosamine.

CLAUSE 12. The compound of any one of clauses 1 to 11, which is a compound set forth in any one of Tables 1, 2, and 3, or is any one of compound Nos. 1-172; or a pharmaceutically acceptable salt or ester thereof.

CLAUSE 13. The compound of any one of clauses 1 to 12, wherein one or more of the C, H, O, and/or N atoms in the compound is isotope-enriched.

CLAUSE 14. The compound of clause 13, wherein the C atoms in the compound are independently $^{12}C$, $^{13}C$, or $^{14}C$.

CLAUSE 15. The compound of clause 13 or 14, wherein the H atoms are independently $^{1}H$, D (2H), or T (3H).

CLAUSE 16. The compound of any one of clauses 13 to 15, wherein the O-atoms are independently $^{16}O$, $^{17}O$, or $^{18}O$.

CLAUSE 17. The compound of any one of clauses 13 to 16, wherein the N atoms are independently $^{14}N$ or $^{15}N$.

CLAUSE 18. A pharmaceutical composition comprising the compound of any one of clauses 1 to 17 and a pharmaceutically acceptable carrier.

CLAUSE 19. The pharmaceutical composition of clause 18, wherein the composition is suitable for oral administration or for topical administration.

CLAUSE 20. The pharmaceutical composition of clause 18 or 19, wherein the composition is in the form of a hard shell gelatin capsule, a soft shell gelatin capsule, a cachet, a pill, a tablet, a lozenge, a powder, a granule, a pellet, a pastille, or a dragee.

CLAUSE 21. The pharmaceutical composition of clause 18 or 19, wherein the composition is in the form of a solution, an aqueous liquid suspension, a non-aqueous liquid suspension, an oil-in-water liquid emulsion, a water-in-oil liquid emulsion, an elixir, a syrup, an ointment, or a medical patch.

CLAUSE 22. The pharmaceutical composition of any one of clauses 18 to 21, wherein the composition is enteric coated.

CLAUSE 23. The pharmaceutical composition of any one of clauses 18 to 22, wherein the composition is formulated for controlled release.

CLAUSE 24. A method for the prevention or treatment of a bone or joint disorder comprising administering an effective amount of the compound of any one of clauses 1 to 17 or the pharmaceutical composition of any one of clauses 18 to 23 to a subject in need thereof, such that the bone or joint disorder is prevented or treated in the subject.

CLAUSE 25. The method of clause 24, wherein the bone or joint disorder is osteoporosis.

CLAUSE 26. The method of clause 24, wherein the bone or joint disorder is osteopenia.

CLAUSE 27. The method of clause 24, wherein the bone or joint disorder is arthritis.

CLAUSE 28. The method of clause 27, wherein the arthritis is osteoarthritis, inflammatory arthritis, traumatic arthritis, degenerative arthritis or dysplastic arthritis.

CLAUSE 29. The method of clause 28, wherein the inflammatory arthritis is rheumatoid arthritis or psoriatic arthritis.

CLAUSE 30. The method of any one of clauses 24 to 29, wherein the subject is a mammal, e.g., a human.

CLAUSE 31. A method for increasing the therapeutic effectiveness of GlcNBu in a subject in need thereof, comprising administering an effective amount of the compound of any one of clauses 1 to 17 or the pharmaceutical composition of any one of clauses 18 to 23 to the subject, such that the therapeutic effectiveness of GlcNBu is increased as compared to administration of GlcNBu.

CLAUSE 32. The method of clause 31, wherein said increasing the therapeutic effectiveness of GlcNBu comprises one or more of the following: increasing bioavailability of GlcNBu; increasing AUC of GlcNBu in blood or plasma; increasing $C_{max}$ of GlcNBu; increasing $T_{max}$ of GlcNBu; increasing $t_{1/2}$ of GlcNBu; improving therapeutic bio-distribution of GlcNBu; increasing therapeutic level of GlcNBu in a selected tissue; increasing bioabsorption of GlcNBu; reducing metabolism of GlcNBu; and reducing side effects of GlcNBu.

CLAUSE 33. The method of clause 31 or 32, wherein the subject suffers from a bone or joint disorder.

CLAUSE 34. The method of clause 33, wherein the bone or joint disorder is osteoporosis, osteopenia or arthritis.

CLAUSE 35. The method of any one of clauses 31 to 34, wherein the subject is a mammal, e.g., a human.

CLAUSE 36. A kit comprising the compound of any one of clauses 1 to 17 or the pharmaceutical composition of any one of clauses 18 to 23 and instructions for use thereof.

CLAUSE 37. A method for treating osteoporosis in a subject, comprising administering an effective amount of the compound of any one of clauses 1 to 17 or the pharmaceutical composition of any one of clauses 18 to 23 to the subject, such that osteoporosis is treated in the subject.

CLAUSE 38. The method of clause 37, wherein compound No. 16 is administered to the subject.

CLAUSE 39. A method for treating osteoarthritis in a subject, comprising administering an effective amount of the compound of any one of clauses 1 to 17 or the pharmaceutical composition of any one of clauses 18 to 23 to the subject, such that osteoporosis is treated in the subject.

CLAUSE 40. The method of clause 39, wherein compound No. 16 is administered to the subject.

CLAUSE 41. A method for treating a bone or joint disorder comprising administering an effective amount of the compound of any one of claims 1 to 10 or the pharmaceutical composition of any one of claims 11 to 15 to a subject in need thereof in combination with one or more second therapeutic agent, such that the bone or joint disorder is prevented or treated in the subject.

CLAUSE 42. The method of clause 41, wherein the one or more second therapeutic agent is a bisphosphonate, denosumab, calcitonic, a selective estrogen receptor modulators (SERM) such as raloxifene, teriparatide, duloxetine, and/or a nonsteroidal anti-inflammatory drugs (NSAIDs).

Although this invention is described in detail with reference to embodiments thereof, these embodiments are offered to illustrate but not to limit the invention. It is possible to make other embodiments that employ the principles of the invention and that fall within its spirit and scope as defined by the claims appended hereto.

The contents of all documents and references cited herein are hereby incorporated by reference in their entirety.

What is claimed is:

1. A pharmaceutical composition comprising a compound of Formula (III), or a pharmaceutically acceptable salt or ester thereof, and a pharmaceutically acceptable carrier:

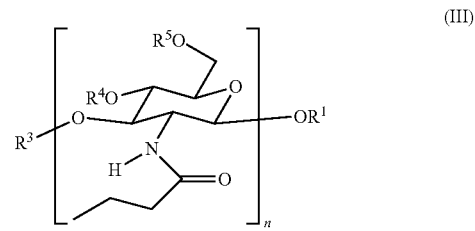

where:
R$^1$ is hydrogen, substituted alkyl, or acyl group derived from a carboxylic acid or a peptide, optionally with a protecting group, a phosphonyl group, or a sulfonyl group;
R$^3$, R$^4$, and R$^5$ are independently hydrogen, substituted or unsubstituted alkyl, aryl, arylalkyl, alkylaryl, cyclic or heterocyclic moiety, or acyl group derived from a carboxylic acid, an amino acid, or a peptide, optionally with a protecting group, a phosphonyl group, or a sulfonyl group, provided that R$^3$, R$^4$, and R$^5$ are not all acyl group at the same time, wherein when R$^5$ is acyl group which is a carbonyl group that is attached through its carbon atom to an alkyl group, the alkyl group is methyl, ethyl, propyl, butyl, hexyl, isopropyl, tert-butyl, sec-butyl, isobutyl, cyclopropyl, cyclopentyl or cyclohexyl; and
n is an integer from 1 to 6;
provided that R$^1$, R$^3$, R$^4$, and R$^5$ are not all hydrogen at the same time; or
one or more of R$^1$, R$^3$, R$^4$, and R$^5$ are independently selected from alkoxycarbonyl, aryloxycarbonyl, and arylalkoxycarbonyl; or
R$^3$ and R$^4$, taken together with the atoms to which they are attached, form a substituted or unsubstituted heterocyclic ring.

2. The pharmaceutical composition of claim 1, wherein the composition is suitable for oral or topical administration.

3. The pharmaceutical composition of claim 1, wherein the composition is in the form of a hard shell gelatin capsule, a soft shell gelatin capsule, a cachet, a pill, a tablet, a lozenge, a powder, a granule, a pellet, a pastille, or a dragee.

4. The pharmaceutical composition of claim 1, wherein the composition is in the form of a solution, an aqueous liquid suspension, a non-aqueous liquid suspension, an oil-in-water liquid emulsion, a water-in-oil liquid emulsion, an elixir, a syrup, an ointment, or a medical patch.

5. The pharmaceutical composition of claim 1, wherein the composition is enteric coated or formulated for controlled release.

6. The pharmaceutical composition of claim 1, wherein n is 1.

7. A method for the treatment of a bone or joint disorder comprising administering an effective amount of the pharmaceutical composition of claim 1 to a subject in need thereof, such that the bone or joint disorder is treated in the subject.

8. The method of claim 7, wherein the bone or joint disorder is osteoporosis, osteopenia, and/or arthritis.

9. The method of claim 8, wherein the arthritis is osteoarthritis, inflammatory arthritis, traumatic arthritis, degenerative arthritis, dysplastic arthritis, rheumatoid arthritis or psoriatic arthritis.

10. A method for the treatment of a bone or joint disorder comprising administering an effective amount of the pharmaceutical composition of claim 6 to a subject in need thereof, such that the bone or joint disorder is treated in the subject.

11. The method of claim 10, wherein the bone or joint disorder is osteoporosis, osteopenia, and/or arthritis.

12. The method of claim 11, wherein the arthritis is osteoarthritis, inflammatory arthritis, traumatic arthritis, degenerative arthritis, dysplastic arthritis, rheumatoid arthritis or psoriatic arthritis.

13. A pharmaceutical composition comprising a compound, or a pharmaceutically acceptable salt or ester thereof, and a pharmaceutically acceptable carrier, wherein the compound is:

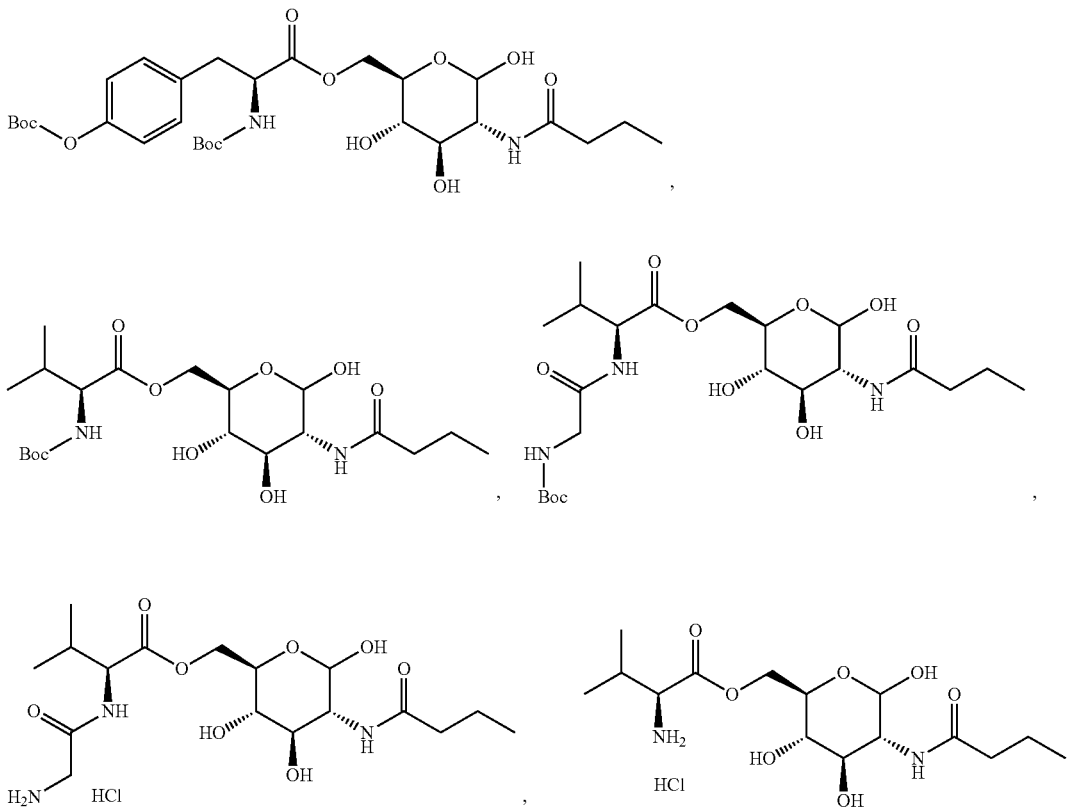

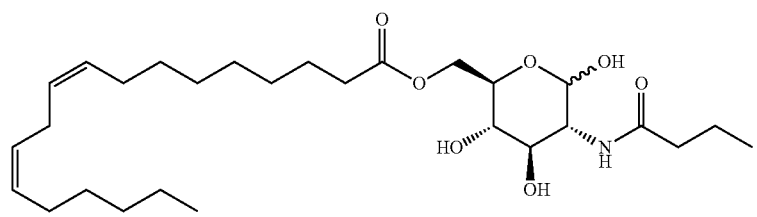
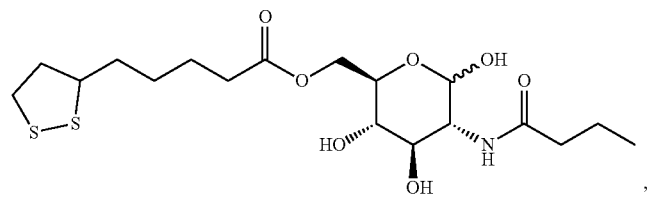
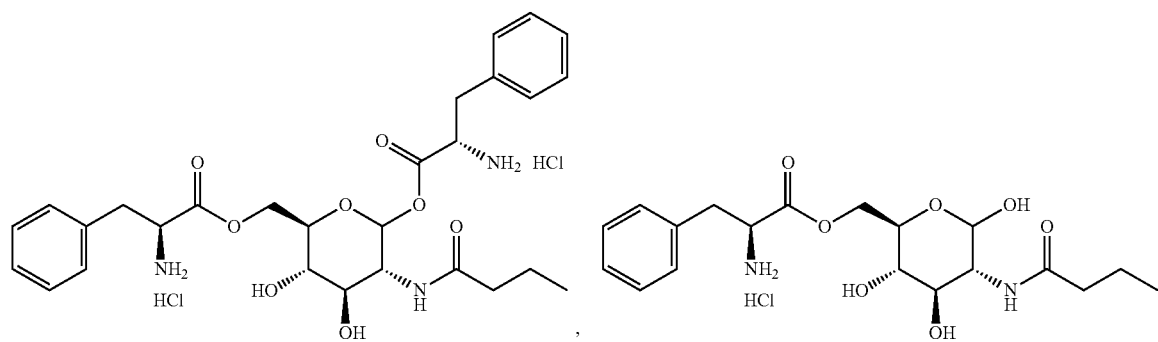
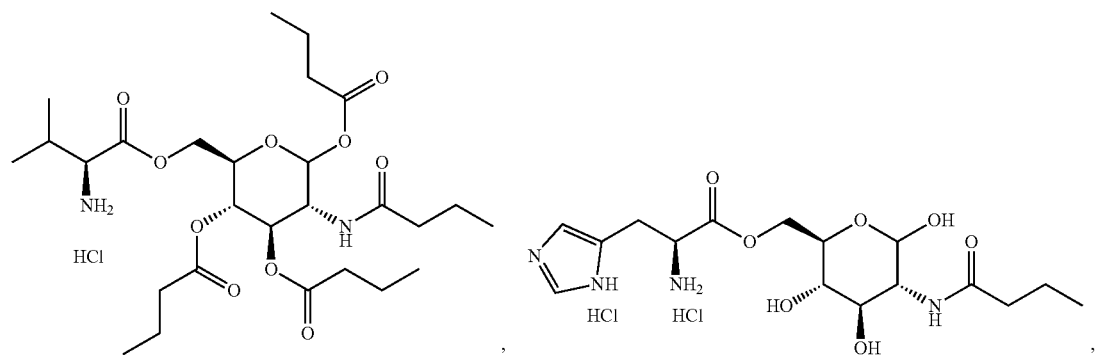
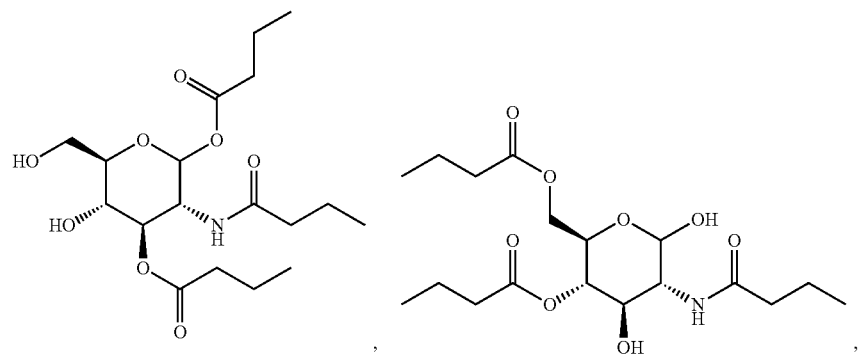

-continued
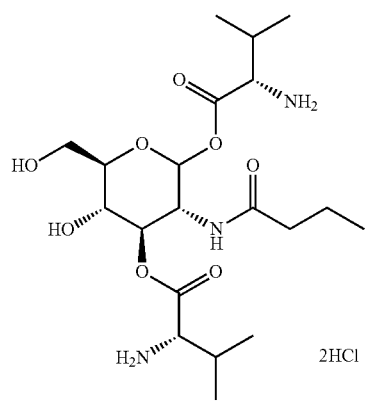
2HCl
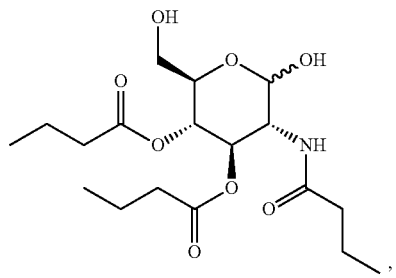
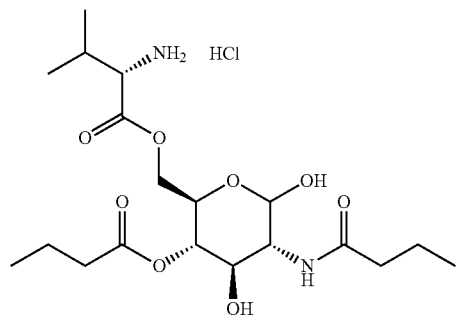
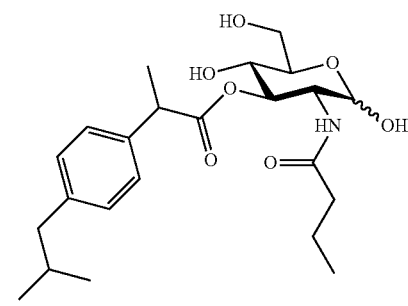
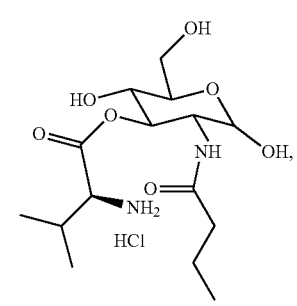
HCl
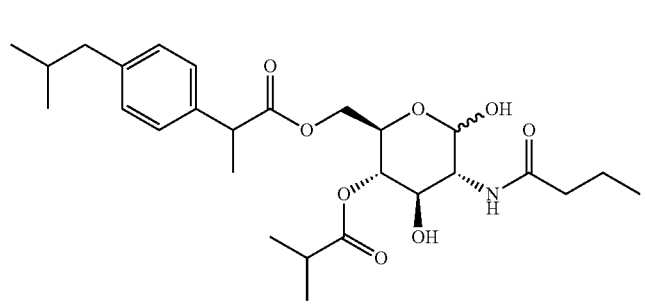
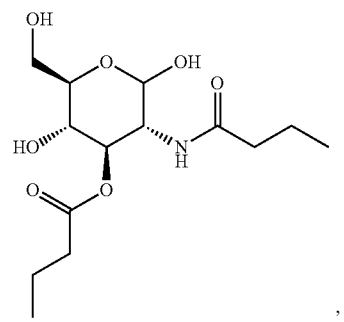
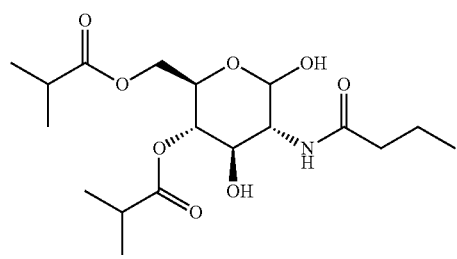
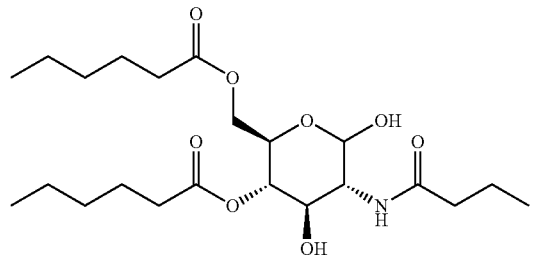
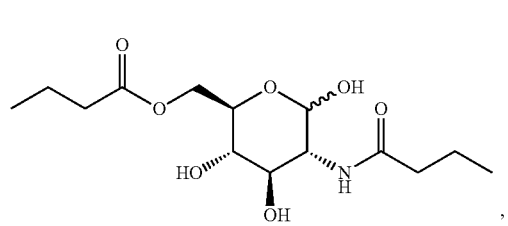
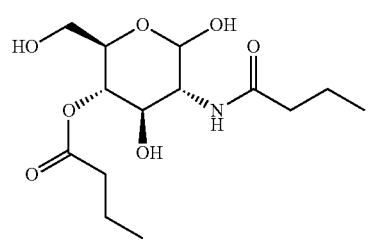

-continued
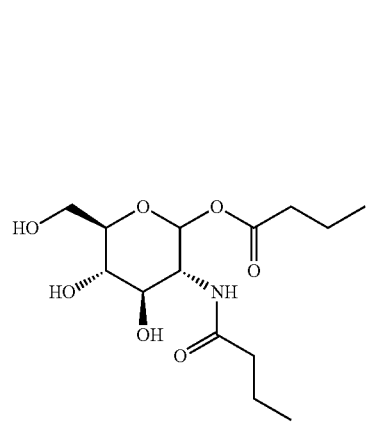
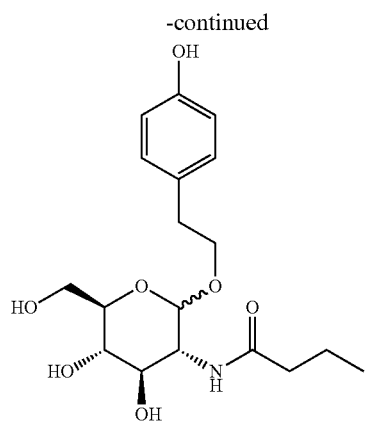
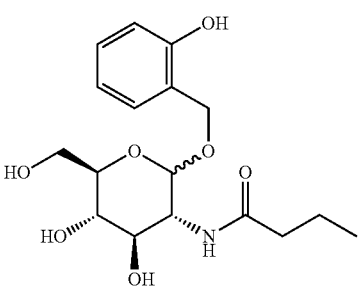
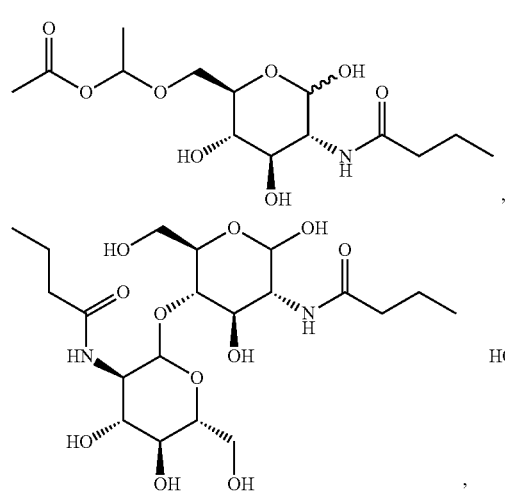
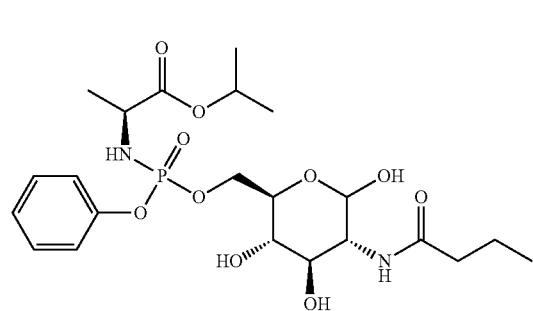
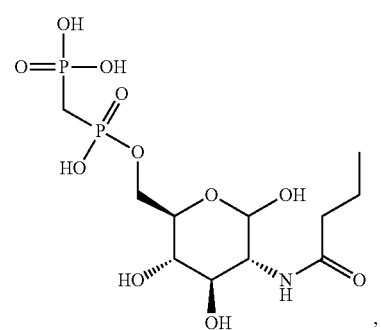
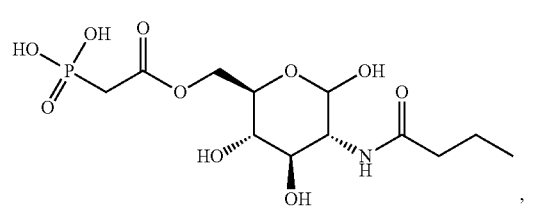
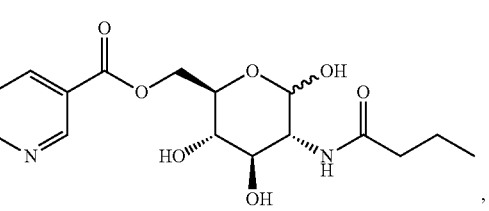
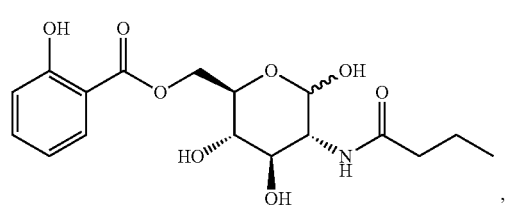
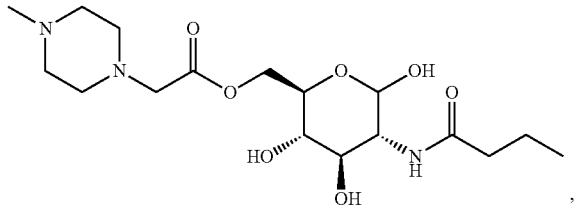

133 134
-continued
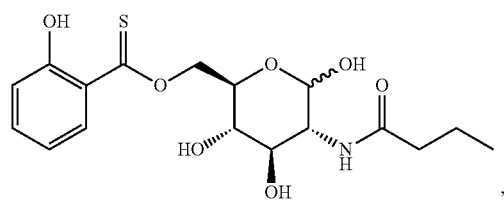
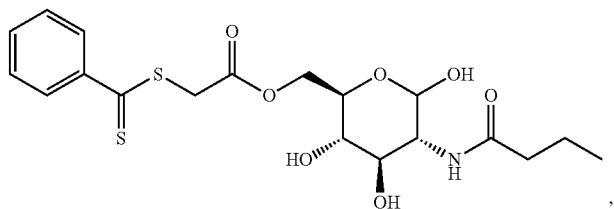
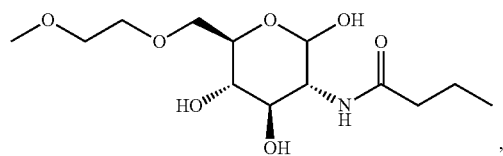
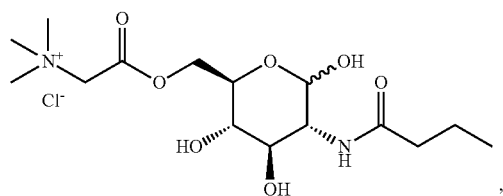
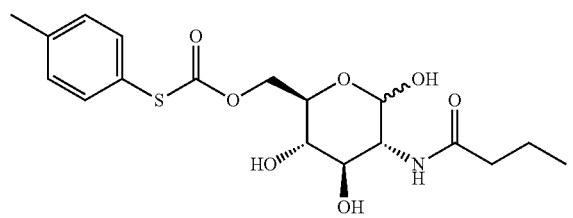
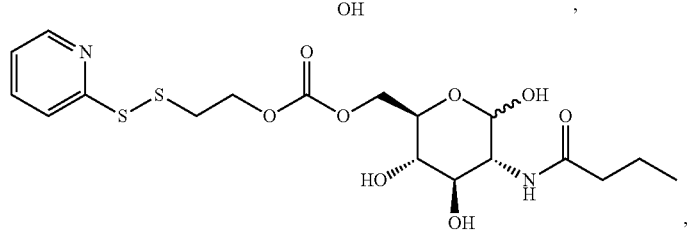
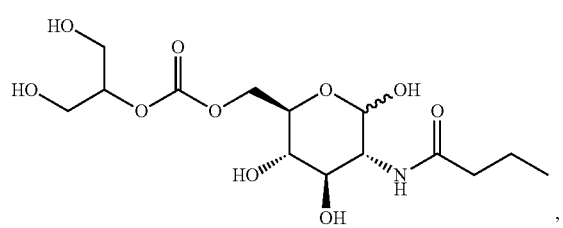
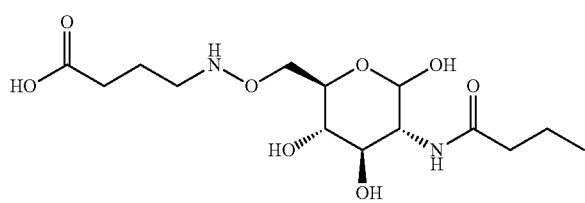
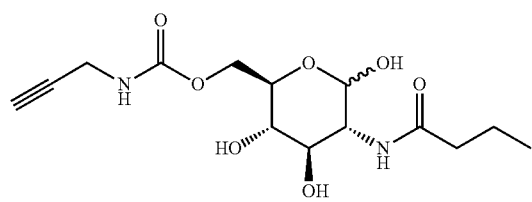
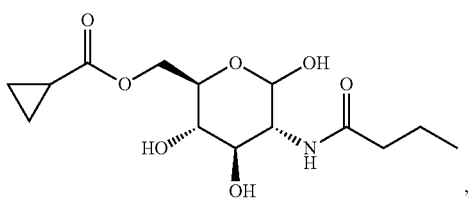

135
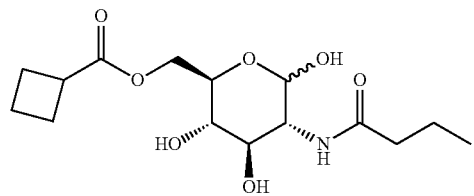
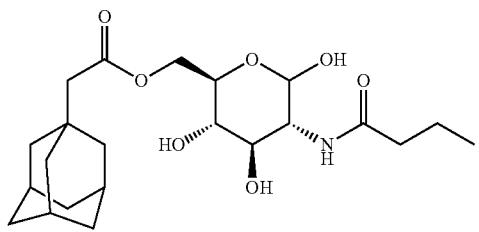
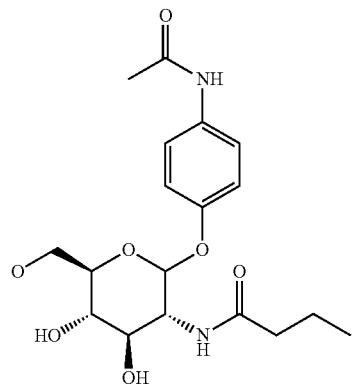
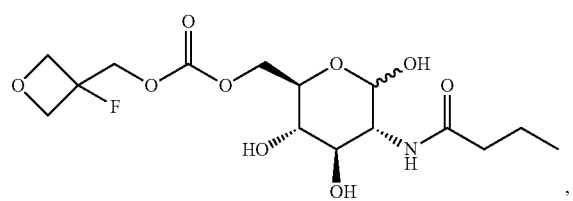
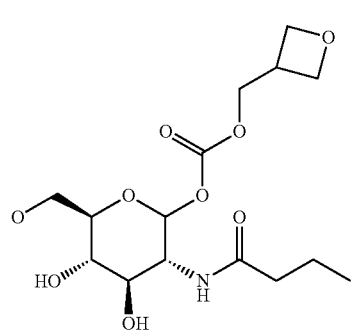
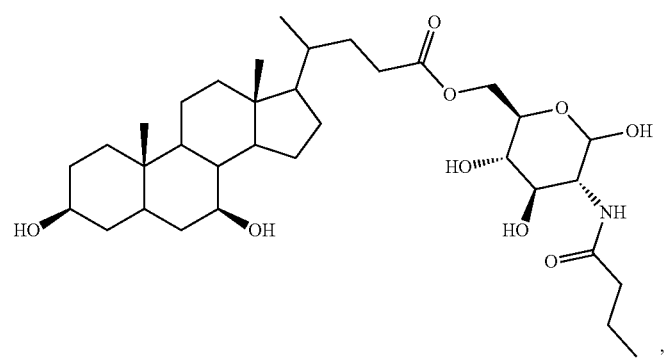
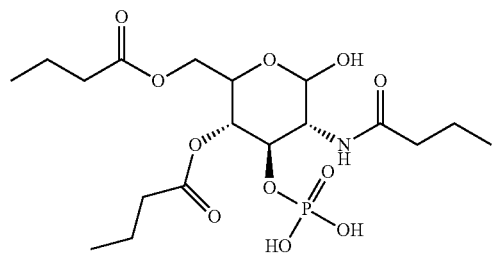
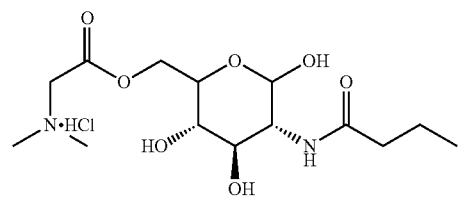
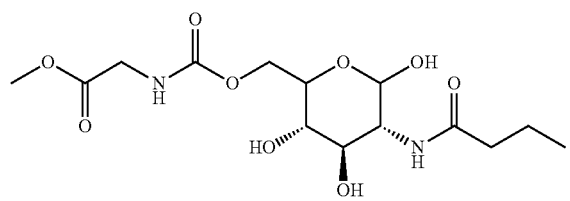
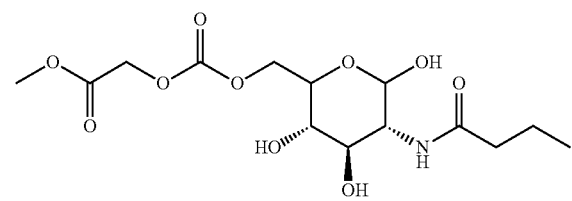
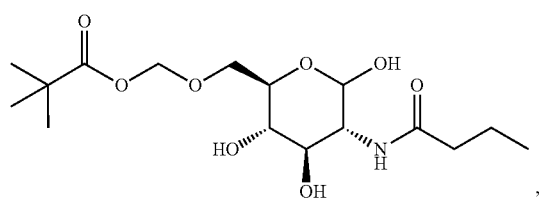
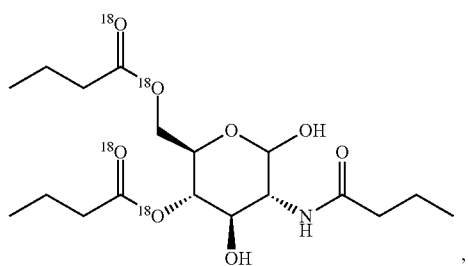

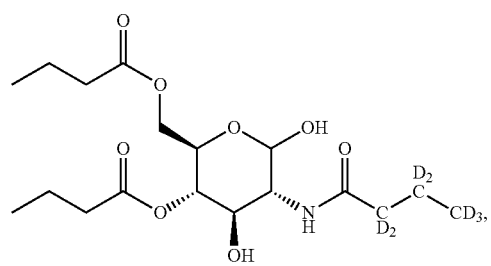
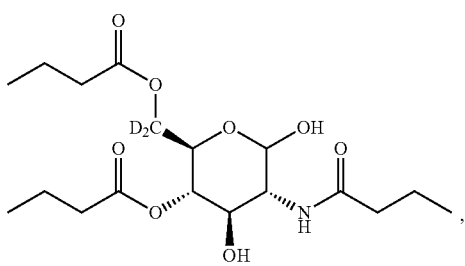
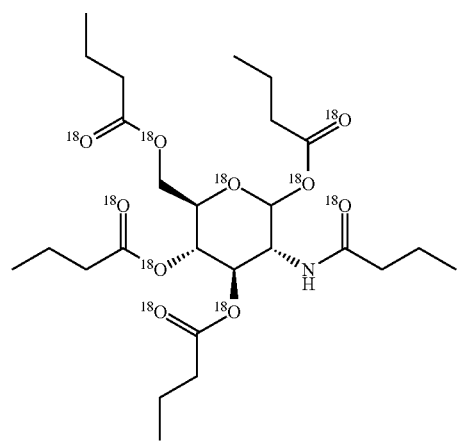
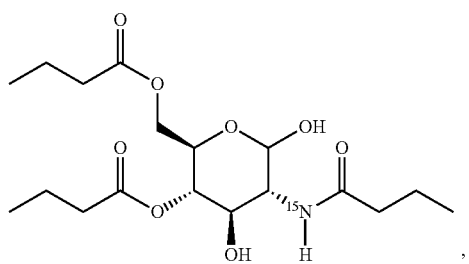
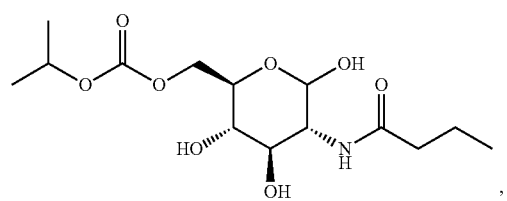
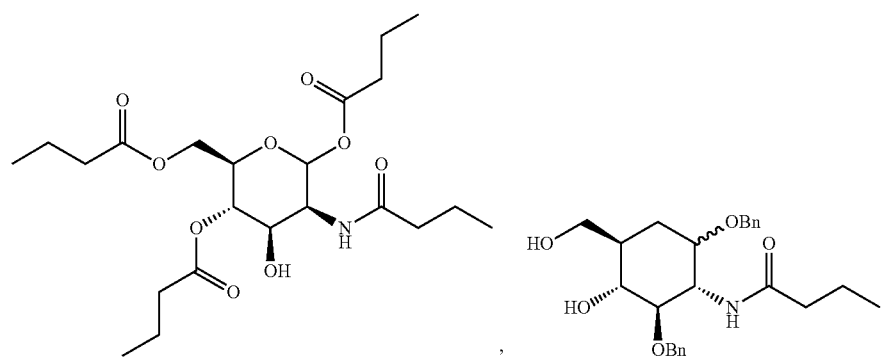
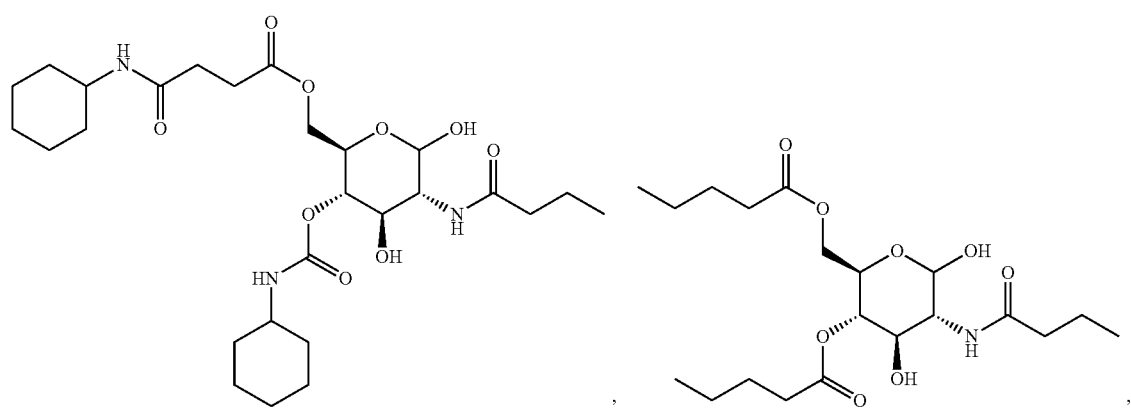

-continued
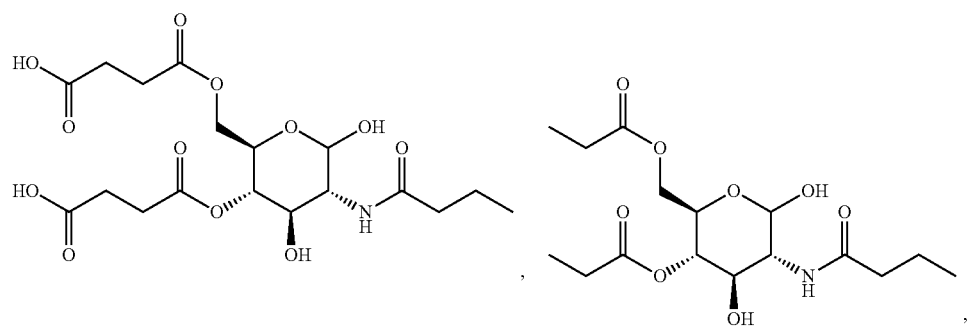
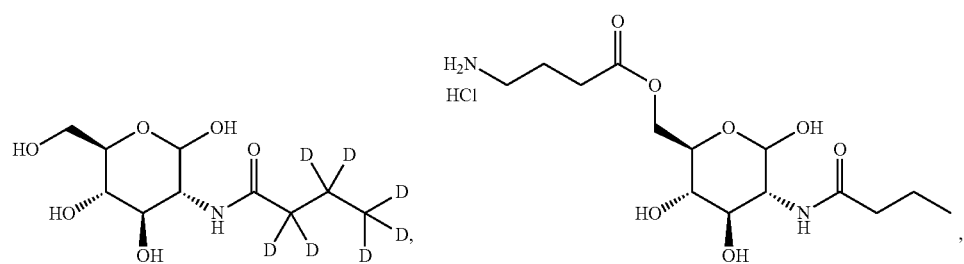
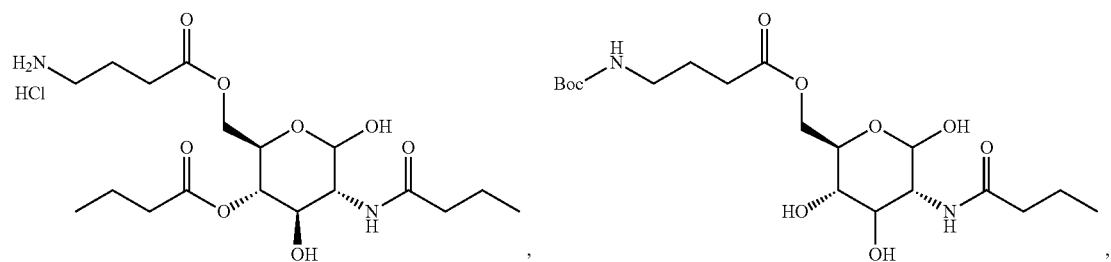
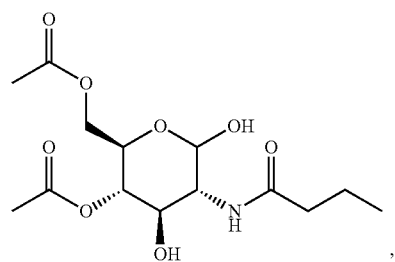
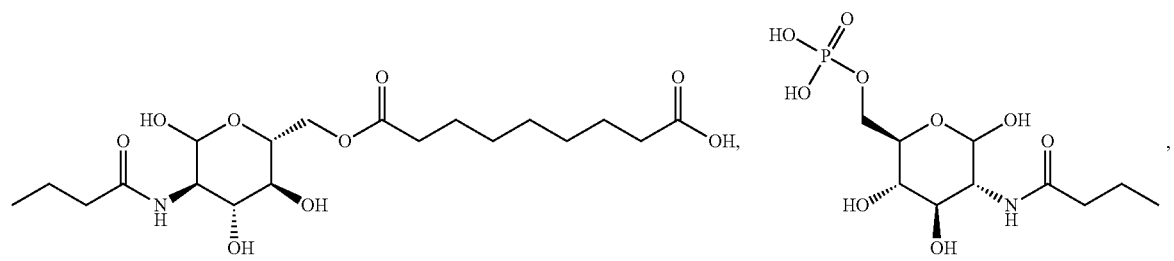

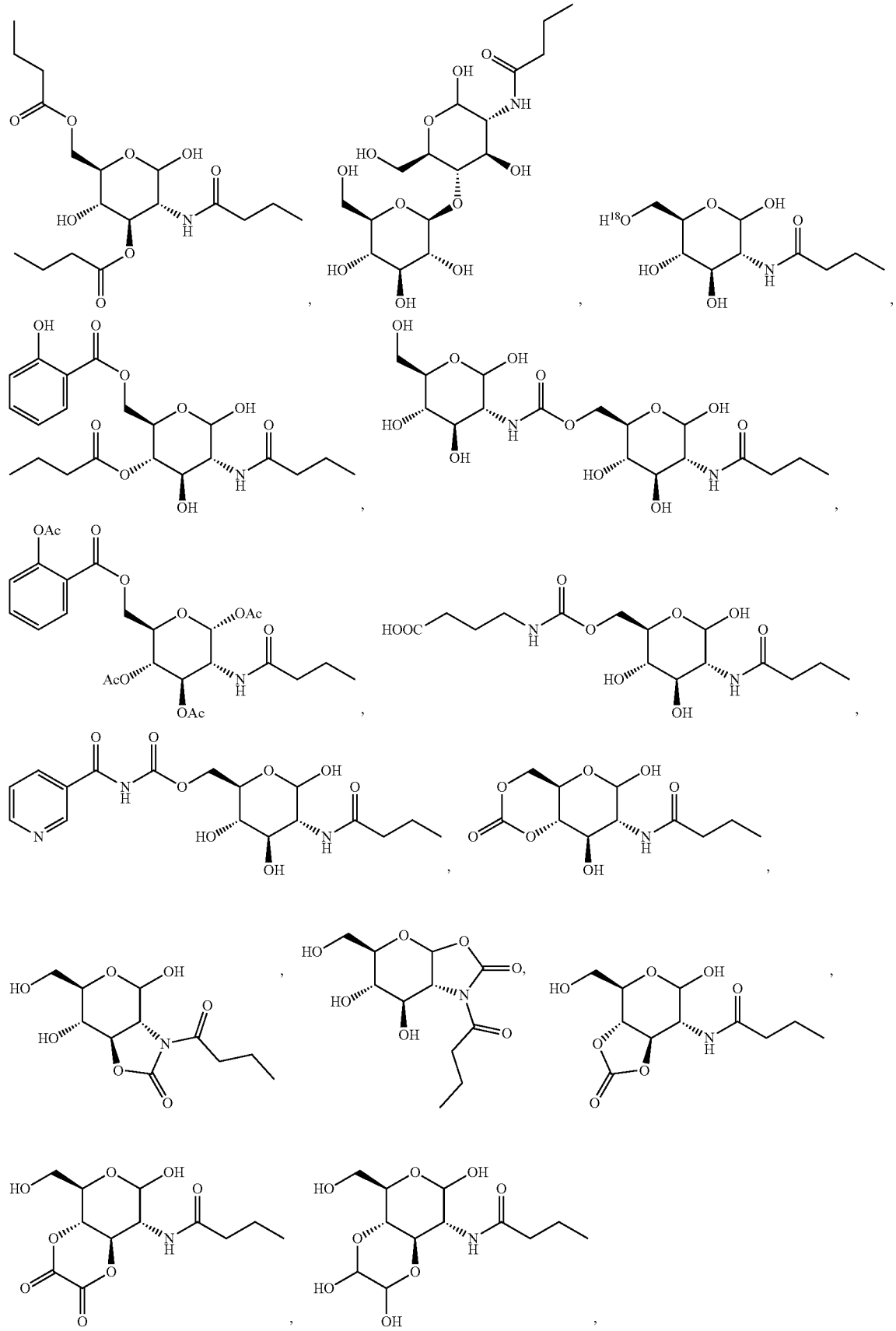

143 144
-continued
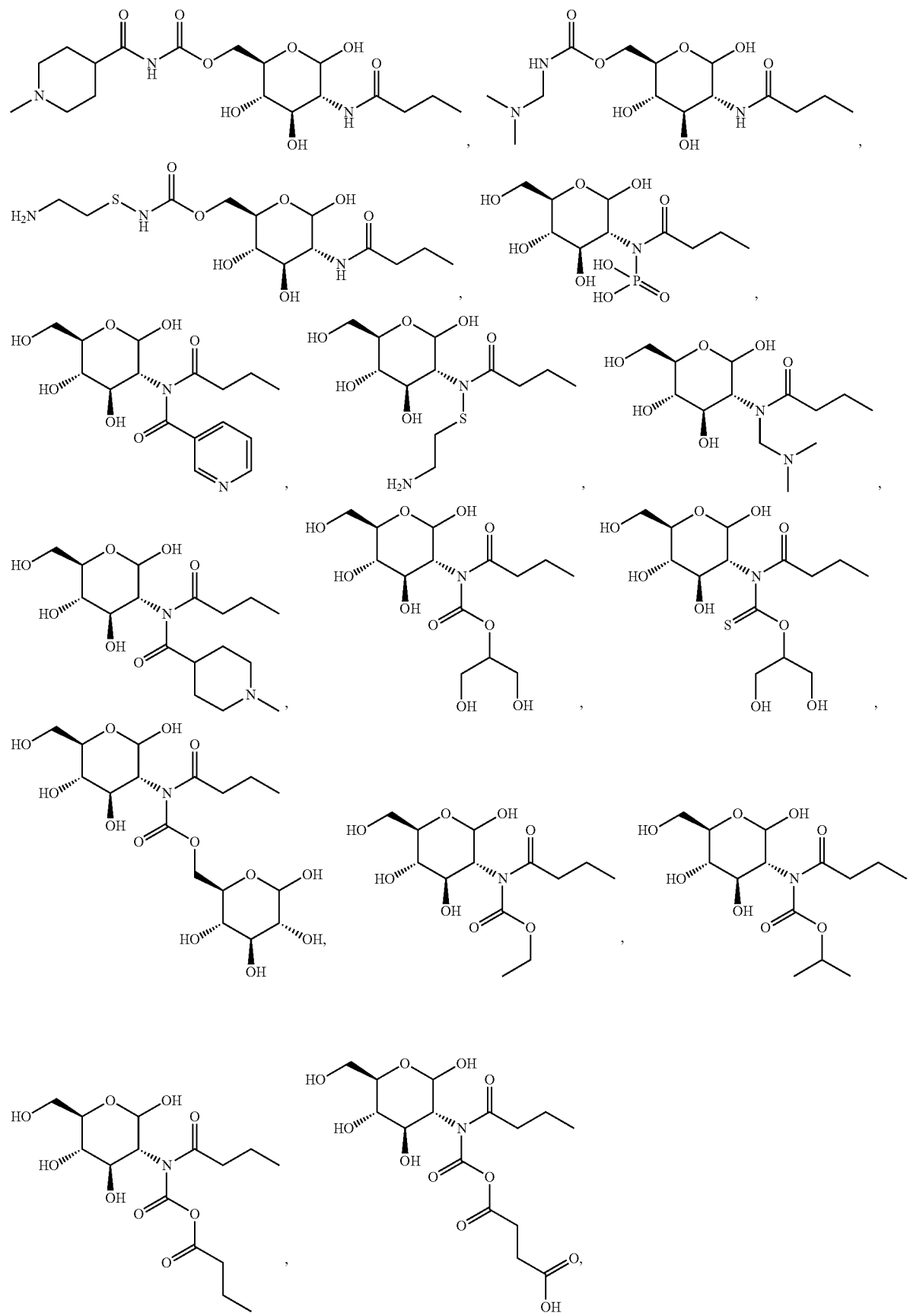

145 -continued 146
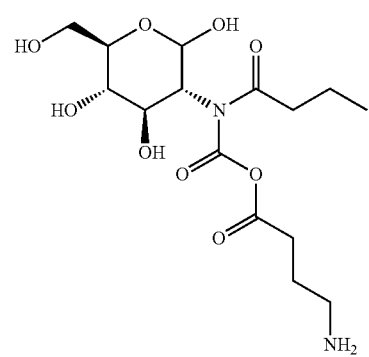
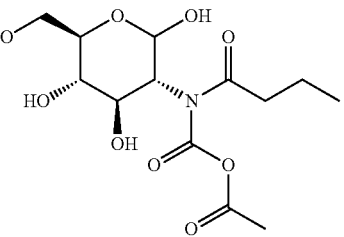
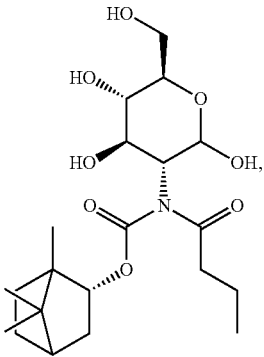
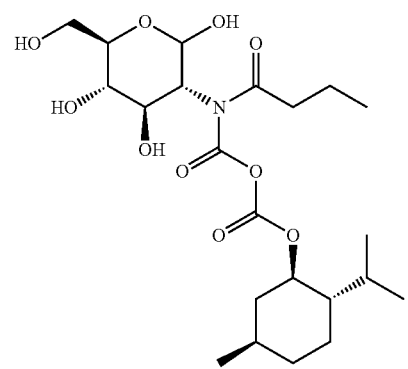
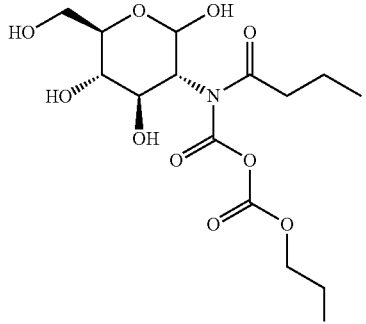
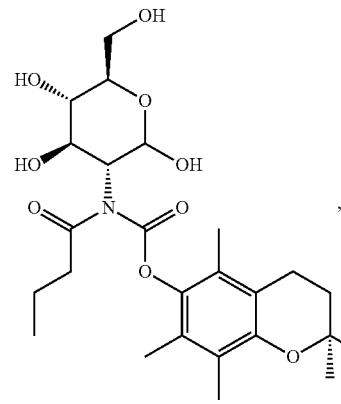
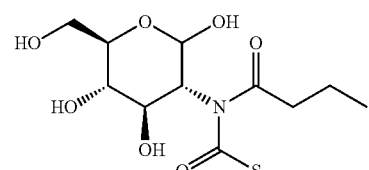
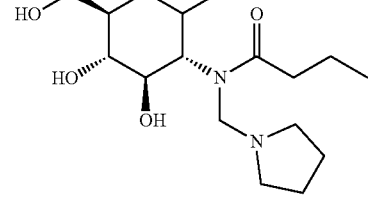
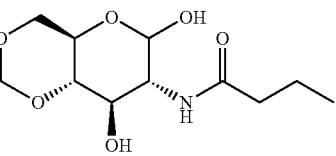
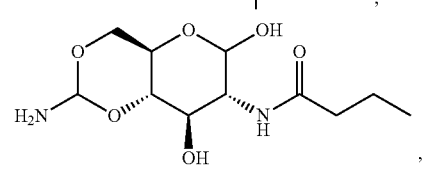
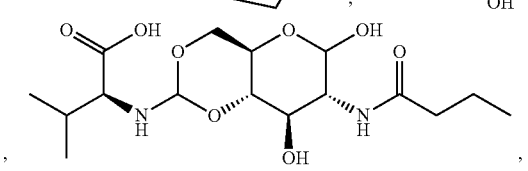

147 148
-continued
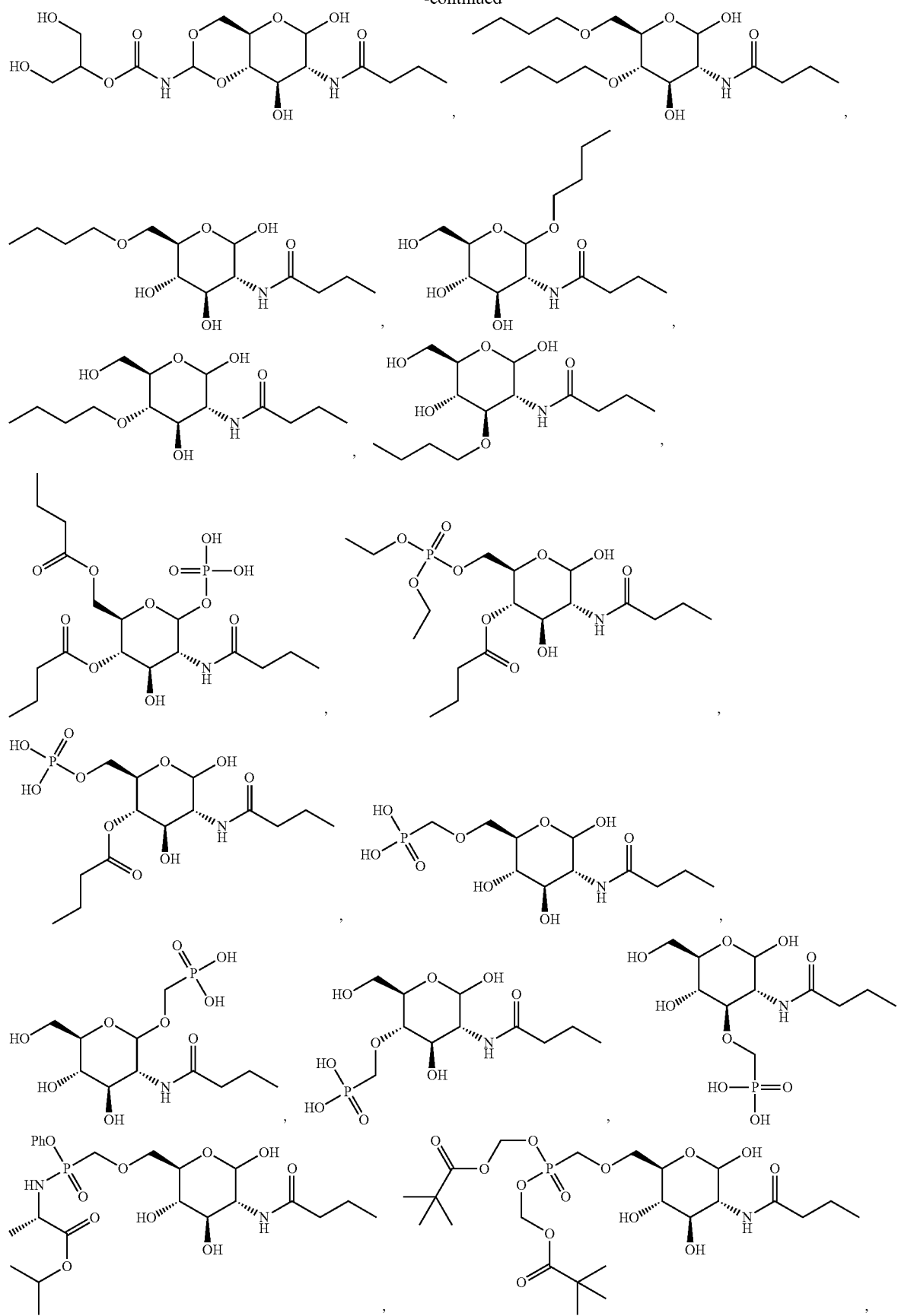

-continued
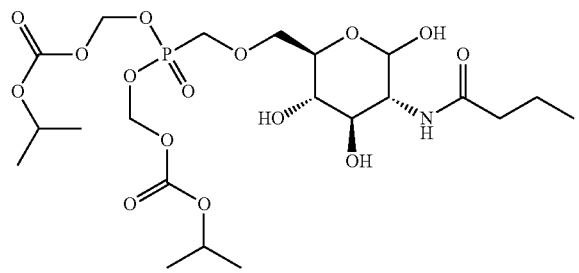
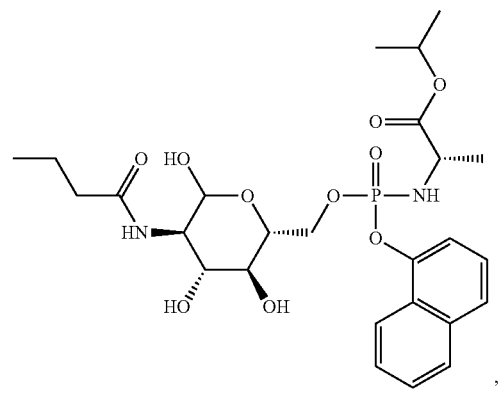
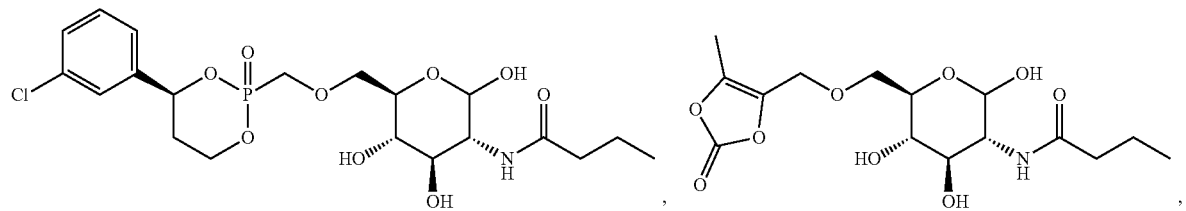
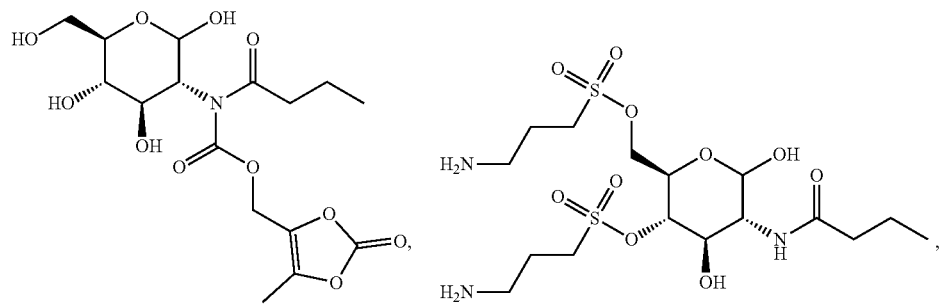
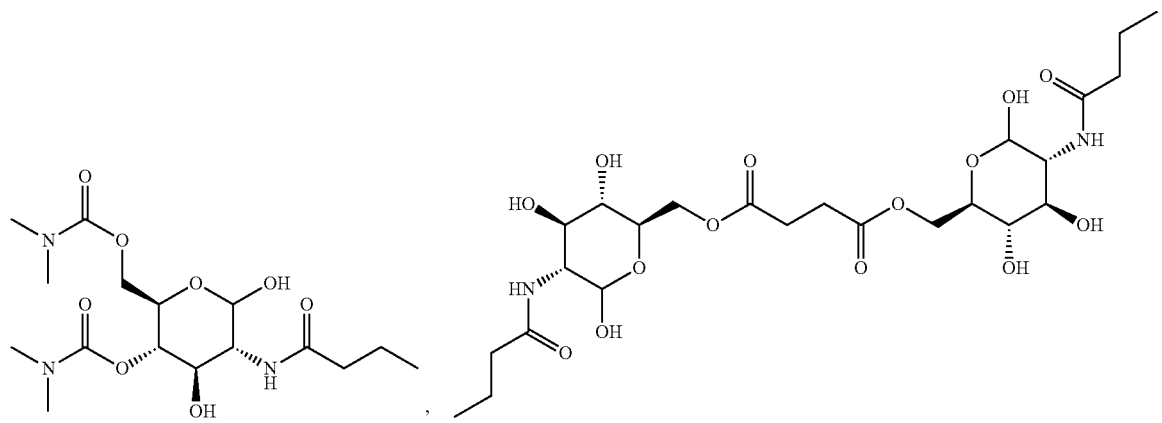

-continued
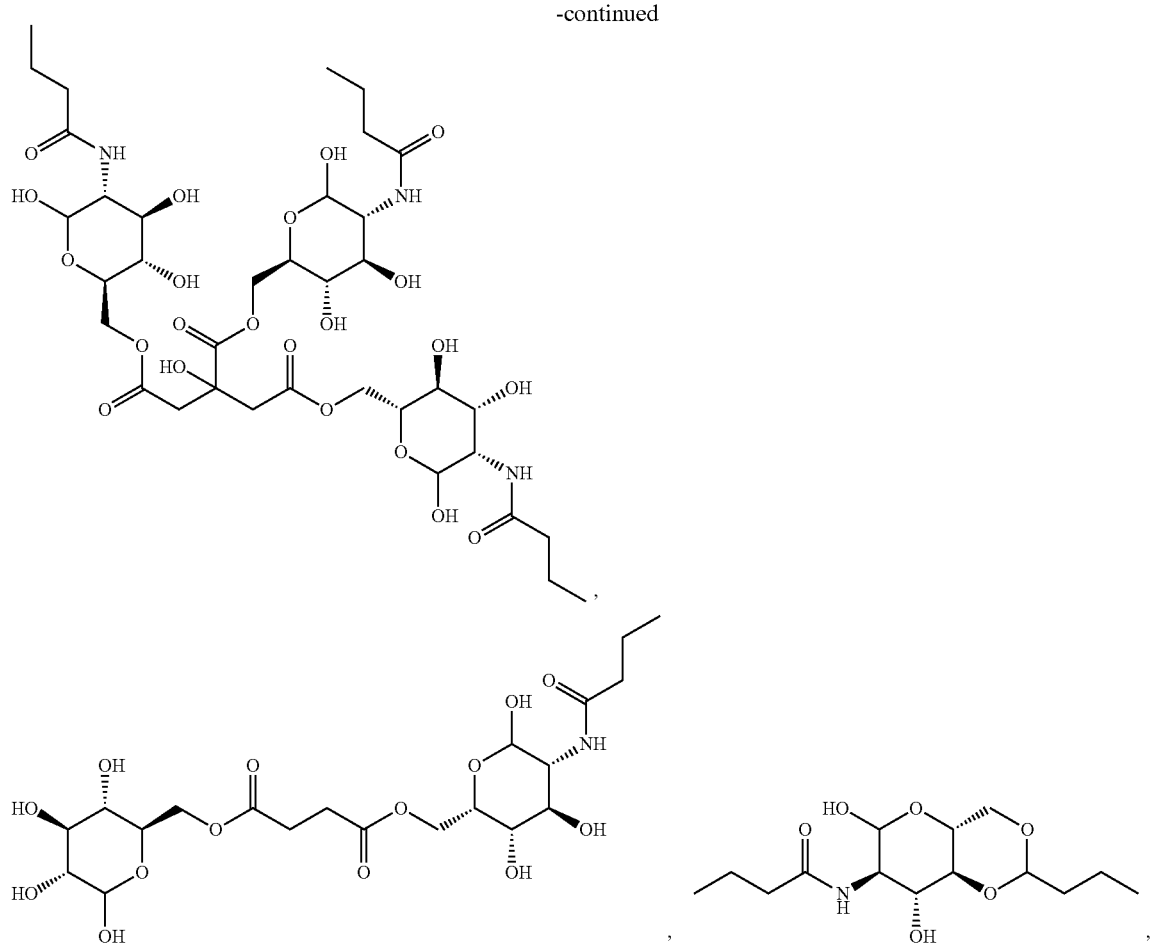
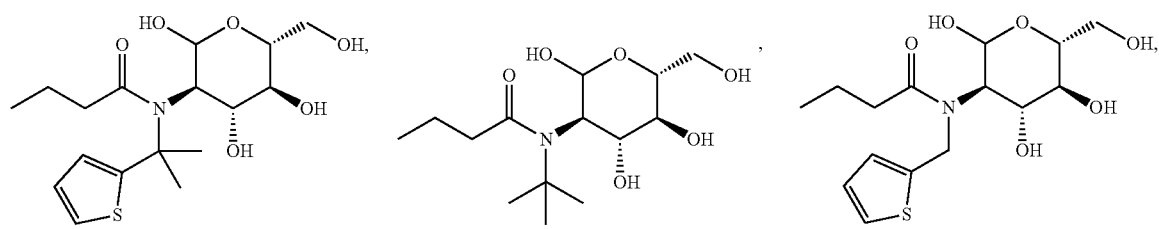
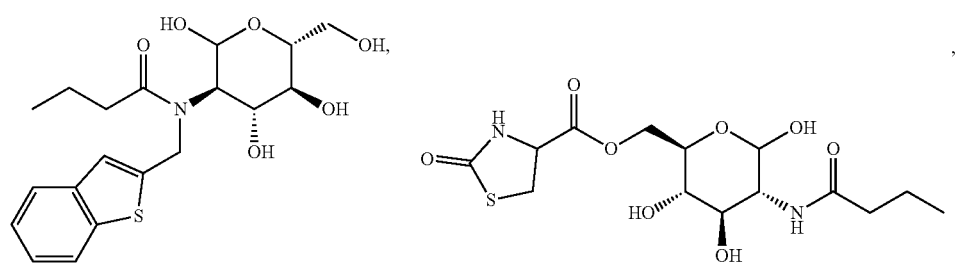

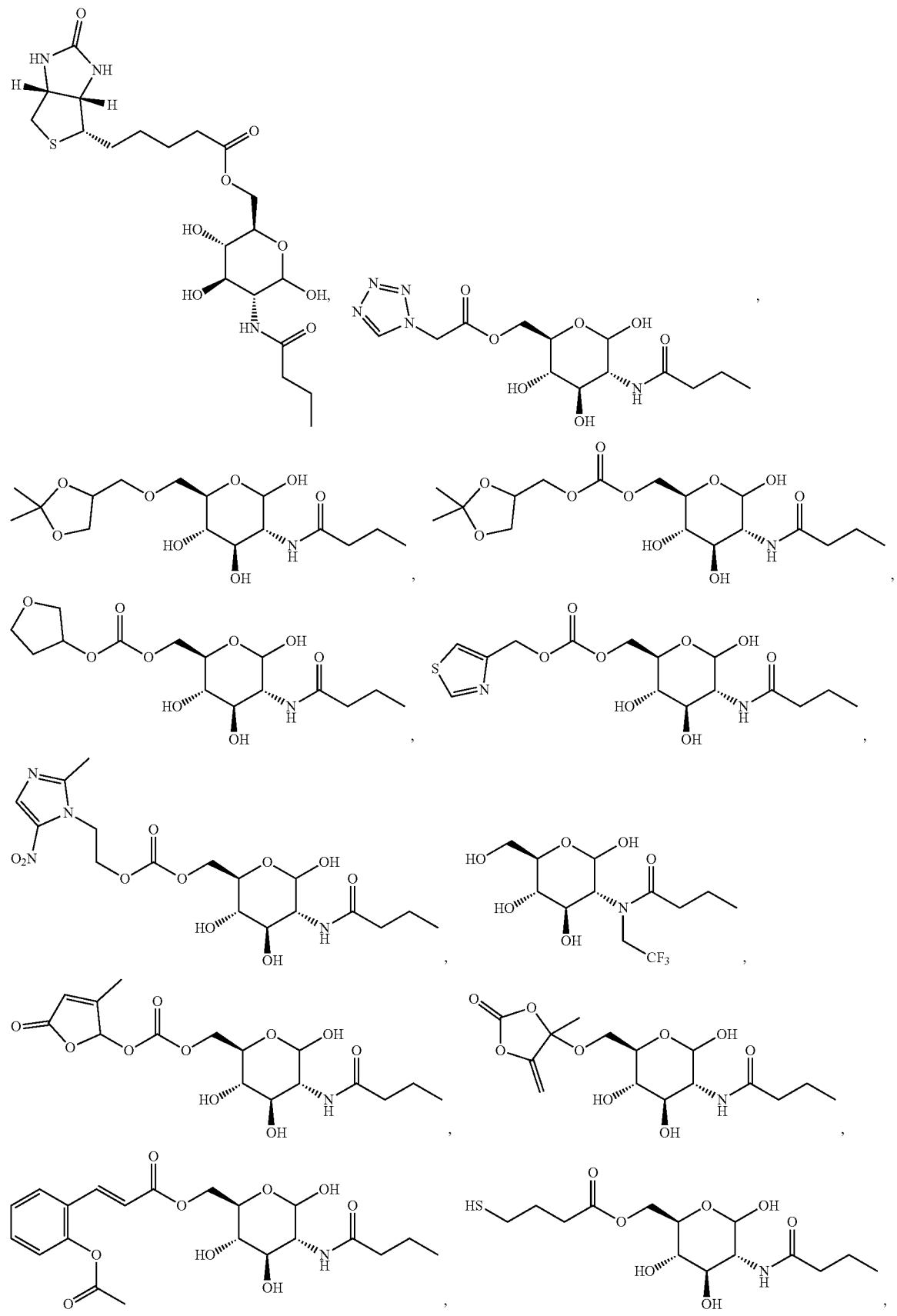

-continued

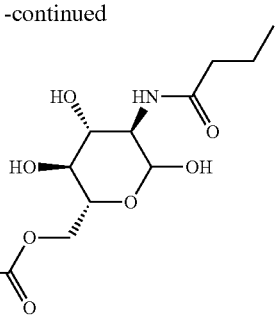
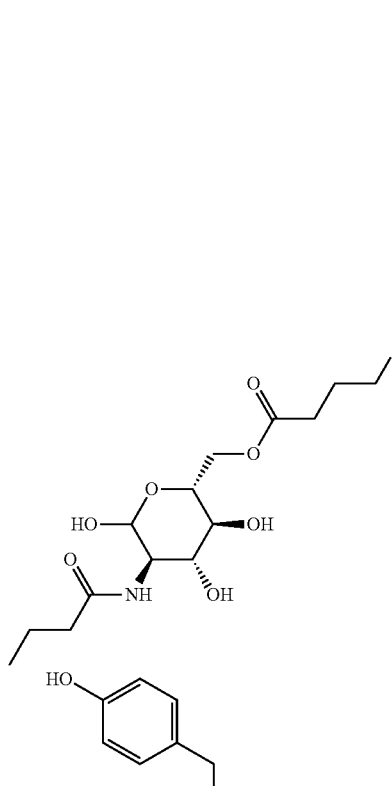
, or

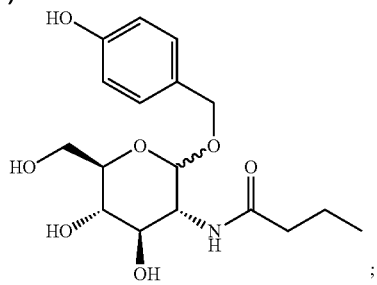
;

14. The pharmaceutical composition of claim 13, wherein the composition is suitable for oral or topical administration.

15. The pharmaceutical composition of claim 13, wherein the composition is in the form of a hard shell gelatin capsule, a soft shell gelatin capsule, a cachet, a pill, a tablet, a lozenge, a powder, a granule, a pellet, a pastille, or a dragee.

16. The pharmaceutical composition of claim 13, wherein the composition is in the form of a solution, an aqueous liquid suspension, a non-aqueous liquid suspension, an oil-in-water liquid emulsion, a water-in-oil liquid emulsion, an elixir, a syrup, an ointment, or a medical patch.

17. The pharmaceutical composition of claim 13, wherein the composition is enteric coated or formulated for controlled release.

18. A method for the treatment of a bone or joint disorder comprising administering an effective amount of the pharmaceutical composition of claim 13 to a subject in need thereof, such that the bone or joint disorder is treated in the subject.

19. The method of claim 18, wherein the bone or joint disorder is osteoporosis, osteopenia, and/or arthritis.

20. The method of claim 19, wherein the arthritis is osteoarthritis, inflammatory arthritis, traumatic arthritis, degenerative arthritis, dysplastic arthritis, rheumatoid arthritis or psoriatic arthritis.

* * * * *